US012252512B2

(12) United States Patent
Schnepp et al.

(10) Patent No.: US 12,252,512 B2
(45) Date of Patent: Mar. 18, 2025

(54) MUTATED POLYPEPTIDES, COMPOSITIONS COMPRISING THE SAME, AND USES THEREOF

(71) Applicant: INTERIUS BIOTHERAPEUTICS, INC., Philadelphia, PA (US)

(72) Inventors: Bruce C. Schnepp, Havertown, PA (US); Philip R. Johnson, Bryn Mawr, PA (US)

(73) Assignee: Interius Biotherapeutics, Inc., Philadelphia, PA (US)

(*) Notice: Subject to any disclaimer, the term of this patent is extended or adjusted under 35 U.S.C. 154(b) by 0 days.

(21) Appl. No.: 18/358,358

(22) Filed: Jul. 25, 2023

(65) Prior Publication Data

US 2024/0059744 A1 Feb. 22, 2024

Related U.S. Application Data

(60) Provisional application No. 63/507,783, filed on Jun. 13, 2023, provisional application No. 63/503,815, filed on May 23, 2023, provisional application No. 63/391,939, filed on Jul. 25, 2022, provisional application No. 63/391,930, filed on Jul. 25, 2022.

(51) Int. Cl.
*C12N 15/86* (2006.01)
*C07K 14/145* (2006.01)

(52) U.S. Cl.
CPC ........ *C07K 14/145* (2013.01); *C07K 2319/03* (2013.01); *C07K 2319/30* (2013.01)

(58) Field of Classification Search
None
See application file for complete search history.

(56) References Cited

U.S. PATENT DOCUMENTS 4,439,196 A 3/1984 Higuchi
4,447,224 A 5/1984 DeCant, Jr. et al.
4,447,233 A 5/1984 Mayfield
4,487,603 A 12/1984 Harris
4,596,556 A 6/1986 Morrow et al.
4,790,824 A 12/1988 Morrow et al.
4,816,567 A 3/1989 Cabilly et al.
4,941,880 A 7/1990 Burns
4,946,778 A 8/1990 Ladner et al.
5,064,413 A 11/1991 Mckinnon et al.
5,260,203 A 11/1993 Ladner et al.
5,312,335 A 5/1994 Mckinnon et al.
5,383,851 A 1/1995 Mckinnon, Jr. et al.
5,399,163 A 3/1995 Peterson et al.
6,005,079 A 12/1999 Casterman et al.
6,096,002 A 8/2000 Landau
6,261,567 B1 7/2001 Hart et al.
6,620,135 B1 9/2003 Weston et al.
11,767,366 B1 9/2023 Russell et al.
2007/0042368 A1 2/2007 Zehentner-Wilkinson et al.
2008/0227736 A1 9/2008 Chen et al.
2009/0324604 A1 12/2009 Liu et al.
2010/0196419 A1 8/2010 Compans et al.
2018/0036429 A1 2/2018 Acharjee
2018/0044425 A1 2/2018 Ågerstam et al.
2018/0371064 A1 12/2018 Fusil et al.
2019/0055568 A1 2/2019 Puléet al.
2019/0241655 A1 8/2019 Cua et al.
2020/0216502 A1 7/2020 Albertini et al.
2020/0371088 A1 11/2020 Birnbaum et al.
2021/0087271 A1 3/2021 Pejchal et al.
2021/0106632 A1 4/2021 Kim et al.
2021/0317209 A1 10/2021 Chu et al.
2021/0347913 A1 11/2021 Sagert et al.
2022/0098271 A1 3/2022 Gill et al.
2022/0133790 A1 5/2022 Gehrke et al.
2023/0279363 A1 9/2023 Russell et al.

FOREIGN PATENT DOCUMENTS

EP 0404097 A2 12/1990
WO WO-1988001649 A1 3/1988
WO WO-1993011161 A1 6/1993
WO WO-1994004678 A1 3/1994
WO WO-1994025591 A1 11/1994
WO WO-1997009433 A1 3/1997
WO WO-2004041862 A2 5/2004
WO WO-2013153391 A1 10/2013
WO WO-2015015489 A1 2/2015
(Continued)

OTHER PUBLICATIONS

Vajdos, F. et al., 2002, JMB, pp. 415-428.*
Bedouelle, H. et al., Febs J., 2006, pp. 34-46.*
50YL Albertini, A.A et al., “50YL, VSV G CR2”, RCSB PDB, Mar. 21, 2018, last revised Apr. 18, 2018, available at https://www.rcsb.org/structure/50YL (last accessed Jan. 3, 2024), 6 pages.
50Y9—Albertini, A.A. et al., “50Y9, VSV G CR3”, RCSB PDB, Mar. 21, 2018, last revised Apr. 18, 2018, available at https://www.rcsb.org/structure/50Y9 (last accessed Jan. 3, 2024), 6 pages.
Albertini et al., “Molecular and Cellular Aspects of Rhabdovirus Entry,” Viruses (2012) 4:117-129.
Baert et al., “Influence of Immunogenicity on the Long-Term Efficacy of Infliximab in Crohn’s Disease,” (2003) New Engl. J. Med. 348:601-608.
Beniaminovitz et al., “Prevention of Rejection in Cardiac Transplantation by Blockade of the Interleukin-2 Receptor with a Monoclonal Antibody,” (2000) New Engl. J. Med. 342(9):613-619.
(Continued)

*Primary Examiner* — Michael D Burkhart
(74) *Attorney, Agent, or Firm* — Goodwin Procter LLP

(57) ABSTRACT

Provided for herein are viral particles comprising a heterologous viral glycoprotein and a targeting moiety, wherein the targeting moiety comprises a polypeptide comprising a formula of T-$S_1$, wherein T is a target binding domain and $S_1$ is a stalk portion. The stalk portion may comprise a variant Fe domain. The stalk portion may comprise a flexible polypeptide domain. The targeting moiety comprising the formula T-$S_1$ may be incorporated into a viral particle to assist with targeting such particles to a specific cell type. Also provided for herein are compositions comprising the same, and methods of using the same.

33 Claims, 57 Drawing Sheets

Specification includes a Sequence Listing.

(56) References Cited

FOREIGN PATENT DOCUMENTS

| | | | |
|---|---|---|---|
| WO | WO-2016065323 | A2 | 4/2016 |
| WO | WO-2018014039 | A1 | 1/2018 |
| WO | WO-2019200007 | A1 | 10/2019 |
| WO | WO-2020223240 | A1 | 11/2020 |
| WO | WO-2021000530 | A1 | 1/2021 |
| WO | WO-2022013872 | A1 | 1/2022 |
| WO | WO-2022023529 | A1 | 2/2022 |
| WO | WO-2022067262 | A1 | 3/2022 |
| WO | WO-2022140556 | A1 | 6/2022 |
| WO | WO-2022183072 | A1 | 9/2022 |
| WO | WO-2023107593 | A2 | 6/2023 |
| WO | WO-2023114884 | A2 | 6/2023 |
| WO | WO-2023170681 | A1 | 9/2023 |

OTHER PUBLICATIONS

C. Dunbar et al, "Gene therapy comes of age", 359 Science 1 (2018).
Chothia et al., "Canonical Structures for the Hypervariable Regions of Immunoglobulins," (1987) J. Mol. Biol. 196:901-917.
Chothia et al., "Conformations of Immunoglobulin Hypervariable Regions," (1989) Nature 342: 877-883.
Clackson et al., "Making Antibody Fragments Using Phage Display Libraries," (1991) Nature 352:624-628. (Abstract Only).
Dobson CS, Reich AN, Gaglione S, Smith BE, Kim EJ, Dong J, Ronsard L, Okonkwo V, Lingwood D, Dougan M, Dougan SK, Birnbaum ME. Antigen identification and high-throughput interaction mapping by reprogramming viral entry. Nat Methods. Apr. 2022; 19(4):449-460. doi: 10.1038/s41592-022-01436-z. Epub Apr. 8, 2022. PMID: 35396484; PMCID: PMC9012700.
Donald J. Voet et al., "Fundamentals of biochemistry" (2008), chapters 3 and 4, 39-82.
Duverge and M. Negroni, "Pseudotyping lentiviral vectors: when the clothes make the virus", 12 VIRUSES 1311 (2020).
E. Pettersen et al., "UCSF Chimera—A visualization system for exploratory research and analysis", 25 J. Comp. Chem. 1605 (2004).
Edelman, G M et al. "The covalent structure of an entire gammaG immunoglobulin molecule." *Proceedings of the National Academy of Sciences of the United States of America* vol. 63,1 (1969): 78-85. doi:10.1073/pnas.63.1.78.
F. Amirache et al, "Mystery solved: VSV-G-LVs do not allow efficient gene transfer into unstimulated T cells, B cells, and HSCs cause they lack the LDL receptor", 123 BLOOD 1422 (2014).
Finkelshtein et al., "LDL Receptor and its Family Members Serve as the Cellular Receptors for Vesicular Stomatitis Virus," PNAS (2013) 110(18): 7306-7311.
Ghosh et al., "Natalizumab for Active Crohn's Disease," (2003) New Engl. J. Med. 348:24-32.
Herold et al., "Anti-CD3 Monoclonal Antibody in New-Onset Type 1 Diabetes Mellitus," (2002) New Engl. J. Med. 346(22): 1692-1698.
Holliger et al., "Diabodies: Small Bivalent and Bispecific Antibody Fragments," (1993) Proc. Natl. Acad. Sci. USA 90: 6444-6448.
Holliger et al., "Engineered Antibody Fragments and the Rise of Single Domains," (2005) Nat. Biotechnol. 23(9): 1126-1136.
Hwang et al., "Engineering a Serum-Resistant and Thermostable Vesicular Stomatitis Virus G Glycoprotein for Pseudotyping Retroviral and Lentiviral Vectors," Gene Ther. (Aug. 2013) 20(8):807-815.
International Search Report and Written Opinion for PCT/US2022/081616, dated Jun. 15, 2023, 14 pages.
J. Rose and C. Gallione, "Nucleotide Sequences of the mRNAs Encoding the Vesicular Stomatitis Virus G and M Proteins Determined from cDNA Clones Containing the Complete Coding Regions", 39 J. Virology 519 (1981).
Kabat et al., "Unusual Distributions of Amino Acids in Complementarity-Determining (Hypervariable) Segments of Heavy and Light Chains of Immunoglobulins and Their Possible Roles in Specificity of Antibody-Combining Sites," (1977) J. Biol. Chem. 252(19):6609-6616.
Kabat, "The Structural Basis for Antibody Complementary," Adv. Prot. Chem. (1978) 32:1-75. (Abstract Only).
*Kelonia Therapeutcis, Inc.* v. *Interius Biotherapeutics, Inc.*, U.S. Pat. No. 11,767,366, Case No. PRG2024-00008, Patent Owner's Preliminary Response.
*Kelonia Therapeutics, Inc.* v. *Interius Biotherapeutics, Inc.*, U.S. Pat. No. 11,767,366, Petition for Post-Grant Review of U.S. Pat. No. 11,767,366.
L. Naldini et al., "In vivo gene delivery and stable transduction of nondividing cells by a lentiviral vector", 272 SCIENCE 263 (1996).
Lathe, "Synthetic Oligonucleotide Probes Deduced from Amino Acid Sequence Data," J. Molec. Biol. (1985) 183:1-12.
Lee et al., "ASTCT Consensus Grading for Cytokine Release Syndrome and Neurologic Toxicity Associated with Immune Effector Cells," Biol. Blood Marrow Transplant (2019) 25:625-638.
Lipsky et al., "Infliximab and Methotrexate in the Treatment of Rheumatoid Arthritis," (2000) New Engl. J. Med. 343(22): 1594-1602.
Liu et al., "Chimeric Mouse-Human IgG1 Antibody that can Mediate Lysis of Cancer Cells," Proc Natl. Acad. Sci., USA (1987) 84:3439-3443.
Liu et al., "Production of a Mouse-Human Chimeric Monoclonal Antibody to CD20 with Potent Fc-Dependent Biologic Activity," J. Immunology (1987) 139(10):3521-3526.
Liu et al., "Randomised, Double Blind, Placebo Controlled Study of Interferon Beta-1a in Relapsing-Remitting Multiple Sclerosis Analysed by Area under Disability/Time Curves," J. Neurol. Neurosurg. Psych. (1999) 67:451-456.
Marks et al., "By-Passing Immunization," J. Mol. Biol. (1991) 222: 581-597.
Michaels et al., "Preclinical proof of concept for VivoVec, a lentiviral-based platform for in vivo CAR T-cell engineering", *J Immunother Cancer* 2023; 11:e006292. doi: 10.1136/jitc-2022-006292, 40 pages.
Milgrom et al., "Treatment of Allergic Asthma with Monoclonal Anti-IgE Antibody," New Engl. J. Med. (1999) 341:1966-1973.
Muller, "[43] Determination of Affinity and Specificity of Anti-Hapten Antibodies by Competitive Radioimmunoassay," Meth. Enzymol. (1983) 92:589-601. (Abstract Only).
Muyldermans et al., "Recognition of Antigens by Single-Domain Antibody Fragments: the Superfluous Luxury of Paired Domains," (2001) Trends Biochem. Sci. 26(4):230-235.
N. Depolo et al, "VSV-G Pseudotyped lentiviral vector produced in human cells are inactivated by human serum", 2 Molecular therapy 218 (2000).
Neelapu et al., "Chimeric Antigen Receptor T-Cell Therapy—Assessment and Management of Toxicities," Nat. Rev. Clin. Oncology (Jan. 2018) 15(1): 47-62.
Nikolic et al., "Structural Basis for the Recognition of LDL-Receptor Family Members by VSV Glycoprotein," Nature Comm. (2018) 9(1029): 1-12.
Notice of Allowance for U.S. Appl. No. 18/066,420 dated Jul. 26, 2023.
Notice of Allowance for U.S. Appl. No. 18/157,421 dated Aug. 25, 2023.
Notification Of Transmittal Of The International Search Report and The Written Opinion Of The International Searching Authority, dated Feb. 22, 2024, 139 pages.
Pluckthun, "Antibodies from *Escherichia coli*," Nature (Oct. 4, 1990) vol. 347, No. 6292, pp. 497-498.
Portielji et al., "IL-12: A Promising Adjuvant for Cancer Vaccination," Cancer Immunol. Immunother. (2003) 52:133-144.
Presta, "Selection, Design, and Engineering of Therapeutic Antibodies," J. Allergy Clin. Immunol. (2005) 116(4):731-736.
R. Florkiewicz and J. Rose, "A Cell Line Expressing Vesicular Stomatitis Virus Glycoprotein fuses at low ph", 225 SCIENCE 721 (1984).
Reichmann et al., "Reshaping Human Antibodies for Therapy," Nature (1988) 332(6162):323-327.
Roche et al., "Crystal Structure of the Low-pH Form of the Vesicular Stomatitis Virus Glycoprotein G," Science (Jul. 14, 2006) 313:187-191.

(56) References Cited

OTHER PUBLICATIONS

Roche et al., "Structure of the Prefusion Form of the Vesicular Stomatitis Virus Glycoprotein G," Science (Feb. 9, 2007) 315:843-848.
S. P. J. Whelan, "Vesicular stomatis Virus", Encyclopedia of virology 291 (Elsevier ltd) (2008).
S. Roche et al, "Structures of vesicular stomatitis virus glycoprotein: membrane fusion revisited", 65 Cell Mol. Life Sci. 1716 (2008).
Slamon et al., "Use of Chemotherapy Plus a Monoclonal Antibody against HER2 for Metastatic Breast Cancer that Overexpresses HER2," (2001) New Engl. J. Med. 344(11):783-792.
Teachey et al., "Identification of Predictive Biomarkers for Cytokine Release Syndrome after Chimeric Antigen Receptor T-cell Therapy for Acute Lymphoblastic Leukemia," Cancer Discov. (Jun. 2016) 6(6):664-679.
Tsurushita et al., "Humanization of a Chicken Anti-IL-12 Monoclonal Antibody," J. Immuno. Methods (2004) vol. 295, pp. 9-19.
Yang et al., "A Randomized Trial of Bevacizumab, an Anti-Vascular Endothelial Growth Factor Antibody, for Metastatic Renal Cancer," (2003) New Engl. J. Med. 349(5): 427-434.
Zardecki et al., "RCSB Protein Data Bank: A Resource for Chemical, Biochemical, and Structural Explorations of large and small biomolecules", 93 J. Chem. Educ. 569(2016).
Declaration of Proffesor John K. Rose, Phd in Support of Petition for Post-Grant Review of U.S. Appl. No. 11,767,366 Before the Patent Trial and Appeal Board *Kelonia Therapeutics, Inc.* Petition v. *Interius Biotherapeutics, Inc*., Patent Owner, Exhibit 1002, 98 pages.

* cited by examiner

Figure 1B:
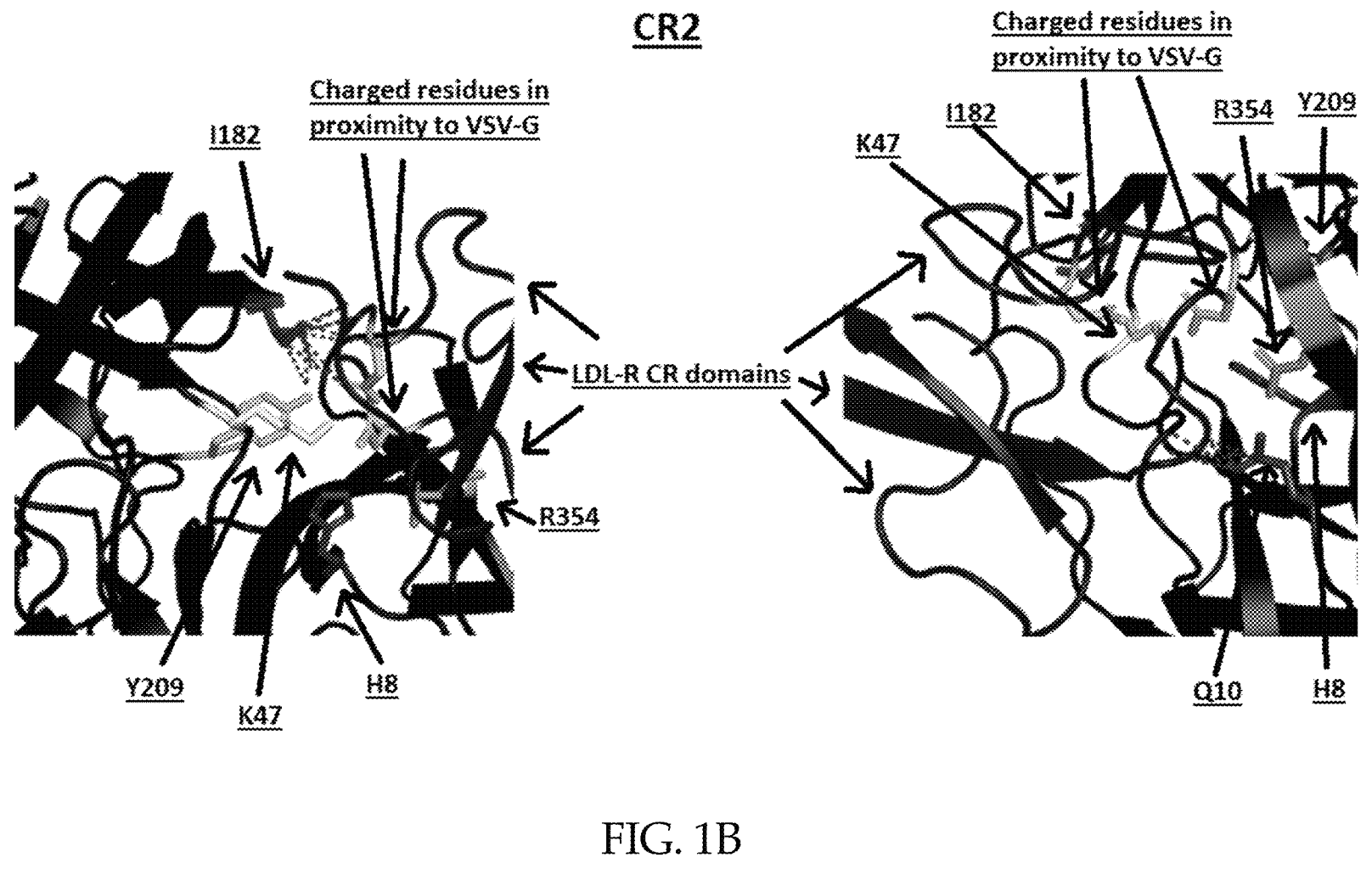

CR2

Charged residues in proximity to VSV-G

I182

K47

R354

Y209

H8

Q10

LDL-R CR domains

Charged residues in proximity to VSV-G

```
SEQ_ID_NO_2    KFTIVFPHNQKGNWKNVPSNYHYCPSSSDLNWHNDLIGIALQVKMPKSHKAIQADGWMCH    60
SEQ_ID_NO_11   KIEIVFPQHTTGDWKEVPHEYNYCPTSADKWSHGTQTGIPVELTMPKGLTTHQVDGFMCH    60
SEQ_ID_NO_13   KFTTVFPHHQKGNWKNVPSTYHYCPSSSDQNWHNDLTGVSLHVKIPKSHKAIQADGWMCH    60
SEQ_ID_NO_15   KITISFPQSLKGDWRPVPKGYNYCPTSADKNLHGDLIDIGLRLRAPKSFKGISADGWMCH    60
SEQ_ID_NO_17   KFTIVFPQSQKGDWKDVPPNYRYCPSSADQNWHGDLLGVNIRAKMPKVHKAIKADGWMCH    60
SEQ_ID_NO_19   KFSIVFPQSQKGNWKNVPSSYHYCPSSSDQNWHNDLLGITMKVKMPKTHKAIQADGWMCH    60
SEQ_ID_NO_21   KFTIVFPHNQRGNWKNVPANYQYCPSSSDLNWHNGLIGTSLQVKMPKSHKAIQADGWMCH    60
               *: * *:  .*:*: **  *.***:*:* * *.    .  :.    **  .  ..**:***

SEQ_ID_NO_2    ASKWVTTCDFRWYGPKYITHSIRSFTPSVEQCKESIEQTKQGTWLNPGFPPQSCGYATVT    120
SEQ_ID_NO_11   SALWMTTCDFRWYGEKYITHSIHNEEPTDYQCLEAIKAYKDGVSFNPGFPPQSCGYGTVT    120
SEQ_ID_NO_13   AAKWVTTCDFRWYGPKYITHSTHSMSPTLEQCKTSIEQTKQGVWINPGFPPQSCGYATVT    120
SEQ_ID_NO_15   AARWITTCDFRWYGPKYITHSIHSFRPSNDQCKEAIRLTNEGNWINPGFPPQSCGYASVT    120
SEQ_ID_NO_17   AAKWVTTCDYRWYGPQYITHSIHSFIPTKAQCEESIKQTKEGVWINPGFPPKNCGYASVS    120
SEQ_ID_NO_19   AAKWITTCDFRWYGPKYITHSIKSIQPTSEQCKESIKQTKQGTWMSPGFPPQNCGYATVT    120
SEQ_ID_NO_21   AAKWVTTCDFRWYGPKYVTHSIKSMIPTVDQCKESIAQTKQGTWLNPGFPPQSCGYASVT    120
               :: *:****:*****:*:*****:.   *:  **  :*    ::*  :.*****:.***.:*:

SEQ_ID_NO_2    DAEAVIVQVTPHHVLVDEYTGEWVDSQFINGKCSNYICPTVHNSTTWHSDYKVKGLCDSN    180
SEQ_ID_NO_11   DAEAHIVIVTPHSVKVDEYTGEWIDPHFIGGRCKGQTCETVHNSTKWFTSSDGESVCSQL    180
SEQ_ID_NO_13   DAEVVVVQATPHHVLVDEYTGEWIDSQLVGGKCSKEVCQTVHNSTVWHADYKITGLCESN    180
SEQ_ID_NO_15   DSESVVVTVTKHQVLVDEYSGSWIDSQFPGGSCTSPICDTVHNSTLWHADHTLDSICDQE    180
SEQ_ID_NO_17   DAESIIVQATAHSVMIDEYSGDWLDSQFPTGRCTGSTCETIHNSTLWYADYQVTGLCDSA    180
SEQ_ID_NO_19   DSVAVVVQATPHRVLVDEYTGEWIDSQFPNGKCETEECETVHNSTVWYSDYKVTGLCDAT    180
SEQ_ID_NO_21   DAEAVIVKATPHQVLVDEYTGEWVDSQFPTGKCNKDICPTVHNSTTWHSDYKVTGLCDAN    180
               *:    :* .* * * :***:*.*:* ::    * *       * *:****  *.:.      .:*.

SEQ_ID_NO_2    LISMDITFFSEDGELSSLGKEGTGFRSNYFAYETGGKACKMQYCKHWGVRLPSGVWFEMA    240
SEQ_ID_NO_11   FTLVGGIFFSDSEEITSMGLPETGIRSNYFPYVSIEGTCKMPFCPKPGYKLKNDLWFQIT    240
SEQ_ID_NO_13   LASVDITFFSEDGQKTSLGKPNTGFRSNHFAYESGEKACRMQYCTQWGIRLPSGVWFELV    240
SEQ_ID_NO_15   FVAMDAVLFTESGKPEEFGKPNSGIRSNYFPYESLKDVCQMDFCKRKGFKLPSGVWFEIE    240
SEQ_ID_NO_17   LVSTEVTFYSEDGLMTSIGRQNTGYRSNYFPYEKGAAACKMKYCTHEGIRLPSGVWFENV    240
SEQ_ID_NO_19   LVDTEITFFSEDGKKESIGKPNTGYRSNYFAYEKGDKVCKMNYCKHAGVRLPSGVWFEFV    240
SEQ_ID_NO_21   LISMDITFFSEDGKLTSLGKEGTGFRSNYFAYENGDKACRMQYCKHWGVRLPSGVWFEMA    240
               :      .::::.      .:*     :* ***:* *  .      *:* :* : * :* ..:**::

SEQ_ID_NO_2    DKDLFA----AARFPECPEGSSISAPSQTSVDVSLIQDVERILDYSLCQETWSKIRAGLP    296
SEQ_ID_NO_11   DPDLDKTVRDLPHIKDCDLSSSIVIPGEHATDISLISDVERILDYALCQNTWSKIEAGEP    300
SEQ_ID_NO_13   DKDLFQ----AAKLPECPRGSSISAPSQTSVDVSLIQDVERILDYSLCQETWSKIRAKLP    296
SEQ_ID_NO_15   DAEKSHKAQVELKIKKCPHGAVISAPNQNAADINLIMDVERILDYSLCQATWSKIQNKEA    300
SEQ_ID_NO_17   DKELLE-----SVQMPECPAGLTISAPTQTSVDVSLILDVERMLDYSLCQETWSKVHSGLP    296
SEQ_ID_NO_19   DQDVYA----AAKLPECPVGATISAPTQTSVDVSLILDVERILDYSLCQETWSKIRSKQP    296
SEQ_ID_NO_21   DKDIYN----DAKFPDCPEGSSIAAPSQTSVDVSLIQDVERILDYSLCQETWSKIRABLP    296
               * :                :: *   .  * :* : :.*:.** ****:***:*** ****:.

SEQ_ID_NO_2    ISPVDLSYLAPKNPGTGPAFTIINGTLKYFETRYIRVDIAAPILSRMVGMISGTTTEREL    356
SEQ_ID_NO_11   ITPVDLSYLGPKNPGAGPVFTIINGSLHYFMSKYLRVELESPVIPRMEGKVAGTRIVRQL    360
SEQ_ID_NO_13   VSPVDLSYLAPKNPGSGPAFTIINGTLKYFETRYIRVDISNPIIPRMVGTMSGTTTEREL    356
SEQ_ID_NO_15   LTPIDISYLGPKNPGPGPAFTIINGTLHYFNTRYIRVDIAGPVTKEITGFVSGTSTSEVL    360
SEQ_ID_NO_17   ISPVDLGYIAPKNPGAGPAFTIVNGILKYFDTRYLRIDTEGPVLKKMTGKVSGTPTKREL    356
SEQ_ID_NO_19   VSPVDLSYLAPKNPGTGPAFTIINGTLKYFETRYIRIDIDNPIISKMVGKISGSQTEREL    356
SEQ_ID_NO_21   ISPVDLSYLSPKNPGTGPAFTIINGTLKYFETRYIRVDIAGPIIPQMPGVISGTTTEREL    356
               ::*:*:.*:.***** **.***:**:*:** ::*:*:::   *:   .: * ::*:    * *

SEQ_ID_NO_2    WDDWAPYEDVEIGPNGVLRTSSGYKFPLYMIGHGMLDSDLHLSSKAQVFEHPHIQDAASQ    416
SEQ_ID_NO_11   WDQWFPFGEVEIGPNGVLKTKQGYKFPLHIIGTGEVDNDIKMERIVKHWEHPHIEAAQTF    420
SEQ_ID_NO_13   WNDWYPKEDVEIGPNGVLKTPTGFKFPLYMIGHGMLDSDLHKSSQAQVFEHPHANDAASQ    416
SEQ_ID_NO_15   WDQWFPYGENSIGPNGLLKTASGYKYPLFMVGTGVLDADIHKLGEATVIEHPHAKEAQKV    420
SEQ_ID_NO_17   WTEWFPYDDVEIGPNGVLKTPEGYKFPLYMIGHGLLDSDLQKTSQAEVFEHPQIAEAVQK    416
SEQ_ID_NO_19   WTEWFPYEGVEIGPNGILKTPTGYKFPLFMIGHGMLDSDLHKTSQAEVFEHPHLAEAPKQ    416
SEQ_ID_NO_21   WTDWYPYEDVEIGPNGVLKTATGYKFPLYMIGHGMLDSDLHISSKAQVFEHPHIQDAASQ    416
               * :* *:      .*****:*:*   *:*:**.::* * :* *::       :      .**:     *

SEQ_ID_NO_2    LP---DDESLFFGDTGLSKNPIELVEGWFSSWKSSIASFFFIIGLIIGLFLVLRVGIHLC    473
SEQ_ID_NO_11   LKKDDTEEVLYYGDTGVSKNPVELVEGWFSGWRSSIMGVLAVIIGFVILIFLIRLIGVLS    480
SEQ_ID_NO_13   LP---DDETLFFGDTGLSKNPVELVEGWFSSWKSTLASFFLIIGLGVALIFIIRIIVAIR    473
SEQ_ID_NO_15   VD---DSEVIFFGDTGVSKNPVEVVEGWFSGWRSSLMSIFGIILLIVCLVLIVRILIALK    477
SEQ_ID_NO_17   LP----DDETLFFGDTGISKNPVEVIEGWFSNWRSSVMAIVFAILLLVITVLMVRLCVAFR    473
SEQ_ID_NO_19   LP----EEETLFFGDTGISKNPVELIEGWFSSWKSTVVIFFFAIGVFILLYVVARIVIAVR    473
SEQ_ID_NO_21   LP---DDETLFFGDTGLSKNPIELVEGWFSGWKSTIASFFFIIGLVIGLYLVLRIGIALC    473
               :         .* :::****:****:*::*****,*:*::    ..    *      :      .: *:     .

SEQ_ID_NO_2    IKLKHTK-KRQIYTDIEMNRLGK---    495
SEQ_ID_NO_11   -SLFRQKRRPIYKSDVEMAHFR-----    501
SEQ_ID_NO_13   YKYKG-RKTQKIYNDVEMSRLGNK-    496
SEQ_ID_NO_15   YCCVRHEKRTIYKEDLEMGRIPRRA    502
SEQ_ID_NO_17   R---FCCQKRHKIYNDLEMNQLRR---    494
SEQ_ID_NO_19   YRYQGSN-NKRIYNDIEMSRFRK--    495
SEQ_ID_NO_21   IKCRVQEKRPKIYTDVEMNRLDR--    496
                     .            *:** ::
```

FIG. 3

With Paramyxoviridae glycoprotein

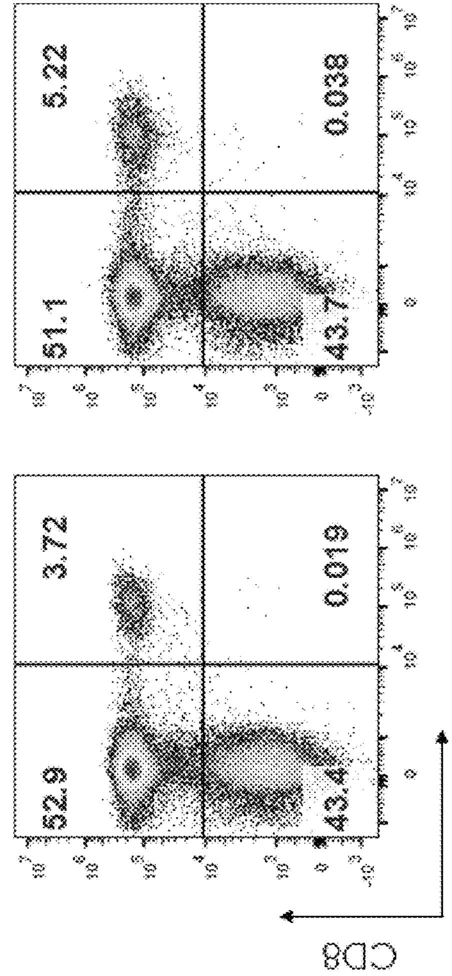
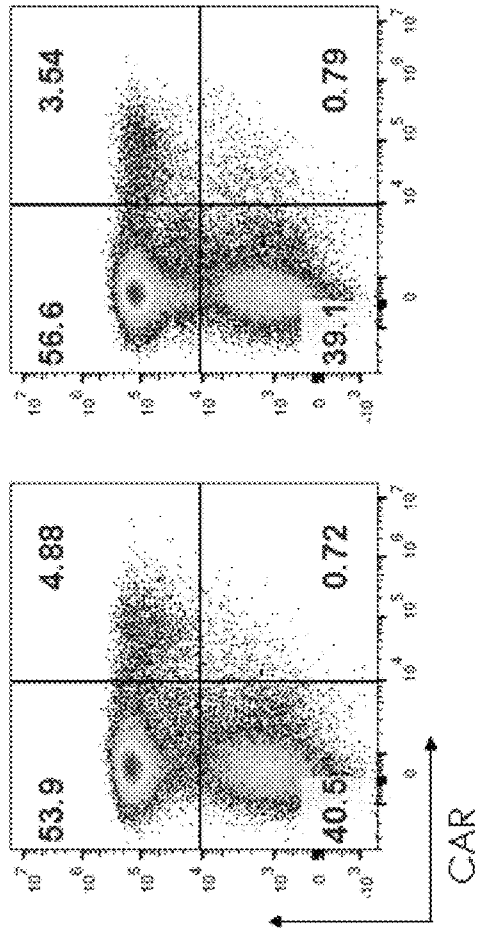
FIG. 9A

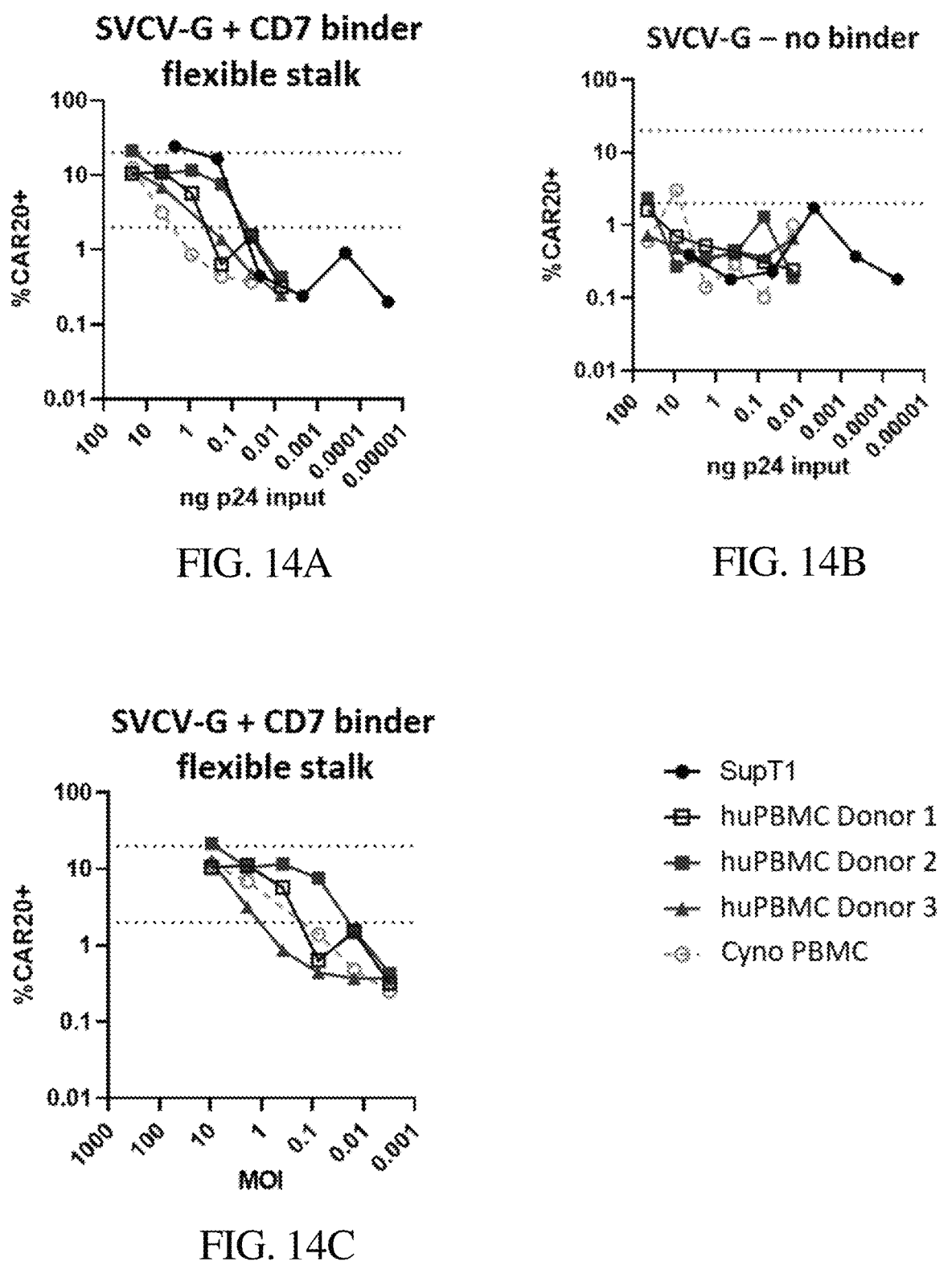

SVCV-G + CD7 binder flexible stalk

%CAR20+

100 10 1 0.1 0.01

100 10 1 0.1 0.01 0.001 0.0001 0.00001 ng p24 input

FIG. 14A

SVCV-G – no binder

%CAR20+

100 10 1 0.1 0.01

100 10 1 0.1 0.01 0.001 0.0001 0.00001 ng p24 input

FIG. 14B

SVCV-G + CD7 binder flexible stalk

%CAR20+

100 10 1 0.1 0.01

1000 100 10 1 0.1 0.01 0.001

MOI

FIG. 14C

SupT1 huPBMC Donor 1 huPBMC Donor 2 huPBMC Donor 3

Cyno PBMC

SupT1
huPBMC Donor 1
huPBMC Donor 2
huPBMC Donor 3
Cyno PBMC

SupT1
huPBMC Donor 1
huPBMC Donor 2
huPBMC Donor 3
Cyno PBMC

Days post-injection

Vector

Buffer

Days post-injection

SEQUENCE LISTING

```
Sequence total quantity: 105
SEQ ID NO: 1            moltype = AA  length = 511
FEATURE                 Location/Qualifiers
source                  1..511
                        mol_type = protein
                        organism = synthetic construct
SEQUENCE: 1
MKCLLYLAFL FIGVNCKFTI VFPHNQKGNW KNVPSNYHYC PSSSDLNWHN DLIGTALQVK  60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLISM DITFFSEDGE LSSLGKEGTG FRSNYFAYET GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTTER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 2            moltype = AA  length = 495
FEATURE                 Location/Qualifiers
source                  1..495
                        mol_type = protein
                        organism = synthetic construct
SEQUENCE: 2
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 3            moltype = AA  length = 495
FEATURE                 Location/Qualifiers
source                  1..495
                        mol_type = protein
                        organism = synthetic construct
SEQUENCE: 3
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LASMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 4            moltype = AA  length = 495
FEATURE                 Location/Qualifiers
source                  1..495
                        mol_type = protein
                        organism = synthetic construct
SEQUENCE: 4
KFTIVFPHNQ KGNWKNVPSN YHYCPSSSDL NWHNDLIGTA LQVKMPKSHK AIQADGWMCH  60
```

```
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LDSMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 5           moltype = AA  length = 495
FEATURE                Location/Qualifiers
source                 1..495
                       mol_type = protein
                       organism = synthetic construct
SEQUENCE: 5
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LESMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 6           moltype = AA  length = 495
FEATURE                Location/Qualifiers
source                 1..495
                       mol_type = protein
                       organism = synthetic construct
SEQUENCE: 6
KFTIVFPANQ KGNWKNVPSN YHYCPSSSDL NWHNDLIGTA LQVKMPQSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 7           moltype = AA  length = 495
FEATURE                Location/Qualifiers
source                 1..495
                       mol_type = protein
                       organism = synthetic construct
SEQUENCE: 7
KFTIVFPHNA KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 8           moltype = AA  length = 495
FEATURE                Location/Qualifiers
source                 1..495
                       mol_type = protein
                       organism = synthetic construct
SEQUENCE: 8
KFTIVFPHNR KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 9           moltype = AA  length = 495
FEATURE                Location/Qualifiers
source                 1..495
                       mol_type = protein
                       organism = synthetic construct
SEQUENCE: 9
```

```
KFTIVFPHNK KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LISMDITFFS EDGELSSLGK EGTGFRSNYF AYETGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TTERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                  495

SEQ ID NO: 10          moltype = AA  length = 517
FEATURE                Location/Qualifiers
source                 1..517
                       mol_type = protein
                       organism = synthetic construct
SEQUENCE: 10
MLSYLIFALV VSPILGKIEI VFPQHTTGDW KRVPHEYNYC PTSADKNSHG TQTGIPVELT  60
MPKGLTTHQV DGFMCHSALW MTTCDFRWYG PKYITHSIHN EEPTDYQCLE AIKAYKDGVS  120
FNPGFPPQSC GYGTVTDAEA HIVTVTPHSV KVDEYTGEWI DPHFIGGRCK GQICETVHNS  180
TKWFTSSDGE SVCSQLFTLV GGTFFSDSEE ITSMGLPETG IRSNYFPYVS TEGICKMPFC  240
RKPGYKLKND LWFQITDPDL DKTVRDLPHI KDCDLSSSIV TPGEHATDIS LISDVERILD  300
YALCQNTWSK IEAGEPITPV DLSYLGPKNP GAGPVFTIIN GSLHYFMSKY LRVELESPVI  360
PRMEGKVAGT RIVRQLWDQW FPFGEVEIGP NGVLKTKQGY KFPLHIIGTG EVDNDIKMER  420
IVKHWEHPHI EAAQTFLKKD DTEEVLYYGD TGVSKNPVEL VEGWFSGWRS SIMGVLAVII  480
GFVILIFLIR LIGVLSSLFR QKRRPIYKSD VEMAHFR                          517

SEQ ID NO: 11          moltype = AA  length = 501
FEATURE                Location/Qualifiers
source                 1..501
                       mol_type = protein
                       organism = synthetic construct
SEQUENCE: 11
KIEIVFPQHT TGDWKRVPHE YNYCPTSADK NSHGTQTGIP VELTMPKGLT THQVDGFMCH  60
SALWMTTCDF RWYGPKYITH SIHNEEPTDY QCLEAIKAYK DGVSFNPGFP PQSCGYGTVT  120
DAEAHIVTVT PHSVKVDEYT GEWIDPHFIG GRCKGQICET VHNSTKWFTS SDGESVCSQL  180
FTLVGGTFFS DSEEITSMGL PETGIRSNYF PYVSTEGICK MPFCRKPGYK LKNDLWFQIT  240
DPDLDKTVRD LPHIKDCDLS SSIVTPGEHA TDISLISDVE RILDYALCQN TWSKIEAGEP  300
ITPVDLSYLG PKNPGAGPVF TIINGSLHYF MSKYLRVELE SPVIPRMEGK VAGTRIVRQL  360
WDQWFPFGEV EIGPNGVLKT KQGYKFPLHI IGTGEVDNDI KMERIVKHWE HPHIEAAQTF  420
LKKDDTEEVL YYGDTGVSKN PVELVEGWFS GWRSSIMGVL AVIIGFVILI FLIRLIGVLS  480
SLFRQKRRPI YKSDVEMAHF R                                           501

SEQ ID NO: 12          moltype = AA  length = 512
FEATURE                Location/Qualifiers
source                 1..512
                       mol_type = protein
                       organism = synthetic construct
SEQUENCE: 12
MLRLFLFCFL ALGAHSKFTI VFPHHQKGNW KNVPSTYHYC PSSSDQNWHN DLTGVSLHVK  60
IPKSHKAIQA DGWMCHAAKW VTTCDFRWYG PKYITHSIHS MSPTLEQCKT SIEQTKQGVW  120
INPGFPPQSC GYATVTDAEV VVVQATPHHV LVDEYTGEWI DSQLVGGKCS KEVCQTVHNS  180
TVWHADYKIT GLCESNLASV DITFFSEDGQ KTSLGKPNTG FRSNHFAYES GEKACRMQYC  240
TQWGIRLPSG VWFELVDKDL FQAAKLPECP RGSSISAPSQ TSVDVSLIQD VERILDYSLC  300
QETWSKIRAK LPVSPVDLSY LAPKNPGSGP AFTIINGTLK YFETRYIRVD ISNPIIPHMV  360
GTMSGTTTER ELWNDWYPYE DVEIGPNGVL KTPTGFKFPL YMIGHGMLDS DLHKSSQAQV  420
FEHPHAKDAA SQLPDDETLF FGDTGLSKNP VELVEGWFSS WKSTLASFFL IIGLGVALIF  480
IIRIIVAIRY KYKGRKTQKI YNDVEMSRLG NK                               512

SEQ ID NO: 13          moltype = AA  length = 496
FEATURE                Location/Qualifiers
source                 1..496
                       mol_type = protein
                       organism = synthetic construct
SEQUENCE: 13
KFTIVFPHHQ KGNWKNVPST YHYCPSSSDQ NWHNDLTGVS LHVKIPKSHK AIQADGWMCH  60
AAKWVTTCDF RWYGPKYITH SIHSMSPTLE QCKTSIEQTK QGVWINPGFP PQSCGYATVT  120
DAEVVVVQAT PHHVLVDEYT GEWIDSQLVG GKCSKEVCQT VHNSTVWHAD YKITGLCESN  180
LASVDITFFS EDGQKTSLGK PNTGFRSNHF AYESGEKACR MQYCTQWGIR LPSGVWFELV  240
DKDLFQAAKL PECPRGSSIS APSQTSVDVS LIQDVERILD YSLCQETWSK IRAKLPVSPV  300
DLSYLAPKNP GSGPAFTIIN GTLKYFETRY IRVDISNPII PHMVGTMSGT TTERELWNDW  360
YPYEDVEIGP NGVLKTPTGF KFPLYMIGHG MLDSDLHKSS QAQVFEHPHA KDAASQLPDD  420
ETLFFGDTGL SKNPVELVEG WFSSWKSTLA SFFLIIGLGV ALIFIIRIIV AIRYKYKGRK  480
TQKIYNDVEM SRLGNK                                                 496

SEQ ID NO: 14          moltype = AA  length = 523
FEATURE                Location/Qualifiers
source                 1..523
                       mol_type = protein
                       organism = synthetic construct
```

```
SEQUENCE: 14
MKMKMVIAGL ILCIGILPAI GKITISFPQS LKGDWRPVPK GYNYCPTSAD KNLHGDLIDI  60
GLRLRAPKSF KGISADGWMC HAARWITTCD FRWYGPKYIT HSIHSFRPSN DQCKEAIRLT  120
NEGNWINPGF PPQSCGYASV TDSESVVVTV TKHQVLVDEY SGSWIDSQFP GGSCTSPICD  180
TVHNSTLWHA DHTLDSICDQ EFVAMDAVLF TESGKFEEFG KPNSGIRSNY FPYESLKDVC  240
QMDFCKRKGF KLPSGVWFEI EDAEKSHKAQ VELKIKRCPH GAVISAPNQN AADINLIMDV  300
ERILDYSLCQ ATWSKIQNKE ALTPIDISYL GPKNPGPGPA FTIINGTLHY FNTRYIRVDI  360
AGPVTKEITG FVSGTSTSRV LWDQWFPYGE NSIGPNGLLK TASGYKYPLF MVGTGVLDAD  420
IHKLGEATVI EHPHAKEAQK VVDDSEVIFF GDTGVSKNPV EVVEGWFSGW RSSLMSIFGI  480
ILLIVCLVLI VRILIALKYC CVRHKKRTIY KEDLEMGRIP RRA                   523

SEQ ID NO: 15          moltype = AA  length = 502
FEATURE                Location/Qualifiers
source                 1..502
                       mol_type = protein
                       organism = synthetic construct
SEQUENCE: 15
KITISFPQSL KGDWRPVPKG YNYCPTSADK NLHGDLIDIG LRLRAPKSFK GISADGWMCH  60
AARWITTCDF RWYGPKYITH SIHSFRPSND QCKEAIRLTN EGNWINPGFP PQSCGYASVT  120
DSESVVVTVT KHQVLVDEYS GSWIDSQFPG GSCTSPICDT VHNSTLWHAD HTLDSICDQE  180
FVAMDAVLFT ESGKFEEFGK PNSGIRSNYF PYESLKDVCQ MDFCKRKGFK LPSGVWFEIE  240
DAEKSHKAQV ELKIKRCPHG AVISAPNQNA ADINLIMDVE RILDYSLCQA TWSKIQNKEA  300
LTPIDISYLG PKNPGPGPAF TIINGTLHYF NTRYIRVDIA GPVTKEITGF VSGTSTSRVL  360
WDQWFPYGEN SIGPNGLLKT ASGYKYPLFM VGTGVLDADI HKLGEATVIE HPHAKEAQKV  420
VDDSEVIFFG DTGVSKNPVE VVEGWFSGWR SSLMSIFGII LLIVCLVLIV RILIALKYCC  480
VRHKKRTIYK EDLEMGRIPR RA                                         502

SEQ ID NO: 16          moltype = AA  length = 511
FEATURE                Location/Qualifiers
source                 1..511
                       mol_type = protein
                       organism = synthetic construct
SEQUENCE: 16
MTPAFILCML LAGSSWAKFT IVFPQSQKGD WKDVPPNYRY CPSSADQNWH GDLLGVNIRA  60
KMPKVHKAIK ADGWMCHAAK WVTTCDYRWY GPQYITHSIH SFIPTKAQCE ESIKQTKEGV  120
WINPGFPPKN CGYASVSDAE SIIVQATAHS VMIDEYSGDW LDSQFPTGRC TGSTCETIHN  180
STLWYADYQV TGLCDSALVS TEVTFYSEDG LMTSIGRQNT GYRSNYFPYE KGAAACRMKY  240
CTHEGIRLPS GVWFEMVDKE LLESVQMPEC PAGLTISAPT QTSVDVSLIL DVERMLDYSL  300
CQETWSKVHS GLPISPVDLG YIAPKNPGAG PAFTIVNGTL KYFDTRYLRI DIEGPVLKKM  360
TGKVSGTPTK RELWTEWFPY DDVEIGPNGV LKTPEGYKFP LYMIGHGLLD SDLQKTSQAE  420
VFHHPQIAEA VQKLPDDETL FFGDTGISKN PVEVIEGWFS NWRSSVMAIV FAILLLVITV  480
LMVRLCVAFR HFCCQKRHKI YNDLEMNQLR R                                511

SEQ ID NO: 17          moltype = AA  length = 494
FEATURE                Location/Qualifiers
source                 1..494
                       mol_type = protein
                       organism = synthetic construct
SEQUENCE: 17
KFTIVFPQSQ KGDWKDVPPN YRYCPSSADQ NWHGDLLGVN IRAKMPKVHK AIKADGWMCH  60
AAKWVTTCDY RWYGPQYITH SIHSFIPTKA QCEESIKQTK EGVWINPGFP PKNCGYASVS  120
DAESIIVQAT AHSVMIDEYS GDWLDSQFPT GRCTGSTCET IHNSTLWYAD YQVTGLCDSA  180
LVSTEVTFYS EDGLMTSIGR QNTGYRSNYF PYEKGAAACR MKYCTHEGIR LPSGVWFEMV  240
DKELLESVQM PECPAGLTIS APTQTSVDVS LILDVERMLD YSLCQETWSK VHSGLPISPV  300
DLGYIAPKNP GAGPAFTIVN GTLKYFDTRY LRIDIEGPVL KKMTGKVSGT PTKRELWTEW  360
FPYDDVEIGP NGVLKTPEGY KFPLYMIGHG LLDSDLQKTS QAEVFHHPQI AEAVQKLPDD  420
ETLFFGDTGI SKNPVEVIEG WFSNWRSSVM AIVFAILLLV ITVLMVRLCV AFRHFCCQKR  480
HKIYNDLEMN QLRR                                                  494

SEQ ID NO: 18          moltype = AA  length = 512
FEATURE                Location/Qualifiers
source                 1..512
                       mol_type = protein
                       organism = synthetic construct
SEQUENCE: 18
MNFLLLTFIV LPLCSHAKFS IVFPQSQKGN WKNVPSSYHY CPSSSDQNWH NDLLGITMKV  60
KMPKTHKAIQ ADGWMCHAAK WITTCDFRWY GPKYITHSIH SIQPTSEQCK ESIKQTKQGT  120
WMSPGFPPQN CGYATVTDSV AVVVQATPHH VLVDEYTGEW IDSQFPNGKC ETEECETVHN  180
STVWYSDYKV TGLCDATLVD TEITFFSEDG KKESIGKPNT GYRSNYFAYE KGDKVCKMNY  240
CKHAGVRLPS GVWFEFVDQD VYAAAKLPEC PVGATISAPT QTSVDVSLIL DVERILDYSL  300
CQETWSKIRS KQPVSPVDLS YLAPKNPGTG PAFTIINGTL KYFETRYIRI DIDNPIISKM  360
VGKISGSQTE RELWTEWFPY EGVEIGPNGI LKTPTGYKFP LFMIGHGMLD SDLHKTSQAE  420
VFEHPHLAEA PKQLPEEETL FFGDTGISKN PVELIEGWFS SWKSTVVTFF FAIGVFILLY  480
VVARIVIAVR YRYQGSNNKR IYNDIEMSRF RK                               512

SEQ ID NO: 19          moltype = AA  length = 495
FEATURE                Location/Qualifiers
source                 1..495
                       mol_type = protein
```

```
                         organism = synthetic construct
SEQUENCE: 19
KFSIVFPQSQ KGNWKNVPSS YHYCPSSSDQ NWHNDLLGIT MKVKMPKTHK AIQADGWMCH  60
AAKWITTCDF RWYGPKYITH SIHSIQPTSE QCKESIKQTK QGTWMSPGFP PQNCGYATVT  120
DSVAVVVQAT PHHVLVDEYT GEWIDSQFPN GKCETEECET VHNSTVWYSD YKVTGLCDAT  180
LVDTEITFFS EDGKKESIGK PNTGYRSNYF AYEKGDKVCK MNYCKHAGVR LPSGVWFEFV  240
DQDVYAAAKL PECPVGATIS APTQTSVDVS LILDVERILD YSLCQETWSK IRSKQPVSPV  300
DLSYLAPKNP GTGPAFTIIN GTLKYFETRY IRIDIDNPII SKMVGKISGS QTERELWTEW  360
FPYEGVEIGP NGILKTPTGY KFPLFMIGHG MLDSDLHKTS QAEVFEHPHL AEAPKQLPEE  420
ETLFFGDTGI SKNPVELIEG WFSSWKSTVV TFFFAIGVFI LLYVVARIVI AVRYRYQGSN  480
NKRIYNDIEM SRFRK                                                   495

SEQ ID NO: 20            moltype = AA  length = 513
FEATURE                  Location/Qualifiers
source                   1..513
                         mol_type = protein
                         organism = synthetic construct
SEQUENCE: 20
MLVLYLLLSL LALGAQCKFT IVFPHNQKGN WKNVPANYQY CPSSSDLNWH NGLIGTSLQV  60
KMPKSHKAIQ ADGWMCHAAK WVTTCDFRWY GPKYVTHSIK SMIPTVDQCK ESIAQTKQGT  120
WLNPGFPPQS CGYASVTDAE AVIVKATPHQ VLVDEYTGEW VDSQFPTGKC NKDICPTVHN  180
STTWHSDYKV TGLCDANLIS MDITFFSEDG KLTSLGKEGT GFRSNYFAYE NGDKACRMQY  240
CKHWGVRLPS GVWFEMADKD IYNDAKFPDC PEGSSIAAPS QTSVDVSLIQ DVERILDYSL  300
CQETWSKIRA HLPISPVDLS YLSPKNPGTG PAFTIINGTL KYFETRYIRV DIAGPIIPQM  360
RGVISGTTTE RELWTDWYPY EDVEIGPNGV LKTATGYKFP LYMIGHGMLD SDLHISSKAQ  420
VFEHPHIQDA ASQLPDDETL FFGDTGLSKN PIELVEGWFS GWKSTIASFF FIIGLVIGLY  480
LVLRIGIALC IKCRVQEKRP KIYTDVEMNR LDR                               513

SEQ ID NO: 21            moltype = AA  length = 496
FEATURE                  Location/Qualifiers
source                   1..496
                         mol_type = protein
                         organism = synthetic construct
SEQUENCE: 21
KFTIVFPHNQ KGNWKNVPAN YQYCPSSSDL NWHNGLIGTS LQVKMPKSHK AIQADGWMCH  60
AAKWVTTCDF RWYGPKYVTH SIKSMIPTVD QCKESIAQTK QGTWLNPGFP PQSCGYASVT  120
DAEAVIVKAT PHQVLVDEYT GEWVDSQFPT GKCNKDICPT VHNSTTWHSD YKVTGLCDAN  180
LISMDITFFS EDGKLTSLGK EGTGFRSNYF AYENGDKACR MQYCKHWGVR LPSGVWFEMA  240
DKDIYNDAKF PDCPEGSSIA APSQTSVDVS LIQDVERILD YSLCQETWSK IRAHLPISPV  300
DLSYLSPKNP GTGPAFTIIN GTLKYFETRY IRVDIAGPII PQMRGVISGT TTERELWTDW  360
YPYEDVEIGP NGVLKTATGY KFPLYMIGHG MLDSDLHISS KAQVFEHPHI QDAASQLPDD  420
ETLFFGDTGL SKNPIELVEG WFSGWKSTIA SFFFIIGLVI GLYLVLRIGI ALCIKCRVQE  480
KRPKIYTDVE MNRLDR                                                  496

SEQ ID NO: 22            moltype = AA  length = 495
FEATURE                  Location/Qualifiers
source                   1..495
                         mol_type = protein
                         organism = synthetic construct
SEQUENCE: 22
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LDSMDITFFS EDGELSSLGK EGTGFRSNYF AYENGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TAERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 23            moltype = AA  length = 495
FEATURE                  Location/Qualifiers
source                   1..495
                         mol_type = protein
                         organism = synthetic construct
SEQUENCE: 23
KFTIVFPHNQ KGNWKNVPSN YHYCPSSSDL NWHNDLIGTA LQVKMPKSHK AIQADGWMCH  60
ASKWVTTCDF RWYGPKYITH SIRSFTPSVE QCKESIEQTK QGTWLNPGFP PQSCGYATVT  120
DAEAVIVQVT PHHVLVDEYT GEWVDSQFIN GKCSNYICPT VHNSTTWHSD YKVKGLCDSN  180
LESMDITFFS EDGELSSLGK EGTGFRSNYF AYENGGKACK MQYCKHWGVR LPSGVWFEMA  240
DKDLFAAARF PECPEGSSIS APSQTSVDVS LIQDVERILD YSLCQETWSK IRAGLPISPV  300
DLSYLAPKNP GTGPAFTIIN GTLKYFETRY IRVDIAAPIL SRMVGMISGT TAERELWDDW  360
APYEDVEIGP NGVLRTSSGY KFPLYMIGHG MLDSDLHLSS KAQVFEHPHI QDAASQLPDD  420
ESLFFGDTGL SKNPIELVEG WFSSWKSSIA SFFFIIGLII GLFLVLRVGI HLCIKLKHTK  480
KRQIYTDIEM NRLGK                                                   495

SEQ ID NO: 24            moltype = AA  length = 511
FEATURE                  Location/Qualifiers
source                   1..511
```

```
                        mol_type = protein
                        organism = synthetic construct
SEQUENCE: 24
MKCLLYLAFL FIGVNCKFTI VFPHNQKGNW KNVPSNYHYC PSSSDLNWHN DLIGTALQVK  60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLDSM DITFFSEDGE LSSLGKEGTG FRSNYFAYEN GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTAER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 25           moltype = AA  length = 511
FEATURE                 Location/Qualifiers
source                  1..511
                        mol_type = protein
                        organism = synthetic construct
SEQUENCE: 25
MKCLLYLAFL FIGVNCKFTI VFPHNQKGNW KNVPSNYHYC PSSSDLNWHN DLIGTALQVK  60
MPKSHKAIQA DGWMCHASKW VTTCDFRWYG PKYITHSIRS FTPSVEQCKE SIEQTKQGTW  120
LNPGFPPQSC GYATVTDAEA VIVQVTPHHV LVDEYTGEWV DSQFINGKCS NYICPTVHNS  180
TTWHSDYKVK GLCDSNLESM DITFFSEDGE LSSLGKEGTG FRSNYFAYEN GGKACKMQYC  240
KHWGVRLPSG VWFEMADKDL FAAARFPECP EGSSISAPSQ TSVDVSLIQD VERILDYSLC  300
QETWSKIRAG LPISPVDLSY LAPKNPGTGP AFTIINGTLK YFETRYIRVD IAAPILSRMV  360
GMISGTTAER ELWDDWAPYE DVEIGPNGVL RTSSGYKFPL YMIGHGMLDS DLHLSSKAQV  420
FEHPHIQDAA SQLPDDESLF FGDTGLSKNP IELVEGWFSS WKSSIASFFF IIGLIIGLFL  480
VLRVGIHLCI KLKHTKKRQI YTDIEMNRLG K                                511

SEQ ID NO: 26           moltype = AA  length = 330
FEATURE                 Location/Qualifiers
source                  1..330
                        mol_type = protein
                        organism = synthetic construct
SEQUENCE: 26
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 27           moltype = AA  length = 325
FEATURE                 Location/Qualifiers
source                  1..325
                        mol_type = protein
                        organism = synthetic construct
SEQUENCE: 27
STKGPSVFPL APCSRSTSES TAALGCLVKD YFPEPVTVSW NSGALTSGVH TFPAVLQSSG  60
LYSLSSVVTV PSSSLGTQTY TCNVDHKPSN TKVDKTVERK CCVECPPCPA PPVAGPSVFL  120
FPPKPKDTLM ISRTPEVTCV VVDVSHEDPE VQFNWYVDGV EVHNAKTKPR EEQFNSTFRV  180
VSVLTVVHQD WLNGKEYKCK VSNKGLPAPI EKTISKTKGQ PREPQVYTLP PSREEMTKNQ  240
VSLTCLVKGF YPSDIAVEWE SNGQPENNYK TTPPMLDSDG SFFLYSKLTV DKSRWQQGNV  300
FSCSVMHEAL HNHYTQKSLS LSPGK                                       325

SEQ ID NO: 28           moltype = AA  length = 326
FEATURE                 Location/Qualifiers
source                  1..326
                        mol_type = protein
                        organism = synthetic construct
SEQUENCE: 28
STKGPSVFPL APCSRSTSES TAALGCLVKD YFPEPVTVSW NSGALTSGVH TFPAVLQSSG  60
LYSLSSVVTV PSSSLGTKTY TCNVDHKPSN TKVDKRVESK YGPPCPSCPA PEFLGGPSVF  120
LFPPKPKDTL MISRTPEVTC VVVDVSQEDP EVQFNWYVDG VEVHNAKTKP REEQFNSTYR  180
VVSVLTVLHQ DWLNGKEYKC KVSNKGLPSS IEKTISKAKG QPREPQVYTL PPSQEEMTKN  240
QVSLTCLVKG FYPSDIAVEW ESNGQPENNY KTTPPVLDSD GSFFLYSRLT VDKSRWQEGN  300
VFSCSVMHEA LHNHYTQKSL SLSLGK                                      326

SEQ ID NO: 29           moltype = AA  length = 240
FEATURE                 Location/Qualifiers
source                  1..240
                        mol_type = protein
                        organism = synthetic construct
SEQUENCE: 29
MAGPPRLLLL PLLLALARGL PGALAAQEVQ QSPHCTTVPV GASVNITCST SGGLRGIYLR  60
QLGPQPQDII YYEDGVVPTT DRRFRGRIDF SGSQDNLTIT MHRLQLSDTG TYTCQAITEV  120
NVYGSGTLVL VTEEQSQGWH RCSDAPPRAS ALPAPPTGSA LPDPQTASAL PDPPAASALP  180
AALAVISFLL GLGLGVACVL ARTQIKKLCS WRDKNSAACV VYEDMSHSRC NTLSSPNQYQ  240
```

```
SEQ ID NO: 30            moltype = AA  length = 7
FEATURE                  Location/Qualifiers
source                   1..7
                         mol_type = protein
                         organism = synthetic construct
SEQUENCE: 30
GYPFTSY                                                            7

SEQ ID NO: 31            moltype = AA  length = 6
FEATURE                  Location/Qualifiers
source                   1..6
                         mol_type = protein
                         organism = synthetic construct
SEQUENCE: 31
DPNSGD                                                             6

SEQ ID NO: 32            moltype = AA  length = 12
FEATURE                  Location/Qualifiers
source                   1..12
                         mol_type = protein
                         organism = synthetic construct
SEQUENCE: 32
SPYYSNDNSM DY                                                      12

SEQ ID NO: 33            moltype = AA  length = 11
FEATURE                  Location/Qualifiers
source                   1..11
                         mol_type = protein
                         organism = synthetic construct
SEQUENCE: 33
RASQSIGTSI H                                                       11

SEQ ID NO: 34            moltype = AA  length = 7
FEATURE                  Location/Qualifiers
source                   1..7
                         mol_type = protein
                         organism = synthetic construct
SEQUENCE: 34
YASESIS                                                            7

SEQ ID NO: 35            moltype = AA  length = 9
FEATURE                  Location/Qualifiers
source                   1..9
                         mol_type = protein
                         organism = synthetic construct
SEQUENCE: 35
QQSNSWPTT                                                          9

SEQ ID NO: 36            moltype = AA  length = 121
FEATURE                  Location/Qualifiers
source                   1..121
                         mol_type = protein
                         organism = synthetic construct
SEQUENCE: 36
QVQLQQPGAE LVKPGASVKL SCKASGYPFT SYWIHWVKQR PGRGLEWLGR IDPNSGDTKY  60
NEKFKNKATL TVDKSSTTAY MQLSSLTSED SAVYYCARSP YYSNDNSMDY WGQGTSVTVS  120
S                                                                  121

SEQ ID NO: 37            moltype = AA  length = 108
FEATURE                  Location/Qualifiers
source                   1..108
                         mol_type = protein
                         organism = synthetic construct
SEQUENCE: 37
DILLTQSPAI LSVSPGERVS FSCRASQSIG TSIHWYQQRT NDSPRLLIKY ASESISGIPS  60
RFSGSGSGTD FTLSINSVES EDIADYYCQQ SNSWPTTFGG GTKLEIKR                108

SEQ ID NO: 38            moltype = AA  length = 249
FEATURE                  Location/Qualifiers
source                   1..249
                         mol_type = protein
                         organism = synthetic construct
SEQUENCE: 38
DILLTQSPAI LSVSPGERVS FSCRASQSIG TSIHWYQQRT NDSPRLLIKY ASESISGIPS  60
RFSGSGSGTD FTLSINSVES EDIADYYCQQ SNSWPTTFGG GTKLEIKRGG GGSGGGGSGG  120
GGSGGGGSQV QLQQPGAELV KPGASVKLSC KASGYPFTSY WIHWVKQRPG RGLEWLGRID  180
PNSGDTKYNE KFKNKATLTV DKSSTTAYMQ LSSLTSEDSA VYYCARSPYY SNDNSMDYWG  240
QGTSVTVSS                                                          249
```

```
SEQ ID NO: 39          moltype = AA  length = 249
FEATURE                Location/Qualifiers
source                 1..249
                       mol_type = protein
                       organism = synthetic construct
SEQUENCE: 39
QVQLQQPGAE LVKPGASVKL SCKASGYPFT SYWIHWVKQR PGRGLEWLGR IDPNSGDTKY  60
NEKFKNKATL TVDKSSTTAY MQLSSLTSED SAVYYCARSP YYSNDNSMDY WGQGTSVTVS  120
SGGGGSGGGG SGGGGSGGGG SDILLTQSPA ILSVSPGERV SFSCRASQSI GTSIHWYQQR  180
TNDSPRLLIK YASESISGIP SRFSGSGSGT DFTLSINSVE SEDIADYYCQ QSNSWPTTFG  240
GGTKLEIKR                                                         249

SEQ ID NO: 40          moltype = AA  length = 235
FEATURE                Location/Qualifiers
source                 1..235
                       mol_type = protein
                       organism = synthetic construct
SEQUENCE: 40
MALPVTALLL PLALLLHAAR PSQFRVSPLD RTWNLGETVE LKCQVLLSNP TSGCSWLFQP  60
RGAAASPTFL LYLSQNKPKA AEGLDTQRFS GKRLGDTFVL TLSDFRRENE GCYFCSALSN  120
SIMYFSHFVP VFLPAKPTTT PAPRPPTPAP TIASQPLSLR PEACRPAAGG AVHTRGLDFA  180
CDIYIWAPLA GTCGVLLLSL VITLYCNHRN RRRVCKCPRP VVKSGDKPSL SARYV       235

SEQ ID NO: 41          moltype = AA  length = 210
FEATURE                Location/Qualifiers
source                 1..210
                       mol_type = protein
                       organism = synthetic construct
SEQUENCE: 41
MRPRLWLLLA AQLTVLHGNS VLQQTPAYIK VQTNKMVMLS CEAKISLSNM RIYWLRQRQA  60
PSSDSHHEFL ALWDSAKGTI HGEEVEQEKI AVFRDASRFI LNLTSVKPED SGIYFCMIVG  120
SPELTFGKGT QLSVVDFLPT TAQPTKKSTL KKRVCRLPRP ETQKGPLCSP ITLGLLVAGV  180
LVLLVSLGVA IHLCCRRRRA RLRFMKQLYK                                  210

SEQ ID NO: 42          moltype = AA  length = 7
FEATURE                Location/Qualifiers
source                 1..7
                       mol_type = protein
                       organism = synthetic construct
SEQUENCE: 42
RYTFTDY                                                           7

SEQ ID NO: 43          moltype = AA  length = 6
FEATURE                Location/Qualifiers
source                 1..6
                       mol_type = protein
                       organism = synthetic construct
SEQUENCE: 43
YPYNGG                                                            6

SEQ ID NO: 44          moltype = AA  length = 12
FEATURE                Location/Qualifiers
source                 1..12
                       mol_type = protein
                       organism = synthetic construct
SEQUENCE: 44
DHRYNEGVSF DY                                                     12

SEQ ID NO: 45          moltype = AA  length = 15
FEATURE                Location/Qualifiers
source                 1..15
                       mol_type = protein
                       organism = synthetic construct
SEQUENCE: 45
RASESVDGFG NSFMN                                                  15

SEQ ID NO: 46          moltype = AA  length = 7
FEATURE                Location/Qualifiers
source                 1..7
                       mol_type = protein
                       organism = synthetic construct
SEQUENCE: 46
LASNLES                                                           7

SEQ ID NO: 47          moltype = AA  length = 9
FEATURE                Location/Qualifiers
source                 1..9
                       mol_type = protein
                       organism = synthetic construct
```

```
SEQUENCE: 47
QQNNEDPYT                                                         9

SEQ ID NO: 48           moltype = AA  length = 121
FEATURE                 Location/Qualifiers
source                  1..121
                        mol_type = protein
                        organism = synthetic construct
SEQUENCE: 48
EVQLQQSGPE LVKPGASVKI SCKASRYTFT DYNLHWVKLS HEKSLEWIGF IYPYNGGTGY  60
NQKFKNKAKL TVDYSSSTAY MELRSLTSVD AAVYYCARDH RYNEGVSFDY WGQGTTLTVS  120
S                                                                 121

SEQ ID NO: 49           moltype = AA  length = 112
FEATURE                 Location/Qualifiers
source                  1..112
                        mol_type = protein
                        organism = synthetic construct
SEQUENCE: 49
NIVLTQSPAS LAVSLGQRAT ISCRASESVD GFGNSFMNWY QQKPGQSPKL LIYLASNLES  60
GVPARFSGSG SRTDFTLTID PVEADDAATY YCQQNNEDPY TFGGGTKLEI KR          112

SEQ ID NO: 50           moltype = AA  length = 253
FEATURE                 Location/Qualifiers
source                  1..253
                        mol_type = protein
                        organism = synthetic construct
SEQUENCE: 50
NIVLTQSPAS LAVSLGQRAT ISCRASESVD GFGNSFMNWY QQKPGQSPKL LIYLASNLES  60
GVPARFSGSG SRTDFTLTID PVEADDAATY YCQQNNEDPY TFGGGTKLEI KRGGGGSGGG  120
GSGGGGSGGG GSEVQLQQSG PELVKPGASV KISCKASRYT FTDYNLHWVK LSHEKSLEWI  180
GFIYPYNGGT GYNQKFKNKA KLTVDYSSST AYMELRSLTS VDAAVYYCAR DHRYNEGVSF  240
DYWGQGTTLT VSS                                                    253

SEQ ID NO: 51           moltype = AA  length = 253
FEATURE                 Location/Qualifiers
source                  1..253
                        mol_type = protein
                        organism = synthetic construct
SEQUENCE: 51
EVQLQQSGPE LVKPGASVKI SCKASRYTFT DYNLHWVKLS HEKSLEWIGF IYPYNGGTGY  60
NQKFKNKAKL TVDYSSSTAY MELRSLTSVD AAVYYCARDH RYNEGVSFDY WGQGTTLTVS  120
SGGGGSGGGG SGGGGSGGGG SNIVLTQSPA SLAVSLGQRA TISCRASESV DGFGNSFMNW  180
YQQKPGQSPK LLIYLASNLE SGVPARFSGS GSRTDFTLTI DPVEADDAAT YYCQQNNEDP  240
YTFGGGTKLE IKR                                                    253

SEQ ID NO: 52           moltype = AA  length = 509
FEATURE                 Location/Qualifiers
source                  1..509
                        mol_type = protein
                        organism = synthetic construct
SEQUENCE: 52
MSIISYIAFL LLIDSNLGIP IFVPSGRNIS WQPVIQPFDY QCPIHGNLPN TMGLSATKLT  60
IKSPSVFSTD KVSGWICHAA EWKTTCDYRW YGPQYITHSI HPISPTIDEC RRIIQRIASG  120
TDEDLGFPPQ SCGWASVTTV SNTNYRVVPH SVHLEPYGGH WIDHEFNGGE CREKVCEMKG  180
NHSIWITEET VQHECAKHIE EVEGIMYGNV PRGDVMYANN FIIDRHHRVY RFGGSCQMKF  240
CNKDGIKFAR GDWVEKTAGT LTTIHDNVPK CVDGTLVSGH RPGLDLIDTV FNLENVVEYT  300
LCEGTKRKIN KQEKLTSVDL SYLAPRIGGF GSVFRVRNGT LERGSTTYIR IEVEGPIVDS  360
LNGTDPRTNA SRVFWDDWEL DGNIYQGFNG VYKGKDGKIH IPLNMIESGI IDDELQHAFQ  420
ADIIPHPHYD DDEIREDDIF FDNTGENGNP VDAVVEWVSG WGTSLKFFGM TLVALILIFL  480
LIRCCVACTY LMKRSKRPAT ESHEMRSLV                                   509

SEQ ID NO: 53           moltype = AA  length = 491
FEATURE                 Location/Qualifiers
source                  1..491
                        mol_type = protein
                        organism = synthetic construct
SEQUENCE: 53
IPIFVPSGRN ISWQPVIQPF DYQCPIHGNL PNTMGLSATK LTIKSPSVFS TDKVSGWICH  60
AAEWKTTCDY RWYGPQYITH SIHPISPTID ECRRIIQRIA SGTDEDLGFP PQSCGWASVT  120
TVSNTNYRVV PHSVHLEPYG GHWIDHEFNG GECREKVCEM KGNHSIWITE ETVQHECAKH  180
IEEVEGIMYG NVPRGDVMYA NNFIIDRHHR VYRFGGSCQM KFCNKDGIKF ARGDWVEKTA  240
GTLTTIHDNV PKCVDGTLVS GHRPGLDLID TVFNLENVVE YTLCEGTKRK INKQEKLTSV  300
DLSYLAPRIG GFGSVFRVRN GTLERGSTTY IRIEVEGPIV DSLNGTDPRT NASRVFWDDW  360
ELDGNIYQGF NGVYKGKDGK IHIPLNMIES GIIDDELQHA FQADIIPHPH YDDDEIREDD  420
IFFDNTGENG NPVDAVVEWV SGWGTSLKFF GMTLVALILI FLLIRCCVAC TYLMKRSKRP  480
ATESHEMRSL V                                                      491

SEQ ID NO: 54           moltype = AA  length = 5
```

```
FEATURE                Location/Qualifiers
source                 1..5
                       mol_type = protein
                       organism = synthetic construct
REPEAT                 1..5
                       note = Sequence may be present n times, wherein n is 1, 2,
                        3, 4, or 5
SEQUENCE: 54
GGGGA                                                                5

SEQ ID NO: 55          moltype = AA  length = 5
FEATURE                Location/Qualifiers
source                 1..5
                       mol_type = protein
                       organism = synthetic construct
REPEAT                 1..5
                       note = Sequence may be present n times, wherein n is 1, 2,
                        3, 4, or 5
SEQUENCE: 55
GGGGS                                                                5

SEQ ID NO: 56          moltype = AA  length = 12
FEATURE                Location/Qualifiers
source                 1..12
                       mol_type = protein
                       organism = synthetic construct
SEQUENCE: 56
GSAGSAAGSG EF                                                        12

SEQ ID NO: 57          moltype = AA  length = 18
FEATURE                Location/Qualifiers
source                 1..18
                       mol_type = protein
                       organism = synthetic construct
SEQUENCE: 57
KESGSVSSEQ LAQFRSLD                                                  18

SEQ ID NO: 58          moltype = AA  length = 14
FEATURE                Location/Qualifiers
source                 1..14
                       mol_type = protein
                       organism = synthetic construct
SEQUENCE: 58
EGKSSGSGSE SKST                                                      14

SEQ ID NO: 59          moltype = AA  length = 55
FEATURE                Location/Qualifiers
source                 1..55
                       mol_type = protein
                       organism = synthetic construct
SEQUENCE: 59
FVPVFLPAKP TTTPAPRPPT PAPTIASQPL SLRPEACRPA AGGAVHTRGL DFACD         55

SEQ ID NO: 60          moltype = AA  length = 40
FEATURE                Location/Qualifiers
source                 1..40
                       mol_type = protein
                       organism = synthetic construct
SEQUENCE: 60
KIEVMYPPPY LDNEKSNGTI IHVKGKHLCP SPLFPGPSKP                          40

SEQ ID NO: 61          moltype = AA  length = 28
FEATURE                Location/Qualifiers
source                 1..28
                       mol_type = protein
                       organism = synthetic construct
SEQUENCE: 61
IYIWAPLAGT CGVLLLSLVI TLYCNHRN                                       28

SEQ ID NO: 62          moltype = AA  length = 27
FEATURE                Location/Qualifiers
source                 1..27
                       mol_type = protein
                       organism = synthetic construct
SEQUENCE: 62
FWVLVVVGGV LACYSLLVTV AFIIFWV                                        27

SEQ ID NO: 63          moltype = AA  length = 8
FEATURE                Location/Qualifiers
```

```
source                  1..8
                        mol_type = protein
                        organism = synthetic construct
SEQUENCE: 63
NRVRQGYS                                                                  8

SEQ ID NO: 64           moltype = AA  length = 11
FEATURE                 Location/Qualifiers
source                  1..11
                        mol_type = protein
                        organism = synthetic construct
SEQUENCE: 64
GGTETSQVAP A                                                              11

SEQ ID NO: 65           moltype = AA  length = 16
FEATURE                 Location/Qualifiers
source                  1..16
                        mol_type = protein
                        organism = synthetic construct
SEQUENCE: 65
MKCLLYLAFL FIGVNC                                                         16

SEQ ID NO: 66           moltype = AA  length = 16
FEATURE                 Location/Qualifiers
source                  1..16
                        mol_type = protein
                        organism = synthetic construct
SEQUENCE: 66
MLSYLIFALV VSPILG                                                         16

SEQ ID NO: 67           moltype = AA  length = 16
FEATURE                 Location/Qualifiers
source                  1..16
                        mol_type = protein
                        organism = synthetic construct
SEQUENCE: 67
MLRLFLFCFL ALGAHS                                                         16

SEQ ID NO: 68           moltype = AA  length = 21
FEATURE                 Location/Qualifiers
source                  1..21
                        mol_type = protein
                        organism = synthetic construct
SEQUENCE: 68
MKMKMVIAGL ILCIGILPAI G                                                   21

SEQ ID NO: 69           moltype = AA  length = 17
FEATURE                 Location/Qualifiers
source                  1..17
                        mol_type = protein
                        organism = synthetic construct
SEQUENCE: 69
MTPAFILCML LAGSSWA                                                        17

SEQ ID NO: 70           moltype = AA  length = 17
FEATURE                 Location/Qualifiers
source                  1..17
                        mol_type = protein
                        organism = synthetic construct
SEQUENCE: 70
MNFLLLTFIV LPLCSHA                                                        17

SEQ ID NO: 71           moltype = AA  length = 17
FEATURE                 Location/Qualifiers
source                  1..17
                        mol_type = protein
                        organism = synthetic construct
SEQUENCE: 71
MLVLYLLLSL LALGAQC                                                        17

SEQ ID NO: 72           moltype = AA  length = 20
FEATURE                 Location/Qualifiers
source                  1..20
                        mol_type = protein
                        organism = synthetic construct
SEQUENCE: 72
GGGGSGGGGS GGGGSGGGGS                                                     20

SEQ ID NO: 73           moltype = AA  length = 5
```

```
FEATURE                Location/Qualifiers
source                 1..5
                       mol_type = protein
                       organism = synthetic construct
REPEAT                 1..5
                       note = Sequence may be present n times, wherein n is 1, 2,
                        3, 4, or 5
SEQUENCE: 73
EAAAK                                                                       5

SEQ ID NO: 74          moltype = AA  length = 7
FEATURE                Location/Qualifiers
source                 1..7
                       mol_type = protein
                       organism = synthetic construct
REPEAT                 2..6
                       note = Sequence may be present n times, wherein n is 1, 2,
                        3, 4, or 5
SEQUENCE: 74
AEAAAKA                                                                     7

SEQ ID NO: 75          moltype = AA  length = 10
FEATURE                Location/Qualifiers
source                 1..10
                       mol_type = protein
                       organism = synthetic construct
REPEAT                 1..2
                       note = The sequence may be present n times, wherein n is 1,
                        2, 3, 4, or 5.  SEQ ID NO: 75 represents the example where
                        n is 5
VARIANT                1
                       note = X may be alanine (A), lysine (K), or glutamate(E).  F
                        or SEQ ID NO: 75 - each X may be, individually, A, K, or E
SEQUENCE: 75
XPXPXPXPXP                                                                  10

SEQ ID NO: 76          moltype = AA  length = 12
FEATURE                Location/Qualifiers
source                 1..12
                       mol_type = protein
                       organism = synthetic construct
SEQUENCE: 76
AEAAAKEAAA KA                                                               12

SEQ ID NO: 77          moltype = AA  length = 5
FEATURE                Location/Qualifiers
source                 1..5
                       mol_type = protein
                       organism = synthetic construct
SEQUENCE: 77
SYWIH                                                                       5

SEQ ID NO: 78          moltype = AA  length = 17
FEATURE                Location/Qualifiers
source                 1..17
                       mol_type = protein
                       organism = synthetic construct
SEQUENCE: 78
RIDPNSGDTK YNEKFKN                                                          17

SEQ ID NO: 79          moltype = AA  length = 8
FEATURE                Location/Qualifiers
source                 1..8
                       mol_type = protein
                       organism = synthetic construct
SEQUENCE: 79
GYPFTSYW                                                                    8

SEQ ID NO: 80          moltype = AA  length = 8
FEATURE                Location/Qualifiers
source                 1..8
                       mol_type = protein
                       organism = synthetic construct
SEQUENCE: 80
IDPNSGDT                                                                    8

SEQ ID NO: 81          moltype = AA  length = 14
FEATURE                Location/Qualifiers
source                 1..14
```

-continued

```
                        mol_type = protein
                        organism = synthetic construct
SEQUENCE: 81
ARSPYYSNDN SMDY                                                14

SEQ ID NO: 82           moltype = AA  length = 6
FEATURE                 Location/Qualifiers
source                  1..6
                        mol_type = protein
                        organism = synthetic construct
SEQUENCE: 82
QSIGTS                                                         6

SEQ ID NO: 83           moltype = AA  length = 5
FEATURE                 Location/Qualifiers
source                  1..5
                        mol_type = protein
                        organism = synthetic construct
SEQUENCE: 83
DYNLH                                                          5

SEQ ID NO: 84           moltype = AA  length = 17
FEATURE                 Location/Qualifiers
source                  1..17
                        mol_type = protein
                        organism = synthetic construct
SEQUENCE: 84
FIYPYNGGTG YNQKFKN                                             17

SEQ ID NO: 85           moltype = AA  length = 8
FEATURE                 Location/Qualifiers
source                  1..8
                        mol_type = protein
                        organism = synthetic construct
SEQUENCE: 85
RYTFTDYN                                                       8

SEQ ID NO: 86           moltype = AA  length = 8
FEATURE                 Location/Qualifiers
source                  1..8
                        mol_type = protein
                        organism = synthetic construct
SEQUENCE: 86
IYPYNGGT                                                       8

SEQ ID NO: 87           moltype = AA  length = 14
FEATURE                 Location/Qualifiers
source                  1..14
                        mol_type = protein
                        organism = synthetic construct
SEQUENCE: 87
ARDHRYNEGV SFDY                                                14

SEQ ID NO: 88           moltype = AA  length = 10
FEATURE                 Location/Qualifiers
source                  1..10
                        mol_type = protein
                        organism = synthetic construct
SEQUENCE: 88
ESVDGFGNSF                                                     10

SEQ ID NO: 89           moltype = AA  length = 122
FEATURE                 Location/Qualifiers
source                  1..122
                        mol_type = protein
                        organism = synthetic construct
SEQUENCE: 89
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                             122

SEQ ID NO: 90           moltype = AA  length = 107
FEATURE                 Location/Qualifiers
source                  1..107
                        mol_type = protein
                        organism = synthetic construct
SEQUENCE: 90
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK            107
```

```
SEQ ID NO: 91           moltype = AA  length = 15
FEATURE                 Location/Qualifiers
source                  1..15
                        mol_type = protein
                        organism = synthetic construct
SEQUENCE: 91
GGGGSGGGGS GGGGS                                                   15

SEQ ID NO: 92           moltype = AA  length = 244
FEATURE                 Location/Qualifiers
source                  1..244
                        mol_type = protein
                        organism = synthetic construct
SEQUENCE: 92
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SSGGGGSGGG GSGGGGSEIV LTQSPATLSL SPGERATLSC RASQSVSSYL AWYQQKPGQA  180
PRLLIYDASN RATGIPARFS GSGSGTDFTL TISSLEPEDF AVYYCQQRSN WPITFGQGTR  240
LEIK                                                               244

SEQ ID NO: 93           moltype = AA  length = 244
FEATURE                 Location/Qualifiers
source                  1..244
                        mol_type = protein
                        organism = synthetic construct
SEQUENCE: 93
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIKGGG GSGGGGSGGG  120
GSEVQLVESG GGLVQPGRSL RLSCAASGFT FNDYAMHWVR QAPGKGLEWV STISWNSGSI  180
GYADSVKGRF TISRDNAKKS LYLQMNSLRA EDTALYYCAK DIQYGNYYYG MDVWGQGTTV  240
TVSS                                                               244

SEQ ID NO: 94           moltype = AA  length = 110
FEATURE                 Location/Qualifiers
source                  1..110
                        mol_type = protein
                        organism = synthetic construct
SEQUENCE: 94
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIKGSTS             110

SEQ ID NO: 95           moltype = AA  length = 122
FEATURE                 Location/Qualifiers
source                  1..122
                        mol_type = protein
                        organism = synthetic construct
SEQUENCE: 95
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SS                                                                 122

SEQ ID NO: 96           moltype = AA  length = 248
FEATURE                 Location/Qualifiers
source                  1..248
                        mol_type = protein
                        organism = synthetic construct
SEQUENCE: 96
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIKGSTS GGGGSGGGGS  120
GGGGSSEVQL QQSGAELVKP GASVKMSCKA SGYTFTSYNM HWVKQTPGQG LEWIGAIYPG  180
NGDTSYNQKF KGKATLTADK SSSTAYMQLS SLTSEDSADY YCARSNYYGS SYWFFDVWGA  240
GTTVTVSS                                                           248

SEQ ID NO: 97           moltype = AA  length = 248
FEATURE                 Location/Qualifiers
source                  1..248
                        mol_type = protein
                        organism = synthetic construct
SEQUENCE: 97
SEVQLQQSGA ELVKPGASVK MSCKASGYTF TSYNMHWVKQ TPGQGLEWIG AIYPGNGDTS  60
YNQKFKGKAT LTADKSSSTA YMQLSSLTSE DSADYYCARS NYYGSSYWFF DVWGAGTTVT  120
VSSGGGGSGG GGSGGGGSDI VLTQSPAILS ASPGEKVTMT CRASSSVNYM DWYQKKPGSS  180
PKPWIYATSN LASGVPARFS GSGSGTSYSL TISRVEAEDA ATYYCQQWSF NPPTFGGGTK  240
LEIKGSTS                                                           248

SEQ ID NO: 98           moltype = AA  length = 609
FEATURE                 Location/Qualifiers
source                  1..609
```

```
                        mol_type = protein
                        organism = synthetic construct
SEQUENCE: 98
METDTLLLWV LLLWVPGSTG DSAQVQLQQP GAELVKPGAS VKLSCKASGY PFTSYWIHWV  60
KQRPGRGLEW LGRIDPNSGD TKYNEKFKNK ATLTVDKSST TAYMQLSSLT SEDSAVYYCA  120
RSPYYSNDNS MDYWGQGTSV TVSSGGGGSG GGGSGGGGSG GGGSDILLTQ SPAILSVSPG  180
ERVSFSCRAS QSIGTSIHWY QQRTNDSPRL LIKYASESIS GIPSRFSGSG SGTDFTLSIN  240
SVESEDIADY YCQQSNSWPT TFGGGTKLEI KRASGGGGSG GGGSGGGGSE PKSCDKTHTC  300
PPCPAPEAAG GPSVFLFPPK PKDTLMASRT PEVTCVVVDV SHEDPEVKFN WYVDGVEVHN  360
AKTKPREEQY ASTYRVVSVL TVLAQDWLNG KEYKCKVSNK ALGAPIEKTI SKAKGQPREP  420
QVYTLPPSRD ELTKNQVSLT CLVKGFYPSD IAVEWESNGQ PENNYKTTPP VLDSDGSFFL  480
YSKLTVDKSR WQQGNVFSCS VMHEALHNAY TQKSLSLSPG KKIEVMYPPP YLDNEKSNGT  540
IIHVKGKHLC PSPLFPGPSK PFWVLVVVGG VLACYSLLVT VAFIIFWVRS KRSRLLHSDY  600
MNRVRQGYS                                                         609

SEQ ID NO: 99           moltype = AA  length = 508
FEATURE                 Location/Qualifiers
source                  1..508
                        mol_type = protein
                        organism = synthetic construct
SEQUENCE: 99
MALPVTALLL PLALLLHAAR PGSEVQLVES GGGLVQPGRS LRLSCAASGF TFNDYAMHWV  60
RQAPGKGLEW VSTISWNSGS IGYADSVKGR FTISRDNAKK SLYLQMNSLR AEDTALYYCA  120
KDIQYGNYYY GMDVWGQGTT VTVSSGGGGS GGGGSGGGGS EIVLTQSPAT LSLSPGERAT  180
LSCRASQSVS SYLAWYQQKP GQAPRLLIYD ASNRATGIPA RFSGSGSGTD FTLTISSLEP  240
EDFAVYYCQQ RSNWPITFGQ GTRLEIKSGL DFVPVFLPAK PTTTPAPRPP TPAPTIASQP  300
LSLRPEACRP AAGGAVHTRG LDFACDIYIW APLAGTCGVL LLSLVITLYC NHRNKRGRKK  360
LLYIFKQPFM RPVQTTQEED GCSCRFPEEE EGGCELRVKF SRSADAPAYQ QGQNQLYNEL  420
NLGRREEYDV LDKRRGRDPE MGGKPRRKNP QEGLYNELQK DKMAEAYSEI GMKGERRRGK  480
GHDGLYQGLS TATKDTYDAL HMQALPPR                                    508

SEQ ID NO: 100          moltype = AA  length = 4
FEATURE                 Location/Qualifiers
source                  1..4
                        mol_type = protein
                        organism = synthetic construct
SEQUENCE: 100
SGLD                                                              4

SEQ ID NO: 101          moltype = AA  length = 42
FEATURE                 Location/Qualifiers
source                  1..42
                        mol_type = protein
                        organism = synthetic construct
SEQUENCE: 101
KRGRKKLLYI FKQPFMRPVQ TTQEEDGCSC RFPEEEEGGC EL                    42

SEQ ID NO: 102          moltype = AA  length = 112
FEATURE                 Location/Qualifiers
source                  1..112
                        mol_type = protein
                        organism = synthetic construct
SEQUENCE: 102
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 103          moltype = AA  length = 232
FEATURE                 Location/Qualifiers
source                  1..232
                        mol_type = protein
                        organism = synthetic construct
SEQUENCE: 103
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNH YTQKSLSLSP GK          232

SEQ ID NO: 104          moltype = AA  length = 232
FEATURE                 Location/Qualifiers
source                  1..232
                        mol_type = protein
                        organism = synthetic construct
SEQUENCE: 104
EPKSCDKTHT CPPCPAPEAA GGPSVFLFPP KPKDTLMASR TPEVTCVVVD VSHEDPEVKF  60
NWYVDGVEVH NAKTKPREEQ YASTYRVVSV LTVLAQDWLN GKEYKCKVSN KALGAPIEKT  120
ISKAKGQPRE PQVYTLPPSR DELTKNQVSL TCLVKGFYPS DIAVEWESNG QPENNYKTTP  180
PVLDSDGSFF LYSKLTVDKS RWQQGNVFSC SVMHEALHNA YTQKSLSLSP GK          232

SEQ ID NO: 105          moltype = AA  length = 98
```

-continued

```
FEATURE              Location/Qualifiers
source               1..98
                     mol_type = protein
                     organism = synthetic construct
SEQUENCE: 105
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKV                          98
```

MUTATED POLYPEPTIDES, COMPOSITIONS COMPRISING THE SAME, AND USES THEREOF

RELATED APPLICATIONS

This application claims the benefit of U.S. Provisional Application Ser. No. 63/391,930 filed Jul. 25, 2022, U.S. Provisional Application Ser. No. 63/391,939 filed Jul. 25, 2022, U.S. Provisional Application Ser. No. 63/503,815 filed May 23, 2023, and U.S. Provisional Application Ser. No. 63/507,783 filed Jun. 13, 2023 each of which are hereby incorporated by reference in their entirety.

REFERENCE TO SEQUENCE LISTING SUBMITTED ELECTRONICALLY

The instant application contains a Sequence Listing which has been submitted electronically in XML format and is hereby incorporated by reference in its entirety. Said XML copy, created on Jul. 21, 2023, is named "INH-020US_SL.xml" and is 114,351 bytes in size.

FIELD

Embodiments provided herein relate to viral particles comprising a heterologous viral glycoprotein and a targeting moiety having the formula T-$S_1$, wherein T is a target binding domain and $S_1$ is a stalk portion. The stalk portion may comprise variant Fc domains. The stalk portion may comprise a flexible peptide domain. Embodiments provided herein further relate to compositions comprising the viral particles provided for herein and methods of using the same.

BACKGROUND

Vesicular stomatitis virus (VSV) is an enveloped, negative-strand RNA virus that belongs to the Vesiculovirus genus of the Rhabdovirus family. It is an arbovirus which can infect insects, cattle, horses and pigs. The VSV genome encodes five structural proteins, among which include a single transmembrane glycoprotein (G). The glycoprotein is a classic type I membrane glycoprotein with an amino-terminal signal peptide, an ectodomain of about 450 amino acids, a single alpha helical transmembrane segment and a small intraviral carboxy-terminal domain. The signal peptide is cleaved in the lumen of the endoplasmic reticulum, and the native mature glycoprotein consists of the ectodomain, the transmembrane domain and the intraviral domain.

G plays a critical role during the initial steps of virus infection (Albertini, A. A. V., Baquero, E., Ferlin, A., and Gaudin, Y. (2012). Molecular and Cellular Aspects of Rhabdovirus Entry. Viruses 4, 117-139), which is hereby incorporated by reference in its entirety. First, it is responsible for virus attachment to specific receptors. After binding, virions enter the cell by a clathrin-mediated endocytic pathway. In the acidic environment of the endocytic vesicle, G triggers the fusion between the viral and endosomal membranes, which releases the genome in the cytosol for the subsequent steps of infection. Fusion is catalyzed by a low-pH-induced large structural transition from a pre-toward a post-fusion conformation which are both trimeric (Roche, S., Bressanelli, S., Rey, F. A., and Gaudin, Y. (2006). Crystal structure of the low-pH form of the vesicular stomatitis virus glycoprotein G. Science 313, 187-191. Roche, S., Rey, F. A., Gaudin, Y., and Bressanelli, S. (2007). Structure of the prefusion form of the vesicular stomatitis virus glycoprotein g. Science 315, 843-848), each of which is hereby incorporated by reference in its entirety).

The polypeptide chain of G ectodomain folds into three distinct domains which are the fusion domain (FD), the pleckstrin homology domain (PHD), and the trimerization domain (TrD). During the structural transition, the FD, the PHD and the TrD retain their tertiary structure. Nevertheless, they undergo large rearrangements in their relative orientation due to secondary changes in hinge segments (S1 to S5) which refold during the low-pH induced conformational change (Roche et al., 2006; Roche et al., 2007).

It has been shown that low-density lipoprotein receptor (LDL-R) and other members of this receptor family serve as VSV receptors (Finkelshtein, D., Werman, A., Novick, D., Barak, S., and Rubinstein, M. (2013). LDL receptor and its family members serve as the cellular receptors for vesicular stomatitis virus. Proceedings of the National Academy of Sciences of the United States of America 110, 7306-7311, which is hereby incorporated by reference in its entirety). VSV-G can be used for pseudotyping other viruses and VSV-G-pseudotyped lentiviruses (VSV-G-LVs) exhibit the same broad tropism as VSV. However, this broad tropism can inhibit the selective targeting of specific cell types. Therefore, there is a need, for modified (mutated or mutant) VSV-G proteins that can be used to pseudotype viruses that abrogate its binding to the LDL receptor. The present embodiments, fulfill these needs as well as others.

BRIEF SUMMARY

In some embodiments, a viral particle is provided. In some embodiments, the viral particle comprises a heterologous viral glycoprotein and a targeting moiety wherein the targeting moiety comprises a polypeptide having the formula T-$S_1$, wherein T is a target binding domain and $S_1$ is a stalk portion.

In some embodiments, the stalk portion $S_1$ comprises variant Fc protein. In some embodiments, the variant Fc protein comprises a transmembrane domain, such as, but not limited to, a CD8 or CD28 transmembrane domain. In some embodiments, the variant Fc protein comprises an effector mutation, wherein the effector mutation inhibits the interaction between the Fc protein and a Fc interacting protein, such as FcγR, C1q, FcRβ, or FcRn.

In some embodiments, the variant Fc protein is a variant IgG1 Fc protein comprising one or more mutations selected from the group consisting of: L234A, L235A, N297A, P329G, I253A, H310A, and H435A.

In some embodiments, the variant IgG1 Fc protein comprises an amino acid sequence having at least 80% identity to SEQ ID NO: 104, at least 85% identity to SEQ ID NO: 104, at least 90% identity to SEQ ID NO: 104, at least 95% identity to SEQ ID NO: 104, at least 98% identity to SEQ ID NO: 104, or at least 100% identity to SEQ ID NO: 104.

In some embodiments, the variant Fc protein is a variant IgG2 Fc protein comprising one or more mutations selected from the group consisting of: N297A, P329G, 1253A, H310A, and H435A.

In some embodiments, the variant Fc protein is a variant IgG4 Fc protein comprising one or more mutations selected from the group consisting of: S228P, L235E, N297A, P329G, I253A, H310A, and H435A.

In some embodiments, the targeting moiety having the formula T-$S_1$ comprises a stalk portion $S_1$ having a formula of $L_1$-Fc-$L_2$-$X_1$, wherein $L_1$ is a linker or absent, Fc is a variant Fc protein, $L_2$ is a linker or absent, and $X_1$ is a polypeptide comprising the transmembrane domain, wherein the targeting moiety having the formula T-$S_1$ has a formula of T-$L_1$-Fc-$L_2$-$X_1$.

In some embodiments, the polypeptide comprising the transmembrane domain ($X_1$) comprises a polypeptide having a formula of ECD-$T_M$-ICD, wherein ECD is an extracellular domain, or a fragment thereof, of a cell surface protein, or is absent; $T_M$ is a transmembrane domain of a transmembrane protein; and ICD is an intracellular domain or a protein that facilitates the incorporation of the targeting moiety into the envelope of the viral particle, or is absent; wherein the targeting moiety having the formula of T-$L_1$-Fc-$L_2$-$X_1$ has a formula of T-$L_1$-Fc-$L_2$-ECD-$T_M$-ICD.

In some embodiments, the stalk portion $S_1$ comprises a formula of $L_3$-$X_1$, wherein $L_3$ is a flexible peptide linker, and $X_1$ is a polypeptide comprising a transmembrane domain; wherein the targeting moiety having the formula T-$S_1$ has a formula of T-$L_3$-$X_1$.

In some embodiments, the polypeptide comprising the transmembrane domain ($X_1$) comprises a polypeptide having a formula of ECD-$T_M$-ICD, wherein ECD is an extracellular domain, or a fragment thereof, of a cell surface protein, or is absent; $T_M$ is a transmembrane domain of a transmembrane protein; and ICD is an intracellular domain or a protein that facilitates the incorporation of the targeting moiety into the envelope of the viral particle, or is absent; wherein the targeting moiety having the formula of T-$L_3$-$X_1$ has a formula of T-$L_3$-ECD-$T_M$-ICD.

In some embodiments, the targeting moiety binds to CD7. In some embodiments, the targeting moiety comprises a polypeptide having a heavy chain variable region comprising a HCDR1 of SEQ ID NO: 30, a HCDR2 of SEQ ID NO: 31, and an HCDR3 of SEQ ID NO: 32, or variants of any of the forging. In some embodiments, the targeting moiety comprises a polypeptide having a light chain variable region comprising a LCDR1 of SEQ ID NO: 33, a LCDR2 of SEQ ID NO: 34, and an LCDR3 of SEQ ID NO: 35, or variants of any of the forging. In some embodiments, the heavy chain comprises a heavy chain variable region having at least 90% sequence identity to SEQ ID NO: 36. In some embodiments, the light chain comprises a light chain variable region having at least 90% sequence identity to SEQ ID NO: 37. In some embodiments, the targeting moiety that binds to CD7 comprises a polypeptide having a sequence having at least 90% sequence identity to SEQ ID NO: 38. In some embodiments, the targeting moiety that binds to CD7 comprises a polypeptide having a sequence having at least 90% sequence identity to SEQ ID NO: 39.

In some embodiments, the targeting moiety binds to CD8. In some embodiments, the targeting moiety comprises a polypeptide having a heavy chain variable region comprising a HCDR1 of SEQ ID NO: 42, a HCDR2 of SEQ ID NO: 43, and an HCDR3 of SEQ ID NO: 44, or variants of any of the forging. In some embodiments, the targeting moiety comprises a polypeptide having a light chain variable region comprising a LCDR1 of SEQ ID NO: 45, a LCDR2 of SEQ ID NO: 46, and an LCDR3 of SEQ ID NO: 47, or variants of any of the forging. In some embodiments, the heavy chain comprises a heavy chain variable region having at least 90% sequence identity to SEQ ID NO: 48. In some embodiments, the light chain comprises a light chain variable region having at least 90% sequence identity to SEQ ID NO: 49. In some embodiments, the targeting moiety that binds to CD8 comprises a polypeptide having a sequence having at least 90% sequence identity to SEQ ID NO: 50. In some embodiments, the targeting moiety that binds to CD8 comprises a polypeptide having a sequence having at least 90% sequence identity to SEQ ID NO: 51.

In some embodiments, the heterologous viral glycoprotein is a SVCV-G polypeptide as provided for herein.

In some embodiments, the heterologous viral glycoprotein is a VSV-G polypeptide. In some embodiments, the VSV-G polypeptide comprises substitutions at positions I182, T214, and T352 of SEQ ID NO: 2. In some embodiments, the substitution at position 182 is I182D or I182E. In some embodiments, the substitution at position 214 is T214N. In some embodiments, the substitution at position 352 is T352A.

In some embodiments, the viral particle provided for herein further comprises a nucleic acid molecule encoding a heterologous molecule of interest. In some embodiments, the heterologous molecule of interest is as provided for herein. In some embodiments, the heterologous molecule of interest is a CAR. In some embodiments, the CAR comprises an antigen binding domain having a heavy chain variable region having at least 95% identity to SEQ ID NO: 89 and a light chain variable region having at least 95% identity to SEQ ID NO: 90. In some embodiments, the CAR comprises an antigen binding domain having a heavy chain variable region having at least 95% identity to SEQ ID NO: 94 and a light chain variable region having at least 95% identity to SEQ ID NO: 95.

In some embodiments, the CAR comprises an antigen binding domain having an amino acid sequence having at least 95% identity to SEQ ID NO: 92. In some embodiments, the CAR comprises an antigen binding domain having an amino acid sequence having at least 95% identity to SEQ ID NO: 93. In some embodiments, the CAR comprises an antigen binding domain having an amino acid sequence having at least 95% identity to SEQ ID NO: 96. In some embodiments, CAR comprises an antigen binding domain having an amino acid sequence having at least 95% identity to SEQ ID NO: 97.

In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a method of infecting a cell is provided. In some embodiments the method comprises contacting the cell with a viral particle as provided for herein.

In some embodiments, a method of infecting a cell in a subject is provided. In some embodiments, the method comprises administering to the subject a pharmaceutical composition comprising a viral particle as provided for herein.

In some embodiments, a method of delivering a heterologous molecule of interest to a cell is provided. In some embodiments, the method comprises contacting the cell with a viral particle as provided for herein, wherein the viral particle comprises a nucleic acid molecule encoding the heterologous molecule of interest.

In some embodiments, a method of delivering a heterologous molecule of interest to a cell in a subject is provided. In some embodiments, the method comprises administering to the subject a viral particle as provided for herein, wherein the viral particle comprises a nucleic acid molecule encoding the heterologous molecule of interest.

In some embodiments, a method of treating a disease or disorder in a subject is provided. In some embodiments, the method comprises administering to the subject a viral particle as provided for herein, wherein the viral particle comprises a nucleic acid molecule encoding a heterologous molecule of interest to treat the disease or disorder.

In some embodiments, a method of delivering a heterologous molecule to a target cell is provided. In some embodiments, the method comprises contacting the cell with a viral particle as provided for herein, wherein the viral particle comprises a nucleic acid molecule encoding the heterologous molecule.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion.

In some embodiments, the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53. In some embodiments, the targeting binding domain comprises a sequence selected from SEQ ID NO: 38, SEQ ID NO: 39, SEQ ID NO: 50, or SEQ ID NO: 51. In some embodiments, the stalk portion $S_1$ comprises a variant Fc protein comprising a sequence that is a variant of SEQ ID NO: 26, SEQ ID NO: 27, or SEQ ID NO: 28. In some embodiments, the variant of SEQ ID NO: 26 comprises one or more mutations selected from the group consisting of L234A, L235A, N297A, P329G, I253A, H310A, and H435A. In some embodiments, the variant of SEQ ID NO: 27 comprises one or more mutations selected from the group consisting of N297A, P329G, I253A, H310A, and H435A. In some embodiments, the variant of SEQ ID NO: 28 comprises one or more mutations selected from the group consisting of S228P, L235E, N297A, P329G, I253A, H310A and H435A. In some embodiments, the variant Fc protein further comprises a transmembrane domain comprising a sequence selected from SEQ ID NO: 61 or SEQ ID NO: 62.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53. In some embodiments, the target binding domain comprises a sequence selected from SEQ ID NO: 38, SEQ ID NO: 39, SEQ ID NO: 50, or SEQ ID NO: 51. In some embodiments, the stalk portion $S_1$ comprises a formula of $L_1$-Fc-$L_2$-$X_1$, wherein $L_1$ is a linker comprising a sequence selected from SEQ ID NO: 54, SEQ ID NO: 55, SEQ ID NO: 56, SEQ ID NO: 57, SEQ ID NO: 58, SEQ ID NO: 73, SEQ ID NO: 74, SEQ ID NO: 75, or SEQ ID NO: 76, or is absent; Fc is a variant Fc protein comprising a sequence that is a variant of SEQ ID NO: 26, SEQ ID NO: 27, or SEQ ID NO: 28, $L_2$ is a linker comprising a sequence selected from SEQ ID NO: 54, SEQ ID NO: 55, SEQ ID NO: 56, SEQ ID NO: 57, SEQ ID NO: 58, SEQ ID NO: 73, SEQ ID NO: 74, SEQ ID NO: 75, or SEQ ID NO: 76, or is absent; and $X_1$ is a polypeptide comprising a transmembrane domain. In some embodiments, the variant of SEQ ID NO: 26 comprises one or more mutations selected from the group consisting of L234A, L235A, N297A, P329G, I253A, H310A, and H435A. In some embodiments, the variant of SEQ ID NO: 27 comprises one or more mutations selected from the group consisting of N297A, P329G, I253A, H310A, and H435A. In some embodiments, the variant of SEQ ID NO: 28 comprises one or more mutations selected from the group consisting of S228P, L235E, N297A, P329G, I253A, H310A and H435A. In some embodiments, the polypeptide comprising a transmembrane domain ($X_1$) has a formula of ECD-$T_M$-ICD, wherein ECD is an extracellular domain having a sequence selected from SEQ ID NO: 59 or SEQ ID NO: 60, or is a fragment thereof, or is absent; $T_M$ is a transmembrane domain having a sequence of SEQ ID NO: 61 or SEQ ID NO: 62 or a fragment thereof; and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53. In some embodiments, the target binding domain comprises a sequence selected from SEQ ID NO: 38, SEQ ID NO: 39, SEQ ID NO: 50, or SEQ ID NO: 51. In some embodiments, the stalk portion $S_1$ comprises a formula of $L_1$-Fc-$L_2$-$X_1$, wherein $L_1$ is a linker comprising a sequence of SEQ ID NO: 55 or is absent; Fc is a variant Fc protein comprises a sequence that is a variant of SEQ ID NO: 26, SEQ ID NO: 27, or SEQ ID NO: 28, $L_2$ is a linker comprising a sequence of SEQ ID NO: 55 or is absent; and $X_1$ is a polypeptide comprising a transmembrane domain. In some embodiments, the variant of SEQ ID NO: 26 comprises one or more mutations selected from the group consisting of L234A, L235A, N297A, P329G, I253A, H310A, and H435A. In some embodiments, the variant of SEQ ID NO: 27 comprises one or more mutations selected from the group consisting of N297A, P329G, I253A, H310A, and H435A. In some embodiments, the variant of SEQ ID NO: 28 comprises one or more mutations selected from the group consisting of S228P, L235E, N297A, P329G, I253A, H310A and H435A. In some embodiments, the polypeptide comprising a transmembrane domain ($X_1$) has a formula of ECD-$T_M$-ICD, wherein ECD is an extracellular domain having a sequence of SEQ ID NO: 60, or a fragment thereof, or is absent; $T_M$ is a transmembrane domain having a sequence of SEQ ID NO: 62 or a fragment thereof; and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, heterologous viral glycoprotein comprises a sequence selected from SEQ ID NO: 23 or SEQ ID NO: 25. In some embodiments, the target binding domain comprises a of SEQ ID NO: 39. In some embodiments, the stalk portion $S_1$ comprises a formula of $L_1$-Fc-$L_2$-$X_1$, wherein $L_1$ is a linker comprising a sequence of SEQ ID NO: 55; Fc is a variant Fc protein comprising a sequence of SEQ ID NO: 104, $L_2$ is a linker and is absent; and $X_1$ is a polypeptide comprising a transmembrane domain. In some embodiments, the polypeptide comprising a transmembrane domain ($X_1$) has a formula of ECD-$T_M$-ICD, wherein ECD is an extracellular domain having a sequence of SEQ ID NO: 60; $T_M$ is a transmembrane domain having a sequence of SEQ ID NO: 62; and ICD is an intracellular domain or protein that facilitates the incorporation of the targeting moiety into the envelope of the viral particle, wherein the ICD comprises an env incorporation motif comprising an amino acid sequence of SEQ ID NO: 63.

In some embodiments, a viral particle is provided, wherein the viral particle comprises a heterologous viral glycoprotein and a targeting moiety. In some embodiments, the heterologous viral glycoprotein comprises an amino acid sequence having at least 90% identity to SEQ ID NO: 23 or SEQ ID NO: 25, having at least 95% identity to SEQ ID NO: 23 or SEQ ID NO: 25, having at least 99% identity to SEQ ID NO: 23 or SEQ ID NO: 25, or having at least 100% identity to SEQ ID NO: 23 or SEQ ID NO: 25. In some embodiments, the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98.

In some embodiments, a viral particle is provided, wherein the viral particle comprises a heterologous viral glycoprotein and a targeting moiety. In some embodiments, the heterologous viral glycoprotein comprises an amino acid sequence having at least 90% identity to SEQ ID NO: 52 or SEQ ID NO: 53, having at least 95% identity to SEQ ID NO: 52 or SEQ ID NO: 53, having at least 99% identity to SEQ ID NO: 52 or SEQ ID NO: 53, or having at least 100% identity to SEQ ID NO: 52 or SEQ ID NO: 53. In some embodiments, the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the target binding domain comprises an amino acid sequence of SEQ ID NO: 38 or SEQ ID NO: 39. In some embodiments, the stalk portion $S_1$ comprises a formula $L_3$-$X_1$, wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58 and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59 or SEQ ID NO: 60, or is a fragment thereof, or is absent, $T_M$ is a transmembrane domain comprising an amino acid sequence of SEQ ID NO: 61 or SEQ ID NO: 62, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the target binding domain comprises an amino acid sequence of SEQ ID NO: 50 or SEQ ID NO: 51. In some embodiments, the stalk portion $S_1$ comprises a formula $L_3$-$X_1$, wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58 and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59 or SEQ ID NO: 60, or is a fragment thereof, or is absent, $T_M$ is a transmembrane domain comprising an amino acid sequence of SEQ ID NO: 61 or SEQ ID NO: 62, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence of SEQ ID NO: 22, SEQ ID NO: 23, SEQ ID NO: 24, SEQ ID NO: 25, SEQ ID NO: 52, or SEQ ID NO: 53. In some embodiments, the target binding domain comprises an amino acid sequence of SEQ ID NO: 38, SEQ ID NO: 39, SEQ ID NO: 50, or SEQ ID NO: 51. In some embodiments, the stalk portion $S_1$ comprises a formula $L_3$-$X_1$, wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58 and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59 or SEQ ID NO: 60, or is a fragment thereof, or is absent, $T_M$ is a transmembrane domain comprising an amino acid sequence of SEQ ID NO: 61 or SEQ ID NO: 62, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence of SEQ ID NO: 22, SEQ ID NO: 23, SEQ ID NO: 24, SEQ ID NO: 25, SEQ ID NO: 52, or SEQ ID NO: 53. In some embodiments, the target binding domain comprises an amino acid sequence of SEQ ID NO: 38, SEQ ID NO: 39, SEQ ID NO: 50, or SEQ ID NO: 51. In some embodiments, the stalk portion $S_1$ comprises a formula $L_3$-$X_1$, wherein $L_3$ is a flexible peptide linker comprising an amino acid sequence of SEQ ID NO: 55, and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59 or SEQ ID NO: 60, or is a fragment thereof, or is absent, $T_M$ is a transmembrane domain comprising an amino acid sequence of SEQ ID NO: 61 or SEQ ID NO: 62, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64, or the ICD is absent.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence of SEQ ID NO: 23 or SEQ ID NO: 25. In some embodiments, the target binding domain comprises an amino acid sequence of SEQ ID NO: 39. In some embodiments, the stalk portion $S_1$ comprises a formula $L_3$-$X_1$, wherein $L_3$ is a flexible peptide linker comprising an amino acid sequence of SEQ ID NO: 55, and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59, $T_M$ is a transmembrane domain comprising an amino acid sequence of SEQ ID NO: 61, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64.

In some embodiments, a viral particle is provided. In some embodiments, the viral particle comprises a heterologous viral glycoprotein and a targeting moiety comprising a polypeptide having the formula T-$S_1$, wherein T is a target binding domain and $S_1$ is a stalk portion. In some embodiments, the heterologous viral glycoprotein comprises a sequence of SEQ ID NO: 52 or SEQ ID NO: 53. In some embodiments, the target binding domain comprises an amino acid sequence of SEQ ID NO: 39. In some embodiments, the stalk portion $S_1$ comprises a formula $L_3$-$X_1$, wherein $L_3$ is a flexible peptide linker comprising an amino acid sequence of SEQ ID NO: 55, and $X_1$ is a polypeptide linker comprising a transmembrane domain. In some embodiments, the polypeptide comprising a transmembrane domain ($X_1$) has a formula of ECD-$T_M$-ICD, wherein ECD is an extracellular domain comprising an amino acid sequence of SEQ ID NO: 59, $T_M$ is a transmembrane domain comprising an amino acid sequence of SEQ ID NO: 61, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64.

In some embodiments, the viral particle as provided for herein further comprises a nucleic acid molecule encoding for a heterologous molecule of interest. In some embodiments, the heterologous molecule of interest is as provided for herein. In some embodiments, the heterologous molecule of interest is a CAR. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

BRIEF DESCRIPTION OF FIGURES

FIG. 1A and FIG. 1B illustrate crystal structures of VSV-G bound to LDL-R. FIG. 1A illustrates the crystal structure of VSV-G bound to CR3 of the LDL-R. FIG. 1B illustrates the crystal structure of VSV-G bound to CR2 of the LDL-R.

FIG. 2A illustrates the titration of VSV-G constructs on SupT1 cells. FIG. 2B illustrates functional titer of each construct calculated from the titration in FIG. 2A.

FIG. 3 illustrates an alignment of the ectodomains of different VSV-G proteins from different strains.

FIG. 9A shows flow cytometry data of human PBMCs transduced with exemplary vectors comprising CD8 binders as disclosed herein.

FIG. 14A illustrates the ability of SVCV-G pseudotyped lentiviral particles harboring a CD7 binder with a flexible stalk to transduce SupT1 cells as well as human and non-human primate PBMCs. FIG. 14B illustrates the transduction of cells in the absence of the CD7 binder. FIG. 14C illustrates the transduction of human and non-human primate PBMCs in terms of MOI calculated from SupT1 titration.

FIG. 18A and FIG. 18B is a comparison of the off target transduction of GFP in a panel of B-cell cell lines as compared to control SupT1 cells. FIG. 18A illustrates the data for VSV-G* pseudotyped lentiviral particles harboring a CD7 binder with a variant Fc stalk. VSV-G* denotes VSV-G (I182E, T214N, T352A). FIG. 18B illustrates the data for SVCV-G pseudotyped lentiviral particles harboring a CD7 binder with a variant Fc stalk.

FIG. 19A and FIG. 19B is a comparison of the off target transduction of a CAR20-T2A-GFP construct in a panel of B-cell cell lines as compared to control SupT1 cells. FIG. 19A illustrates the data for VSV-G* pseudotyped lentiviral particles harboring a CD7 binder with a variant Fc stalk. VSV-G* denotes VSV-G (I182E, T214N, T352A). FIG. 19B illustrates the data for SVCV-G pseudotyped lentiviral particles harboring a CD7 binder with a variant Fc stalk.

FIG. 20A illustrates that CD7 negative B-cell tumor lines were not transduced by the pseudotyped lentiviral particles. FIG. 20B illustrates that primary PBMCs isolated from patients with B cell malignancies were not transduced by the pseudotyped lentiviral particles.

FIG. 21A and FIG. 21B is a comparison of the off target transduction of GFP in a panel of B-cell cell lines as compared to control SupT1. FIG. 21A illustrates the data for VSV-G* pseudotyped lentiviral particles harboring a CD7 binder with a flexible stalk. VSV-G* denotes VSV-G (I182E, T214N, T352A). FIG. 21B illustrates the data for SVCV-G pseudotyped lentiviral particles harboring a CD7 binder with a flexible stalk.

FIG. 22A illustrates the data for VSV-G* pseudotyped lentiviral particles harboring a CD7 binder with a flexible stalk. VSV-G* denotes VSV-G (I182E, T214N, T352A). FIG. 22B illustrates the data for SVCV-G pseudotyped lentiviral particles harboring a CD7 binder with a flexible stalk.

FIG. 23A illustrates the breakdown of CAR positive PBMCs generated by the VSV-G* pseudotyped lentiviral particles harboring a CD7 binder with a variant Fc stalk. FIG. 23B illustrates the ability of CAR20 positive PBMCs to kill Raji lymphoma cells. FIG. 23C illustrates the ability of CAR20 positive PBMCs to kill Daudi lymphoma cells.

FIG. 25A illustrates the experimental design. FIG. 25B illustrates the ability of CAR20 positive PBMCs to kill B cells expressing GFP or CAR20 and GFP. FIG. 25C illustrates the results of GFP assessment of remaining cells.

FIG. 27A illustrates that the VSV-G* pseudotyped lentiviral particles are able to deplete CD20+ B-cells. FIG. 27B illustrates that mice injected with the VSV-G* pseudotyped lentiviral particles generate CAR20+ cells that were detectable in blood samples for the duration of the study.

FIG. 28A depicts the experimental design. FIG. 28B illustrates that mice receiving i.v. lentiviral particles as provided for herein prior to Raji tumor infusion had significantly lower tumor burden than mice receiving control (GFP) vector or untreated mice. Tumor burden measured via IVIS imaging.

FIG. 29A depicts the experimental design. FIG. 29B illustrates that mice receiving i.v. lentiviral particles as provided for herein after 6 days after Raji tumor infusion had their tumor burdens diminished below the limit of detection. FIG. 29C illustrates the results for a similar study with varying viral concentrations. FIG. 29D illustrates that mice receiving the highest viral concentration developed CAR20 positive cells that were detectable in blood samples for the duration of the study. Tumor burden measured via IVIS imaging.

FIG. 30A illustrates the data for Animal 1. FIG. 30B illustrates the data for Animal 2. FIG. 30C illustrates the data for Animal 3. FIG. 30D illustrates the data for Animal 4. FIG. 30E illustrates the data for Animal 5. FIG. 30F illustrates the data for Animal 6.

FIG. 32A illustrates the data for Animal 1. FIG. 32B illustrates the data for Animal 2. FIG. 32C illustrates the data for Animal 3. FIG. 32D illustrates the data for Animal 4. FIG. 32E illustrates the data for control animal 1, receiving only buffer. FIG. 32F illustrates the data for control animal 2, receiving only buffer.

FIG. 34A illustrates the data for Animal 1. FIG. 34B illustrates the data for Animal 2. FIG. 34C illustrates the data for Animal 3. FIG. 34D illustrates the data for Animal 4. FIG. 34E illustrates the data for Animal 5. FIG. 34F illustrates the data for Animal 6. FIG. 34G illustrates the data for control animal 1, receiving only buffer. FIG. 34H illustrates the data for control animal 2, receiving only buffer.

FIG. 36A illustrates the detection of anti-CD20 specific antibodies in the plasma of animals receiving a CD20 CAR molecule having an antigen binding domain of SEQ ID NO: 96. FIG. 36B illustrates the levels of INF-γ and TNF-α in animals receiving a CD20 CAR molecule having an antigen binding domain of SEQ ID NO: 96, indicators of a T cell response. FIG. 36C illustrates the detection of anti-CD20 specific antibodies in the plasma of animals receiving a CD20 CAR molecule having an antigen binding domain of SEQ ID NO: 92. FIG. 36D illustrates the levels of INF-γ and TNF-α in animals receiving a CD20 CAR molecule having an antigen binding domain of SEQ ID NO: 92, indicators of a T cell response.

FIG. 38A illustrates the data for Animal 1. FIG. 38B illustrates the data for Animal 2. FIG. 38C illustrates the data for control animal 1, receiving only buffer. FIG. 38D illustrates the data for control animal 2, receiving only buffer.

DETAILED DESCRIPTION

Figure 1A:
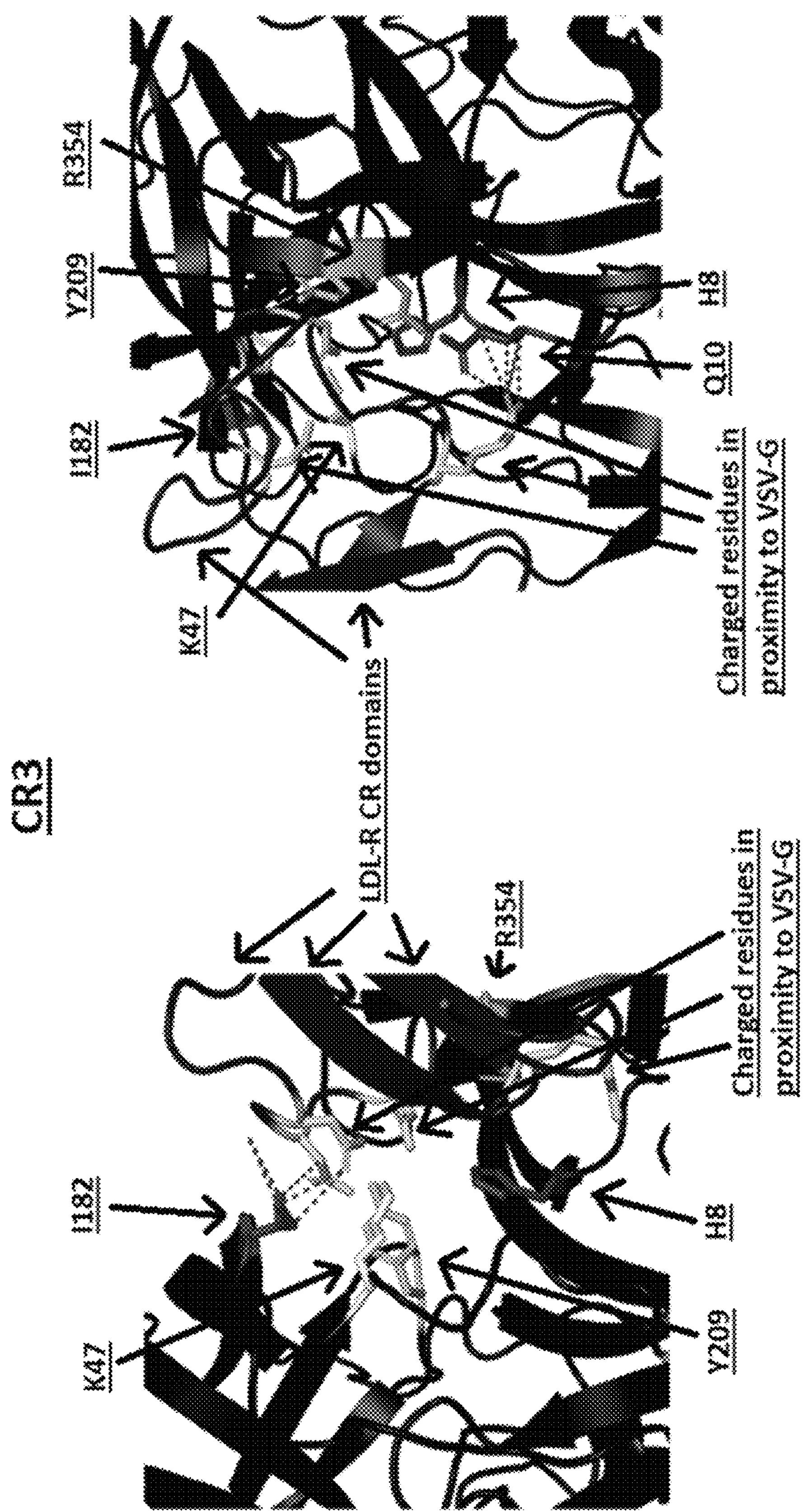

Provided for herein are viral particles comprising a heterologous viral glycoprotein and a targeting moiety, wherein the targeting moiety comprises a polypeptide having the formula of T-$S_1$, wherein T is a target binding domain, and $S_1$ is a stalk portion. In some embodiments, $S_1$ comprises a mutant Fc polypeptide that can be, for example, linked to a transmembrane domain as provided for herein. In some embodiments, $S_1$ comprises flexible polypeptides as provided for herein. The mutant Fc polypeptides or the flexible polypeptides can be incorporated into a viral particle to help facilitate the targeting of the viral particle to a specific cell type.

Additionally, the viral particle can comprise VSV-G proteins that can be used, for example, to pseudotype a virus, such as a lentivirus. In some embodiments, the pseudotyped viral-like particles are pseudotyped using viral glycoproteins of a vesicular stomatitis New Jersey virus strain, a vesicular stomatitis Indiana virus strain, a vesicular stomatitis Alagoas virus strain, a vesicular stomatitis Maraba virus strain, or a vesicular stomatitis Carajas virus strain. Examples of such proteins are provided for herein.

The pseudotyped viruses comprising the mutant VSV-G proteins, such as those provided for herein, can be used in conjunction with a targeting moiety to facilitate the fusion of the pseudotyped virus with a specific cell or tissue based on the expression of the target on the cell or the tissue. As provided for herein, the targeting moiety can be linked to a Fc protein, which can be referred to a stalk protein that comprises a transmembrane domain to facilitate the attachment of the targeting moiety to the surface of the virus. In some embodiments, the Fc protein comprises a Fc effector mutation, such as those provided for herein.

Unless defined otherwise, all technical and scientific terms have the same meaning as is commonly understood by one of ordinary skill in the art to which the embodiments disclosed belongs.

As used herein, the terms “a” or “an” means that “at least one” or “one or more” unless the context clearly indicates otherwise.

As used herein, the term “about” means that the numerical value is approximate and small variations would not significantly affect the practice of the disclosed embodiments. Where a numerical limitation is used, unless indicated otherwise by the context, “about” means the numerical value can vary by ±10% and remain within the scope of the disclosed embodiments.

Additionally, where a phrase recites “about x to y,” the term “about” modifies both x and y and can be used interchangeably with the phrase “about x to about y” unless context dictates differently.

As used herein, the term “individual” or “subject,” or “patient” used interchangeably, means any animal, including mammals, such as mice, rats, other rodents, rabbits, dogs, cats, swine, cattle, sheep, horses, or primates, such as humans.

As used herein, the terms “comprising” (and any form of comprising, such as “comprise”, “comprises”, and “comprised”), “having” (and any form of having, such as “have” and “has”), “including” (and any form of including, such as “includes” and “include”), or “containing” (and any form of containing, such as “contains” and “contain”), are inclusive or open-ended and do not exclude additional, unrecited elements or method steps. Any step or composition that uses the transitional phrase of “comprise” or “comprising” can also be said to describe the same with the transitional phase of "consisting of" or "consists."

As used herein, the term "contacting" means bringing together of two elements in an in vitro system or an in vivo system. For example, "contacting" virus or vector described herein with an individual or patient or cell includes the administration of the virus to an individual or patient, such as a human, as well as, for example, introducing a compound into a sample containing a cellular or purified preparation containing the cell.

As used herein, the term "fused" or "linked" when used in reference to a protein having different domains or heterologous sequences means that the protein domains are part of the same peptide chain that are connected to one another with either peptide bonds or other covalent bonding. The domains or section can be linked or fused directly to one another or another domain or peptide sequence can be between the two domains or sequences and such sequences would still be considered to be fused or linked to one another. In some embodiments, the various domains or proteins provided for herein are linked or fused directly to one another or a linker sequences, such as the glycine/serine sequences described herein link the two domains together.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune cell activation compared to the immune cell activation detected in the absence of the composition. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system.

Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the phrase "ex vivo" in reference to a cell being transduced, transfected or transformed ex vivo, refers to a cell being transduced, transfected or transformed outside of the subject, that is with the cells being removed from the subject before such cells are transduced, transfected or transformed.

"Identity" as used herein refers to the subunit sequence identity between two polymeric molecules such as between two nucleic acid or amino acid molecules, such as, between two polynucleotide or polypeptide molecules. When two amino acid sequences have the same residues at the same positions; e.g., if a position in each of two polypeptide molecules is occupied by an Arginine, then they are identical at that position. The identity or extent to which two amino acid or two nucleic acid sequences have the same residues at the same positions in an alignment is often expressed as a percentage. The identity between two amino acid or two nucleic acid sequences is a direct function of the number of matching or identical positions; e.g., if half of the positions in two sequences are identical, the two sequences are 50% identical; if 90% of the positions (e.g., 9 of 10), are matched or identical, the two amino acids sequences are 90% identical.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). In some embodiments, such a sequence is at least 60%, 80% or 85%, or 90%, 95% or even 99% identical at the amino acid level or nucleic acid to the sequence used for comparison. Other percentages of identity in reference to specific sequences are described herein.

Sequence identity can be measured/determined using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e3 and e100 indicating a closely related sequence. In some embodiments, sequence identity is determined by using BLAST with the default settings.

To the extent embodiments provided for herein, includes composition comprising various proteins, these proteins may, in some instances, comprise amino acid sequences that have sequence identity to the amino acid sequences disclosed herein. Therefore, in certain embodiments, depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more) to the SEQ ID NOs disclosed herein. In addition to these percentages, other percentages of identity are provided for herein. Identity between polypeptides can be determined by the Smith-Waterman homology search algorithm as implemented in the MPSRCH program (Oxford Molecular), using an affine gap search with parameters gap open penalty—12 and gap extension penalty=1.

These proteins may, compared to the disclosed proteins, include one or more (e.g. 1, 2, 3, 4, 5, 6, 7, 8, 9, 10, etc.) conservative amino acid replacements i.e. replacements of one amino acid with another which has a related side chain. Genetically-encoded amino acids are generally divided into four families: (1) acidic i.e. aspartate, glutamate; (2) basic i.e. lysine, arginine, histidine; (3) non polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, Substitution of single amino acids within these families does not have a major effect on the biological activity. The proteins may have one or more (e.g. 1, 2, 3, 4, 5, 6, 7, 8, 9, 10, etc.) single amino acid deletions relative to the disclosed protein sequences. The proteins may also include one or more (e.g. 1, 2, 3, 4, 5, 6, 7, 8, 9, 10, etc.) insertions (e.g. each of 1, 2, 3, 4 or 5 amino acids) relative to the disclosed protein sequences.

As used herein, the phrase "in vivo" in reference to a cell being transduced, transfected or transformed in vivo, refers to a cell being transduced, transfected or transformed in the subject without the cells being removed from the subject before such cells are transduced, transfected or transformed.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family that is able to infect non-dividing cells. Non-limiting examples of lentiviruses are HIV, SIV, and FIV. Vectors or viral-like particles derived from lentiviruses can be used to transduce cells and deliver genes or other molecules and have them expressed in a cell either in vitro (ex-vivo) or in vivo.

By the term "modified" as used herein, is meant a changed state or structure of a molecule or cell as provided herein. Molecules may be modified in many ways, including chemically, structurally, and functionally, such as mutations, substitutions, insertions, or deletions (e.g. internal deletions truncations). Cells may be modified through the introduction of nucleic acids or the expression of heterologous proteins.

By the term "modulating," as used herein, is meant mediating an increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, such as, a human.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "oligonucleotide" typically refers to short polynucleotides. It will be understood that when a nucleotide sequence is represented by a DNA sequence (i.e., A, T, C, G), this also provides the corresponding RNA sequence (i.e., A, U, C, G) in which "U" replaces "T."

"Parenteral" administration of a composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, the terms "nucleic acids" and "polynucleotides" as used herein are interchangeable. As used herein polynucleotides include, but are not limited to, all nucleic acid sequences which are obtained by any methods available in the art, including, without limitation, recombinant methods, i.e., the cloning of nucleic acid sequences from a recombinant library or a cell genome, using cloning technology and PCR, and the like, and by synthetic means.

As used herein, the terms "peptide," "polypeptide," and "protein" are used interchangeably, and refer to a compound comprised of a plurality of amino acid residues covalently linked by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Unless explicitly stated otherwise, the terms "heterologous viral structural protein" and "heterologous viral glycoprotein" as used herein are used synonymously and interchangeably. Accordingly, unless explicitly stated otherwise, an embodiment referring to a "heterologous viral structural protein" is understood to be referring to a "heterologous viral glycoprotein" and vice versa.

The term "pseudotyped" or "pseudotyped viral particle", as used herein, refers to a viral particle bearing glycoproteins derived from other viruses having envelopes or a viral vector encoding envelope glycoproteins from a virus that is different from the parental virus. The host range of the vector particles can thus be expanded or altered depending on the type of cell surface receptor used by the glycoprotein. For example, a virus can be pseudotyped with a VSV-G mutant protein as provided for herein.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In some embodiments, the targeting moieties described herein that can be used to target the viral particles comprising the mutant VSV-G protein, or other viral structural proteins used to pseudotype a virus, can specifically bind to their target.

The term "subject" includes living organisms, including those in which an immune response can be elicited (e.g., mammals). A "subject" or "patient," as used therein, may be a human or non-human mammal. Non-human mammals include, for example, livestock and pets, such as ovine, bovine, porcine, canine, non-human primates, feline and murine mammals. In some embodiments, the subject is human.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into a cell. A "transfected" or "transformed" or "transduced" cell is one which has been transfected, transformed or transduced with exogenous nucleic acid. The cell includes the primary subject cell and its progeny. In some embodiments, the transfection, transformation, or transduction is performed or occurs in vivo.

To "treat" a disease as the term is used herein, means to reduce the frequency or severity of at least one sign or symptom of a disease or disorder experienced by a subject.

A "vector" is a composition of matter which comprises an isolated nucleic acid encoding a protein or a peptide. Numerous vectors are known in the art including, but not limited to, linear polynucleotides, plasmids, DNA, and RNA. Examples of viral vectors include, but are not limited to, Sendai viral vectors, adenoviral vectors, adeno-associated virus vectors, retroviral vectors, lentiviral vectors, and the like.

A "carrier" or "delivery vehicle" includes viral particles, viruses, polylysine compounds, and liposomes, which facilitate transfer of nucleic acid into cells. A carrier or delivery vehicle can also be used to deliver a protein or peptide to a cell.

Ranges: throughout this disclosure, various aspects of the embodiments can be presented in a range format. It should be understood that the description in range format is merely for convenience and brevity and should not be construed as an inflexible limitation. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. Unless otherwise explicitly stated to the contrary, a range that is disclosed also includes the endpoints of the range.

In some embodiments, a polypeptide is provided comprising a variant Fc polypeptide. In some embodiments, the variant Fc polypeptide is a variant of a Fc polypeptide comprising the amino acid sequence of SEQ ID NO: 26 (IgG1 Fc), SEQ ID NO: 27 (IgG2 Fc), or SEQ ID NO: 28 (IgG4 Fc). In some embodiments, the variant comprises a N-terminal deletion. In some embodiments, the N-terminal deletion does not comprise up to 100 amino acid residues from the N-terminus of SEQ ID NO: 26, SEQ ID NO: 27, or SEQ ID NO: 28. In some embodiments, the N-terminal deletion does not comprise up to 98 amino acid residues as counted from the N-terminus of SEQ ID NO: 26, SEQ ID NO: 27, or SEQ ID NO: 28. In some embodiments, the N-terminal deletion does not comprise 98 amino acid residues as counted from the N-terminus of SEQ ID NO: 26, SEQ ID NO: 27, or SEQ ID NO: 28. In some embodiments, the N-terminal deletion does not comprise 98 amino acid residues as counted from the N-terminus of SEQ ID NO: 26. In some embodiments, the N-terminal deletion does not comprise 90-98 amino acid residues as counted from the N-terminus of SEQ ID NO: 26, SEQ ID NO: 27, or SEQ ID NO: 28. In some embodiments, the N-terminal deletion does not comprise 75-98 amino acid residues as counted from the N-terminus of SEQ ID NO: 26, SEQ ID NO: 27, or SEQ ID NO: 28. In some embodiments, the N-terminal deletion does not comprise 60-98 amino acid residues as counted from the N-terminus of SEQ ID NO: 26, SEQ ID NO: 27, or SEQ ID NO: 28. In some embodiments, the N-terminal deletion does not comprise 50-98 amino acid residues as counted from the N-terminus of SEQ ID NO: 26, SEQ ID NO: 27, or SEQ ID NO: 28. In some embodiments, the N-terminal deletion does not comprise 40-98 amino acid residues as counted from the N-terminus of SEQ ID NO: 26, SEQ ID NO: 27, or SEQ ID NO: 28. In some embodiments, the N-terminal deletion does not comprise 30-98 amino acid residues as counted from the N-terminus of SEQ ID NO: 26, SEQ ID NO: 27, or SEQ ID NO: 28. In some embodiments, the N-terminal deletion does not comprise 10-98 amino acid residues as counted from the N-terminus of SEQ ID NO: 26, SEQ ID NO: 27, or SEQ ID NO: 28. In some embodiments, the N-terminal deletion does not comprise 5-98 amino acid residues as counted from the N-terminus of SEQ ID NO: 26, SEQ ID NO: 27, or SEQ ID NO: 28. In some embodiments, the N-terminal deletion does not comprise 1-98 amino acid residues as counted from the N-terminus of SEQ ID NO: 26, SEQ ID NO: 27, or SEQ ID NO: 28. In some embodiments, the variant Fc polypeptide does not comprise the amino acid sequence of (SEQ ID NO: 105)

ASTKGPSVFPLAPSSKSTSGGTAALGCLVKDYFPEPVTVSWN

SGALTSGVHTFPAVLQSSGLYSLSSVVTVPSSSLGTQTYICN

VNHKPSNTKVDKKV

In some embodiments, the variant Fc polypeptide does not comprise any of the sequence of SEQ ID NO: 105. In some embodiments, the variant Fc polypeptide does not comprise the entirety of the sequence of SEQ ID NO: 105. As used herein, the phrase "as counted from the N-terminus" in regards to a N-terminal deletion of a reference sequence means that one is treating the first residue of the reference sequence as residue 1 even if under a numbering scheme, such as the EU numbering scheme for Fc polypeptides, the first residue would have a different number. Thus, for example, the phrase a "N-terminal deletion does not comprise 3 amino acid residues as counted from the N-terminus of SEQ ID NO: 26" refers to the residues "ASK" being deleted as they are first three residues of SEQ ID NO: 26. In some embodiments, the variant Fc polypeptide comprises the amino acid sequence of SEQ ID NO: 103. In some embodiments, the variant Fc polypeptide either with or without a N-terminal deletion, as provided for herein, comprises one or more mutations at a position that corresponds to L234, L235, M297, P329, 1253, H310, or H435. The positions refer to the EU numbering of the Fc polypeptide. In some embodiments, the variant Fc polypeptide either with or without a N-terminal deletion, as provided for herein, comprises mutations positions that corresponds to L234, L235, M297, P329, 1253, H310, and H435. In some embodiments, the variant Fc polypeptide either with or without a N-terminal deletion, as provided for herein, comprises mutations at positions that corresponds to L234, and L235. In some embodiments, the variant Fc polypeptide either with or without a N-terminal deletion, as provided for herein, comprises a mutation at a position that corresponds to M297. In some embodiments, the variant Fc polypeptide either with or without a N-terminal deletion, as provided for herein, comprises a mutation at a position that corresponds to P329. In some embodiments, the variant Fc polypeptide either with or without a N-terminal deletion, as provided for herein, comprises a mutation at a position that corresponds to 1253. In some embodiments, the variant Fc polypeptide either with or without a N-terminal deletion, as provided for herein, comprises a mutation at a position that corresponds to H310. In some embodiments, the variant Fc polypeptide either with or without a N-terminal deletion, as provided for herein, comprises a mutation at a position that corresponds to H435. In some embodiments, the variant Fc polypeptide either with or without a N-terminal deletion, as provided for herein, comprises one or more mutations that correspond to L234A, L235A, M297A, P329G, I253A, H310A, or H435A. In some embodiments, the variant Fc polypeptide either with or without a N-terminal deletion, as provided for herein, comprises mutations that correspond to L234A, L235A, M297A, P329G, I253A, H310A, and H435A. In some embodiments, the Fc variant polypeptide comprises an amino acid sequence that is at least 85%, 90%, 91%, 92%, 93%, 94%, 95%, 96%, 97%, 98%, or 99% identical to the amino acid sequence of SEQ ID NO: 103, provided that the Fc variant does not comprise the amino acid sequence of SEQ ID NO: 105, and provided that the variant comprises one or more mutations that correspond to L234A, L235A, M297A, P329G, I253A, H310A, or H435A. In some embodiments, the Fc variant polypeptide comprises an amino acid sequence that is at least 85%, 90%, 91%, 92%, 93%, 94%, 95%, 96%, 97%, 98%, or 99% identical to the amino acid sequence of SEQ ID NO: 103, provided that the Fc variant does not comprise the amino acid sequence of SEQ ID NO: 105, and provided that the variant comprises mutations that correspond to L234A, L235A, M297A, P329G, I253A, H310A, and H435A. In some embodiments, the Fc variant polypeptide comprises an amino acid sequence that is at least 85%, 90%, 91%, 92%, 93%, 94%, 95%, 96%, 97%, 98%, or 99% identical to the amino acid sequence of SEQ ID NO: 104, provided that the Fc variant does not comprise the amino acid sequence of SEQ ID NO: 105. In some embodiments, the Fc variant polypeptide comprises the sequence of SEQ ID NO: 104, provided that the Fc variant does not comprise the amino acid sequence of SEQ ID NO: 105. As used herein, the positions referenced in the Fc polypeptide refer to the positions according to the EU numbering scheme. The EU numbering scheme is known in the art. For example, in the polypeptide of SEQ ID NO: 104, position 234 refers to residue 19 of SEQ ID NO: 104, position 235 refers to residue 20 of SEQ ID NO: 104, and so on and so forth.

As provided for herein, the Fc variants can, in some embodiments, be fused or linked to another protein, such as a targeting moiety. The Fc variant can also be fused or linked to a transmembrane domain and/or an intracellular domain so that it can be inserted into a cellular membrane or a viral envelope, such as the envelope of a lentivirus. In some embodiments, the targeting moiety is linked or fused to the N-terminus of the Fc variant polypeptide. In some embodiments, the Fc variant polypeptide is linked to a transmembrane domain at the C-terminus of the Fc variant polypeptide.

In some embodiments, viral particles are provided comprising the variant Fc polypeptides provided for herein, such as those described herein, including those described above and below.

Viral Particles Comprising Heterologous Viral Glycoprotein and Targeting Moiety

In some embodiments, viral particles are provided comprising a heterologous viral glycoprotein and a targeting moiety. In some embodiments, the targeting moiety comprises a polypeptide having the formula T-$S_1$, wherein T is a target binding domain, and $S_1$ is a stalk portion. In some embodiments, $S_1$ comprises a variant Fc protein, wherein the variant Fc protein comprises a transmembrane domain, such as, but not limited to a CD8 or CD28 transmembrane domain. Accordingly, in some embodiments, the stalk portion $S_1$ comprises an N-terminus to C-terminus orientation of variant Fc—transmembrane domain. In some embodiments, the variant Fc protein comprises an effector mutation, wherein the effector mutation inhibits the interaction between the Fc protein and a Fc interacting protein, such as FcγR, C1q, FcRβ, or FcRn.

In some embodiments, the $S_1$ stalk portion is attached to the surface of the viral particle through the transmembrane domain. For example, the transmembrane domain can pass through or is inserted in the envelope of an enveloped virus (e.g. lentivirus or other viruses provided for herein). Thus, the $S_1$ stalk portion linked to the transmembrane domain is presented on the outer surface of the enveloped virus.

In some embodiments, the variant Fc protein is a variant of an IgG1 Fc, IgG2 Fc or IgG4 Fc protein. In some embodiments, the variant Fc protein comprises a variant of a sequence of SEQ ID NO: 26 (IgG1 Fc), SEQ ID NO: 27 (IgG2 Fc), or SEQ ID NO: 28 (IgG4 Fc).

In some embodiments, the variant Fc protein is a variant IgG1 Fc protein (SEQ ID NO: 26). In some embodiments, the variant IgG1 Fc protein comprises one or more of the mutations that corresponds to those selected from the group consisting of: L234A, L235A, N297A, P329G, I253A, H310A, and H435A of SEQ ID NO: 26, numbered according to the EU numbering index of Kabat as described in Edelman, G M et al. "The covalent structure of an entire gammaG immunoglobulin molecule." *Proceedings of the National Academy of Sciences of the United States of America* vol. 63, 1 (1969): 78-85. doi:10.1073/pnas.63.178, hereby incorporated by reference in its entirety. Any of the mutations L234A, L235A, N297A, P329G, 1253A, H310A, and H435A of SEQ ID NO: 26 may be present or absent and the mutations may be combined in any combination. In some embodiments, the variant IgG1 Fc protein comprises a mutation that corresponds to L234A and L235A of SEQ ID NO: 26. In some embodiments, the variant IgG1 Fc protein comprises a mutation that corresponds to N297A of SEQ ID NO: 26. In some embodiments, the variant IgG1 Fc protein comprises a mutation that corresponds to P329G of SEQ ID NO: 26. In some embodiments, the variant IgG1 Fc protein comprises a mutation that corresponds to L234A, L235A, N297A, and P329G of SEQ ID N: 26. In some embodiments, the variant IgG1 Fc protein comprises a mutation that corresponds to I253A of SEQ ID NO: 26. In some embodiments, the variant IgG1 Fc protein comprises a mutation that corresponds to H310A of SEQ ID NO: 26. In some embodiments, the variant IgG1 Fc protein comprises a mutation that corresponds to H435A of SEQ ID NO: 26. In some embodiments, the variant IgG1 Fc protein comprises a mutation that corresponds to I253A, H310A, and H435A of SEQ ID NO: 26. In some embodiments, the variant IgG1 Fc protein comprises a mutation that corresponds to L234A, L235A, N297A, P329G, I253A, H310A, and H435A of SEQ ID NO: 26.

In some embodiments, the variant Fc protein comprising a variant IgG1 Fc protein comprises a truncation of the IgG1 Fc sequence. The truncation can comprise the deletion of any number of amino acids from the N-terminus, the C-terminus, or both of the IgG1 Fc sequence. In some embodiments, the variant Fc protein comprising a variant IgG1 Fc protein comprises a truncation of SEQ ID NO: 26. The truncation can comprises the deletion of any number of amino acids from the N-terminus, the C-terminus, or both of SEQ ID NO: 26. In some embodiments, the truncation comprises the deletion of amino acids from the N-terminus of SEQ ID NO: 26. In some embodiments, the truncation comprises the deletion of amino acids from the C-terminus of SEQ ID NO: 26. In some embodiments, the truncation comprises the deletion of amino acids from both the N-terminus and the C-terminus of SEQ ID NO: 26. In some embodiments, the truncation of SEQ ID NO: 26 comprises an amino acid sequence of SEQ ID NO: 103:

```
                                                   (SEQ ID NO: 103)
EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGK
```

In some embodiments, the variant IgG1 Fc protein comprises one or more mutations relative to SEQ ID NO: 103 selected from the group consisting of: L19A, L20A, N82A, P114G, I38A, H95A, and H220A. It is to be understood that the positions L19, L20, N82, P114, 138, H95, and H220 are in reference to SEQ ID NO: 103 only. The skilled artisan would readily recognize that positions L234, L235, N297, P329, 1253, H310, and H435 numbered according to the EU numbering system of Kabat correspond to positions L19, L20, N82, P114, I38, H95, and H220, respectively, of SEQ ID NO: 103. Any of the mutations L19A, L20A, N82A, P114G, I38A, H95A, and H220A of SEQ ID NO: 103 may be present of absent and the mutations may be combined in any combination. In some embodiments, the variant IgG1 Fc protein comprises a mutation that corresponds to L19A and L20A of SEQ ID NO: 103. In some embodiments, the variant IgG1 Fc protein comprises a mutation that corresponds to N82A of SEQ ID NO: 103. In some embodiments, the variant IgG1 Fc comprises a mutation that corresponds to P114G of SEQ ID NO: 103. In some embodiments, the variant IgG1 Fc comprises a mutation that corresponds to L19A, L20A, N82A, and P114G of SEQ ID NO: 103. In some embodiments, the variant IgG1 Fc protein comprises a mutation that corresponds to I38A of SEQ ID NO: 103. In some embodiments, the variant IgG1 Fc protein comprises a mutation that corresponds to H95A of SEQ ID NO: 103.

In some embodiments, the variant IgG1 Fc protein comprises a mutation that corresponds to H220A of SEQ ID NO: 103. In some embodiments, the variant IgG1 Fc protein comprises a mutation that corresponds to I38A, H95A, and H220A of SEQ ID NO: 103. In some embodiments, the variant IgG1 Fc protein comprises a mutation that corresponds to L19A, L20A N82A, P114G, I38A, H95A, and H220A of SEQ ID NO: 103. In some embodiments, the variant IgG1 Fc protein comprises a mutation that corresponds to each of L19A, L20A N82A, P114G, 138A, H95A, and H220A of SEQ ID NO: 103. An exemplary variant IgG1 protein that comprises each of L19A, L20A N82A, P114G, I38A, H95A, and H220A is shown below in the amino acid sequence of SEQ ID NO: 104:

```
                                                   (SEQ ID NO: 104)
EPKSCDKTHTCPPCPAPEAAGGPSVFLFPPKPKDTLMASRTPEVTCVVVD

VSHEDPEVKFNWYVDGVEVHNAKTKPREEQYASTYRVVSVLTVLAQDWLN

GKEYKCKVSNKALGAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNAYTQKSLSLSPGK
```

In some embodiments, the variant Fc protein is a variant IgG2 Fc protein (SEQ ID NO: 27). In some embodiments, the variant IgG2 Fc protein comprises one or more mutations selected from the group consisting of: N297A, P329G, I253A, H310A, and H435A as those position correspond to SEQ ID NO: 27, numbered according to the EU numbering index of Kabat. Any of the mutations N297A, P329G, I253A, H310A, and H435A of SEQ ID NO: 27 may be present or absent and the mutations may be combined in any combination. In some embodiments, the variant IgG2 Fc protein comprises a mutation that corresponds to N297A of SEQ ID NO: 27. In some embodiments, the variant IgG2 Fc protein comprises a mutation that corresponds to P329G of SEQ ID NO: 27. In some embodiments, the variant IgG2 Fc protein comprises a mutation that corresponds to N297A and P329G of SEQ ID NO: 27. In some embodiments, the variant IgG2 Fe protein comprises a mutation that corresponds to I253A of SEQ ID NO: 27. In some embodiments, the variant IgG2 Fc protein comprises a mutation that corresponds to H310A of SEQ ID NO: 27. In some embodiments, the variant IgG2 Fc protein comprises a mutation that corresponds to H435A of SEQ ID NO: 27. In some embodiments, the variant IgG2 Fc protein comprises a mutation that corresponds to I253A, H310A, and H435A of SEQ ID NO: 27.

In some embodiments, the variant Fc protein comprising a variant IgG2 Fc protein comprises a truncation of the IgG2 Fc sequence. The truncation can comprise the deletion of any number of amino acids from the N-terminus, the C-terminus, or both of the IgG2 Fc sequence. In some embodiments, the variant Fc protein comprising a variant IgG2 Fc protein comprises a truncation of SEQ ID NO: 27. The truncation can comprises the deletion of any number of amino acids from the N-terminus, the C-terminus, or both of SEQ ID NO: 27. In some embodiments, the truncation comprises the deletion of amino acids from the N-terminus of SEQ ID NO: 27. In some embodiments, the truncation comprises the deletion of amino acids from the C-terminus of SEQ ID NO: 27. In some embodiments, the truncation comprises the deletion of amino acids from both the N-terminus and the C-terminus of SEQ ID NO: 27.

In some embodiments, the variant Fc protein is a variant IgG4 Fc protein (SEQ ID NO: 28). In some embodiments, the variant IgG4 Fc protein comprises one or more mutations selected from the group consisting of: S228P, L235E, N297A, P329G, I253A, H310A, and H435A as those positions correspond to SEQ ID NO: 28, numbered according to the EU numbering index of Kabat. Any of the mutations S228P, L235E, N297A, P329G, I253A, H310A, and H435A of SEQ ID NO: 28 may be present or absent and the mutations may be combined in any combination. In some embodiments, the variant IgG4 Fc protein comprises a mutation that corresponds to S228P of SEQ ID NO: 28. In some embodiments, the variant IgG4 Fc protein comprises a mutation that corresponds to L235E of SEQ ID NO: 28. In some embodiments, the variant IgG4 Fc protein comprises a mutation that corresponds to N297A of SEQ ID NO: 28. In some embodiments, the variant IgG4 Fc protein comprises a mutation that corresponds to P329G of SEQ ID NO: 28. In some embodiments, the variant IgG4 Fc protein comprises a mutation that corresponds to S228P, L235E, N297A, and P329G of SEQ ID NO: 28. In some embodiments, the variant IgG4 Fc protein comprises a mutation that corresponds to I253A of SEQ ID NO: 28. In some embodiments, the variant IgG4 Fc protein comprises a mutation that corresponds to H310A of SEQ ID NO: 28. In some embodiments, the variant IgG4 Fc protein comprises a mutation that corresponds to H435A of SEQ ID NO: 28. In some embodiments, the variant IgG4 Fc protein comprises a mutation that corresponds to I253A, H310A, and H435A of SEQ ID NO: 28.

In some embodiments, the variant Fc protein comprising a variant IgG4 Fc protein comprises a truncation of the IgG4 Fc sequence. The truncation can comprise the deletion of any number of amino acids from the N-terminus, the C-terminus, or both of the IgG4 Fc sequence. In some embodiments, the variant Fc protein comprising a variant IgG4 Fc protein comprises a truncation of SEQ ID NO: 28. The truncation can comprises the deletion of any number of amino acids from the N-terminus, the C-terminus, or both of SEQ ID NO: 28. In some embodiments, the truncation comprises the deletion of amino acids from the N-terminus of SEQ ID NO: 28. In some embodiments, the truncation comprises the deletion of amino acids from the C-terminus of SEQ ID NO: 28. In some embodiments, the truncation comprises the deletion of amino acids from both the N-terminus and the C-terminus of SEQ ID NO: 28.

In some embodiments, the stalk portion $S_1$ comprising a variant Fc protein is given by the formula $L_1$-Fc-$L_2$-$X_1$, wherein $L_1$ is a linker or absent; Fc is the variant Fc protein; $L_2$ is a linker or absent; and $X_1$ is a polypeptide comprising the transmembrane domain. Accordingly, the targeting moiety comprising the formula T-$S_1$ may also be given by the formula T-$L_1$-Fc-$L_2$-$X_1$, wherein: T is a target binding domain; $L_1$ is a linker or absent; Fc is the variant Fc protein; $L_2$ is a linker or absent; and $X_1$ is a polypeptide comprising the transmembrane domain. Therefore, it is to be understood that, in some embodiments, the stalk portion $S_1$ may be given by the formula $L_1$-Fc-$L_2$-$X_1$. In some embodiments, the target binding domain T is as provided for herein. In some embodiments, the variant Fc protein is as provided for herein.

In some embodiments, $L_1$ and $L_2$ are each, independently, a polypeptide linker. In some embodiments, the polypeptide linker comprises $(GGGGA)_n$ (SEQ ID NO: 54), $(GGGGS)_n$ (SEQ ID NO: 55), $(EAAAK)_n$ (SEQ ID NO: 73)$_n$A (EAAAK)$_n$A (SEQ ID NO: 74), $(XP)_n$(SEQ ID NO: 75), wherein X is Ala, Lys, or Glu, GSAGSAAGSGEF (SEQ ID NO: 56), KESGSVSSEQLAQFRSLD (SEQ ID NO: 57), EGKSSGSGSESKST (SEQ ID NO: 58), AEAAAKEAAAKA (SEQ ID NO: 76), or a combination thereof, wherein each n is, independently, 1-5. In some embodiments, each n is, independently, 1. In some embodiments, each n is, independently, 2. In some embodiments, each n is, independently, 3. In some embodiments, each n is, independently, 4. In some embodiments, each n is, independently, 5. In some embodiments, each n is, independently, greater than 5. In some embodiments, $L_1$ is absent. In some embodiments, $L_1$ is $(GGGGA)_n$ (SEQ ID NO: 54) or $(GGGGS)_n$ (SEQ ID NO: 55), wherein each n is, independently, 1-5. In some embodiments, $L_1$ is $(GGGGA)_n$ (SEQ ID NO: 54) or $(GGGGS)_n$ (SEQ ID NO: 55), wherein each n is, independently, 1. In some embodiments, $L_1$ is $(GGGGA)_n$ (SEQ ID NO: 54) or $(GGGGS)_n$ (SEQ ID NO: 55), wherein each n is, independently, 2. In some embodiments, $L_1$ is $(GGGGA)_n$ (SEQ ID NO: 54) or $(GGGGS)_n$ (SEQ ID NO: 55), wherein each n is, independently, 3. In some embodiments, $L_1$ is $(GGGGA)_n$ (SEQ ID NO: 54) or $(GGGGS)_n$ (SEQ ID NO: 55), wherein each n is, independently, 4. In some embodiments, $L_1$ is $(GGGGA)_n$ (SEQ ID NO: 54) or $(GGGGS)_n$ (SEQ ID NO: 55), wherein each n is, independently, 5. In some embodiments, $L_1$ is $(GGGGA)_n$ (SEQ ID NO: 54) or $(GGGGS)_n$ (SEQ ID NO: 55), wherein each n is, independently, greater than 5. In some embodiments, $L_2$ is absent. In some embodiments, $L_2$ is $(GGGGA)_n$ (SEQ ID NO: 54) or $(GGGGS)_n$ (SEQ ID NO: 55), wherein each n is, independently, 1-5. In some embodiments, $L_2$ is $(GGGGA)_n$ (SEQ ID NO: 54) or $(GGGGS)_n$ (SEQ ID NO: 55), wherein each n is, independently, 1. In some embodiments, $L_2$ is $(GGGGA)_n$ (SEQ ID NO: 54) or $(GGGGS)_n$ (SEQ ID NO: 55), wherein each n is, independently, 2. In some embodiments, $L_2$ is $(GGGGA)_n$ (SEQ ID NO: 54) or $(GGGGS)_n$ (SEQ ID NO: 55), wherein each n is, independently, 3. In some embodiments, $L_2$ is $(GGGGA)_n$ (SEQ ID NO: 54) or (GGGGS) n (SEQ ID NO: 55), wherein each n is, independently, 4. In some embodiments, $L_2$ is (GGGGA) n (SEQ ID NO: 54) or $(GGGGS)_n$ (SEQ ID NO: 55), wherein each n is, independently, 5. In some embodiments, $L_2$ is $(GGGGA)_n$ (SEQ ID NO: 54) or $(GGGGS)_n$ (SEQ ID NO: 55), wherein each n is, independently, greater than 5.

In some embodiments, $X_1$ comprises a polypeptide having a formula of ECD-$T_M$-ICD, wherein ECD is an extracellular domain, or a fragment thereof, of a cell surface protein, or is absent; $T_M$ is a transmembrane domain of a transmembrane protein; and ICD is an intracellular domain of a protein or a protein that facilitates the incorporation of the targeting moiety into the envelope of the viral particle, or is absent. Accordingly, in some embodiments, the targeting moiety comprising the formula T-$S_1$ that may also be given by the formula T-$L_1$-Fc-$L_2$-$X_1$ may also be given by the formula T-$L_1$-Fc-$L_2$-ECD-$T_M$-ICD, wherein T is a target binding domain; $L_1$ is a linker or absent; Fc is the variant Fc protein; $L_2$ is a linker or absent; ECD is an extracellular domain, or a fragment thereof, of a cell surface protein, or is absent; $T_M$ is a transmembrane domain of a transmembrane protein; and ICD is an intracellular domain of a protein or a protein that facilitates the incorporation of the targeting moiety into the envelope of the viral particle, or is absent. Therefore, it is to be understood that, in some embodiments, the stalk portion $S_1$ may be given by the formula $L_1$-Fc-$L_2$-ECD-$T_M$-ICD.

In some embodiments, the stalk portion $S_1$ does not comprise a variant Fc region. In some embodiments, the stalk portion $S_1$ is given by the formula $L_3$-$X_1$, wherein $L_3$ is a flexible peptide linker and $X_1$ is a polypeptide comprising a transmembrane domain as provided for herein. Accordingly, in some embodiments, the targeting moiety comprising the formula T-$S_1$ may also be given by the formula T-$L_3$-$X_1$, wherein T is a target binding domain, $L_3$ is a flexible peptide linker, and $X_1$ is a polypeptide comprising a transmembrane domain as provided for herein. Therefore, it is to be understood that, in some embodiments, the stalk portion $S_1$ may be given by the formula $L_3$-$X_1$. In some embodiments, the $S_1$ stalk portion is attached to the surface of the viral particle through the transmembrane domain.

In some embodiments, the flexible peptide linker $L_3$ may be any flexible peptide linker. In some embodiments, $L_3$ is selected from the group of flexible linkers including, but not limited to, $(GGGGA)_n$ (SEQ ID NO: 54), $(GGGGS)_n$ (SEQ ID NO: 55), GSAGSAAGSGEF (SEQ ID NO: 56), KESGSVSSEQLAQFRSLD (SEQ ID NO: 57), EGKSSGSGSESKST (SEQ ID NO: 58), or any combination thereof, wherein each n is, independently, an integer selected from 1-4. In some embodiments, each n is, independently, an integer selected from 1-4, 1-5, 1-6, 1-7, 1-8, 1-9, or 1-10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, each n is, independently, greater than 10. In some embodiments, $L_3$ is $(GGGGA)_n$ (SEQ ID NO: 54) and n is 1. In some embodiments, $L_3$ is $(GGGGA)_n$ (SEQ ID NO: 54) and n is 2. In some embodiments, $L_3$ is $(GGGGA)_n$ (SEQ ID NO: 54) and n is 3. In some embodiments, $L_3$ is $(GGGGA)_n$ (SEQ ID NO: 54) and n is 4. In some embodiments, $L_3$ is $(GGGGA)_n$ (SEQ ID NO: 54) and n is 5. In some embodiments, $L_3$ is $(GGGGA)_n$ (SEQ ID NO: 54) and n is 6. In some embodiments, $L_3$ is $(GGGGA)_n$ (SEQ ID NO: 54) and n is 7. In some embodiments, $L_3$ is $(GGGGA)_n$ (SEQ ID NO: 54) and n is 8. In some embodiments, $L_3$ is $(GGGGA)_n$ (SEQ ID NO: 54) and n is 9. In some embodiments, $L_3$ is $(GGGGA)_n$ (SEQ ID NO: 54) and n is 10. In some embodiments, $L_3$ is $(GGGGA)_n$ (SEQ ID NO: 54) and n is greater than 10. In some embodiments, $L_3$ is $(GGGGS)_n$ (SEQ ID NO: 55) and n is 1. In some embodiments, $L_3$ is $(GGGGS)_n$ (SEQ ID NO: 55) and n is 2. In some embodiments, $L_3$ is $(GGGGS)_n$ (SEQ ID NO: 55) and n is 3. In some embodiments, $L_3$ is $(GGGGS)_n$ (SEQ ID NO: 55) and n is 4. In some embodiments, $L_3$ is $(GGGGS)_n$ (SEQ ID NO: 55) and n is 5. In some embodiments, $L_3$ is $(GGGGS)_n$ (SEQ ID NO: 55) and n is 6. In some embodiments, $L_3$ is $(GGGGS)_n$ (SEQ ID NO: 55) and n is 7. In some embodiments, $L_3$ is $(GGGGS)_n$ (SEQ ID NO: 55) and n is 8. In some embodiments, $L_3$ is $(GGGGS)_n$ (SEQ ID NO: 55) and n is 9. In some embodiments, $L_3$ is $(GGGGS)_n$ (SEQ ID NO: 55) and n is 10. In some embodiments, $L_3$ is $(GGGGS)_n$ (SEQ ID NO: 55) and n is greater than 10. In some embodiments, $L_3$ is GSAGSAAGSGEF (SEQ ID NO: 56). In some embodiments, $L_3$ is KESGSVSSEQLAQFRSLD (SEQ ID NO: 57). In some embodiments, $L_3$ is EGKSSGSGSESKST (SEQ ID NO: 58).

In some embodiments, the flexible peptide linker $L_3$ may be any flexible peptide linker. In some embodiments, $L_3$ is selected from the group of flexible linkers including, but not limited to, $(GGGGA)_n$ (SEQ ID NO: 54), $(GGGGS)_n$ (SEQ ID NO: 55), GSAGSAAGSGEF (SEQ ID NO: 56), KESGSVSSEQLAQFRSLD (SEQ ID NO: 57), EGKSSGSGSESKST (SEQ ID NO: 58), or any combination thereof, wherein each n is, independently, an integer selected from 1-4. In some embodiments, n is 1. In some embodiments, n is 2. In some embodiments, n is 3. In some embodiments, n is 4. In some embodiments, $L_3$ is $(GGGGA)_n$ (SEQ ID NO: 54) and n is 1. In some embodiments, $L_3$ is $(GGGGA)_n$ (SEQ ID NO: 54) and n is 2. In some embodiments, $L_3$ is $(GGGGA)_n$ (SEQ ID NO: 54) and n is 3. In some embodiments, $L_3$ is $(GGGGA)_n$ (SEQ ID NO: 54) and n is 4. In some embodiments, $L_3$ is $(GGGGS)_n$ (SEQ ID NO: 55) and n is 1. In some embodiments, $L_3$ is $(GGGGS)_n$ (SEQ ID NO: 55) and n is 2. In some embodiments, $L_3$ is $(GGGGS)_n$ (SEQ ID NO: 55) and n is 3. In some embodiments, $L_3$ is $(GGGGS)_n$ (SEQ ID NO: 55) and n is 4. In some embodiments, $L_3$ is GSAGSAAGSGEF (SEQ ID NO: 56). In some embodiments, $L_3$ is KESGSVSSEQLAQFRSLD (SEQ ID NO: 57). In some embodiments, $L_3$ is EGKSSGSGSESKST (SEQ ID NO: 58).

In some embodiments, $L_3$ is selected from the group of flexible linkers including, but not limited to, $(GGGGA)_n$ (SEQ ID NO: 54), $(GGGGS)_n$ (SEQ ID NO: 55), GSAGSAAGSGEF (SEQ ID NO: 56), KESGSVSSEQLAQFRSLD (SEQ ID NO: 57), EGKSSGSGSESKST (SEQ ID NO: 58), or any combination thereof, wherein each n is, independently, an integer selected from 1, 2, or 4. In some embodiments, n is 1. In some embodiments, n is 2. In some embodiments, n is 4. In some embodiments, $L_3$ is $(GGGGA)_n$ (SEQ ID NO: 54) and n is 1. In some embodiments, $L_3$ is $(GGGGA)_n$ (SEQ ID NO: 54) and n is 2. In some embodiments, $L_3$ is $(GGGGA)_n$ (SEQ ID NO: 54) and n is 4. In some embodiments, $L_3$ is $(GGGGS)_n$ (SEQ ID NO: 55) and n is 1. In some embodiments, $L_3$ is $(GGGGS)_n$ (SEQ ID NO: 55) and n is 2. In some embodiments, $L_3$ is $(GGGGS)_n$ (SEQ ID NO: 55) and n is 4. In some embodiments, $L_3$ is GSAGSAAGSGEF (SEQ ID NO: 56). In some embodiments, $L_3$ is KESGSVSSEQLAQFRSLD (SEQ ID NO: 57). In some embodiments, $L_3$ is EGKSSGSGSESKST (SEQ ID NO: 58).

In some embodiments, $X_1$ comprises a polypeptide having a formula of ECD-$T_M$-ICD, wherein ECD is an extracellular domain, or a fragment thereof, of a cell surface protein, or is absent; $T_M$ is a transmembrane domain of a transmembrane protein; and ICD is an intracellular domain of a protein or a protein that facilitates the incorporation of the targeting moiety into the envelope of the viral particle, or is absent. Accordingly, in some embodiments, the targeting moiety comprising the formula T-$S_1$ that may also be given by the formula T-$L_3$-$X_1$, may also be given by the formula T-$L_3$-ECD-$T_M$-ICD, wherein T is a target binding domain, $L_3$ is a flexible peptide linker ECD is an extracellular domain, or a fragment thereof, of a cell surface protein, or is absent; $T_M$ is a transmembrane domain of a transmembrane protein; and ICD is an intracellular domain of a protein or a protein that facilitates the incorporation of the targeting moiety into the envelope of the viral particle, or is absent. Therefore, it is to be understood that, in some embodiments, the stalk portion $S_1$ may be given by the formula $L_3$-ECD-$T_M$-ICD.

In some embodiments, the ECD is absent. In some embodiments, the ECD can be any appropriate extracellular domain or fragment thereof. In some embodiments, the ECD is from a different protein as compared to the transmembrane domain. The ECD domain can be the entire ECD domain or a fragment thereof. In some embodiments, the ECD domain is a CD8 or CD28 ECD domain, or a fragment thereof. In some embodiments, the ECD domain is a CD8 ECD domain or fragment thereof. In some embodiments, the CD8 ECD domain comprises the polypeptide of FVPVFLPAKPTTTPAPRPPTPAPTIASQPLSLRPEACRPAAGGAVHTRGLDFACD (SEQ ID NO: 59). In some embodiments, the CD8 ECD domain consists or consists essentially of the polypeptide of FVPVFLPAKPTTTPAPRPPTPAPTIASQPLSLRPEACRPAAGGAVHTRGLDFACD (SEQ ID NO: 59). In some embodiments, the ECD domain comprises a polypeptide that is 25-45 amino acids in length. In some embodiments, the ECD comprises a polypeptide that is at least, or is about, 80, 85, 90, 91, 92, 93, 94, 95, 96, 97, 98, or 99% identical to a peptide of FVPVFLPAKPTTTPAPRPPTPAPTIASQPLSLRPEACRPAAGGAVHTRGLDFACD (SEQ ID NO: 59). In some embodiments, the ECD domain is a CD28 ECD domain or fragment thereof. In some embodiments, the CD28 ECD domain comprises the polypeptide of KIEVMYPPPYLDNEKSNGTIIHVKGKHLCPSPLFPGPSKP (SEQ ID NO: 60). In some embodiments, the CD28 ECD domain consists or consists essentially of the polypeptide of KIEVMYPPPYLDNEKSNGTIIHVKGKHLCPSPLFPGPSKP (SEQ ID NO: 60). In some embodiments, the ECD domain comprises a polypeptide that is 25-45 amino acids in length. In some embodiments, the ECD comprises a polypeptide that is at least, or is about, 80, 85, 90, 91, 92, 93, 94, 95, 96, 97, 98, or 99% identical to a peptide of KIEVMYPPPYLDNEKSNGTIIHVKGKHLCPSPLFPGPSKP (SEQ ID NO: 60).

In some embodiments, the $T_M$ can be any appropriate transmembrane domain or fragment thereof. In some embodiments, the $T_M$ domain is a CD8 or CD28 $T_M$ domain or a fragment thereof. In some embodiments, the $T_M$ domain is a CD8 $T_M$ domain or fragment thereof. In some embodiments, the CD8 $T_M$ domain comprises the polypeptide of IYIWAPLAGTCGVLLLSLVITLYCNHRN (SEQ ID NO: 61). In some embodiments, the CD8 $T_M$ domain consists or consists essentially of the polypeptide of IYIWAPLAGTCGVLLLSLVITLYCNHRN (SEQ ID NO: 61). In some embodiments, the $T_M$ comprises a polypeptide that is at least, or is about, 80, 85, 90, 91, 92, 93, 94, 95, 96, 97, 98, or 99% identical to a peptide of IYIWAPLAGTCGVLLLSLVITLYCNHRN (SEQ ID NO: 61). In some embodiments, the $T_M$ domain is a CD28 $T_M$ domain or fragment thereof. In some embodiments, the CD28 $T_M$ domain comprises the polypeptide of FWVLVVVGGVLACYSLLVTVAFIIFWV (SEQ ID NO: 62). In some embodiments, the CD28 $T_M$ domain consists or consists essentially of the polypeptide of FWVLVVVGGVLACYSLLVTVAFIIFWV (SEQ ID NO: 62). In some embodiments, the $T_M$ comprises a polypeptide that is at least, or is about, 80, 85, 90, 91, 92, 93, 94, 95, 96, 97, 98, or 99% identical to a peptide of FWVLVVVGGVLACYSLLVTVAFIIFWV (SEQ ID NO: 62).

In some embodiments, the $T_M$ domain is from the same protein as the ECD. In some embodiments, the $T_M$ domain is from a different protein as the ECD. In some embodiments, the $T_M$ domain is a CD8, or CD28 $T_M$ domain or a fragment thereof and the ECD domain is a CD8, or CD28 ECD domain or fragment thereof. In some embodiments, the $T_M$ domain is at least, or is about, 80, 85, 90, 91, 92, 93, 94, 95, 96, 97, 98, or 99% identical to a peptide of IYIWAPLAGTCGVLLLSLVITLYCNHRN (SEQ ID NO: 61) and the ECD domain is at least, or is about, 80, 85, 90, 91, 92, 93, 94, 95, 96, 97, 98, or 99% identical to a peptide of FVPVFLPAKPTTTPAPRPPTPAPTIASQPLSLRPEACRPAAGGAVHTRGLDFACD (SEQ ID NO: 59). In some embodiments, the $T_M$ domain is at least, or is about, 80, 85, 90, 91, 92, 93, 94, 95, 96, 97, 98, or 99% identical to a peptide of IYIWAPLAGTCGVLLLSLVITLYCNHRN (SEQ ID NO: 61) and the ECD domain is at least, or is about, 80, 85, 90, 91, 92, 93, 94, 95, 96, 97, 98, or 99% identical to a peptide of KIEVMYPPPYLDNEKSNGTIIHVKGKHLCPSPLFPGPSKP (SEQ ID NO: 60). In some embodiments, the $T_M$ domain is at least, or is about, 80, 85, 90, 91, 92, 93, 94, 95, 96, 97, 98, or 99% identical to a peptide of FWVLVVVGGVLACYSLLVTVAFIIFWV (SEQ ID NO: 62) and the ECD domain is at least, or is about, 80, 85, 90, 91, 92, 93, 94, 95, 96, 97, 98, or 99% identical to a peptide of FVPVFLPAKPTTTPAPRPPTPAPTIASQPLSLRPEACRPAAGGAVHTRGLDFACD (SEQ ID NO: 59). In some embodiments, the $T_M$ domain is at least, or is about, 80, 85, 90, 91, 92, 93, 94, 95, 96, 97, 98, or 99% identical to a peptide of FWVLVVVGGVLACYSLLVTVAFIIFWV (SEQ ID NO: 62) and the ECD domain is at least, or is about, 80, 85, 90, 91, 92, 93, 94, 95, 96, 97, 98, or 99% identical to a peptide of KIEVMYPPPYLDNEKSNGTIIHVKGKHLCPSPLFPGPSKP (SEQ ID NO: 60).

In some embodiments, the transmembrane domain is linked to an intracellular domain (ICD) of a cellular transmembrane protein, or a fragment thereof. In some embodiments, the ICD is absent. In some embodiments, the ICD is from the same or different protein as the TM domain. In some embodiments, the ICD comprises an Env incorporation motif. An Env incorporation motif is a molecule, e.g., polypeptide, that can help to facilitate the incorporation of a protein into the envelope of the virus. A non-limiting example of an Env incorporation motif is a polypeptide comprising the amino acid sequence of NRVRQGYS (SEQ ID NO: 63). This is a non-limiting example and other peptide sequences can be used, such as, but not limited to, GGTETSQVAPA (SEQ ID NO: 64). In some embodiments, the Env incorporation motif comprises an amino acid sequence of SEQ ID NO: 63, SEQ ID NO: 64, or a combination thereof. In some embodiments, the Env incorporation motif comprises an amino acid sequence of SEQ ID NO: 63. In some embodiments, the Env incorporation motif comprises an amino acid sequence of SEQ ID NO: 64.

In some embodiments, the target binding domain "T" is any polypeptide or polynucleotide that may be used to bind to a desired target. In some embodiments, T is any polypeptide, polynucleotide, or fragment thereof that binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of lmprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRC5D); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4) bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIV1 envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; IL13Ra2; IL1 1Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-11Ra); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis (Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Gly cation Endproducts (RAGE-1); Receptor tyrosine kinase-like orphan receptor 1 (ROR1); Receptor tyrosine-protein kinase ERBB2 or Her-22/neu; Renal ubiquitous 1 (RU1); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAP1; Survivin; Synovial sarcoma X breakpoint 2 (SSX2); TCR Gamma Alternate Reading Frame Protein (TARP); TCR-beta-1 chain; TCR-beta2 chain; TCR-delta chain; TCR-gamma chain; TCRgamma-delta; Telomerase; TGFbetaR2: The antigen recognized by TNT antibody; Thyroid stimulating hormone receptor (TSHR); Timl-/HVCR1; Tissue Factor 1 (TF1); Tn ag; Tn antigen ((Tn Ag) or (GalNAcaSer/Ther)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1). In some embodiments, the targeting moiety "T" binds to CD7. In some embodiments, the target binding domain "T" binds to CD8. In some embodiments, the target binding domain "T" is an antibody. It is to be understood that in the context of the present disclosure "antibody" not only refers to a "complete" antibody comprising two identical heavy chains, two identical light chains, and two antigen binding fragments, but also refers to antibodies of any isotype, fragments of antibodies including, but not limited to, Fab, Fv, scFv, and Fd fragments, chimeric antibodies, humanized antibodies, single chain antibodies (scAb), single domain antibodies (dAb), single domain heavy chain antibodies, single domain light chain antibodies, bi-specific antibodies, multi-specific antibodies, and fusion proteins comprising an antigen-binding portion of an antibody and a non-antibody protein. In some embodiments, the antibody is selected from the group comprising a scFv, Fab, VHH, single domain antibody, and the like. In some embodiments, the antibody is a scFv. In some embodiments the antibody is a Fab. In some embodiments, the antibody is a VHH. In some embodiments, the antibody is a single domain antibody.

In some embodiments, the polypeptide represented by the formula of T-$S_1$ can form a dimer when present on the surface of the viral particle. The dimer can, for example, can be formed by interaction between the stalk portions of the polypeptide molecules. For example, when the stalk portion comprises the Fe domain or a variant Fe domain as provided for herein, the Fe domains of the polypeptide molecules will interact with one another on the surface of the virus and form a dimer. Without being bound to any particular theory, the dimer can also, in some embodiments, improve specificity due to increased avidity to the target protein through the target binding domain (T) compared to a polypeptide that does not or cannot form a dimer. Accordingly, in some embodiments, the viral particle comprises a dimer, which can be a homodimer or heterodimer, comprising two polypeptides having the formula of T-$S_1$. In some embodiments, the homodimer refers to two polypeptides having the formula of T-$S_1$ having the exact same amino acid sequence. A dimer can also be formed by two polypeptides having either different targeting binding domains (T) or two different $S_1$ portions, such as two different Fe domains, including variant Fe domains. A dimer formed by two polypeptides having either different targeting binding domains or different Fe domains can be referred to as a heterodimer. In some embodiments, the heterodimer is formed by a first polypeptide having the formula of T-$S_1$ and a second polypeptide having the formula of T-$S_1$, wherein the first polypeptide has a first targeting binding domain and a first $S_1$ polypeptide and the second polypeptide has a second targeting binding domain and a second $S_1$ polypeptide. In some embodiments, the first and second targeting binding domain are the same. In some embodiments, the first and second targeting binding domains are different. In some embodiments, the first and second targeting binding domains bind to the same target, but at different epitopes. In some embodiments, the first and second $S_1$ polypeptides are the same. In some embodiments, the first and second $S_1$ polypeptides are different. In some embodiments, the first and second $S_1$ polypeptides are the same, except that they have different Fe domains. The Fe domains that can be used herein can also, in some embodiments, be engineered to not form a dimer.

In some embodiments, the viral particles provided for herein are pseudotyped viral particles. In some embodiments, the viral particles are pseudotyped using viral glycoproteins of viruses of the Paramyxoviridae family. In some embodiments, the pseudotyped viral-like particles are pseudotyped using viral glycoproteins of morbillivirus, such as Measles virus. In some embodiments, the pseudotyped viral-like particles are pseudotyped using viral glycoproteins of the Measles virus. In some embodiments, the pseudotyped viral-like particles are pseudotyped using viral glycoproteins of henipavirus, such as Nipah virus, Cedar virus, or Hendra virus. In some embodiments, the pseudotyped viral-like particles are pseudotyped using viral glycoproteins of the Nipah virus. In some embodiments, a polypeptide or an antibody as provided herein is linked via a linker to an envelope glycoprotein G or H of a virus of the Paramyxoviridae family. In some embodiments, the virus of the Paramyxoviridae family is a morbillivirus, such as Measles virus. In some embodiments, the virus of the Paramyxoviridae family is a henipavirus, such as Nipah virus, Cedar virus, or Hendra virus.

As provided for herein, the viruses can be pseudotyped with a VSV-G protein, either wild-type or mutant of the same. Without being bound to any particular theory, the mutant VSV-G protein that can be used to pseudotype a virus (e.g. lentivirus) comprising a mutation at position 182 can be used to pseudotype a virus and transduce a cell when the virus comprises a targeting moiety. This mutation inhibits or reduces the VSV-G affinity to its natural co-receptor, the LDL-R. The mutant VSV-G proteins as provided can be used, in some embodiments, to transduce a target cell and deliver a heterologous molecule to the targeted cells.

In some embodiments, a VSV-G protein is provided that comprises a mutation at position 198 as compared to SEQ ID NO: 1 or at position 182 as compared to SEQ ID NO: 2. SEQ ID NO: 1 is the full length protein and SEQ ID NO: 2 is the ectodomain of the VSV-G protein. The 16-mer signal peptide of MKCLLYLAFLFIGVNC (SEQ ID NO: 65) as shown at the N-terminus of SEQ ID NO: 1 is cleaved leaving a protein of SEQ ID NO: 2. Thus, although a mutation may be referred to in the context of SEQ ID NO: 2, it should be understood to also be made in the context of SEQ ID NO: 1, which contains the leader sequence, and thus would be a position number that is 16 more than the position recited for SEQ ID NO: 2. In some embodiments, the mutation inhibits or decreases the binding of the VSV-G protein to the LDL receptor (LDL-R). In some embodiments, the mutation is a I182D mutation as compared to SEQ ID NO: 2. In some embodiments, the mutation is a I182E mutation as compared to SEQ ID NO: 2.

In some embodiments, a VSV-G protein is provided that comprises a mutation at position 198 as compared to SEQ ID NO: 10 or at position 182 as compared to SEQ ID NO: 11. SEQ ID NO: 10 is the full length protein and SEQ ID NO: 11 is the ectodomain of the VSV-G protein. The 16-mer signal peptide of MLSYLIFALVVSPILG (SEQ ID NO: 66) as shown at the N-terminus of SEQ ID NO: 10 is cleaved leaving a protein of SEQ ID NO: 11. Thus, although a mutation may be referred to in the context of SEQ ID NO: 11, it should be understood to also be made in the context of SEQ ID NO: 10, which contains the leader sequence, and thus would be a position number that is 16 more than the position recited for SEQ ID NO: 11. In some embodiments, the mutation inhibits or decreases the binding of the VSV-G protein to the LDL receptor (LDL-R). In some embodiments, the mutation is a T182D mutation as compared to SEQ ID NO: 11. In some embodiments, the mutation is a T182E mutation as compared to SEQ ID NO: 11.

In some embodiments, a VSV-G protein is provided that comprises a mutation at position 198 as compared to SEQ ID NO: 12 or at position 182 as compared to SEQ ID NO: 13. SEQ ID NO: 12 is the full length protein and SEQ ID NO: 13 is the ectodomain of the VSV-G protein. The 16-mer signal peptide of MLRLFLFCFLALGAHS (SEQ ID NO: 67) as shown at the N-terminus of SEQ ID NO: 12 is cleaved leaving a protein of SEQ ID NO: 13. Thus, although a mutation may be referred to in the context of SEQ ID NO: 13, it should be understood to also be made in the context of SEQ ID NO: 12, which contains the leader sequence, and thus would be a position number that is 16 more than the position recited for SEQ ID NO: 13. In some embodiments, the mutation inhibits or decreases the binding of the VSV-G protein to the LDL receptor (LDL-R). In some embodiments, the mutation is a A182D mutation as compared to SEQ ID NO: 13. In some embodiments, the mutation is a A182E mutation as compared to SEQ ID NO: 13.

In some embodiments, a VSV-G protein is provided that comprises a mutation at position 203 as compared to SEQ ID NO: 14 or at position 182 as compared to SEQ ID NO: 15. SEQ ID NO: 14 is the full length protein and SEQ ID NO: 15 is the ectodomain of the VSV-G protein. The 21-mer signal peptide of MKMKMVIAGLILCIGILPAIG (SEQ ID NO: 68) as shown at the N-terminus of SEQ ID NO: 14 is cleaved leaving a protein of SEQ ID NO: 15. Thus, although a mutation may be referred to in the context of SEQ ID NO: 15, it should be understood to also be made in the context of SEQ ID NO: 14, which contains the leader sequence, and thus would be a position number that is 21 more than the position recited for SEQ ID NO: 15. In some embodiments, the mutation inhibits or decreases the binding of the VSV-G protein to the LDL receptor (LDL-R). In some embodiments, the mutation is a V182D mutation as compared to SEQ ID NO: 15. In some embodiments, the mutation is a V182E mutation as compared to SEQ ID NO: 15.

In some embodiments, a VSV-G protein is provided that comprises a mutation at position 199 as compared to SEQ ID NO: 16 or at position 182 as compared to SEQ ID NO: 17. SEQ ID NO: 16 is the full length protein and SEQ ID NO: 17 is the ectodomain of the VSV-G protein. The 17-mer signal peptide of MTPAFILCMLLAGSSWA (SEQ ID NO: 69) as shown at the N-terminus of SEQ ID NO: 16 is cleaved leaving a protein of SEQ ID NO: 17. Thus, although a mutation may be referred to in the context of SEQ ID NO: 17, it should be understood to also be made in the context of SEQ ID NO: 16, which contains the leader sequence, and thus would be a position number that is 17 more than the position recited for SEQ ID NO: 17. In some embodiments, the mutation inhibits or decreases the binding of the VSV-G protein to the LDL receptor (LDL-R). In some embodiments, the mutation is a V182D mutation as compared to SEQ ID NO: 17. In some embodiments, the mutation is a V182E mutation as compared to SEQ ID NO: 17.

In some embodiments, a VSV-G protein is provided that comprises a mutation at position 199 as compared to SEQ ID NO: 18 or at position 182 as compared to SEQ ID NO: 19. SEQ ID NO: 18 is the full length protein and SEQ ID NO: 19 is the ectodomain of the VSV-G protein. The 17-mer signal peptide of MNFLLLTFIVLPLCSHA (SEQ ID NO: 70) as shown at the N-terminus of SEQ ID NO: 18 is cleaved leaving a protein of SEQ ID NO: 19. Thus, although a mutation may be referred to in the context of SEQ ID NO: 19, it should be understood to also be made in the context of SEQ ID NO: 18, which contains the leader sequence, and thus would be a position number that is 17 more than the position recited for SEQ ID NO: 19. In some embodiments, the mutation inhibits or decreases the binding of the VSV-G protein to the LDL receptor (LDL-R). In some embodiments, the mutation is a V182D mutation as compared to SEQ ID NO: 19. In some embodiments, the mutation is a V182E mutation as compared to SEQ ID NO: 19.

In some embodiments, a VSV-G protein is provided that comprises a mutation at position 199 as compared to SEQ ID NO: 20 or at position 182 as compared to SEQ ID NO: 21. SEQ ID NO: 20 is the full length protein and SEQ ID NO: 21 is the ectodomain of the VSV-G protein. The 17-mer signal peptide of MLVLYLLLSLLALGAQC (SEQ ID NO: 71) as shown at the N-terminus of SEQ ID NO: 20 is cleaved leaving a protein of SEQ ID NO: 21. Thus, although a mutation may be referred to in the context of SEQ ID NO: 21, it should be understood to also be made in the context of SEQ ID NO: 20, which contains the leader sequence, and thus would be a position number that is 17 more than the position recited for SEQ ID NO: 21. In some embodiments, the mutation inhibits or decreases the binding of the VSV-G protein to the LDL receptor (LDL-R). In some embodiments, the mutation is a I182D mutation as compared to SEQ ID NO: 21. In some embodiments, the mutation is a I182E mutation as compared to SEQ ID NO: 21.

As used herein, when a polypeptide is said to have a mutation as compared to a reference sequence, such comparison is based on an alignment such as using BlastP or ClustalW or ClutalOmega alignment software using default parameters. For example, position 182 can be found in SEQ ID NO: 2 and also as compared to the other strains as illustrated in FIG. 3. FIG. 3 illustrates a clustal alignment of the wild-type sequences of the ectodomains of the various strains of the VSV-G protein. The residue that is bolded and underlined are the residues that align to position 182 of SEQ ID NO: 2 of the various strains. SEQ ID NO: 2 refers to ectodomain of the VSV-G protein of the Indiana strain. SEQ ID NO: 11 refers to ectodomain of the VSV-G protein of the New Jersey strain. SEQ ID NO: 13 refers to ectodomain of the VSV-G protein of the Marraba strain. SEQ ID NO: 15 refers to ectodomain of the VSV-G protein of the Carajas strain. SEQ ID NO: 17 refers to ectodomain of the VSV-G protein of the Alagoa strain. SEQ ID NO: 19 refers to ectodomain of the VSV-G protein of the Cocal strain. SEQ ID NO: 21 refers to ectodomain of the VSV-G protein of the Morreton strain. Accordingly, the residue that aligns to residues 182 as compared to SEQ ID NO: 2 can also be mutated as provided for herein.

In some embodiments, the mutation at position 182 as compared to SEQ ID NO: 2 is not an alanine. In some embodiments, the mutation at position 182 as compared to SEQ ID NO: 2 is not a valine.

In some embodiments, the mutation at position 182 as compared to SEQ ID NO: 2 is I182S, I182H, I182T, I182Q, or I182N. In some embodiments, the mutation at position 182 as compared to SEQ ID NO: 11 is T182S, T182H, T182Q, or T182N. In some embodiments, the mutation at position 182 as compared to SEQ ID NO: 13 is A182S, A182H, A182T, A182Q, or A182N. In some embodiments, the mutation at position 182 as compared to SEQ ID NO: 15 is V182S, V182H, V182T, V182Q, or V182N. In some embodiments, the mutation at position 182 as compared to SEQ ID NO: 17 is V182S, V182H, V182T, V182Q, or V182N. In some embodiments, the mutation at position 182 as compared to SEQ ID NO: 19 is V182S, V182H, V182T, V182Q, or V182N. In some embodiments, the mutation at position 182 as compared to SEQ ID NO: 21 is I182S, I182H, I182T, I182Q, or I182N. In some embodiments, the mutation at position 182 is not a hydrophobic residue. In some embodiments, the mutation at position 182 is a charged residue. In some embodiments, the mutation at position 182 is a negatively charged residue.

Although, the mutations may be described in reference to SEQ ID NO: 1 or SEQ ID NO: 2, which is the VSV-G protein from the Indiana strain, the mutation can also be used in other strains of the VSV-G protein. For example, the mutation can be made in the New Jersey Strain of VSV-G, the Marraba strain of VSV-G, the Carajas strain of VSV-G, the Alagoa strain of VSV-G, the Cocal strain of VSV-G, or the Morreton strain of VSV-G. In some embodiments, the sequences of each are as provided herein. Examples of these can be found, for example in U.S. Patent Application Publication No. 20200216502, which is hereby incorporated by reference. For example, the wild-type full length or ectodomain of the New Jersey Strain of VSV-G are SEQ ID NO: 10 and SEQ ID NO: 11, respectively, the wild-type full length or ectodomain of Marraba strain of VSV-G are SEQ ID NO: 12 and SEQ ID NO: 13, respectively, the wild-type full length or ectodomain of Carajas strain of VSV-G are SEQ ID NO: 14 and SEQ ID NO: 15, respectively, the wild-type full length or ectodomain of Alagoa strain of VSV-G are SEQ ID NO: 16 and SEQ ID NO: 17, respectively, the wild-type full length or ectodomain of Cocal strain of VSV-G are SEQ ID NO: 18 and SEQ ID NO: 19, respectively, or the wild-type full length or ectodomain of Morreton strain of VSV-G are SEQ ID NO: 20 and SEQ ID NO: 21, respectively.

A VSV-G protein comprising a mutation at position 182 as compared to SEQ ID NO: 2 can also comprise other mutations, such as those described in U.S. Patent Application Publication No. 20200216502, which is hereby incorporated by reference in its entirety. For example, the VSV-G protein can comprise a mutation at a position that corresponds to positions of 8, 47, 209 and/or 354 of SEQ ID NO: 2.

In some embodiments, the substitution at position 8 is by any amino acid different from the amino acid indicated at that position in the sequence SEQ ID NO: 2, except Y. In some embodiments, the substitution at position 209 is by any amino acid different from the amino acid indicated at that position in the sequence SEQ ID NO: 2, except H. In some embodiments, the substitution at position 47 is by any amino acid different from the amino acid indicated at that position in the sequence SEQ ID NO: 2, except K or R. In some embodiments, the substitution at position 354 is by any amino acid different from the amino acid indicated at that position in the sequence SEQ ID NO: 2, except K or R.

In some embodiments, the substitution is at position 47 or at position 354, or at both positions 47 and 354 are substituted by A, G, F or Q. In some embodiments, the substitution is A or Q.

In some embodiments, the substitution at position 8 is an alanine, i.e., H8A.

In some embodiments, the substitution at position 47 is Q or N, i.e., K47Q or K47N.

In some embodiments, the protein comprises a mutation (substitution) at position 10. In some embodiments, the substitution/mutation is Q10A, Q10R, or Q10K.

In some embodiments, a protein comprising a mutation at position 182 as compared to SEQ ID NO: 2 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 2 (or SEQ ID NO: 1 if using the full length protein). In some embodiments, the polypeptide comprises a I182D or I182E mutation. In some embodiments, the VSV-G protein comprises a I182S, I182H, I182T, I182Q, or I182N mutation.

In some embodiments, a protein comprising a mutation at position 182 as compared to SEQ ID NO: 11 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 11 (or SEQ ID NO: 10 if using the full length protein). In some embodiments, the polypeptide comprises a T182D or T182E mutation. In some embodiments, the VSV-G protein comprises a T182S, T182H, T182Q, or T182N mutation.

In some embodiments, a protein comprising a mutation at position 182 as compared to SEQ ID NO: 13 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 13 (or SEQ ID NO: 12 if using the full length protein). In some embodiments, the polypeptide comprises a A182D or A182E mutation. In some embodiments, the VSV-G protein comprises a A182S, A182H, A182T, A182Q, or A182N mutation.

In some embodiments, a protein comprising a mutation at position 182 as compared to SEQ ID NO: 15 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 15 (or SEQ ID NO: 14 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 17 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 17 (or SEQ ID NO: 16 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 19 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 19 (or SEQ ID NO: 18 if using the full length protein). In some embodiments, the polypeptide comprises a V182D or V182E mutation. In some embodiments, the VSV-G protein comprises a V182S, V182H, V182T, V182Q, or V182N mutation.

In some embodiments, a protein comprising a mutation at position 182 as compared to SEQ ID NO: 21 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 21 (or SEQ ID NO: 20 if using the full length protein). In some embodiments, the polypeptide comprises a I182D or I182E mutation. In some embodiments, the VSV-G protein comprises a I182S, I182H, I182T, I182Q, or I182N mutation.

Viral Glycoproteins

The mutant VSV-G proteins can be used, for example, to pseudotype a virus, such as, but not limited to a lentivirus. Accordingly, in some embodiments, a viral particle comprising a mutant VSV-G protein as provided herein are provided. In some embodiments, the viral particle comprises a VSV-G protein comprising a mutation at position 198 as compared to SEQ ID NO: 1. In some embodiments, a protein comprising a mutation at position 182 as compared to SEQ ID NO: 2 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 2 (or SEQ ID NO: 1 if using the full length protein). In some embodiments, the polypeptide comprises a I182D or I182E mutation as compared to SEQ ID NO: 2. In some embodiments, the VSV-G protein comprises a I182S, I182H, I182T, I182Q, or I182N mutation.

In some embodiments, the viral particle comprises a VSV-G protein comprising a mutation at position 198 as compared to SEQ ID NO: 10. In some embodiments, a protein comprising a mutation at position 182 as compared to SEQ ID NO: 11 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 11 (or SEQ ID NO: 10 if using the full length protein). In some embodiments, the polypeptide comprises a T182D or T182E mutation as compared to SEQ ID NO: 11. In some embodiments, the VSV-G protein comprises a T182S, T182H, T182Q, or T182N mutation.

In some embodiments, the viral particle comprises a VSV-G protein comprising a mutation at position 198 as compared to SEQ ID NO: 12. In some embodiments, a protein comprising a mutation at position 182 as compared to SEQ ID NO: 13 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 13 (or SEQ ID NO: 12 if using the full length protein). In some embodiments, the polypeptide comprises a A182D or A182E mutation as compared to SEQ ID NO: 13. In some embodiments, the VSV-G protein comprises a A182S, A182H, A182T, A182Q, or A182N mutation.

In some embodiments, the viral particle comprises a VSV-G protein comprising a mutation at position 203 as compared to SEQ ID NO: 14. In some embodiments, a protein comprising a mutation at position 182 as compared to SEQ ID NO: 15 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 15 (or SEQ ID NO: 14 if using the full length protein). In some embodiments, the polypeptide comprises a V182D or V182E mutation as compared to SEQ ID NO: 15. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 16. In some embodiments, a protein comprising a mutation at position 182 as compared to SEQ ID NO: 17 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 17 (or SEQ ID NO: 16 if using the full length protein). In some embodiments, the polypeptide comprises a V182D or V182E mutation as compared to SEQ ID NO: 17. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 18. In some embodiments, a protein comprising a mutation at position 182 as compared to SEQ ID NO: 19 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 19 (or SEQ ID NO: 18 if using the full length protein). In some embodiments, the polypeptide comprises a V182D or V182E mutation as compared to SEQ ID NO: 19. In some embodiments, the VSV-G protein comprises a V182S, V182H, V182T, V182Q, or V182N mutation.

In some embodiments, the viral particle comprises a VSV-G protein comprising a mutation at position 199 as compared to SEQ ID NO: 20. In some embodiments, a protein comprising a mutation at position 182 as compared to SEQ ID NO: 21 comprises a mutation at position 182 and at least, or about, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identical as compared to SEQ ID NO: 21 (or SEQ ID NO: 20 if using the full length protein). In some embodiments, the polypeptide comprises a I182D or I182E mutation as compared to SEQ ID NO: 21. In some embodiments, the VSV-G protein comprises a I182S, I182H, I182T, I182Q, or I182N mutation.

In some embodiments, the VSV-G protein further comprises a mutation at position that corresponds to positions 214 and/or 352 of SEQ ID NO: 2. In some embodiments, the residue that corresponds to position 214 of SEQ ID NO: 2 is T214. In some embodiments, the residue that corresponds to position 352 of SEQ ID NO: is T352. In some embodiments, the VSV-G protein comprises mutation that corresponds to T214N mutation as compared to SEQ ID NO: 2. In some embodiments, the VSV-G protein comprises mutation that corresponds to T352A mutation as compared to SEQ ID NO: 2. In some embodiments, the VSV-G protein comprises a T214N and T352A mutations as compared to SEQ ID NO: 2. These mutations can be combined with any other mutations as provided for herein. In some embodiments, the T214N and/or T352A mutations are combined with the I182E or I182D mutations. In some embodiments, a VSV-G protein comprises an amino acid sequence of SEQ ID NO: 22 and SEQ ID NO: 23, which combines the I182D or I182E, respectively, with the T214N and T352A mutations. The sequences are also illustrated below with the leader sequences, which are removed during protein processing.

```
VSV-G Protein_I196D, T230N and T368A mutations
(with leader sequence and adjusted numbering)
                                                    (SEQ ID NO: 24)
MKCLLYLAFLFIGVNCKFTIVFPHNQKGNWKNVPSNYHYCPSSSDLNWH

NDLIGTALQVKMPKSHKAIQADGWMCHASKWVTTCDFRWYGPKYITHSI

RSFTPSVEQCKESIEQTKQGTWLNPGFPPQSCGYATVTDAEAVIVQVTPH

HVLVDEYTGEWVDSQFINGKCSNYICPTVHNSTTWHSDYKVKGLCDSNL

DSMDITFFSEDGELSSLGKEGTGFRSNYFAYENGGKACKMQYCKHWGVR

LPSGVWFEMADKDLFAAARFPECPEGSSISAPSQTSVDVSLIQDVERILDY

SLCQETWSKIRAGLPISPVDLSYLAPKNPGTGPAFTIINGTLKYFETRYIRV

DIAAPILSRMVGMISGTTAERELWDDWAPYEDVEIGPNGVLRTSSGYKFP

LYMIGHGMLDSDLHLSSKAQVFEHPHIQDAASQLPDDESLFFGDTGLSKN
```

-continued

PIELVEGWFSSWKSSIASFFFIIGLIIGLFLVLRVGIHLCIKLKHTKKRQIYTD

IEMNRLGK

VSV-G Protein_I182D, T214N and T352A mutations
(without leader sequence)

(SEQ ID NO: 22)

KFTIVFPHNQKGNWKNVPSNYHYCPSSSDLNWHNDLIGTALQVKMPKSH

KAIQADGWMCHASKWVTTCDFRWYGPKYITHSIRSFTPSVEQCKESIEQT

KQGTWLNPGFPPQSCGYATVTDAEAVIVQVTPHHVLVDEYTGEWVDSQF

INGKCSNYICPTVHNSTTWHSDYKVKGLCDSNLDSMDITFFSEDGELSSLG

KEGTGFRSNYFAYENGGKACKMQYCKHWGVRLPSGVWFEMADKDLFA

AARFPECPEGSSISAPSQTSVDVSLIQDVERILDYSLCQETWSKIRAGLPISP

VDLSYLAPKNPGTGPAFTIINGTLKYFETRYIRVDIAAPILSRMVGMISGTT

AERELWDDWAPYEDVEIGPNGVLRTSSGYKFPLYMIGHGMLDSDLHLSS

KAQVFEHPHIQDAASQLPDDESLFFGDTGLSKNPIELVEGWESSWKSSIAS

FFFIIGLIIGLFLVLRVGIHLCIKLKHTKKRQIYTDIEMNRLGK

VSV-G Protein with I196E, T230N and T368A mutations
(with leader sequence and adjusted numbering)

(SEQ ID NO: 25)

MKCLLYLAFLFIGVNCKFTIVFPHNQKGNWKNVPSNYHYCPSSSDLNWH

NDLIGTALQVKMPKSHKAIQADGWMCHASKWVTTCDFRWYGPKYITHSI

RSFTPSVEQCKESIEQTKQGTWLNPGFPPQSCGYATVTDAEAVIVQVTPH

HVLVDEYTGEWVDSQFINGKCSNYICPTVHNSTTWHSDYKVKGLCDSNL

ESMDITFFSEDGELSSLGKEGTGFRSNYFAYENGGKACKMQYCKHWGVR

LPSGVWFEMADKDLFAAARFPECPEGSSISAPSQTSVDVSLIQDVERILDY

SLCQETWSKIRAGLPISPVDLSYLAPKNPGTGPAFTIINGTLKYFETRYIRV

DIAAPILSRMVGMISGTTAERELWDDWAPYEDVEIGPNGVLRTSSGYKFP

LYMIGHGMLDSDLHLSSKAQVFEHPHIQDAASQLPDDESLFFGDTGLSKN

PIELVEGWFSSWKSSIASFFFIIGLIIGLFLVLRVGIHLCIKLKHTKKRQIYTD

IEMNRLGK

VSV-G Protein with I182E, T214N and T352A mutations
(without leader sequences)

(SEQ ID NO: 23)

KFTIVFPHNQKGNWKNVPSNYHYCPSSSDLNWHNDLIGTALQVKMPKSH

KAIQADGWMCHASKWVTTCDFRWYGPKYITHSIRSFTPSVEQCKESIEQT

KQGTWLNPGFPPQSCGYATVTDAEAVIVQVTPHHVLVDEYTGEWVDSQF

INGKCSNYICPTVHNSTTWHSDYKVKGLCDSNLESMDITFFSEDGELSSLG

KEGTGFRSNYFAYENGGKACKMQYCKHWGVRLPSGVWFEMADKDLFA

AARFPECPEGSSISAPSQTSVDVSLIQDVERILDYSLCQETWSKIRAGLPISP

VDLSYLAPKNPGTGPAFTIINGTLKYFETRYIRVDIAAPILSRMVGMISGTT

AERELWDDWAPYEDVEIGPNGVLRTSSGYKFPLYMIGHGMLDSDLHLSS

KAQVFEHPHIQDAASQLPDDESLFFGDTGLSKNPIELVEGWFSSWKSSIAS

FFFIIGLIIGLFLVLRVGIHLCIKLKHTKKRQIYTDIEMNRLGK

The other strains of the VSV-G protein as described herein can also comprises the mutations that correspond to T214N and/or T352A in SEQ ID NO: 2 and as illustrated in SEQ ID NO: 22 and SEQ ID NO: 23.

In some embodiments, the composition comprises a mutation as described in Hwang et al., Gene Ther 2013 August; 20(8):807-15. (Epub 2013 Jan. 31), which is hereby incorporated by reference in its entirety. For example, the mutations can be, at positions 230, 368, 66, and/or 162 that corresponds to SEQ ID NO: 1. The positions will be 16 positions less as compared to SEQ ID NO: 2, when the leader sequence is removed. In some embodiments, the mutations at those positions are, for example, T230N, T368A, K66T, S162T, or any combination thereof. In some embodiments, the VSV-G protein comprises a T230N and a T368A mutation. In some embodiments, the VSV-G polypeptide comprises a K66T, S162T, T230N, and a T368A. These positions are those that correspond to the positions in the full length protein (SEQ ID NO: 1). In some embodiments, the VSV-G protein comprises T230N mutation, a T368A mutation, a K66T mutation, a S162T mutation, or any combination thereof. In some embodiments, the VSV-G protein further comprises one or more mutations in addition to the mutation that corresponds to position 182 of SEQ ID NO: 2, such as those described in U.S. Patent Application Publication No. 20200216502, which is hereby incorporated by reference in its entirety. For example, the VSV-G protein can further comprise a mutation at a position that corresponds to positions of 8, 47, 209 and/or 354 of SEQ ID NO: 2.

In some embodiments, the substitution at position 8 is by any amino acid different from the amino acid indicated at that position in the sequence SEQ ID NO: 2, except Y. In some embodiments, the substitution at position 209 is by any amino acid different from the amino acid indicated at that position in the sequence SEQ ID NO: 2, except H. In some embodiments, the substitution at position 47 is by any amino acid different from the amino acid indicated at that position in the sequence SEQ ID NO: 2, except K or R. In some embodiments, the substitution at position 354 is by any amino acid different from the amino acid indicated at that position in the sequence SEQ ID NO: 2, except K or R. In some embodiments, the substitution is at position 47 or at position 354, or at both positions 47 and 354 are substituted by A, G, F or Q. In some embodiments, the substitution is A or Q. In some embodiments, the substitution at position 8 is an alanine, i.e., H8A. In some embodiments, the substitution at position 47 is Q or N, i.e., K47Q or K47N. In some embodiments, the protein comprises a mutation (substitution) at position 10. In some embodiments, the substitution/mutation is Q10A, Q10R, or Q10K.

Additionally, in some embodiments, instead of the VSV-G protein or mutant thereof, the viruses can be pseudotyped with other viral structural proteins.

For example, the viral particle can be pseudotyped with a Spring viremia of carp virus G (SVCV-G) protein and transduce a cell when the virus comprises a targeting moiety. The Spring viremia of carp virus G protein as provided can be used, in some embodiments, to transduce a target cell and deliver a heterologous molecule to the targeted cells. In some embodiments, a Spring viremia of carp virus G protein is provided that comprises SEQ ID NO: 52. SEQ ID NO: 52 is the full length protein and SEQ ID NO: 53 is the ectodomain of the Spring viremia of carp virus G protein that has the N-terminal signal peptide removed. Accordingly, in some embodiments, the protein comprises an amino acid sequence of SEQ ID NO: 53. The Spring viremia of carp virus G protein can be used, for example, to pseudotype a virus, such as, but not limited to a lentivirus. Accordingly, in some embodiments, a viral particle comprising a Spring viremia of carp virus G protein as provided herein are provided. In some embodiments, the viral particle comprises a Spring viremia of carp virus G protein comprising SEQ ID NO: 52 or SEQ ID NO: 53 or sequence that is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identical to a sequence of SEQ ID NO: 52 or SEQ ID NO: 53.

```
The sequence of Spring Viremia of Carp Virus-G
(SEQ ID NO: 52-with leader sequence)
MSIISYIAFLLLIDSNLGIPIFVPSGRNISWQPVIQPFDYQCPIHGNLPNTMGLSATKLTIKSP

SVFSTDKVSGWICHAAEWKTTCDYRWYGPQYITHSIHPISPTIDECRRIIQRIASGTDEDLGFP

PQSCGWASVTTVSNTNYRVVPHSVHLEPYGGHWIDHEFNGGECREKVCEMKGNHSIWITEETVQ

HECAKHIEEVEGIMYGNVPRGDVMYANNFIIDRHHRVYRFGGSCQMKFCNKDGIKFARGDWVEK

TAGTLTTIHDNVPKCVDGTLVSGHRPGLDLIDTVFNLENVVEYTLCEGTKRKINKQEKLTSVDL

SYLAPRIGGFGSVFRVRNGTLERGSTTYIRIEVEGPIVDSLNGTDPRTNASRVFWDDWELDGNI

YQGFNGVYKGKDGKIHIPLNMIESGIIDDELQHAFQADIIPHPHYDDDEIREDDIFFDNTGENG

NPVDAVVEWVSGWGTSLKFFGMTLVALILIFLLIRCCVACTYLMKRSKRPATESHEMRSLV

The sequence of Spring Viremia of Carp Virus-G
(SEQ ID NO: 53-without leader sequence):
IPIFVPSGRNISWQPVIQPFDYQCPIHGNLPNTMGLSATKLTIKSPSVFSTDKVSGWICHAAEW

KTTCDYRWYGPQYITHSIHPISPTIDECRRIIQRIASGTDEDLGFPPQSCGWASVTTVSNTNYR

VVPHSVHLEPYGGHWIDHEFNGGECREKVCEMKGNHSIWITEETVQHECAKHIEEVEGIMYGNV

PRGDVMYANNFIIDRHHRVYRFGGSCQMKFCNKDGIKFARGDWVEKTAGILTTIHDNVPKCVDG

TLVSGHRPGLDLIDTVFNLENVVEYTLCEGTKRKINKQEKLTSVDLSYLAPRIGGFGSVFRVRN
```

-continued

```
GTLERGSTTYIRIEVEGPIVDSLNGTDPRTNASRVFWDDWELDGNIYQGFNGVYKGKDGKIHIP

LNMIESGIIDDELQHAFQADIIPHPHYDDDEIREDDIFFDNTGENGNPVDAVVEWVSGWGTSLK

FFGMTLVALILIFLLIRCCVACTYLMKRSKRPATESHEMRSLV
```

Targeting Moieties

In some embodiments, the viral particle comprises a targeting moiety having the formula T-$S_1$, wherein T is a target binding domain and $S_1$ is a stalk portion. The targeting moiety can be used to target the viral particle comprising the mutant VSV-G protein or the SVCV-G protein to a cell that expresses the target to which the targeting moiety binds to. In some embodiments, the target binding domain is an antibody, a scFv antibody, an antigen binding domain, an ankyrin repeat (e.g., DARPIN), a VHH domain antibody, a nanobody, single domain antibody, a FN3 domain, or any combination thereof. The target binding domain can be attached to the viral surface through a variant Fc protein (e.g. $L_1$-Fc-$L_2$-$X_1$) as provided for herein or through a flexible polypeptide (e.g., $L_3$-$X_1$) as provided for herein. In some embodiments, the targeting moiety is attached (fused or linked) an envelope glycoprotein G or H of a virus of the Paramyxoviridae family, such as a morbillivirus, such as Measles virus, or a henipavirus, such as Nipah virus, Cedar virus, or Hendra virus. In some embodiments, the targeting moiety can be attached (fused or linked) to a glycoprotein of a virus of the Rhabdoviridae family, such as a vesicular stomatitis New Jersey virus, a vesicular stomatitis Indiana virus, a vesicular stomatitis Alagoas virus, a vesicular stomatitis Maraba virus, a vesicular stomatitis Carajas virus, Parainfluenza virus, *Spodoptera frugiperda* rhabdovirus isolate Sf G, *Drosophila obscura* sigmavirus 10A, Wuhan insect virus 7, Perch virus, or Spring viremia of carp virus. In some embodiments, the VSV protein is the mutated proteins, such as those provided for herein. In some embodiments, the targeting moiety is attached to a glycoprotein of a virus of the Filoviridae family, such as Ebola virus or a glycoprotein of a virus of the Arenaviridae family, such as Machupo virus.

In some embodiments, the target binding domain is a scFv. In some embodiments, the target binding domain is a single domain antibody. In some embodiments, the target binding domain is a VHH.

In some embodiments, the targeting moiety binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of lmprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (FRa or FR1); Folate receptor beta (FRb); Follicle stimulating hormone receptor (FSHR); Fos-related antigen 1; Fucosyl-GM1; G protein coupled receptor class C group 5 member D (GPRC5D); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4) bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIV1 envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVl-Tax; Human papilloma virus E6 (HPV E6); Human papilloma virus E7 (HPV E7); Human Telomerase reverse transcriptase (hTERT); IgE; IL13Ra2; IL1 1Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-11Ra); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1;

O-acetyl-GD2 ganglioside (OAcGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Gly cation Endproducts (RAGE-1); Receptor tyrosine kinase-like orphan receptor 1 (ROR1); Receptor tyrosine-protein kinase ERBB2 or Her-22/neu; Renal ubiquitous 1 (RU1); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAP1; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1). In some embodiments, the targeting moiety binds to CD7. In some embodiments, the targeting moiety binds to CD8.

In some embodiments, the targeting moiety binds to a target that is present on a cell, such as an immune cell. In some embodiments, the cell is an immune cell, such as, but not limited to, T cell, B cell; NK cell, dendritic cell, neutrophils, macrophages, a cancer cell; or, for example, CD3+ T cell; CD4+ T cell; CD7+ T cell, CD8+ T cell; CD19+B cell; CD19+ cancer cell; CD20+ B cell; CD20+ cancer cell; CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte. In some embodiments, the cell is a T cell. In some embodiments, the cell is a B cell. In some embodiments, the cell is a CD7+ T cell and/or CD8+ T cell.

CD7 Binding Polypeptides

In some embodiments, the targeting moiety (e.g. polypeptide) binds to CD7.

In some embodiments, the polypeptide that binds to CD7 is an antibody which binds to non-human primate CD7. In some embodiments, the polypeptide that binds to CD7 is an antibody which binds to human CD7. The sequence of human CD7 (UniProtKB P09564) is as follows (SEQ ID NO: 29):

```
                                        (SEQ ID NO: 29)
MAGPPRLLLLPLLLALARGLPGALAAQEVQQSPHCTTVPVGASVNITCST

SGGLRGIYLRQLGPQPQDIIYYEDGVVPTTDRRFRGRIDFSGSQDNLTIT

MHRLQLSDTGTYTCQAITEVNVYGSGTLVLVTEEQSQGWHRCSDAPPRAS

ALPAPPTGSALPDPQTASALPDPPAASALPAALAVISFLLGLGLGVACVL

ARTQIKKLCSWRDKNSAACVVYEDMSHSRCNTLSSPNQYQ.
```

In some embodiments, the CD7 that the polypeptide binds to is expressed on the surface of a cell. In some embodiments, the cell is an immune cell. In some embodiments, the immune cell is a CD7+ T cell, CD4+ T cell, CD8+ T cell, NK cell, alpha-beta T cell, gamma-delta T cell, lymphoid progenitor cell, hematopoietic stem cell, myeloid cell, monocyte, macrophage, central memory T cell, effector memory T cell, stem-cell like memory T cells, naïve T cell, activated T cell, regulatory T cell (TReg), terminally differentiated effector memory T cell (TEMRA), resident memory T cell (TRM) or a T-cellCD8+CCR7+.

In some embodiments, the antibody comprises a Fc region. The Fc region can be linked to the heavy or light chain of the antibody. In some embodiments, the Fc region is an IgG Fc. In some embodiments, the IgG is selected from IgG1, IgG2, IgG3, or IgG4. In some embodiments, the IgG fc is IgG1 Fc. In some embodiments, the antibody comprises an Fc constant region as set forth herein, such as SEQ ID NO: 26, 27, or 28 or a mutant thereof as provided for herein.

In some embodiments, polypeptides (e.g. CD7-binding polypeptide) are provided herein. In some embodiments, antibodies (e.g. an anti-CD7 antibody) are provided herein. In some embodiments, the antibody is a recombinant antibody that binds to CD7. In some embodiments, the CD7 protein is a human CD7 protein. In some embodiments, the CD7 protein is a non-human CD7 protein (e.g., mouse, rat, pig, dog, non-human primate). As used herein, the term "recombinant antibody" refers to an antibody that is not naturally occurring. In some embodiments, the term "recombinant antibody" refers to an antibody that is not isolated from a human subject.

In some embodiments, an antibody, or antigen binding fragment thereof is provided, wherein the antibody or antibody fragment comprises a peptide selected from the following table, which illustrate the CDRs based on Kabat numbering.

| Kabat CDRs | | | | | | |
|---|---|---|---|---|---|---|
| Ab ID No | HCDR1 | HCDR2 | HCDR3 | LCDR1 | LCDR2 | LCDR3 |
| CD7AB1 | GYPFTSY (SEQ | DPNSGD (SEQ ID | SPYYSNDNSMDY (SEQ ID | RASQSIGTSIH (SEQ | YASESIS (SEQ ID NO: 34) | QQSNSWPTT (SEQ ID |

-continued

| Kabat CDRs | | | | | | |
|---|---|---|---|---|---|---|
| Ab ID No | HCDR1 | HCDR2 | HCDR3 | LCDR1 | LCDR2 | LCDR3 |
| | ID NO: 30) | NO: 31) | NO: 32) | ID NO: 33) | | NO: 35) |

In some embodiments, a polypeptide, an antibody, or antibody binding fragment thereof, comprises a heavy or light chain CDR as provided in the tables above. In some embodiments, a polypeptide, an antibody, or antibody binding fragment thereof, comprises a heavy or light chain CDR as provided in the tables above and binds to non-human primate CD7. In some embodiments, a polypeptide, an antibody, or antibody binding fragment thereof, comprises a heavy or light chain CDR as provided in the tables above and binds to human CD7. In some embodiments, a polypeptide, an antibody, or antibody binding fragment thereof, comprises a light chain CDR having a sequence selected from SEQ ID NO: 33-35. In some embodiments, a polypeptide, an antibody, or antibody binding fragment thereof, comprises a light chain CDR having a sequence of SEQ ID NO: 33. In some embodiments, a polypeptide, an antibody, or antibody binding fragment thereof, comprises a light chain CDR having a sequence of SEQ ID NO: 34. In some embodiments, a polypeptide, an antibody, or antibody binding fragment thereof, comprises a light chain CDR having a sequence of SEQ ID NO: 35. In some embodiments, a polypeptide, an antibody, or antibody binding fragment thereof, comprises a heavy chain CDR having a sequence selected from SEQ ID NO: 30-32. In some embodiments, a polypeptide, an antibody, or antibody binding fragment thereof, comprises a heavy chain CDR having a sequence of SEQ ID NO: 30. In some embodiments, a polypeptide, an antibody, or antibody binding fragment thereof, comprises a heavy chain CDR having a sequence of SEQ ID NO: 31. In some embodiments, a polypeptide, an antibody, or antibody binding fragment thereof, comprises a heavy chain CDR having a sequence of SEQ ID NO: 32. The CDRs referenced in the embodiments throughout the present specification can be interchanged with the CDRs that are characterized by different formats, such as Chothia and IMGT.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 33, the LCDR2 has a sequence of SEQ ID NO: 34, and the LCDR3 has a sequence of SEQ ID NO: 35.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 30, the HCDR2 has a sequence of SEQ ID NO: 31, and the HCDR3 has a sequence of SEQ ID NO: 32.

In some embodiments, a polypeptide, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences.

The different CDR motifs can be combined in any combination including those not depicted in the table above. For example, the following embodiments are provided as non-limiting examples of such combinations.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 33; the light chain CDR2 has the amino acid sequence of SEQ ID NO: 34; and the light chain CDR3 sequence has the amino acid sequence of SEQ ID NO: 35; and (ii) a heavy chain variable region comprising heavy chain CDR1, CDR2, and CDR3 sequences, wherein the heavy chain CDR1 sequence has the amino acid sequence of SEQ ID NO: 30; the heavy chain CDR2 sequence has the amino acid sequence of SEQ ID NO: 31; and the heavy chain CDR3 sequence has the amino acid sequence of SEQ ID NO: 32; or variants of any of the foregoing.

Although the preceding paragraphs may make reference to CDRs under the Kabat system the equivalent CDR sequences can be used from the IMGT and CHOTHIA designations.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other heavy chain CDR1 sequences. In some embodiments, the heavy chain variable region CDR2 is replaced with any of the other heavy chain CDR2 sequences. In some embodiments, the heavy chain variable region CDR3 is replaced with any of the other heavy chain CDR3 sequences.

In some embodiments, the polypeptide comprises a heavy chain variable region peptide having one of the following sequences, or a variant thereof:

| SEQ ID NO: | AB ID NO. | Sequence |
|---|---|---|
| 36 | CD7AB1 | QVQLQQPGAELVKPGASVKLSCKASGYPFTSYWI HWVKQRPGRGLEWLGRIDPNSGDTKYNEKFKNKA TLTVDKSSTTAYMQLSSLTSEDSAVYYCARSPYY SNDNSMDYWGQGTSVTVSS |

In some embodiments, the polypeptide comprises a light chain variable region peptide having one of the following sequences, or a variant thereof:

| SEQ ID NO: | AB ID NO. | Sequence |
|---|---|---|
| 37 | CD7AB1 | DILLTQSPAILSVSPGERVSFSCRASQSIGTSIHWYQ QRINDSPRLLIKYASESISGIPSRFSGSGSGTDFTLS INSVESEDIADYYCQQSNSWPTTFGGGTKLEIKR |

In some embodiments, a polypeptide, an antibody, or antigen binding fragment thereof, comprises a $V_H$ peptide of SEQ ID NO: 36. I*n some embodiments, a polypeptide, an antibody, or antigen binding fragment thereof, comprises a* $V_L$ *peptide of* SEQ ID NO: 37. I*n some embodiments, a polypeptide, an antibody, or antigen binding fragment thereof, comprises a* $V_H$ *peptide and a* $V_L$ *peptide, wherein the wherein the* $V_H$ *peptide comprises a sequence of* SEQ ID NO: 36, *or a variant thereof; and the* $V_L$ *peptide comprises a sequence of* SEQ ID NO: 37, *or a variant thereof.* I*n some embodiments, a polypeptide, an antibody, or antigen binding fragment thereof, comprises a* $V_H$ *peptide and a* $V_L$ *peptide, wherein the wherein the* $V_H$ *peptide comprises a sequence of* SEQ ID NO: 36, *or a variant thereof; and the* $V_L$ *peptide comprises a sequence of* SEQ ID NO: 37, *or a variant thereof, and the polypeptide, the antibody, or antigen binding fragment thereof, binds to non-human primate* CD7. I*n some embodiments, a polypeptide, an antibody, or antigen binding fragment thereof, comprises a* $V_H$ *peptide and a* $V_L$ *peptide, wherein the wherein the* $V_H$ *peptide comprises a sequence of* SEQ ID NO: 36, *or a variant thereof; and the* $V_L$ *peptide comprises a sequence of* SEQ ID NO: 37, *or a variant thereof, and the polypeptide, the antibody, or antigen binding fragment thereof, binds to human* CD7. I*n some embodiments, the* $V_H$ *peptide comprises a sequence of* SEQ ID NO: 36; *and the* $V_L$ *peptide comprises a sequence of* SEQ ID NO: 37.

The $V_H$ and the $V_L$ sequences can be in any format, including, but not limited to an scFv format where the $V_H$ and $V_L$ regions are linked with a peptide linker. Examples of peptide linkers that can be used to link various peptides provided for herein include, but are not limited to: $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. In some embodiments, the variable regions are not linked with a peptide linker. In some embodiments, the polypeptide comprises SEQ ID NO: 36 and SEQ ID NO: 37.

As provided for herein, the polypeptide, antibodies, or antigen binding fragments thereof can be variants of the sequences.

The sequences of the polypeptides or antibodies can be modified to yield human IgG antibodies. The conversion of the sequences provided herein can be modified to yield other types of antibodies. The CDRs can also be linked to other antibodies, proteins, or molecules to create antibody fragments that bind CD7.

In some embodiments, a polypeptide or an antibody as provided herein is a targeting moiety on the surface of an engineered viral particle. In some embodiments, the targeting moiety allows for binding to a target cell. In some embodiments, the targeting moiety is a CD7 binding moiety, such as a polypeptide or an antibody as provided herein. In some embodiments, the target binding domain ("T") comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38:

```
                                            (SEQ ID NO: 38)
DILLTQSPAILSVSPGERVSFSCRASQSIGTSIHWYQQRINDSPRLLIK

YASESISGIPSRFSGSGSGTDFTLSINSVESEDIADYYCQQSNSWPTTF

GGGTKLEIKRGGGGSGGGGSGGGGSGGGGSQVQLQQPGAELVKPGASVK

LSCKASGYPFTSYWIHWVKQRPGRGLEWLGRIDPNSGDTKYNEKFKNKA

TLTVDKSSTTAYMQLSSLTSEDSAVYYCARSPYYSNDNSMDYWGQGTSV

TVSS
```

or is substantially similar to SEQ ID NO: 38, or is an active fragment of SEQ ID NO: 38. In some embodiments, the target binding domain ("T") comprises a sequence that is at least 90% identical to a sequence of SEQ ID NO: 38. In some embodiments, the target binding domain ("T") comprises a sequence that is at least 95% identical to a sequence of SEQ ID NO: 38. In some embodiments, the target binding domain ("T") comprises a sequence that is at least 99% identical to a sequence of SEQ ID NO: 38. In some embodiments, the target binding domain ("T") comprises a sequence as set forth in SEQ ID NO: 38. In some embodiments, the target binding domain ("T") as set forth in SEQ ID NO: 38 is an antibody, or an antigen binding fragment thereof. In some embodiments, the target binding domain ("T") is an anti-CD7 antibody.

In some embodiments, a polypeptide or an antibody as provided for herein is a targeting moiety on the surface of an engineered viral particle. In some embodiments, the engineered viral particle is a pseudotyped viral-like particle. In some embodiments, the targeting moiety allows for binding to a target cell. In some embodiments, the targeting moiety is a CD7 binding moiety, such as a polypeptide or an antibody as provided herein. In some embodiments, the target binding domain ("T") comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39. In some embodiments, the target binding domain ("T") comprises a sequence that is at least 90% identical to a sequence of SEQ ID NO: 39.

```
                                            (SEQ ID NO: 39)
QVQLQQPGAELVKPGASVKLSCKASGYPFTSYWIHWVKQRPGRGLEWLG

RIDPNSGDTKYNEKFKNKATLTVDKSSTTAYMQLSSLTSEDSAVYYCAR

SPYYSNDNSMDYWGQGTSVTVSSGGGGSGGGGSGGGGSGGGGSDILLTQ

SPAILSVSPGERVSFSCRASQSIGTSIHWYQQRINDSPRLLIKYASESI

SGIPSRFSGSGSGTDFTLSINSVESEDIADYYCQQSNSWPTTFGGGTKL

EIKR
```

or is substantially similar to SEQ ID NO: 39, or is an active fragment of SEQ ID NO: 39. In some embodiments, the target binding domain ("T") comprises a sequence that is at least 95% identical to a sequence of SEQ ID NO: 39. In some embodiments, the target binding domain ("T") comprises a sequence that is at least 99% identical to a sequence of SEQ ID NO: 39. In some embodiments, the target binding domain ("T") comprises a sequence as set forth in SEQ ID NO: 39. In some embodiments, the target binding domain ("T") as set forth in SEQ ID NO: 39 is an antibody, or an antigen binding fragment thereof. In some embodiments, the target binding domain ("T") is an anti-CD7 antibody. In some embodiments, the anti-CD7 antibody binds to non-human primate CD7. In some embodiments, the anti-CD7 antibody binds to human CD7.

CD8 Binding Polypeptides

In some embodiments, the targeting moiety (e.g. a polypeptide) can bind to CD8.

In some embodiments, the polypeptide binds to CD8. In some embodiments, the polypeptide binds to CD8-alpha. In some embodiments, the polypeptide binds to CD8-beta. In some embodiments, the polypeptide binds to CD8 heterodimer. In some embodiments, the CD8 heterodimer comprises CD8-alpha and CD8-beta subunits. In some embodiments, the polypeptide binds to CD8-alpha homodimer. In some embodiments, the polypeptide that binds to CD8 is an antibody which binds to non-human primate CD8. In some embodiments, the antibody that binds to non-human primate CD8 is an antibody which binds to non-human primate CD8-alpha. In some embodiments, the antibody that binds to non-human primate CD8 is an antibody which binds to non-human primate CD8-beta. In some embodiments, the antibody that binds to non-human primate CD8 is an antibody which binds to non-human primate CD8-alpha homodimer. In some embodiments, the antibody that binds to non-human primate CD8 is an antibody which binds to non-human primate CD8 heterodimer. In some embodiments, the polypeptide that binds to CD8 is an antibody which binds to human CD8. In some embodiments, the antibody that binds to human CD8 is an antibody which binds to human CD8-alpha. In some embodiments, the antibody that binds to human CD8 is an antibody which binds to human CD8-beta. In some embodiments, the antibody that binds to human CD8 is an antibody which binds to human CD8-alpha homodimer.

In some embodiments, the antibody that binds to human CD8 is an antibody which binds to human CD8 heterodimer. The sequence of human CD8-alpha (UniProtKB Q8TAW8) is as follows (SEQ ID NO: 40):

```
                                         (SEQ ID NO: 40)
MALPVTALLLPLALLLHAARPSQFRVSPLDRTWNLGETVELKCQVLLSN

PTSGCSWLFQPRGAAASPTFLLYLSQNKPKAAEGLDTQRFSGKRLGDTF

VLTLSDFRRENEGCYFCSALSNSIMYFSHFVPVFLPAKPTTTPAPRPPT
```

-continued

```
PAPTIASQPLSLRPEACRPAAGGAVHTRGLDFACDIYIWAPLAGTCGVL

LLSLVITLYCNHRNRRRVCKCPRPVVKSGDKPSLSARYV
```

The sequence of human CD8-beta (UniProtKB Q8TD28) is as follows (SEQ ID NO: 41):

```
                                         (SEQ ID NO: 41)
MRPRLWLLLAAQLTVLHGNSVLQQTPAYIKVQTNKMVMLSCEAKISLSN

MRIYWLRQRQAPSSDSHHEFLALWDSAKGTIHGEEVEQEKIAVFRDASR

FILNLTSVKPEDSGIYFCMIVGSPELTFGKGTQLSVVDFLPTTAQPTKK

STLKKRVCRLPRPETQKGPLCSPITLGLLVAGVLVLLVSLGVAIHLCCR

RRRARLRFMKQLYK.
```

In some embodiments, the CD8 that the polypeptide binds to is expressed on the surface of a cell. In some embodiments, the cell is an immune cell. In some embodiments, the immune cell is a CD7+ T cell, CD4+ T cell, CD8+ T cell, NK cell, alpha-beta T cell, gamma-delta T cell, lymphoid progenitor cell, hematopoietic stem cell, myeloid cell, monocyte, macrophage, central memory T cell, effector memory T cell, stem-cell like memory T cells, naïve T cell, activated T cell, regulatory T cell (TReg), terminally differentiated effector memory T cell (TEMRA), resident memory T cell (TRM) or a T-cell CD8+CCR7+. In some embodiments, the cell is a CD8+ T cell. In some embodiments, the cell is a CD8+ cell.

In some embodiments, the antibody comprises a Fc region. The Fc region can be linked to the heavy or light chain of the antibody. In some embodiments, the Fc region is an IgG Fc. In some embodiments, the IgG is selected from IgG1, IgG2, IgG3, or IgG4. In some embodiments, the IgG Fc is IgG1 Fc. In some embodiments, the antibody comprises an Fc constant region as set forth herein, such as SEQ ID NO: 26, 27, or 28 or a variant thereof.

In some embodiments, polypeptides (e.g. CD8-binding polypeptide) are provided herein. In some embodiments, antibodies (e.g. an anti-CD8 antibody) are provided herein. In some embodiments, the antibody is a recombinant antibody that binds to CD8. In some embodiments, the CD8 protein is a human CD8 protein. In some embodiments, the CD8 protein is a non-human CD8 protein (e.g., mouse, rat, pig, dog, non-human primate). As used herein, the term "recombinant antibody" refers to an antibody that is not naturally occurring. In some embodiments, the term "recombinant antibody" refers to an antibody that is not isolated from a human subject.

In some embodiments, an antibody, or antigen binding fragment thereof is provided, wherein the antibody or antibody fragment comprises a peptide selected from the following table, which illustrate the CDRs based on Kabat numbering.

| Kabat CDRs | | | | | | |
|---|---|---|---|---|---|---|
| Ab ID No | HCDR1 | HCDR2 | HCDR3 | LCDR1 | LCDR2 | LCDR3 |
| CD8AB1 | RYTFTDY (SEQ ID NO: 42) | YPYNGG (SEQ ID NO: 43) | DHRYNEGVSFDY (SEQ ID NO: 44) | RASESVDGFGNSEMN (SEQ ID NO: 45) | LASNLES (SEQ ID NO: 46) | QQNNEDPYT (SEQ ID NO: 47) |

In some embodiments, a polypeptide, an antibody, or antibody binding fragment thereof, comprises a heavy or light chain CDR as provided in the tables above. In some embodiments, a polypeptide, an antibody, or antibody binding fragment thereof, comprises a heavy or light chain CDR as provided in the tables above and binds to non-human primate CD8. In some embodiments, a polypeptide, an antibody, or antibody binding fragment thereof, comprises a heavy or light chain CDR as provided in the tables above and binds to human CD8. In some embodiments, a polypeptide, an antibody, or antibody binding fragment thereof, comprises a light chain CDR having a sequence selected from SEQ ID NO: 45-47. In some embodiments, a polypeptide, an antibody, or antibody binding fragment thereof, comprises a light chain CDR having a sequence of SEQ ID NO: 45. In some embodiments, a polypeptide, an antibody, or antibody binding fragment thereof, comprises a light chain CDR having a sequence of SEQ ID NO: 46. In some embodiments, a polypeptide, an antibody, or antibody binding fragment thereof, comprises a light chain CDR having a sequence of SEQ ID NO: 47. In some embodiments, a polypeptide, an antibody, or antibody binding fragment thereof, comprises a heavy chain CDR having a sequence selected from SEQ ID NO: 42-44. In some embodiments, a polypeptide, an antibody, or antibody binding fragment thereof, comprises a heavy chain CDR having a sequence of SEQ ID NO: 42. In some embodiments, a polypeptide, an antibody, or antibody binding fragment thereof, comprises a heavy chain CDR having a sequence of SEQ ID NO: 43. In some embodiments, a polypeptide, an antibody, or antibody binding fragment thereof, comprises a heavy chain CDR having a sequence of SEQ ID NO: 44. The CDRs referenced in the embodiments throughout the present specification can be interchanged with the CDRs that are characterized by different formats, such as Chothia and IMGT.

In some embodiments, a polypeptide, an antibody, or antibody binding fragment thereof, comprises a light chain variable region having a LCDR1, a LCDR2, and a LCDR3, wherein the LCDR1 has a sequence of SEQ ID NO: 45, the LCDR2 has a sequence of SEQ ID NO: 46, and the LCDR3 has a sequence of SEQ ID NO: 47.

In some embodiments, a polypeptide, an antibody, or antibody binding fragment thereof, comprises a heavy chain variable region having a HCDR1, a HCDR2, and a HCDR3, wherein the HCDR1 has a sequence of SEQ ID NO: 42, the HCDR2 has a sequence of SEQ ID NO: 43, and the HCDR3 has a sequence of SEQ ID NO: 44.

In some embodiments, a polypeptide, an antibody or antibody binding fragment thereof, comprises: (i) a light chain having any one of the foregoing recited combinations of LCDR1, LCDR2, and LCDR3 sequences; and (ii) a heavy chain having any one of the foregoing recited combinations of HCDR1, HCDR2, and HCDR3 sequences.

The different CDR motifs can be combined in any combination including those not depicted in the table above. For example, the following embodiments are provided as non-limiting examples of such combinations.

In some embodiments, a polypeptide, an antibody, or antigen binding fragment thereof, comprises: (i) a light chain variable region comprising light chain CDR1, CDR2, and CDR3 sequences, wherein the light chain CDR1 sequence has the amino acid sequence of SEQ ID NO: 45; the light chain CDR2 has the amino acid sequence of SEQ ID NO: 46; and the light chain CDR3 sequence has the amino acid sequence of SEQ ID NO: 47; and (ii) a heavy chain variable region comprising heavy chain CDR1, CDR2, and CDR3 sequences, wherein the heavy chain CDR1 sequence has the amino acid sequence of SEQ ID NO: 42; the heavy chain CDR2 sequence has the amino acid sequence of SEQ ID NO: 43; and the heavy chain CDR3 sequence has the amino acid sequence of SEQ ID NO: 44; or variants of any of the foregoing.

Although the preceding paragraphs may make reference to CDRs under the Kabat system the equivalent CDR sequences can be used from the IMGT and CHOTHIA designations.

In some embodiments, the light chain variable region CDR1 is replaced with any of the other light chain CDR1 sequences. In some embodiments, the light chain variable region CDR2 is replaced with any of the other light chain CDR2 sequences. In some embodiments, the light chain variable region CDR3 is replaced with any of the other light chain CDR3 sequences. In some embodiments, the heavy chain variable region CDR1 is replaced with any of the other heavy chain CDR1 sequences. In some embodiments, the heavy chain variable region CDR2 is replaced with any of the other heavy chain CDR2 sequences. In some embodiments, the heavy chain variable region CDR3 is replaced with any of the other heavy chain CDR3 sequences.

In some embodiments, the polypeptide comprises a heavy chain variable region peptide having one of the following sequences, or a variant thereof:

| SEQ ID NO: | AB ID NO. | Sequence |
|---|---|---|
| 48 | CD8AB1 | EVQLQQSGPELVKPGASVKISCKASRYTFTDYNLHWVKLSHEKSLEWIGFIYPYNGGTGYNQKFKNKAKLTVDYSSSTAYMELRSLTSVDAAVYYCARDHRYNEGVSFDYWGQGTTLTVSS |

In some embodiments, the polypeptide comprises a light chain variable region peptide having one of the following sequences, or a variant thereof:

| SEQ ID NO: | AB ID NO. | Sequence |
|---|---|---|
| 49 | CD8AB1 | NIVLTQSPASLAVSLGQRATISCRASESVDGFGNSFMNWYQQKPGQSPKLLIYLASNLESGVPARFSGSGSRTDFTLTIDPVEADDAATYYCQQNNEDPYTFGGGTKLEIKR |

In some embodiments, a polypeptide, an antibody, or antigen binding fragment thereof, comprises a $V_H$ peptide of SEQ ID NO: 48. In some embodiments, a polypeptide, an antibody, or antigen binding fragment thereof, comprises a $V_L$ peptide of SEQ ID NO: 49. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 48, or a variant thereof; and the $V_L$ peptide comprises a sequence of SEQ ID NO: 49, or a variant thereof. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 48, or a variant thereof; and the $V_L$ peptide comprises a sequence of SEQ ID NO: 49, or a variant thereof, and the polypeptide, the antibody, or antigen binding fragment thereof, binds to non-human primate CD8. In some embodiments, a polypeptide, an antibody, or antigen binding fragment thereof, comprises a $V_H$ peptide and a $V_L$ peptide, wherein the wherein the $V_H$ peptide comprises a sequence of SEQ ID NO: 48, or a variant thereof; and the $V_L$ peptide comprises a sequence of SEQ ID NO: 49, or a variant thereof, and the polypeptide, the antibody, or antigen binding fragment thereof, binds to human CD8. In some embodiments, the $V_H$ peptide comprises a sequence of SEQ ID NO: 48; and the $V_L$ peptide comprises a sequence of SEQ ID NO: 49.

The $V_H$ and the $V_L$ sequences can be in any format, including, but not limited to an scFv format where the $V_H$ and $V_L$ regions are linked with a peptide linker. Examples of peptide linkers that can be used to link various peptides provided for herein include, but are not limited to: $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. In some embodiments, the variable regions are not linked with a peptide linker. In some embodiments, the polypeptide comprises SEQ ID NO: 48 and SEQ ID NO: 49.

As provided for herein, the polypeptide, antibodies, or antigen binding fragments thereof can be variants of the sequences.

The sequences of the polypeptides or antibodies can be modified to yield human IgG antibodies. The conversion of the sequences provided herein can be modified to yield other types of antibodies. The CDRs can also be linked to other antibodies, proteins, or molecules to create antibody fragments that bind CD8.

In some embodiments, a polypeptide or an antibody as provided herein is a targeting moiety on the surface of an engineered viral particle. In some embodiments, the targeting moiety allows for binding to a target cell. In some embodiments, the target binding domain ("T") is a CD8 binding moiety, such as a polypeptide or an antibody as provided herein. In some embodiments, the target binding domain ("T") comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50:

```
                                                 (SEQ ID NO: 50)
NIVLTQSPASLAVSLGORATISCRASESVDGFGNSFMNWYQQKPGQSPKL

LIYLASNLESGVPARFSGSGSRTDFTLTIDPVEADDAATYYCOONNEDPY

TFGGGTKLEIKRGGGGSGGGGSGGGGSGGGGSEVQLQQSGPELVKPGASV

KISCKASRYTFTDYNLHWVKLSHEKSLEWIGFIYPYNGGTGYNQKFKNKA

KLTVDYSSSTAYMELRSLTSVDAAVYYCARDHRYNEGVSFDYWGQGTTLT

VSS
```

or is substantially similar to SEQ ID NO: 50, or is an active fragment of SEQ ID NO: 50. In some embodiments, the target binding domain ("T") comprises a sequence that is at least 90% identical to a sequence of SEQ ID NO: 50. In some embodiments, the target binding domain ("T") comprises a sequence that is at least 95% identical to a sequence of SEQ ID NO: 50. In some embodiments, the target binding domain ("T") comprises a sequence that is at least 99% identical to a sequence of SEQ ID NO: 50. In some embodiments, the target binding domain ("T") comprises a sequence as set forth in SEQ ID NO: 50. In some embodiments, the target binding domain ("T") as set forth in SEQ ID NO: 50 is an antibody, or an antigen binding fragment thereof. In some embodiments, the targeting moiety is an anti-CD8 antibody.

In some embodiments, a polypeptide or an antibody as provided for herein is a targeting moiety on the surface of an engineered viral particle. In some embodiments, the engineered viral particle is a pseudotyped viral-like particle. In some embodiments, the targeting moiety allows for binding to a target cell. In some embodiments, the target binding domain ("T") is a CD8 binding moiety, such as a polypeptide or an antibody as provided herein. In some embodiments, the target binding domain ("T") comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51:

```
                                                 (SEQ ID NO: 51)
EVQLQQSGPELVKPGASVKISCKASRYTFTDYNLHWVKLSHEKSLEWIGF

IYPYNGGTGYNQKFKNKAKLTVDYSSSTAYMELRSLTSVDAAVYYCARDH

RYNEGVSFDYWGQGTTLTVSSGGGGSGGGGSGGGGSGGGGSNIVLTQSPA
```

-continued

```
SLAVSLGQRATISCRASESVDGFGNSFMNWYQQKPGQSPKLLIYLASNLE

SGVPARFSGSGSRTDFTLTIDPVEADDAATYYCOONNEDPYTFGGGTKLE

IKR
```

or is substantially similar to SEQ ID NO: 51, or is an active fragment of SEQ ID NO: 51. In some embodiments, the target binding domain ("T") comprises a sequence that is at least 90% identical to a sequence of SEQ ID NO: 51. In some embodiments, the target binding domain ("T") comprises a sequence that is at least 95% identical to a sequence of SEQ ID NO: 51. In some embodiments, the target binding domain ("T") comprises a sequence that is at least 99% identical to a sequence of SEQ ID NO: 51. In some embodiments, the target binding domain ("T") comprises a sequence as set forth in SEQ ID NO: 51. In some embodiments, the target binding domain ("T") as set forth in SEQ ID NO: 51 is an antibody, or an antigen binding fragment thereof. In some embodiments, the targeting moiety is an anti-CD8 antibody. In some embodiments, the anti-CD8 antibody binds to non-human primate CD8. In some embodiments, the anti-CD8 antibody binds to human CD8.

Targeting Moieties Comprising an Fc Domain

In some embodiments, the $V_H$ and $V_L$ polypeptides are linked to a stalk portion S1 comprising an Fc region. In some embodiments, the Fc region is as provided for herein. In some embodiments, the Fc region is a variant Fc region as provided for herein. Non-limiting mutations in the Fc region are provided for herein. In some embodiments, the variant Fc region comprises a sequence that is a variant of SEQ ID NO: 26, SEQ ID NO: 27, or SEQ ID NO: 28 as provided for herein. In some embodiments, the variant of SEQ ID NO: 26 comprises one or more mutations selected from the group consisting of L234A, L235A, N297A, P329G, I253A, H310A, and H435A as provided for herein. In some embodiments, the variant of SEQ ID NO: 27 comprises one or more mutations selected from the group consisting of N297A, P329G, I253A, H310A, and H435A as provided for herein. In some embodiments, the variant of SEQ ID NO: 28 comprises one or more mutations selected from the group consisting of S228P, L235E, N297A, P329G, I253A, H310A, and H435A as provided for herein. As provided for herein, the heavy chain can be linked to a Fc region. In some embodiments, the Fc region further comprises (e.g.linked to) a transmembrane domain. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. Examples of ECD include, but are not limited to, a CD8 and/or CD28 extracellular domain as provided for herein. Examples of $T_M$ include, but are not limited to, a CD8 and/or CD28 transmembrane domain as provided for herein. In some embodiments, $X_1$ comprises a $T_M$ and the ECD and ICD are absent. In some embodiments, $X_1$ comprises an ECD, a $T_M$, and the ICD is absent. In some embodiments, $X_1$ comprises a $T_M$ and an ICD and the ECD is absent. In some embodiments, $X_1$ comprises an ECD, a $T_M$, and an ICD. In any of the following embodiments, it is to be understood that the ECD, the ICD, or both may be optionally absent.

Accordingly, an embodiment wherein $X_1$ comprises a CD8 and/or CD28 ECD, a CD8 and/or CD28 $T_M$, and an ICD comprising an Env incorporation motif is understood to encompass the following $X_1$ members: i) a CD8 and/or CD28 ECD, a CD8 and/or CD28 $T_M$, and an ICD comprising an Env incorporation motif; ii) a CD8 and/or CD28 $T_M$, and an ICD comprising an Env incorporation motif wherein the ECD is absent; iii) a CD8 and/or CD28 ECD, and a CD8 and/or CD28 $T_M$, wherein the ICD is absent; and iv) a CD8 and/or CD28 $T_M$ wherein both the ECD and the ICD are absent. Similarly, an embodiment wherein $X_1$ comprises a CD8 and/or CD28 $T_M$ and an ICD comprising an Env incorporation motif is understood to encompass the following $X_1$ members: i) a CD8 and/or CD28 $T_M$ and an ICD comprising an Env incorporation motif; and ii) a CD8 and/or CD28 $T_M$ wherein the ICD is absent. Similarly, an embodiment wherein $X_1$ comprises a CD8 and/or CD28 ECD and a CD8 and/or CD28 $T_M$ is understood to encompass the following $X_1$ members: i) a CD8 and/or CD28 ECD and a CD8 and/or CD28 $T_M$; and ii) a CD8 and/or CD28 $T_M$ wherein the ECD is absent. It is to be further understood that the preceding explanation is also true in embodiments where a specific ECD, $T_M$, or ICD are not recited. For example, an embodiment wherein $X_1$ comprises an ECD, a CD8 and/or CD28 $T_M$, and an ICD would be understood to encompass the following $X_1$ members: i) an ECD, a CD8 and/or CD28 $T_M$, and an ICD; ii) an ECD, and a CD8 and/or CD28 $T_M$ wherein the ICD is absent; iii) a CD8 and/or CD28 $T_M$, and an ICD wherein the ECD is absent; and iv) a CD8 and/or CD28 $T_M$ wherein the ECD and the ICD are absent. Similarly, an embodiment wherein $X_1$ comprises a CD8 and/or CD28 $T_M$ and an ICD is understood to encompass the following $X_1$ members: i) a CD8 and/or CD28 $T_M$ and an ICD; and ii) a CD8 and/or CD28 $T_M$ wherein the ICD is absent. Similarly, an embodiment wherein $X_1$ comprises an ECD and a CD8 and/or CD28 $T_M$ is understood to encompass the following $X_1$ members: i) an ECD and a CD8 and/or CD28 $T_M$; and ii) a CD8 and/or CD28 $T_M$ wherein the ECD is absent. Unless explicitly stated, the preceding examples and explanations are applicable to any embodiments that follow.

In some embodiments, $X_1$ comprises a CD8 and/or CD28 ECD, a $T_M$, and an ICD. In some embodiments, $X_1$ comprises an ECD, a CD8 and/or CD28 $T_M$, and an ICD. In some embodiments, $X_1$ comprises a CD8 and/or CD28 ECD, a CD8 and/or CD28 $T_M$, and an ICD. In some embodiments, $X_1$ comprises an ECD, a $T_M$, and an ICD, wherein the ICD comprises an env incorporation motif as provided for herein. In some embodiments, $X_1$ comprises a CD8 and/or CD28 ECD, a $T_M$, and an ICD, wherein the ICD comprises an env incorporation motif as provided for herein. In some embodiments, $X_1$ comprises an ECD, a CD8 and/or CD28 $T_M$, and an ICD, wherein the ICD comprises an env incorporation motif as provided for herein. In some embodiments, $X_1$ comprises a CD8 and/or CD28 ECD, a CD8 and/or CD28 $T_M$, and an ICD, wherein the ICD comprises an env incorporation motif as provided for herein.

In some embodiments, the $V_H$ and $V_L$ polypeptides provided herein are linked to a stalk portion ($S_1$) comprising an Fc region as provided for herein. In some embodiments, the $V_H$ and $V_L$ polypeptides provided herein are linked to a stalk portion ($S_1$) comprising an Fc region comprising a transmembrane domain as provided for herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or absent, $T_M$ is a transmembrane domain as provided for herein, and ICD is an intracellular domain as provided for herein or absent. In some embodiments, the $V_H$ and $V_L$ polypeptides provided herein are linked to a stalk portion ($S_1$) comprising an Fc region ($L_1$-Fc-$L_2$-$X_1$) comprising a CD8 and/or CD28 ECD, a $T_M$, and an ICD. In some embodiments, the $V_H$ and $V_L$ polypeptides provided herein are linked to a stalk portion ($S_1$) comprising an Fc region ($L_1$-Fc-$L_2$-$X_1$) comprising an ECD, a CD8 and/or CD28 $T_M$, and an ICD. In some embodiments, the $V_H$ and $V_L$ polypeptides provided herein are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the $V_H$ and $V_L$ polypeptides provided herein are linked to a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the $V_H$ and $V_L$ polypeptides provided herein are linked to a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the $V_H$ and $V_L$ polypeptides provided herein are linked to a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the $V_H$ and $V_L$ polypeptides provided herein are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the $V_H$ and $V_L$ polypeptides provided herein linked to a stalk portion ($S_1$) comprising an Fc region ($L_1$-Fc-$L_2$-$X_1$) comprising an ECD, a $T_M$, and an ICD are anchored to the surface of a viral particle, such as those provided for herein. In some embodiments, the identities of $L_1$, Fe, $L_2$, ECD, $T_M$, and ICD are as provided for herein. In some embodiments, the $V_H$ and $V_L$ polypeptides bind to an immune cell, such as those provided herein.

In some embodiments, a $V_H$ peptide having a sequence as set forth in SEQ ID NO: 36 and a $V_L$ peptide having a sequence as set forth in SEQ ID NO: 37 are linked to an a stalk portion ($S_1$) comprising Fc region ($L_1$-Fc-$L_2$-$X_1$) comprising an ECD, a $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising a CD8 and/or CD28 ECD, a $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising an ECD, a CD8 and/or CD28 $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the $V_H$ peptide having a sequence as set forth in SEQ ID NO: 36 and $V_L$ peptide having a sequence as set forth in SEQ ID NO: 37 linked to a stalk portion ($S_1$) comprising an Fc region ($L_1$-Fc-$L_2$-$X_1$) comprising an ECD, a $T_M$, and an ICD are anchored to the surface of a viral particle, such as those provided for herein. In some embodiments, the identities of $L_1$, Fc, $L_2$, ECD, $T_M$, and ICD are as provided for herein. In some embodiments, the $V_H$ and $V_L$ polypeptides bind to an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region comprising a transmembrane domain as provided for herein. In some embodiments, the Fc region further comprising a transmembrane domain has a formula of $L_1$-Fc-$L_2$-$X_1$, wherein $L_1$ is a linker as provided for herein or is Fc is a variant Fc region as provided for herein, $L_2$ is a linker as provided for herein or absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or absent, $T_M$ is a transmembrane domain as provided for herein, and ICD is an intracellular domain as provided for herein or absent. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising an ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising a CD8 and/or CD28 ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising an ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO:

37 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 linked to a stalk portion ($S_1$) comprising an Fc region ($L_1$-Fc-$L_2$-$X_1$) comprising an ECD, a $T_M$, and an ICD are anchored to the surface of a viral particle, such as those provided for herein. In some embodiments, the identities of $L_1$, Fc, $L_2$, ECD, $T_M$, and ICD are as provided for herein. In some embodiments, the $V_H$ and $V_L$ polypeptides bind to an immune cell, such as those provided herein.

In some embodiments, a polypeptide is provided comprising a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_H$ peptide and a $V_L$ peptide comprises a light chain CDR having a sequence of SEQ ID NO: 33-35; and/or a heavy chain CDR having a sequence of SEQ ID NO: 30-32. In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_H$ peptide and a $V_L$ peptide comprise a light chain CDR1 having a sequence of SEQ ID NO: 33; a light chain CDR2 having a sequence of SEQ ID NO: 34; a light chain CDR3 having a sequence of SEQ ID NO: 35; and/or a heavy chain CDR1 having a sequence of SEQ ID NO: 30; a heavy chain CDR2 having a sequence of SEQ ID NO: 31; and a heavy chain CDR3 having a sequence of SEQ ID NO: 32. In some embodiments, the CDRs in the $V_H$ or $V_L$ chain are as set forth in the combinations provided for herein.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_L$ peptide comprises a LCDR1 having a sequence of SEQ ID NO: 33; a LCDR2 having a sequence of SEQ ID NO: 34; and a LCDR3 having a sequence of SEQ ID NO: 35; and the $V_H$ peptide comprises a HCDR1 having a sequence of SEQ ID NO: 30; a HCDR2 having a sequence of SEQ ID NO: 31; and a HCDR3 having a sequence of SEQ ID NO: 32.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_L$ peptide comprises a LCDR1 having a sequence of SEQ ID NO: 33, wherein the LCDR1 comprises at most 1 conservative amino acid substitution, a LCDR2 having a sequence of SEQ ID NO: 34, wherein the LCDR2 comprises at most 1 conservative amino acid substitution, and a LCDR3 having a sequence of SEQ ID NO: 35, wherein the LCDR3 comprises at most 1 conservative amino acid substitution; and the $V_H$ peptide comprises a HCDR1 having a sequence of SEQ ID NO: 30, wherein the HCDR1 comprises at most 1 conservative amino acid substitution, a HCDR2 having a sequence of SEQ ID NO: 31, wherein the HCDR2 comprises at most 1 conservative amino acid substitution, and a HCDR3 having a sequence of SEQ ID NO: 32, wherein the HCDR3 comprises at most 1 conservative amino acid substitution.

In some embodiments, the polypeptide comprises a $V_H$ peptide and a $V_L$ peptide, wherein the $V_H$ peptide comprises a sequence of SEQ ID NO: 36 and the $V_L$ peptide comprises a sequence of SEQ ID NO: 37.

In some embodiments, the polypeptide as provided herein binds to non-human primate CD7. In some embodiments, the polypeptide as provided herein binds to human CD7.

As provided for herein, the different polypeptides ($V_H$ or $V_L$) described herein can be linked with a peptide linker or not linked with a peptide linker and instead for a continuous sequence. In some embodiments, the peptide linker comprises a sequence of $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5.

In some embodiments, the polypeptide comprising the linked peptide represented by a formula of $V_L$-Z-$V_H$ comprises a heavy chain variable region as set forth in SEQ ID NO: 36 linked via a linker sequence GGGGSGGGGSGGGGSGGGGS (SEQ ID NO: 72) to a light chain variable region as set forth in SEQ ID NO: 37. In some embodiments, the polypeptide comprising a $V_L$ linked via a peptide linker to a $V_H$ has the sequence as set forth below,

```
                                              (SEQ ID NO: 38)
DILLTQSPAILSVSPGERVSFSCRASQSIGTSIHWYQQRTNDSPRLLIKY

ASESISGIPSRFSGSGSGTDFTLSINSVESEDIADYYCQQSNSWPTTFGG

GTKLEIKRGGGGSGGGGSGGGGSGGGGSQVQLQQPGAELVKPGASVKLSC
```

-continued

```
KASGYPFTSYWIHWVKQRPGRGLEWLGRIDPNSGDTKYNEKFKNKATLTV

DKSSTTAYMQLSSLTSEDSAVYYCARSPYYSNDNSMDYWGQGTSVTVSS.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38. In some embodiments, the polypeptide comprises a sequence that is at least 90% identical to a sequence of SEQ ID NO: 38. In some embodiments, the polypeptide comprises a sequence that is at least 95% identical to a sequence of SEQ ID NO: 38. In some embodiments, the polypeptide comprises a sequence that is at least 99% identical to a sequence of SEQ ID NO: 38. In some embodiments, the polypeptide comprises a sequence as set forth in SEQ ID NO: 38. In some embodiments, the polypeptide as set forth in SEQ ID NO: 38 is an antibody, or an antigen binding fragment thereof. In some embodiments, the antibody is an anti-CD7 antibody. In some embodiments, the anti-CD7 antibody binds to non-human primate CD7. In some embodiments, the anti-CD7 antibody binds to human CD7.

In some embodiments, the polypeptide comprising the linked peptide represented by a formula of $V_H$-Z-$V_L$ comprises a light chain variable region as set forth in SEQ ID NO: 37 linked via a linker sequence GGGGSGGGGSGGGGSGGGGS (SEQ ID NO: 72) to a heavy chain variable region as set forth in SEQ ID NO: 36. In some embodiments, the polypeptide comprising a $V_H$ linked via a peptide linker to a $V_L$ has the sequence as set forth below,

```
                                       (SEQ ID NO: 39)
QVQLQQPGAELVKPGASVKLSCKASGYPFTSYWIHWVKQRPGRGLEWLGR

IDPNSGDTKYNEKFKNKATLTVDKSSTTAYMQLSSLTSEDSAVYYCARSP

YYSNDNSMDYWGQGTSVTVSSGGGGSGGGGSGGGGSGGGGSDILLTQSPA

ILSVSPGERVSFSCRASQSIGTSIHWYQQRTNDSPRLLIKYASESISGIP

SRFSGSGSGTDFTLSINSVESEDIADYYCQQSNSWPTTFGGGTKLEIKR.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39. In some embodiments, the polypeptide comprises a sequence that is at least 90% identical to a sequence of SEQ ID NO: 39. In some embodiments, the polypeptide comprises a sequence that is at least 95% identical to a sequence of SEQ ID NO: 39. In some embodiments, the polypeptide comprises a sequence that is at least 99% identical to a sequence of SEQ ID NO: 39. In some embodiments, the polypeptide comprises a sequence as set forth in SEQ ID NO: 39. In some embodiments, the polypeptide as set forth in SEQ ID NO: 39 is an antibody, or an antigen binding fragment thereof. In some embodiments, the antibody is an anti-CD7 antibody. In some embodiments, the anti-CD7 antibody binds to non-human primate CD7. In some embodiments, the anti-CD7 antibody binds to human CD7.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region, such as those provided herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region, said Fc region further comprising a transmembrane domain such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region, such as those provided herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region, said Fc region further comprising a transmembrane domain such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or absent, $T_M$ is a transmembrane domain as provided for herein, and ICD is an intracellular domain as provided for herein or absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 38 and comprises a stalk portion ($S_1$) comprising an Fc region, such as those provided herein. In some embodiments, the polypeptide comprises a sequence having a sequence as set forth in SEQ ID NO: 38 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence having a sequence as set forth in SEQ ID NO: 38 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence having a sequence as set forth in SEQ ID NO: 38 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 39 and comprises a stalk portion ($S_1$) comprising an Fc region, such as those provided herein. In some embodiments, the polypeptide comprises a sequence having a sequence as set forth in SEQ ID NO: 39 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or absent, $T_M$ is a transmembrane domain as provided for herein, and ICD is an intracellular domain as provided for herein or absent. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence having a sequence as set forth in SEQ ID NO: 39 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence having a sequence as set forth in SEQ ID NO: 39 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide provided for herein comprising the formula of T-$S_1$, wherein T is a target binding domain and $S_1$ is a stalk portion, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98:

```
                                              (SEQ ID NO: 98)
METDTLLLWVLLLWVPGSTGDSAQVQLQQPGAELVKPGASVKLSCKASGY
PFTSYWIHWVKQRPGRGLEWLGRIDPNSGDTKYNEKFKNKATLTVDKSST
TAYMQLSSLTSEDSAVYYCARSPYYSNDNSMDYWGQGTSVTVSSGGGGSG
GGGSGGGGSGGGGSDILLTQSPAILSVSPGERVSFSCRASQSIGTSIHWY
QQRTNDSPRLLIKYASESISGIPSRFSGSGSGTDFTLSINSVESEDIADY
YCQQSNSWPTTFGGGTKLEIKRASGGGGSGGGGSGGGGSEPKSCDKTHTC
PPCPAPEAAGGPSVFLFPPKPKDTLMASRTPEVTCVVVDVSHEDPEVKFN
WYVDGVEVHNAKTKPREEQYASTYRVVSVLTVLAQDWLNGKEYKCKVSNK
ALGAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCS
VMHEALHNAYTQKSLSLSPGKKIEVMYPPPYLDNEKSNGTIIHVKGKHLC
PSPLFPGPSKPFWVLVVVGGVLACYSLLVTVAFIIFWVRSKRSRLLHSDY
MNRVRQGYS
```

or is substantially similar to SEQ ID NO: 98, or is an active fragment of SEQ ID NO: 98. In some embodiments, the polypeptide provided for herein comprising the formula of T-$S_1$ comprises an amino acid sequence that is at least 90% identical to a sequence of SEQ ID NO: 98. In some embodiments, the polypeptide provided for herein comprising the formula of T-$S_1$ comprises an amino acid sequence that is at least 95% identical to a sequence of SEQ ID NO: 98. In some embodiments, the polypeptide provided for herein comprising the formula of T-$S_1$ comprises an amino acid sequence that is at least 98% identical to a sequence of SEQ ID NO: 98. In some embodiments, the polypeptide provided for herein comprising the formula of T-$S_1$ comprises an amino acid sequence of SEQ ID NO: 98.

In some embodiments, the polypeptide provided for herein comprising the formula of T-$S_1$, wherein T is a target binding domain and $S_1$ is a stalk portion, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the target binding domain "T" of the polypeptide corresponds to amino acids 25-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence that is at least 90% identical to a sequence of SEQ ID NO: 98, wherein the target binding domain "T" of the polypeptide corresponds to amino acids 25-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence that is at least 95% identical to a sequence of SEQ ID NO: 98, wherein the target binding domain "T" of the polypeptide corresponds to amino acids 25-283 of SEQ ID NO: 98, and wherein the stalk portion "S1" of the polypeptide corresponds to amino acids 284-634 of SEQ ID NO: 98. In some embodiments, the polypeptide provided for herein comprising the formula of T-$S_1$ comprises an amino acid sequence that is at least 98% identical to a sequence of SEQ ID NO: 98, wherein the target binding domain "T" of the polypeptide corresponds to amino acids 25-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence of SEQ ID NO: 98, wherein the target binding domain "T" of the polypeptide corresponds to amino acids 25-283 of SEQ ID NO: 98, and wherein the stalk portion "$S_1$" of the polypeptide corresponds to amino acids 284-634 of SEQ ID NO: 98.

In some embodiments, the polypeptide provided for herein comprising the formula of T-$S_1$, wherein T is a target binding domain comprising a $V_H$ and a $V_L$, and S1 is a stalk portion, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence that is at least 90% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence that is at least 95% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence that is at least 98% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, and wherein the stalk portion "$S_1$" of the polypeptide corresponds to amino acids 284-634 of SEQ ID NO: 98. In some embodiments, the polypeptide provided for herein comprising the formula of T-$S_1$ comprises an amino acid sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, and wherein the stalk portion "$S_1$" of the polypeptide corresponds to amino acids 284-634 of SEQ ID NO: 98.

In some embodiments, the polypeptide provided for herein comprising the formula of T-$L_1$-Fc-$L_2$-$X_1$, wherein T is a target binding domain, $L_1$ is a polypeptide linker or is absent, Fc is a variant Fc domain as provided for herein, $L_2$ is a polypeptide linker or is absent, and $X_1$ is a polypeptide comprising a transmembrane domain, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the target binding domain "T" of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 90% identical to a sequence of SEQ ID NO: 98, wherein the target binding domain "T" of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 95% identical to a sequence of SEQ ID NO: 98, wherein the target binding domain "T" of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 98% identical to a sequence of SEQ ID NO: 98, wherein the target binding domain "T" of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98.

In some embodiments, the polypeptide provided for herein comprising the formula of T-$L_1$-Fc-$L_2$-$X_1$, wherein T is a target binding domain comprising a $V_H$ and a $V_L$, $L_1$ is a polypeptide linker or is absent, Fc is a variant Fc domain as provided for herein, $L_2$ is a polypeptide linker or is absent, and $X_1$ is a polypeptide comprising a transmembrane domain, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 90% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 95% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence that is at least 98% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98. In some embodiments, the polypeptide provided for herein comprising the formula of T-$L_1$-Fc-$L_2$-$X_1$ comprises an amino acid sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent, and $X_1$ corresponds to amino acids 543-634 of SEQ ID NO: 98.

In some embodiments, the polypeptide provided for herein comprising the formula of T-$L_1$-Fc-$L_2$-ECD-$T_M$-ICD, wherein T is a target binding domain, $L_1$ is a polypeptide linker or is absent, Fc is a variant Fc domain as provided for herein, $L_2$ is a polypeptide linker or is absent, ECD is an extracellular domain, $T_M$ is a transmembrane domain, and ICD is an intracellular domain comprising a env incorporation motif, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 90% identical to a sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 95% identical to a sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 98% identical to a sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence of SEQ ID NO: 98, wherein the target binding domain “T” of the polypeptide corresponds to amino acids 25-283 of SEQ ID NO: 98, $L_1$ comprises amino acids 284-301 of SEQ ID NO: 98, Fc comprises amino acids 302-542 of SEQ ID NO: 98, $L_2$ is absent, ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98.

In some embodiments, the polypeptide provided for herein comprising the formula of T-$L_1$-Fc-$L_2$-ECD-$T_M$-ICD, wherein T is a target binding domain comprising a $V_H$ and a $V_L$, $L_1$ is a polypeptide linker or is absent, Fc is a variant Fc domain as provided for herein, $L_2$ is a polypeptide linker or is absent, ECD is an extracellular domain, $T_M$ is a transmembrane domain, and ICD is an intracellular domain comprising a env incorporation motif, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 90% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 95% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 98% identical to a sequence of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98. In some embodiments, the polypeptide provided for herein comprising the formula of T-$L_1$-Fc-$L_2$-ECD-$T_M$-ICD comprises an amino acid of SEQ ID NO: 98, wherein the $V_H$ of the target binding domain corresponds to amino acids 25-150 of SEQ ID NO: 98, the $V_L$ of the target binding domain corresponds to amino acids 172-283 of SEQ ID NO: 98, $L_1$ comprises amino acids 284-301 of SEQ ID NO: 98, Fc comprises amino acids 302-542 of SEQ ID NO: 98, $L_2$ is absent ECD comprises amino acids 543-584 of SEQ ID NO: 98, $T_M$ comprises amino acids 585-612 of SEQ ID NO: 98, and ICD comprises amino acids 613-634 of SEQ ID NO: 98, wherein the env incorporation motif comprises amino acids 627-634 of SEQ ID NO: 98.

In some embodiments, the polypeptide provided for herein comprising the formula of T-$L_1$-Fc-$L_2$-ECD-$T_M$-ICD, wherein T is a target binding domain, $L_1$ is a polypeptide linker or is absent, Fc is a variant Fc domain as provided for herein, $L_2$ is a polypeptide linker or is absent, ECD is an extracellular domain, $T_M$ is a transmembrane domain, and ICD is an intracellular domain comprising a env incorporation motif, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the target binding domain "T" of the polypeptide comprises an amino acid sequence SEQ ID NO: 39 and corresponds to amino acids 25-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 90% identical to a sequence of SEQ ID NO: 98, wherein the target binding domain "T" of the polypeptide comprises an amino acid sequence SEQ ID NO: 39 and corresponds to amino acids 25-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 95% identical to a sequence of SEQ ID NO: 98, wherein the target binding domain "T" of the polypeptide comprises an amino acid sequence SEQ ID NO: 39 and corresponds to amino acids 25-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 98% identical to a sequence of SEQ ID NO: 98, wherein the target binding domain "T" of the polypeptide comprises an amino acid sequence SEQ ID NO: 39 and corresponds to amino acids 25-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence of SEQ ID NO: 98, wherein the target binding domain "T" of the polypeptide comprises an amino acid sequence SEQ ID NO: 39 and corresponds to amino acids 25-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98.

In some embodiments, the polypeptide provided for herein comprising the formula of T-$L_1$-Fc-$L_2$-ECD-$T_M$-ICD, wherein T is a target binding domain comprising a $V_H$ and a $V_L$, $L_1$ is a polypeptide linker or is absent, Fc is a variant Fc domain as provided for herein, $L_2$ is a polypeptide linker or is absent, ECD is an extracellular domain, $T_M$ is a transmembrane domain, and ICD is an intracellular domain comprising a env incorporation motif, comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 98, wherein the $V_H$ of the target binding domain comprises an amino acid sequence of SEQ ID NO: 36 and corresponds to amino acids 25-150 of SEQ ID NO: 98, the $V_L$ of the target binding domain comprises an amino acid sequence of SEQ ID NO: 37 and corresponds to amino acids 172-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 90% identical to a sequence of SEQ ID NO: 98, wherein the $V_H$ of the target binding domain comprises an amino acid sequence of SEQ ID NO: 36 and corresponds to amino acids 25-150 of SEQ ID NO: 98, the $V_L$ of the target binding domain comprises an amino acid sequence of SEQ ID NO: 37 and corresponds to amino acids 172-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 95% identical to a sequence of SEQ ID NO: 98, wherein the $V_H$ of the target binding domain comprises an amino acid sequence of SEQ ID NO: 36 and corresponds to amino acids 25-150 of SEQ ID NO: 98, the $V_L$ of the target binding domain comprises an amino acid sequence of SEQ ID NO: 37 and corresponds to amino acids 172-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence that is at least 98% identical to a sequence of SEQ ID NO: 98, wherein the $V_H$ of the target binding domain comprises an amino acid sequence of SEQ ID NO: 36 and corresponds to amino acids 25-150 of SEQ ID NO: 98, the $V_L$ of the target binding domain comprises an amino acid sequence of SEQ ID NO: 37 and corresponds to amino acids 172-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98. In some embodiments, the polypeptide provided for herein comprising the formula of T-$L_1$-Fc-$L_2$-ECD-$T_M$-ICD comprises an amino acid sequence of SEQ ID NO: 98, wherein the $V_H$ of the target binding domain comprises an amino acid sequence of SEQ ID NO: 36 and corresponds to amino acids 25-150 of SEQ ID NO: 98, the $V_L$ of the target binding domain comprises an amino acid sequence of SEQ ID NO: 37 and corresponds to amino acids 172-283 of SEQ ID NO: 98, $L_1$ comprises an amino acid sequence of SEQ ID NO: 72 and corresponds to amino acids 284-301 of SEQ ID NO: 98, Fc comprises an amino acid sequence of SEQ ID NO: 104 and corresponds to amino acids 302-542 of SEQ ID NO: 98, $L_2$ is absent, ECD comprises an amino acid sequence of SEQ ID NO: 60 and corresponds to amino acids 543-584 of SEQ ID NO: 98, $T_M$ comprises an amino acid sequence of SEQ ID NO: 62 and corresponds to amino acids 585-612 of SEQ ID NO: 98, and ICD comprises amino acids 613-634 of SEQ ID NO: 98, wherein the env incorporation motif comprises an amino acids sequence of SEQ ID NO: 63 and corresponds to amino acids 627-634 of SEQ ID NO: 98.

In some embodiments, a $V_H$ peptide having a sequence as set forth in SEQ ID NO: 48 and a $V_L$ peptide having a sequence as set forth in SEQ ID NO: 49 are linked to a stalk portion ($S_1$) comprising an Fc region ($L_1$-Fc-$L_2$-$X_1$) comprising an ECD, a $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising a CD8 and/or CD28 ECD, a $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising an ECD, a CD8 and/or CD28 $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the $V_H$ peptide having a sequence as set forth in SEQ ID NO: 48 and $V_L$ peptide having a sequence as set forth in SEQ ID NO: 49 linked to a stalk portion ($S_1$) comprising an Fc region ($L_1$-Fc-$L_2$-$X_1$) comprising an ECD, a $T_M$, and an ICD are anchored to the surface of a viral particle, such as those provided for herein. In some embodiments, the identities of $L_1$, Fc, $L_2$, ECD, $T_M$, and ICD are as provided for herein. In some embodiments, the $V_H$ and $V_L$ peptides bind to an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region further comprising a transmembrane domain. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, TM is a transmembrane domain as provided for herein, and ICD is an intracellular domain as provided for herein or is absent. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising an ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising a CD8 and/or CD28 ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to an a stalk portion ($S_1$) comprising Fc region ($L_1$-Fc-$L_2$-$X_1$) comprising an ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 linked to a stalk portion ($S_1$) comprising an Fc region ($L_1$-Fc-$L_2$-$X_1$) comprising an ECD, a $T_M$, and an ICD are anchored to the surface of a viral particle, such as those provided for herein. In some embodiments, the identities of $L_1$, Fc, $L_2$, ECD, $T_M$, and ICD are as provided for herein. In some embodiments, $V_H$ and $V_L$ peptides bind to an immune cell, such as those provided herein.

In some embodiments, a polypeptide is provided comprising a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_H$ peptide and a $V_L$ peptide comprises a light chain CDR having a sequence of SEQ ID NO: 45-47; and/or a heavy chain CDR having a sequence of SEQ ID NO: 42-44. In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_H$ peptide and a $V_L$ peptide comprise a light chain CDR1 having a sequence of SEQ ID NO: 45; a light chain CDR2 having a sequence of SEQ ID NO: 46; a light chain CDR3 having a sequence of SEQ ID NO: 47; and/or a heavy chain CDR1 having a sequence of SEQ ID NO: 42; a heavy chain CDR2 having a sequence of SEQ ID NO: 43; and a heavy chain CDR3 having a sequence of SEQ ID NO: 44. In some embodiments, the CDRs in the $V_H$ or $V_L$ chain are as set forth in the combinations provided for herein.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_L$ peptide comprises a LCDR1 having a sequence of SEQ ID NO: 45; a LCDR2 having a sequence of SEQ ID NO: 46; and a LCDR3 having a sequence of SEQ ID NO: 47; and the $V_H$ peptide comprises a HCDR1 having a sequence of SEQ ID NO: 42; a HCDR2 having a sequence of SEQ ID NO: 43; and a HCDR3 having a sequence of SEQ ID NO: 44.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_L$ peptide comprises a LCDR1 having a sequence of SEQ ID NO: 45, wherein the LCDR1 comprises at most 1 conservative amino acid substitution, a LCDR2 having a sequence of SEQ ID NO: 46, wherein the LCDR2 comprises at most 1 conservative amino acid substitution, and a LCDR3 having a sequence of SEQ ID NO: 47, wherein the LCDR3 comprises at most 1 conservative amino acid substitution; and the $V_H$ peptide comprises a HCDR1 having a sequence of SEQ ID NO: 42, wherein the HCDR1 comprises at most 1 conservative amino acid substitution, a HCDR2 having a sequence of SEQ ID NO: 43, wherein the HCDR2 comprises at most 1 conservative amino acid substitution, and a HCDR3 having a sequence of SEQ ID NO: 44, wherein the HCDR3 comprises at most 1 conservative amino acid substitution.

In some embodiments, the polypeptide comprises a $V_H$ peptide and a $V_L$ peptide, wherein the $V_H$ peptide comprises a sequence of SEQ ID NO: 48 and the $V_L$ peptide comprises a sequence of SEQ ID NO: 49.

In some embodiments, the polypeptide as provided herein binds to non-human primate CD8. In some embodiments, the polypeptide as provided herein binds to human CD8.

As provided for herein, the different polypeptides ($V_H$ or $V_L$) described herein can be linked with a peptide linker or not linked with a peptide linker and instead for a continuous sequence. In some embodiments, the peptide linker comprises a sequence of $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5.

In some embodiments, the polypeptide comprising the linked peptide represented by a formula of $V_L$-Z-$V_H$ comprises a heavy chain variable region as set forth in SEQ ID NO: 48 linked via a linker sequence GGGGSGGGGSGGGGSGGGGS (SEQ ID NO: 72) to a light chain variable region as set forth in SEQ ID NO: 49. In some embodiments, the polypeptide comprising a $V_L$ linked via a peptide linker to a $V_H$ has the sequence as set forth below,

```
                                         (SEQ ID NO: 50)
NIVLTQSPASLAVSLGQRATISCRASESVDGFGNSFMNWYQQKPGQSPKL

LIYLASNLESGVPARFSGSGSRTDFTLTIDPVEADDAATYYCQQNNEDPY

TFGGGTKLEIKRGGGGSGGGGSGGGGSGGGGSEVQLQQSGPELVKPGASV

KISCKASRYTFTDYNLHWVKLSHEKSLEWIGFIYPYNGGTGYNQKFKNKA

KLTVDYSSSTAYMELRSLTSVDAAVYYCARDHRYNEGVSFDYWGQGTTLT

VSS.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50. In some embodiments, the polypeptide comprises a sequence that is at least 90% identical to a sequence of SEQ ID NO: 50. In some embodiments, the polypeptide comprises a sequence that is at least 95% identical to a sequence of SEQ ID NO: 50. In some embodiments, the polypeptide comprises a sequence that is at least 99% identical to a sequence of SEQ ID NO: 50. In some embodiments, the polypeptide comprises a sequence as set forth in SEQ ID NO: 50. In some embodiments, the polypeptide as set forth in SEQ ID NO: 50 is an antibody, or an antigen binding fragment thereof. In some embodiments, the antibody is an anti-CD8 antibody. In some embodiments, the anti-CD8 antibody binds to non-human primate CD8. In some embodiments, the anti-CD8 antibody binds to human CD8.

In some embodiments, the polypeptide comprising the linked peptide represented by a formula of $V_H$-Z-$V_L$ comprises a light chain variable region as set forth in SEQ ID NO: 49 linked via a linker sequence GGGGSGGGGSGGGGSGGGGS (SEQ ID NO: 72) to a heavy chain variable region as set forth in SEQ ID NO: 48. In some embodiments, the polypeptide comprising a $V_H$ linked via a peptide linker to a $V_L$ has the sequence as set forth below,

```
                                         (SEQ ID NO: 51)
EVQLQQSGPELVKPGASVKISCKASRYTFTDYNLHWVKLSHEKSLEWIGF

IYPYNGGTGYNQKFKNKAKLTVDYSSSTAYMELRSLTSVDAAVYYCARDH

RYNEGVSFDYWGQGTTLTVSSGGGGSGGGGSGGGGSGGGGSNIVLTQSPA

SLAVSLGQRATISCRASESVDGFGNSFMNWYQQKPGQSPKLLIYLASNLE

SGVPARFSGSGSRTDFTLTIDPVEADDAATYYCQQNNEDPYTFGGGTKLE

IKR
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51. In some embodiments, the polypeptide comprises a sequence that is at least 90% identical to a sequence of SEQ ID NO: 51. In some embodiments, the polypeptide comprises a sequence that is at least 95% identical to a sequence of SEQ ID NO: 51. In some embodiments, the polypeptide comprises a sequence that is at least 99% identical to a sequence of SEQ ID NO: 51. In some embodiments, the polypeptide comprises a sequence as set forth in SEQ ID NO: 51. In some embodiments, the polypeptide as set forth in SEQ ID NO: 51 is an antibody, or an antigen binding fragment thereof. In some embodiments, the antibody is an anti-CD8 antibody. In some embodiments, the anti-CD8 antibody binds to non-human primate CD8. In some embodiments, the anti-CD8 antibody binds to human CD8.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region, such as those provided herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising an ECD, a CD8 and/or CD28 $T_M$, and an ICD In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region, such as those provided herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising an ECD, a TM, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising an ECD, a CD8 and/or CD28 $T_M$, and an ICD In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 50 and comprises a stalk portion ($S_1$) comprising an Fc region, such as those provided herein. In some embodiments, the polypeptide comprises a sequence having a sequence as set forth in SEQ ID NO: 50 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence having a sequence as set forth in SEQ ID NO: 50 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence having a sequence as set forth in SEQ ID NO: 50 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 51 and comprises a stalk portion ($S_1$) comprising an Fc region, such as those provided herein. In some embodiments, the polypeptide comprises a sequence having a sequence as set forth in SEQ ID NO: 51 and comprises a stalk portion ($S_1$) comprising an Fc region, said Fc region further comprising a transmembrane domain, such as those provided herein. In some embodiments, the Fc region further comprising a transmembrane domain has a formula of $L_1$-Fc-$L_2$-$X_1$, wherein $L_1$ is a linker as provided for herein or is absent, Fc is a variant Fc region as provided for herein, $L_2$ is a linker as provided for herein or is absent, and $X_1$ is a polypeptide comprising a transmembrane domain as provided for herein. As provided for herein, $X_1$ may comprises a polypeptide having the formula ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising an ECD, a $T_M$, and an ICD. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising a CD8 and/or CD28 ECD, a $T_M$, and an ICD. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising an ECD, a CD8 and/or CD28 $T_M$, and an ICD. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising an ECD, a $T_M$, and an ICD, wherein the ICD comprises an env incorporation motif as provided for herein. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising a CD8 and/or CD28 ECD, a $T_M$, and an ICD, wherein the ICD comprises an env incorporation motif as provided for herein. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising an ECD, a CD8 and/or CD28 $T_M$, and an ICD, wherein the ICD comprises an env incorporation motif as provided for herein. In some embodiments, the polypeptide comprises a sequence having a sequence as set forth in SEQ ID NO: 51 and comprises a stalk portion ($S_1$) comprising an Fc region ($L_1$-Fc-$L_2$-$X_1$) comprising a CD8 and/or CD28 ECD, a CD8 and/or CD28 $T_M$, and an ICD, wherein the ICD comprises an env incorporation motif as provided for herein. In some embodiments, the polypeptide comprising a sequence having a sequence as set forth in SEQ ID NO: 51 and comprising a stalk portion ($S_1$) comprising an Fc region ($L_1$-Fc-$L_2$-$X_1$) comprising an ECD, a $T_M$, and an ICD, is anchored to the surface of a viral particle, such as those provided for herein. In some embodiments, the identities of $L_1$, Fc, $L_2$, ECD, $T_M$, and ICD are as provided for herein. In some embodiments, the polypeptide bind to an immune cell, such as those provided herein.

Targeting Moieties Comprising Flexible Polypeptides

In some embodiments, the $V_H$ and $V_L$ polypeptides are linked to a stalk portion ($S_1$) comprising a flexible polypeptide ($L_3$) as provided for herein. In some embodiments, the $V_H$ and $V_L$ polypeptides are linked to a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is as provided for herein. As provided for herein, $X_1$ may comprise a polypeptide having the formula of ECD-$T_M$-ICD, wherein ECD is an extracellular domain, or a fragment thereof as provided for herein or is absent, $T_M$ is a transmembrane domain as provided for herein, and ICD is an intracellular domain as provided for herein or is absent. Examples of ECD include, but are not limited to, a CD8 and/or CD28 ECD as provided for herein. Examples of $T_M$ include, but are not limited to, a CD8 and/or CD28 transmembrane domain as provided for herein. In any of the following embodiments, it is to be understood that the ECD, the ICD, or both may be optionally absent. Accordingly, an embodiment wherein $X_1$ comprises a CD8 and/or CD28 ECD, a CD8 and/or CD28 $T_M$, and an ICD comprising an Env incorporation motif is understood to encompass the following $X_1$ members: i) a CD8 and/or CD28 ECD, a CD8 and/or CD28 $T_M$, and an ICD comprising an Env incorporation motif; ii) a CD8 and/or CD28 $T_M$, and an ICD comprising an Env incorporation motif wherein the ECD is absent; iii) a CD8 and/or CD28 ECD, and a CD8 and/or CD28 $T_M$, wherein the ICD is absent; and iv) a CD8 and/or CD28 $T_M$ wherein both the ECD and the ICD are absent. Similarly, an embodiment wherein $X_1$ comprises a CD8 and/or CD28 $T_M$ and an ICD comprising an Env incorporation motif is understood to encompass the following $X_1$ members: i) a CD8 and/or CD28 $T_M$ and an ICD comprising an Env incorporation motif; and ii) a CD8 and/or CD28 $T_M$ wherein the ICD is absent. Similarly, an embodiment wherein $X_1$ comprises a CD8 and/or CD28 ECD and a CD8 and/or CD28 $T_M$ is understood to encompass the following $X_1$ members: i) a CD8 and/or CD28 ECD and a CD8 and/or CD28 $T_M$; and ii) a CD8 and/or CD28 $T_M$ wherein the ECD is absent. It is to be further understood that the preceding explanation is also true in embodiments where a specific ECD, $T_M$, or ICD are not recited. For example, an embodiment wherein $X_1$ comprises an ECD, a CD8 and/or CD28 $T_M$, and an ICD would be understood to encompass the following $X_1$ members: i) an ECD, a CD8 and/or CD28 $T_M$, and an ICD; ii) an ECD, and a CD8 and/or CD28 $T_M$ wherein the ICD is absent; iii) a CD8 and/or CD28 $T_M$, and an ICD wherein the ECD is absent; and iv) a CD8 and/or CD28 $T_M$ wherein the ECD and the ICD are absent. Similarly, an embodiment wherein $X_1$ comprises a CD8 and/or CD28 $T_M$ and an ICD is understood to encompass the following $X_1$ members: i) a CD8 and/or CD28 $T_M$ and an ICD; and ii) a CD8 and/or CD28 $T_M$ wherein the ICD is absent. Similarly, an embodiment wherein $X_1$ comprises an ECD and a CD8 and/or CD28 $T_M$ is understood to encompass the following $X_1$ members: i) an ECD and a CD8 and/or CD28 $T_M$; and ii) a CD8 and/or CD28 $T_M$ wherein the ECD is absent. Unless explicitly stated, the preceding examples and explanations are applicable to any embodiments that follow.

In some embodiments, $X_1$ comprises a CD8 and/or CD28 ECD, a $T_M$, and an ICD. In some embodiments, $X_1$ comprises an ECD, a CD8 and/or CD28 $T_M$, and an ICD. In some embodiments, $X_1$ comprises a CD8 and/or CD28 ECD, a CD8 and/or CD28 $T_M$, and an ICD. In some embodiments, $X_1$ comprises an ECD, a $T_M$, and an ICD, wherein the ICD comprises an Env incorporation motif as provided for herein. In some embodiments, $X_1$ comprises a CD8 and/or CD28 ECD, a $T_M$, and an ICD, wherein the ICD comprises an Env incorporation motif as provided for herein. In some embodiments, $X_1$ comprises an ECD, a CD8 and/or CD28 $T_M$, and an ICD, wherein the ICD comprises an Env incorporation motif as provided for herein. In some embodiments, $X_1$ comprises a CD8 and/or CD28 ECD, a CD8 and/or CD28 $T_M$, and an ICD, wherein the ICD comprises an Env incorporation motif as provided for herein.

In some embodiments, the $V_H$ and $V_L$ polypeptides provided herein are linked to a stalk portion ($S_1$) comprising a flexible polypeptide ($L_3$) as provided for herein. In some embodiments, the $V_H$ and $V_L$ polypeptides provided herein are linked to a stalk portion ($S_1$) comprising a flexible polypeptide ($L_3$) further comprising a polypeptide comprising a transmembrane domain as provided for herein. In some embodiments the flexible polypeptide ($L_3$) further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or a fragment thereof as provided for herein, or is absent; $T_M$ is a transmembrane domain as provided for herein; and ICD is an intracellular domain as provided for herein. In some embodiments, the $V_H$ and $V_L$ polypeptides provided herein are linked to a stalk portion ($S_1$) comprising a flexible polypeptide ($L_3$-$X_1$) comprising a CD8 and/or CD28 ECD, a $T_M$, and an ICD. In some embodiments, the $V_H$ and $V_L$ polypeptides provided herein are linked to a stalk portion ($S_1$) comprising a flexible polypeptide ($L_3$-$X_1$) comprising an ECD, a CD8 and/or CD28 $T_M$, and an ICD. In some embodiments, the $V_H$ and $V_L$ polypeptides provided herein are linked to a stalk portion ($S_1$) comprising a flexible polypeptide ($L_3$-$X_1$) comprising a CD8 and/or CD28 ECD, a CD8 and/or CD28 $T_M$, and an ICD. In some embodiments, the $V_H$ and $V_L$ polypeptides provided herein are linked to a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the $V_H$ and $V_L$ polypeptides provided herein are linked to a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the $V_H$ and $V_L$ polypeptides provided herein are linked to a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the $V_H$ and $V_L$ polypeptides provided herein are linked to a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the $V_H$ and $V_L$ polypeptides provided herein linked to a stalk portion ($S_1$) comprising a flexible polypeptide ($L_3$-$X_1$) comprising an ECD, a $T_M$, and an ICD are anchored to the surface of a viral particle, such as those provided for herein. In some embodiments, the identities of $L_3$, $X_1$, ECD, $T_M$, and ICD are as provided for herein. In some embodiments, the $V_H$ and $V_L$ polypeptides bind to an immune cell, such as those provided herein.

In some embodiments, a $V_H$ peptide having a sequence as set forth in SEQ ID NO: 36 and a $V_L$ peptide having a sequence as set forth in SEQ ID NO: 37 are linked to a stalk portion ($S_1$) comprising a flexible polypeptide ($L_3$-$X_1$) comprising an ECD, a $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising a CD8 and/or CD28 ECD, a $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising an ECD, a CD8 and/or CD28 $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising a CD8 and/or CD28 ECD, a CD8 and/or CD28 $T_M$, and an ICD. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the $V_H$ peptide having a sequence as set forth in SEQ ID NO: 36 and $V_L$ peptide having a sequence as set forth in SEQ ID NO: 37 are linked to a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the $V_H$ peptide having a sequence as set forth in SEQ ID NO: 36 and $V_L$ peptide having a sequence as set forth in SEQ ID NO: 37 linked to a stalk portion ($S_1$) comprising a flexible polypeptide ($L_3$-$X_1$) comprising an ECD, a $T_M$, and an ICD are anchored to the surface of a viral particle, such as those provided for herein. In some embodiments, the identities of $L_3$, $X_1$, ECD, $T_M$, and ICD are as provided for herein. In some embodiments, the $V_H$ and $V_L$ peptides bind to an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$) as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$) further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein, or is absent. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising a CD8 and/or CD28 ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising an ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising a CD8 and/or CD28 ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 are linked to a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 37 linked to a stalk portion ($S_1$) comprising a flexible polypeptide ($L_3$-$X_1$) comprising an ECD, a $T_M$, and an ICD are anchored to the surface of a viral particle, such as those provided for herein. In some embodiments, the identities of $L_3$, $X_1$, ECD, $T_M$, and ICD are as provided for herein. In some embodiments, the $V_H$ and $V_L$ peptides bind to an immune cell, such as those provided herein.

In some embodiments, a polypeptide is provided comprising a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_H$ peptide and a $V_L$ peptide comprises a light chain CDR having a sequence of SEQ ID NO: 33-35; and/or a heavy chain CDR having a sequence of SEQ ID NO: 30-32. In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_H$ peptide and a $V_L$ peptide comprise a light chain CDR1 having a sequence of SEQ ID NO: 33; a light chain CDR2 having a sequence of SEQ ID NO: 34; a light chain CDR3 having a sequence of SEQ ID NO: 35; and/or a heavy chain CDR1 having a sequence of SEQ ID NO: 30; a heavy chain CDR2 having a sequence of SEQ ID NO: 31; and a heavy chain CDR3 having a sequence of SEQ ID NO: 32. In some embodiments, the CDRs in the $V_H$ or $V_L$ chain are as set forth in the combinations provided for herein.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_L$ peptide comprises a LCDR1 having a sequence of SEQ ID NO: 33; a LCDR2 having a sequence of SEQ ID NO: 34; and a LCDR3 having a sequence of SEQ ID NO: 35; and the $V_H$ peptide comprises a HCDR1 having a sequence of SEQ ID NO: 30; a HCDR2 having a sequence of SEQ ID NO: 31; and a HCDR3 having a sequence of SEQ ID NO: 32.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 36; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 37; provided that the $V_L$ peptide comprises a LCDR1 having a sequence of SEQ ID NO: 33, wherein the LCDR1 comprises at most 1 conservative amino acid substitution, a LCDR2 having a sequence of SEQ ID NO: 34, wherein the LCDR2 comprises at most 1 conservative amino acid substitution, and a LCDR3 having a sequence of SEQ ID NO: 35, wherein the LCDR3 comprises at most 1 conservative amino acid substitution; and the $V_H$ peptide comprises a HCDR1 having a sequence of SEQ ID NO: 30, wherein the HCDR1 comprises at most 1 conservative amino acid substitution, a HCDR2 having a sequence of SEQ ID NO: 31, wherein the HCDR2 comprises at most 1 conservative amino acid substitution, and a HCDR3 having a sequence of SEQ ID NO: 32, wherein the HCDR3 comprises at most 1 conservative amino acid substitution.

In some embodiments, the polypeptide comprises a $V_H$ peptide and a $V_L$ peptide, wherein the $V_H$ peptide comprises a sequence of SEQ ID NO: 36 and the $V_L$ peptide comprises a sequence of SEQ ID NO: 37.

In some embodiments, the polypeptide as provided herein binds to non-human primate CD7. In some embodiments, the polypeptide as provided herein binds to human CD7.

As provided for herein, the different polypeptides ($V_H$ or $V_L$) described herein can be linked with a peptide linker or not linked with a peptide linker and instead for a continuous sequence. In some embodiments, the peptide linker comprises a sequence of $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5.

In some embodiments, the polypeptide comprising the linked peptide represented by a formula of $V_L$-Z-$V_H$ comprises a heavy chain variable region as set forth in SEQ ID NO: 36 linked via a linker sequence GGGGSGGGGSGGGGSGGGGS (SEQ ID NO: 72) to a light chain variable region as set forth in SEQ ID NO: 37. In some embodiments, the polypeptide comprising a $V_L$ linked via a peptide linker to a $V_H$ has the sequence as set forth below,

```
                                        (SEQ ID NO: 38)
DILLTQSPAILSVSPGERVSFSCRASQSIGTSIHWYQQRTNDSPRLLIKY

ASESISGIPSRFSGSGSGTDFTLSINSVESEDIADYYCQQSNSWPTTFGG

GTKLEIKRGGGGSGGGGSGGGGSGGGGSQVQLQQPGAELVKPGASVKLSC

KASGYPFTSYWIHWVKQRPGRGLEWLGRIDPNSGDTKYNEKFKNKATLTV

DKSSTTAYMQLSSLTSEDSAVYYCARSPYYSNDNSMDYWGQGTSVTVSS
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38. In some embodiments, the polypeptide comprises a sequence that is at least 90% identical to a sequence of SEQ ID NO: 38. In some embodiments, the polypeptide comprises a sequence that is at least 95% identical to a sequence of SEQ ID NO: 38. In some embodiments, the polypeptide comprises a sequence that is at least 99% identical to a sequence of SEQ ID NO: 38. In some embodiments, the polypeptide comprises a sequence as set forth in SEQ ID NO: 38. In some embodiments, the polypeptide as set forth in SEQ ID NO: 38 is an antibody, or an antigen binding fragment thereof. In some embodiments, the antibody is an anti-CD7 antibody. In some embodiments, the anti-CD7 antibody binds to non-human primate CD7. In some embodiments, the anti-CD7 antibody binds to human CD7.

In some embodiments, the polypeptide comprising the linked peptide represented by a formula of $V_H$-Z-$V_L$ comprises a light chain variable region as set forth in SEQ ID NO: 37 linked via a linker sequence GGGGSGGGGSGGGGSGGGGS (SEQ ID NO: 72) to a heavy chain variable region as set forth in SEQ ID NO: 36. In some embodiments, a polypeptide comprising a $V_H$ linked via a peptide linker to a $V_L$ has the sequence as set forth below,

```
                                        (SEQ ID NO: 39)
QVQLQQPGAELVKPGASVKLSCKASGYPFTSYWIHWVKQRPGRGLEWLGR

IDPNSGDTKYNEKFKNKATLTVDKSSTTAYMQLSSLTSEDSAVYYCARSP

YYSNDNSMDYWGQGTSVTVSSGGGGSGGGGSGGGGSGGGGSDILLTQSPA

ILSVSPGERVSFSCRASQSIGTSIHWYQQRTNDSPRLLIKYASESISGIP

SRFSGSGSGTDFTLSINSVESEDIADYYCQQSNSWPTTFGGGTKLEIKR.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39. In some embodiments, the polypeptide comprises a sequence that is at least 90% identical to a sequence of SEQ ID NO: 39. In some embodiments, the polypeptide comprises a sequence that is at least 95% identical to a sequence of SEQ ID NO: 39. In some embodiments, the polypeptide comprises a sequence that is at least 99% identical to a sequence of SEQ ID NO: 39. In some embodiments, the polypeptide comprises a sequence as set forth in SEQ ID NO: 39. In some embodiments, the polypeptide as set forth in SEQ ID NO: 39 is an antibody, or an antigen binding fragment thereof. In some embodiments, the antibody is an anti-CD7 antibody. In some embodiments, the anti-CD7 antibody binds to non-human primate CD7. In some embodiments, the anti-CD7 antibody binds to human CD7.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$) as provided for herein. In some embodiments, a polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 38 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$) as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein, or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 39 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 38 and comprises a stalk portion ($S_1$) comprising a flexible polypeptide ($L_3$) as provided for herein. In some embodiments, the polypeptide comprises a sequence having a sequence as set forth in SEQ ID NO: 38 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the polypeptide comprises a sequence having a sequence as set forth in SEQ ID NO: 38 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence having a sequence as set forth in SEQ ID NO: 38 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence having a sequence as set forth in SEQ ID NO: 38 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 38 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence having a sequence as set forth in SEQ ID NO: 38 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence having a sequence as set forth in SEQ ID NO: 38 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence having a sequence as set forth in SEQ ID NO: 38 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence having a sequence as set forth in SEQ ID NO: 38 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 39 and comprises a stalk portion ($S_1$) comprising a flexible polypeptide ($L_3$) as provided for herein. In some embodiments, a polypeptide comprises a sequence having a sequence as set forth in SEQ ID NO: 39 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain or fragment thereof as provided for herein, or is absent; $T_M$ is a transmembrane domain as provided for herein; and ICD is an intracellular domain as provided for herein, or is absent. In some embodiments, the polypeptide comprises a sequence having a sequence as set forth in SEQ ID NO: 39 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence having a sequence as set forth in SEQ ID NO: 39 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence having a sequence as set forth in SEQ ID NO: 39 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 39 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence having a sequence as set forth in SEQ ID NO: 39 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence having a sequence as set forth in SEQ ID NO: 39 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence having a sequence as set forth in SEQ ID NO: 39 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence having a sequence as set forth in SEQ ID NO: 39 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, a $V_H$ peptide having a sequence as set forth in SEQ ID NO: 48 and a $V_L$ peptide having a sequence as set forth in SEQ ID NO: 49 are linked to a stalk portion ($S_1$) comprising a flexible polypeptide ($L_3$) as provided for herein. In some embodiments, the $V_H$ peptide having a sequence as set forth in SEQ ID NO: 48 and the $V_L$ peptide having a sequence as set forth in SEQ ID NO: 49 are linked to a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain or fragment thereof as provided for herein, or is absent; $T_M$ is a transmembrane domain as provided for herein; and ICD is an intracellular domain as provided for herein, or is absent. In some embodiments, the $V_H$ peptide having a sequence as set forth in SEQ ID NO: 48 and the $V_L$ peptide having a sequence as set forth in SEQ ID NO: 49 are linked to a stalk portion ($S_1$) comprising a flexible polypeptide ($L_3$-$X_1$) comprising a CD8 and/or CD28 ECD, a $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising an ECD, a CD8 and/or CD28 $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising a CD8 and/or CD28 ECD, a CD8 and/or CD28 $T_M$, and an ICD. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the $V_H$ peptide having a sequence as set forth in SEQ ID NO: 48 and $V_L$ peptide having a sequence as set forth in SEQ ID NO: 49 are linked to a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the $V_H$ peptide having a sequence as set forth in SEQ ID NO: 48 and $V_L$ peptide having a sequence as set forth in SEQ ID NO: 49 linked to a stalk portion ($S_1$) comprising a flexible polypeptide ($L_3$-$X_1$) comprising an ECD, a $T_M$, and an ICD are anchored to the surface of a viral particle, such as those provided for herein. In some embodiments, the identities of $L_3$, $X_1$, ECD, $T_M$, and ICD are as provided for herein. In some embodiments, the $V_H$ and $V_L$ peptides bind to an immune cell, such as those provided herein.

In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$) as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising a CD8 and/or CD28 ECD, a $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising an ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising a CD8 and/or CD28 ECD, a CD8 and/or CD28 $T_M$, and an ICD. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 49 are linked to a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the $V_H$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprising a sequence that is at least 85%, 86%, 87%, 88%, 89%, 90%, 91%, 92%, 93%, 94%, 95%, 96%, 97%, 98%, or 99% identical to a sequence of SEQ ID NO:

49 linked to a stalk portion ($S_1$) comprising a flexible polypeptide ($L_3$-$X_1$) comprising an ECD, a $T_M$, and an ICD are anchored to the surface of a viral particle, such as those provided for herein. In some embodiments, the identities of $L_3$, $X_1$, ECD, $T_M$, and ICD are as provided for herein. In some embodiments, the $V_H$ and $V_L$ peptides bind to an immune cell, such as those provided herein.

In some embodiments, a polypeptide is provided comprising a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_H$ peptide and a $V_L$ peptide comprise a light chain CDR having a sequence of SEQ ID NO: 45-47; and/or a heavy chain CDR having a sequence of SEQ ID NO: 42-44. In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_H$ peptide and a $V_L$ peptide comprise a light chain CDR1 having a sequence of SEQ ID NO: 45; a light chain CDR2 having a sequence of SEQ ID NO: 46; a light chain CDR3 having a sequence of SEQ ID NO: 47; and/or a heavy chain CDR1 having a sequence of SEQ ID NO: 42; a heavy chain CDR2 having a sequence of SEQ ID NO: 43; and a heavy chain CDR3 having a sequence of SEQ ID NO: 44. In some embodiments, the CDRs in the $V_H$ or $V_L$ chain are as set forth in the combinations provided for herein.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_L$ peptide comprises a LCDR1 having a sequence of SEQ ID NO: 45; a LCDR2 having a sequence of SEQ ID NO: 46; and a LCDR3 having a sequence of SEQ ID NO: 47; and the $V_H$ peptide comprises a HCDR1 having a sequence of SEQ ID NO: 42; a HCDR2 having a sequence of SEQ ID NO: 43; and a HCDR3 having a sequence of SEQ ID NO: 44.

In some embodiments, the polypeptide comprises a $V_H$ peptide and a $V_L$ peptide, wherein the $V_H$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 48; and the $V_L$ peptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 49; provided that the $V_L$ peptide comprises a LCDR1 having a sequence of SEQ ID NO: 45, wherein the LCDR1 comprises at most 1 conservative amino acid substitution, a LCDR2 having a sequence of SEQ ID NO: 46, wherein the LCDR2 comprises at most 1 conservative amino acid substitution, and a LCDR3 having a sequence of SEQ ID NO: 47, wherein the LCDR3 comprises at most 1 conservative amino acid substitution; and the $V_H$ peptide comprises a HCDR1 having a sequence of SEQ ID NO: 42, wherein the HCDR1 comprises at most 1 conservative amino acid substitution, a HCDR2 having a sequence of SEQ ID NO: 43, wherein the HCDR2 comprises at most 1 conservative amino acid substitution, and a HCDR3 having a sequence of SEQ ID NO: 44, wherein the HCDR3 comprises at most 1 conservative amino acid substitution.

In some embodiments, the polypeptide comprises a $V_H$ peptide and a $V_L$ peptide, wherein the $V_H$ peptide comprises a sequence of SEQ ID NO: 48 and the $V_L$ peptide comprises a sequence of SEQ ID NO: 49.

In some embodiments, the polypeptide as provided herein binds to non-human primate CD8. In some embodiments, a polypeptide as provided herein binds to human CD8.

As provided for herein, the different polypeptides ($V_H$ or $V_L$) described herein can be linked with a peptide linker or not linked with a peptide linker and instead for a continuous sequence. In some embodiments, the peptide linker comprises a sequence of $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5. The linked peptide format can be represented by a formula of $V_H$-Z-$V_L$ or $V_L$-Z-$V_H$, wherein Z is the peptide linker. In some embodiments, Z is $(GGGGS)_n$ (SEQ ID NO: 55), wherein each n is independently 1-5. In some embodiments, n is 1. In some embodiments, n is 2. In some embodiments, n is 3. In some embodiments, n is 4. In some embodiments, n is 5.

In some embodiments, the polypeptide comprising the linked peptide represented by a formula of $V_L$-Z-$V_H$ comprises a heavy chain variable region as set forth in SEQ ID NO: 48 linked via a linker sequence GGGGSGGGGSGGGGSGGGGS (SEQ ID NO: 72) to a light chain variable region as set forth in SEQ ID NO: 49. In some embodiments, the polypeptide comprising a $V_L$ linked via a peptide linker to a $V_H$ has the sequence as set forth below,

```
                                          (SEQ ID NO: 50)
NIVLTQSPASLAVSLGQRATISCRASESVDGFGNSFMNWYQQKPGQSPKL

LIYLASNLESGVPARFSGSGSRTDFTLTIDPVEADDAATYYCQQNNEDPY

TFGGGTKLEIKRGGGGSGGGGSGGGGSGGGGSEVQLQQSGPELVKPGASV

KISCKASRYTFTDYNLHWVKLSHEKSLEWIGFIYPYNGGTGYNQKFKNKA

KLTVDYSSSTAYMELRSLTSVDAAVYYCARDHRYNEGVSFDYWGQGTTLT

VSS.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50. In some embodiments, the polypeptide comprises a sequence that is at least 90% identical to a sequence of SEQ ID NO: 50. In some embodiments, the polypeptide comprises a sequence that is at least 95% identical to a sequence of SEQ ID NO: 50. In some embodiments, the polypeptide comprises a sequence that is at least 99% identical to a sequence of SEQ ID NO: 50. In some embodiments, the polypeptide comprises a sequence as set forth in SEQ ID NO: 50. In some embodiments, the polypeptide as set forth in SEQ ID NO: 50 is an antibody, or an antigen binding fragment thereof. In some embodiments, the antibody is an anti-CD8 antibody. In some embodiments, the anti-CD8 antibody binds to non-human primate CD8. In some embodiments, the anti-CD8 antibody binds to human CD8.

In some embodiments, the polypeptide comprising the linked peptide represented by a formula of $V_H$-Z-$V_L$ comprises a light chain variable region as set forth in SEQ ID NO: 49 linked via a linker sequence GGGGSGGGGSGGGGSGGGGS (SEQ ID NO: 72) to a heavy chain variable region as set forth in SEQ ID NO: 48. In some embodiments, the polypeptide comprising a $V_H$ linked via a peptide linker to a $V_L$ has the sequence as set forth below,

```
                                    (SEQ ID NO: 51)
EVQLQQSGPELVKPGASVKISCKASRYTFTDYNLHWVKLSHEKSLEWIGF

IYPYNGGTGYNQKFKNKAKLTVDYSSSTAYMELRSLTSVDAAVYYCARDH

RYNEGVSFDYWGQGTTLTVSSGGGGSGGGGSGGGGSGGGGSNIVLTQSPA

SLAVSLGQRATISCRASESVDGFGNSFMNWYQQKPGQSPKLLIYLASNLE

SGVPARFSGSGSRTDFTLTIDPVEADDAATYYCQQNNEDPYTFGGGTKLE

IKR.
```

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51. In some embodiments, the polypeptide comprises a sequence that is at least 90% identical to a sequence of SEQ ID NO: 51. In some embodiments, the polypeptide comprises a sequence that is at least 95% identical to a sequence of SEQ ID NO: 51. In some embodiments, the polypeptide comprises a sequence that is at least 99% identical to a sequence of SEQ ID NO: 51. In some embodiments, the polypeptide comprises a sequence as set forth in SEQ ID NO: 51. In some embodiments, the polypeptide as set forth in SEQ ID NO: 51 is an antibody, or an antigen binding fragment thereof. In some embodiments, the antibody is an anti-CD8 antibody. In some embodiments, the anti-CD8 antibody binds to non-human primate CD8. In some embodiments, the anti-CD8 antibody binds to human CD8.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$) as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 50 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$) as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence that is at least 85%, 86%, 87%, 88%, 89%, 90%, 91%, 92%, 93%, 94%, 95%, 96%, 97%, 98%, or 99% identical to a sequence of SEQ ID NO: 51 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 50 and comprises a stalk portion ($S_1$) comprising a flexible polypeptide ($L_3$) as provided for herein. In some embodiments, the polypeptide comprises a sequence having a sequence as set forth in SEQ ID NO: 50 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein or is absent. In some embodiments, the polypeptide comprises a sequence having a sequence as set forth in SEQ ID NO: 50 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence having a sequence as set forth in SEQ ID NO: 50 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence having a sequence as set forth in SEQ ID NO: 50 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 50 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence having a sequence as set forth in SEQ ID NO: 50 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence having a sequence as set forth in SEQ ID NO: 50 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence having a sequence as set forth in SEQ ID NO: 50 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence having a sequence as set forth in SEQ ID NO: 50 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

In some embodiments, the polypeptide comprises a sequence having a sequence as set forth in SEQ ID NO: 51 and comprises a stalk portion ($S_1$) comprising a flexible polypeptide ($L_3$) as provided for herein. In some embodiments, the polypeptide comprises a sequence having a sequence as set forth in SEQ ID NO: 51 and comprises a stalk portion ($S_1$) comprising a flexible polypeptide further comprising a polypeptide comprising a transmembrane domain as provided for herein. In some embodiments, the flexible polypeptide further comprising a polypeptide comprising a transmembrane domain is represented by the formula $L_3$-$X_1$, wherein $L_3$ is a flexible polypeptide as provided for herein and $X_1$ is a polypeptide comprising a transmembrane domain as provided for herein. As provided for herein, $X_1$ may comprise a polypeptide having the formula of ECD-$T_M$-ICD, wherein ECD is an extracellular domain, or fragment thereof as provided for herein, or is absent; $T_M$ is a transmembrane domain as provided for herein; and ICD is an intracellular domain as provided for herein, or is absent. In some embodiments, the polypeptide comprises a sequence having a sequence as set forth in SEQ ID NO: 51 and comprises a stalk portion ($S_1$) comprising a flexible polypeptide ($L_3$-$X_1$) comprising a CD8 and/or CD28 ECD, a $T_M$, and an ICD. In some embodiments, the polypeptide comprises a sequence having a sequence as set forth in SEQ ID NO: 51 and comprises a stalk portion ($S_1$) comprising a flexible polypeptide ($L_3$-$X_1$) comprising an ECD, a CD8 and/or CD28 $T_M$, and an ICD. In some embodiments, the polypeptide comprises a sequence having a sequence as set forth in SEQ ID NO: 51 and comprises a stalk portion ($S_1$) comprising a flexible polypeptide ($L_3$-$X_1$) comprising a CD8 and/or CD28 ECD, a CD8 and/or CD28 $T_M$, and an ICD. In some embodiments, the polypeptide comprises a sequence having a sequence as set forth in SEQ ID NO: 51 and comprises a stalk portion ($S_1$) comprising a flexible polypeptide ($L_3$-$X_1$) comprising an ECD, a $T_M$, and an ICD, wherein the ICD comprises an Env incorporation motif as provided for herein. In some embodiments, the polypeptide comprises a sequence having a sequence as set forth in SEQ ID NO: 51 and comprises a stalk portion ($S_1$) comprising a flexible polypeptide ($L_3$-$X_1$) comprising a CD8 and/or CD28 ECD, a $T_M$, and an ICD, wherein the ICD comprises an Env incorporation motif as provided for herein. In some embodiments, the polypeptide comprises a sequence having a sequence as set forth in SEQ ID NO: 51 and comprises a stalk portion ($S_1$) comprising a flexible polypeptide ($L_3$-$X_1$) comprising an ECD, a CD8 and/or CD28 $T_M$, and an ICD, wherein the ICD comprises an Env incorporation motif as provided for herein. In some embodiments, the polypeptide comprises a sequence having a sequence as set forth in SEQ ID NO: 51 and comprises a stalk portion ($S_1$) comprising a flexible polypeptide ($L_3$-$X_1$) comprising a CD8 and/or CD28 ECD, a CD8 and/or CD28 $T_M$, and an ICD, wherein the ICD comprises an Env incorporation motif as provided for herein. In some embodiments, the polypeptide comprising a sequence having a sequence as set forth in SEQ ID NO: 51 and comprising a stalk portion ($S_1$) comprising a flexible polypeptide ($L_3$-$X_1$) comprising an ECD, a $T_M$, and an ICD, is anchored to the surface of a viral particle, such as those provided for herein. In some embodiments, the identities of $L_3$, ECD, $T_M$, and ICD are as provided for herein. In some embodiments, the polypeptide bind to an immune cell, such as those provided herein.

Expressed Polypeptides of Interest

In some embodiments, the viral particle comprising a heterologous viral glycoprotein and a targeting moiety further comprises a nucleic acid molecule encoding for a heterologous molecule of interest or "cargo." In some embodiments, the heterologous viral glycoprotein is as provided for herein. In some embodiments, the targeting moiety is as provided for herein. As used herein, heterologous molecule of interest is meant to refer to any product that may be encoded by a nucleic acid molecule. As non-limiting examples, "cargo" or "heterologous molecule of interest" may refer to an siRNA, an shRNA, a peptide, a polypeptide, a protein, a viral payload, a viral genome, or a combination thereof. In some embodiments, the heterologous molecule of interest is an siRNA, an shRNA, a non-coding RNA (e.g. a guide RNA for a CRISPR system), a peptide, a polypeptide, a protein, a viral payload, a viral genome, a chimeric antigen receptor ("CAR"), or a combination thereof. In some embodiments, the polypeptide is a CAR.

A "chimeric antigen receptor" or "CAR" as used herein refers to an antigen-binding domain that is fused, directly, or indirectly (e.g. via a hinge or transmembrane domain to an intracellular signaling domain capable of activating or stimulating an immune cell. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries). In various embodiments, this scFv is fused to a transmembrane domain and then to an intracellular signaling domain. However, the antigen binding domain can be any molecule that can bind to the target on the cell. For example, the antigen binding domain of a CAR can be an antibody, a scFv antibody, an antigen binding domain, an ankyrin repeat (e.g. DARPIN), a VHH domain antibody, a nanobody, single domain antibody, a FN3 domain, or any combination thereof. In some embodiments, a CAR includes those that solely provide CD3ξ (signals upon antigen binding. In some embodiments, the CAR includes those that provide both costimulation (e.g. CD28 or CD137) and activation (CD3 ξ). In some embodiments, the CARs include those that provide multiple costimulation (e.g. CD28 and CD137) and activation (CD3 ξ). In various embodiments, the CAR is selected to have high affinity or avidity for the antigen. In some embodiments, the antigen-binding domain binds to CD20. In some embodiments, the antigen-binding domain comprises a CD20 antibody, or fragment thereof. In some embodiments, antibody fragments are as provided for herein, such as but not limited to a scFv antibody, an antigen binding domain, an ankyrin repeat (e.g. DARPIN), a VHH domain antibody, a nanobody, single domain antibody, a FN3 domain, or any combination thereof.

In some embodiments, the antigen-binding domain of the CAR comprises a $V_H$ domain, a $V_L$ domain, or a $V_H$ and a $V_L$ domain. In some embodiments, the $V_H$ domain comprises an amino acid sequence having at least 75%, 80%, 85%, 86%, 87%, 88%, 89%, 90%, 91%, 92%, 93%, 94%, 95%, 96%, 97%, 98%, 99%, or 100% identity to SEQ ID NO: 89, or any value or range in-between.

(SEQ ID NO: 89)

```
EVQLVESGGGLVQPGRSLRLSCAASGFTFNDYAMHWVRQAPGKGLEWVST

ISWNSGSIGYADSVKGRFTISRDNAKKSLYLQMNSLRAEDTALYYCAKDI

QYGNYYYGMDVWGQGTTVTVSS
```

In some embodiments, the $V_H$ domain comprises an amino acid sequence having at least 90% identity to SEQ ID NO: 89. In some embodiments, the $V_H$ domain comprises an amino acid sequence having at least 95% identity to SEQ ID NO: 89. In some embodiments, the $V_H$ domain comprises an amino acid sequence having at least 98% identity to SEQ ID NO: 89. In some embodiments, the $V_H$ domain comprises an amino acid sequence having at least 99% identity to SEQ ID NO: 89. In some embodiments, the $V_H$ domain comprises an amino acid sequence having the sequence of SEQ ID NO: 89.

In some embodiments, the $V_L$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 90, or any value or range in-between.

(SEQ ID NO: 90)

```
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPITFGQ

GTRLEIK
```

In some embodiments, the $V_L$ domain comprises an amino acid sequence having at least 90% identity to SEQ ID NO: 90. In some embodiments, the $V_L$ domain comprises an amino acid sequence having at least 95% identity to SEQ ID NO: 90. In some embodiments, the $V_L$ domain comprises an amino acid sequence having at least 98% identity to SEQ ID NO: 90. In some embodiments, the $V_L$ domain comprises an amino acid sequence having at least 99% identity to SEQ ID NO: 90. In some embodiments, the $V_L$ domain comprises an amino acid sequence having the sequence of SEQ ID NO: 90.

In some embodiments, the antigen-binding domain of the CAR comprises a $V_H$ domain and a $V_L$ domain. In some embodiments, the $V_H$ and $V_L$ domain are not linked by a linker peptide. In some embodiments, the $V_H$ and $V_L$ domain are linked by a linker peptide, such as those as provided for herein, including but not limited to: $(GGGGS)_n$ (SEQ ID NO: 55), wherein each n is independently 1-5. In some embodiment n is 1. In some embodiment n is 2. In some embodiment n is 3. In some embodiment n is 4. In some embodiment n is 5.

In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having at least 90% identity to SEQ ID NO: 90. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having at least 95% identity to SEQ ID NO: 90. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having at least 98% identity to SEQ ID NO: 90. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having at least 99% identity to SEQ ID NO: 90. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 89, and comprises a $V_L$ having the sequence of SEQ ID NO: 90. In some embodiments, the antigen-binding domain of the CAR comprising a $V_H$ domain and a $V_L$ domain comprises a $V_H$ domain having at least 90% identity to SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having at least 95% identity to SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having at least 98% identity to SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having at least 99% identity to SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having an amino acid sequence of SEQ ID NO: 89, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 90. In some embodiments, the antigen-binding domain of the CAR comprising a $V_H$ domain and a $V_L$ domain comprises a $V_H$ domain having at least 90% identity to SEQ ID NO: 89, and comprises a $V_L$ having at least 90% identity to SEQ ID NO: 90. In some embodiments, the antigen-binding domain of the CAR comprising a $V_H$ domain and a $V_L$ domain comprises a $V_H$ domain having at least 95% identity to SEQ ID NO: 89, and comprises a $V_L$ having at least 90% identity to SEQ ID NO: 90. In some embodiments, the antigen-binding domain of the CAR comprising a $V_H$ domain and a $V_L$ domain comprises a $V_H$ domain having at least 90% identity to SEQ ID NO: 89, and comprises a $V_L$ having at least 95% identity to SEQ ID NO: 90. In some embodiments, the antigen-binding domain of the CAR comprising a $V_H$ domain and a $V_L$ domain comprises a $V_H$ domain having at least 95% identity to SEQ ID NO: 89, and comprises a $V_L$ having at least 95% identity to SEQ ID NO: 90. In some embodiments, the antigen-binding domain of the CAR comprising a $V_H$ domain and a $V_L$ domain comprises a $V_H$ domain having at least 98% identity to SEQ ID NO: 89, and comprises a $V_L$ having at least 98% identity to SEQ ID NO: 90. In some embodiments, the antigen-binding domain of the CAR comprising a $V_H$ domain and a $V_L$ domain comprises a $V_H$ domain having at least 99% identity to SEQ ID NO: 89, and comprises a $V_L$ having at least 99% identity to SEQ ID NO: 90. In some embodiments, the antigen-binding domain of the CAR comprising a $V_H$ domain and a $V_L$ domain comprises a $V_H$ domain having an amino acid sequence of SEQ ID NO: 89, and comprises a $V_L$ having an amino acid sequence of SEQ ID NO: 90.

In some embodiments, the antigen-binding domain of the CAR comprises a formula of $V_H$-Z-$V_L$, wherein $V_H$ is a heavy chain variable region comprising the amino acid sequence of SEQ ID NO: 89, Z is a linker comprising the amino acid sequence GGGGSGGGGSGGGGS (SEQ ID NO: 91), and $V_L$ is a light chain variable region comprising the amino acid sequence of SEQ ID NO: 90. In some embodiments, the antigen-binding domain of the CAR comprising a formula of $V_H$-Z-$V_L$ has an amino acid sequence as set forth below:

(SEQ ID NO: 92)

```
EVQLVESGGGLVQPGRSLRLSCAASGFTENDYAMHWVRQAPGKGLEWVST

ISWNSGSIGYADSVKGRFTISRDNAKKSLYLQMNSLRAEDTALYYCAKDI

QYGNYYYGMDVWGQGTTVTVSSGGGGSGGGGSGGGGSEIVLTQSPATLSL

SPGERATLSCRASQSVSSYLAWYQQKPGQAPRLLIYDASNRATGIPARFS

GSGSGTDFTLTISSLEPEDFAVYYCQQRSNWPITFGQGTRLEIK
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 92. In some embodiments, the antigen-binding domain of the CAR comprises an amino acid sequence having at least 90% identity to a sequence of SEQ ID NO: 92. In some embodiments, the antigen-binding domain of the CAR comprises an amino acid sequence having at least 95% identity to a sequence of SEQ ID NO: 92. In some embodiments, the antigen-binding domain of the CAR comprises an amino acid sequence having at least 98% identity to a sequence of SEQ ID NO: 92. In some embodiments, the antigen-binding domain of the CAR comprises an amino acid sequence having at least 99% identity to a sequence of SEQ ID NO: 92. In some embodiments, the antigen-binding domain of the CAR comprises the amino acid sequence of SEQ ID NO: 92.

In some embodiments, the antigen-binding domain of the CAR comprises a formula of $V_L$-Z-$V_H$, wherein $V_L$ is a light chain variable region comprising the amino acid sequence of SEQ ID NO: 90, Z is a linker comprising the amino acid sequence GGGGSGGGGSGGGGS (SEQ ID NO: 91), and $V_H$ is a light chain variable region comprising the amino acid sequence of SEQ ID NO: 89. In some embodiments, the antigen-binding domain of the CAR comprising a formula of $V_L$-Z-$V_H$ has an amino acid sequence as set forth below:

(SEQ ID NO: 93)

```
EIVLTQSPATLSLSPGERATLSCRASQSVSSYLAWYQQKPGQAPRLLIYD

ASNRATGIPARFSGSGSGTDFTLTISSLEPEDFAVYYCQQRSNWPITFGQ

GTRLEIKGGGGSGGGGSGGGGSEVQLVESGGGLVQPGRSLRLSCAASGFT

ENDYAMHWVRQAPGKGLEWVSTISWNSGSIGYADSVKGRFTISRDNAKKS

LYLQMNSLRAEDTALYYCAKDIQYGNYYYGMDVWGQGTTVTVSS
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 93. In some embodiments, the antigen-binding domain of the CAR comprises an amino acid sequence having at least 90% identity to a sequence of SEQ ID NO: 93. In some embodiments, the antigen-binding domain of the CAR comprises an amino acid sequence having at least 95% identity to a sequence of SEQ ID NO: 93. In some embodiments, the antigen-binding domain of the CAR comprises an amino acid sequence having at least 98% identity to a sequence of SEQ ID NO: 93. In some embodiments, the antigen-binding domain of the CAR comprises an amino acid sequence having at least 99% identity to a sequence of SEQ ID NO: 93. In some embodiments, the antigen-binding domain of the CAR comprises the amino acid sequence of SEQ ID NO: 93.

In some embodiments, the antigen-binding domain of the CAR comprises a $V_H$ domain, a $V_L$ domain, or a $V_H$ and a $V_L$ domain. In some embodiments, the $V_H$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, or any value or range in-between.

(SEQ ID NO: 94)

```
DIVLTQSPAILSASPGEKVTMTCRASSSVNYMDWYQKKPGSSPKPWIYAT

SNLASGVPARFSGSGSGTSYSLTISRVEAEDAATYYCQQWSFNPPTFGGG

TKLEIKGSTS
```

In some embodiments, the $V_H$ domain comprises an amino acid sequence having at least 90% identity to SEQ ID NO: 94. In some embodiments, the $V_H$ domain comprises an amino acid sequence having at least 95% identity to SEQ ID NO: 94. In some embodiments, the $V_H$ domain comprises an amino acid sequence having at least 98% identity to SEQ ID NO: 94. In some embodiments, the $V_H$ domain comprises an amino acid sequence having at least 99% identity to SEQ ID NO: 94. In some embodiments, the $V_H$ domain comprises an amino acid sequence having the sequence of SEQ ID NO: 94.

In some embodiments, the $V_L$ domain comprises an amino acid sequence having at least 75%, 80%, 85%, 85%, 87%, 88%, 89%, 90%, 91%, 92%, 93%, 94%, 95%, 96%, 97%, 98%, 99%, or 100% identity to SEQ ID NO: 95, or any value or range in-between.

(SEQ ID NO: 95)

```
EVQLQQSGAELVKPGASVKMSCKASGYTFTSYNMHWVKQTPGQGLEWIGA

IYPGNGDTSYNQKFKGKATLTADKSSSTAYMQLSSLTSEDSADYYCARSN

YYGSSYWFFDVWGAGTTVTVSS
```

In some embodiments, the $V_L$ domain comprises an amino acid sequence having at least 90% identity to SEQ ID NO:

95. In some embodiments, the $V_L$ domain comprises an amino acid sequence having at least 95% identity to SEQ ID NO: 95. In some embodiments, the $V_L$ domain comprises an amino acid sequence having at least 98% identity to SEQ ID NO: 95. In some embodiments, the $V_L$ domain comprises an amino acid sequence having at least 99% identity to SEQ ID NO: 95. In some embodiments, the $V_L$ domain comprises an amino acid sequence having the sequence of SEQ ID NO: 95.

In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having at least 90% identity to SEQ ID NO: 95. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having at least 95% identity to SEQ ID NO: 95. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having at least 98% identity to SEQ ID NO: 95. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having at least 99% identity to SEQ ID NO: 95. In some embodiments, the antigen-binding domain of the CAR comprising a $V_H$ domain and a $V_L$ domain comprises a $V_H$ domain having at least 75%, 80%, 85%, 85%, 87%, 88%, 89%, 90%, 91%, 92%, 93%, 94%, 95%, 96%, 97%, 98%, 99%, or 100% identity to SEQ ID NO: 94, and comprises a $V_L$ having the sequence of SEQ ID NO: 95. In some embodiments, the antigen-binding domain of the CAR comprising a $V_H$ domain and a $V_L$ domain comprises a $V_H$ domain having at least 90% identity to SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having at least 95% identity to SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having at least 98% identity to SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having at least 99% identity to SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having an amino acid sequence of SEQ ID NO: 94, and comprises a $V_L$ having at least 75%, 80%, 85%, 85%, 87%, 88%, 89%, 90%, 91%, 92%, 93%, 94%, 95%, 96%, 97%, 98%, 99%, or 100% identity to SEQ ID NO: 95. In some embodiments, the antigen-binding domain of the CAR comprising a $V_H$ domain and a $V_L$ domain comprises a $V_H$ domain having at least 90% identity to SEQ ID NO: 94, and comprises a $V_L$ having at least 90% identity to SEQ ID NO: 95. In some embodiments, the antigen-binding domain of the CAR comprising a $V_H$ domain and a $V_L$ domain comprises a $V_H$ domain having at least 95% identity to SEQ ID NO: 94, and comprises a $V_L$ having at least 90% identity to SEQ ID NO: 95. In some embodiments, the antigen-binding domain of the CAR comprising a $V_H$ domain and a $V_L$ domain comprises a $V_H$ domain having at least 90% identity to SEQ ID NO: 94, and comprises a $V_L$ having at least 95% identity to SEQ ID NO: 95. In some embodiments, the antigen-binding domain of the CAR comprising a $V_H$ domain and a $V_L$ domain comprises a $V_H$ domain having at least 95% identity to SEQ ID NO: 94, and comprises a $V_L$ having at least 95% identity to SEQ ID NO: 95. In some embodiments, the antigen-binding domain of the CAR comprising a $V_H$ domain and a $V_L$ domain comprises a $V_H$ domain having at least 98% identity to SEQ ID NO: 94, and comprises a $V_L$ having at least 98% identity to SEQ ID NO: 95. In some embodiments, the antigen-binding domain of the CAR comprising a $V_H$ domain and a $V_L$ domain comprises a $V_H$ domain having at least 99% identity to SEQ ID NO: 94, and comprises a $V_L$ having at least 99% identity to SEQ ID NO: 95. In some embodiments, the antigen-binding domain of the CAR comprising a $V_H$ domain and a $V_L$ domain comprises a $V_H$ domain having an amino acid sequence of SEQ ID NO: 94, and comprises a $V_L$ having an amino acid sequence of SEQ ID NO: 95.

In some embodiments, the antigen-binding domain of the CAR comprises a formula of $V_H$-Z-$V_L$, wherein $V_H$ is a heavy chain variable region comprising the amino acid sequence of SEQ ID NO: 94, Z is a linker comprising the amino acid sequence GGGGSGGGGSGGGGS (SEQ ID NO: 91), and $V_L$ is a light chain variable region comprising the amino acid sequence of SEQ ID NO: 95. In some embodiments, the antigen-binding domain of the CAR comprising a formula of $V_H$-Z-$V_L$ has an amino acid sequence as set forth below:

```
                                       (SEQ ID NO: 96)
DIVLTQSPAILSASPGEKVTMTCRASSSVNYMDWYQKKPGSSPKPWIYAT

SNLASGVPARFSGSGSGTSYSLTISRVEAEDAATYYCQQWSFNPPTFGGG

TKLEIKGSTSGGGGSGGGGSGGGGSSEVQLQQSGAELVKPGASVKMSCKA

SGYTFTSYNMHWVKQTPGQGLEWIGAIYPGNGDTSYNQKFKGKATLTADK

SSSTAYMQLSSLTSEDSADYYCARSNYYGSSYWFFDVWGAGTTVTVSS
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 96. In some embodiments, the antigen-binding domain of the CAR comprises an amino acid sequence having at least 90% identity to a sequence of SEQ ID NO: 96. In some embodiments, the antigen-binding domain of the CAR comprises an amino acid sequence having at least 95% identity to a sequence of SEQ ID NO: 96. In some embodiments, the antigen-binding domain of the CAR comprises an amino acid sequence having at least 98% identity to a sequence of SEQ ID NO: 96. In some embodiments, the antigen-binding domain of the CAR comprises an amino acid sequence having at least 99% identity to a sequence of SEQ ID NO: 96. In some embodiments, the antigen-binding domain of the CAR comprises the amino acid sequence of SEQ ID NO: 96.

In some embodiments, the antigen-binding domain of the CAR comprises a formula of $V_L$-Z-$V_H$, wherein $V_L$ is a light chain variable region comprising the amino acid sequence of SEQ ID NO: 95, Z is a linker comprising the amino acid sequence GGGGSGGGGSGGGGS (SEQ ID NO: 91), and $V_H$ is a light chain variable region comprising the amino acid sequence of SEQ ID NO: 94. In some embodiments, the antigen-binding domain of the CAR comprising a formula of $V_L$-Z-$V_H$ has an amino acid sequence as set forth below:

```
                                          (SEQ ID NO: 97)
SEVQLQQSGAELVKPGASVKMSCKASGYTFTSYNMHWVKQTPGQGLEWIG

AIYPGNGDTSYNQKFKGKATLTADKSSSTAYMQLSSLTSEDSADYYCARS

NYYGSSYWFFDVWGAGTTVTVSSGGGGSGGGGSGGGGSDIVLTQSPAILS

ASPGEKVTMTCRASSSVNYMDWYQKKPGSSPKPWIYATSNLASGVPARFS

GSGSGTSYSLTISRVEAEDAATYYCQQWSFNPPTFGGGTKLEIKGSTS
```

In some embodiments, the antigen-binding domain of the CAR comprises an amino acid sequence having at least 85%, 86%, 87%, 88%, 89%, 90%, 91%, 92%, 93%, 94%, 95%, 96%, 97%, 98%, 99%, or 100% identity to a sequence of SEQ ID NO: 97. In some embodiments, the antigen-binding domain of the CAR comprises an amino acid sequence having at least 90% identity to a sequence of SEQ ID NO: 97. In some embodiments, the antigen-binding domain of the CAR comprises an amino acid sequence having at least 95% identity to a sequence of SEQ ID NO: 97. In some embodiments, the antigen-binding domain of the CAR comprises an amino acid sequence having at least 98% identity to a sequence of SEQ ID NO: 97. In some embodiments, the antigen-binding domain of the CAR comprises an amino acid sequence having at least 99% identity to a sequence of SEQ ID NO: 97. In some embodiments, the antigen-binding domain of the CAR comprises the amino acid sequence of SEQ ID NO: 97.

In some embodiments, the antigen-binding domain of the CAR comprises rituximab, ocrelizumab, obinutuzumab, ofatumumab, ibritumomab tiuxetan, tositumomab, or ublituximab. In some embodiment, the antigen-binding domain comprises rituximab. In some embodiment, the antigen-binding domain comprises ofatumumab. In some embodiments, the CAR comprises the 4-1BB domain as well.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99:

```
                                          (SEQ ID NO: 99)
MALPVTALLLPLALLLHAARPGSEVQLVESGGGLVQPGRSLRLSCAASGF

TENDYAMHWVRQAPGKGLEWVSTISWNSGSIGYADSVKGRFTISRDNAKK
```

-continued

```
SLYLQMNSLRAEDTALYYCAKDIQYGNYYYGMDVWGQGTTVTVSSGGGGS

GGGGSGGGGSEIVLTQSPATLSLSPGERATLSCRASQSVSSYLAWYQQKP

GQAPRLLIYDASNRATGIPARFSGSGSGTDFTLTISSLEPEDFAVYYCQQ

RSNWPITFGQGTRLEIKSGLDFVPVFLPAKPTTTPAPRPPTPAPTIASQP

LSLRPEACRPAAGGAVHTRGLDFACDIYIWAPLAGTCGVLLLSLVITLYC

NHRNKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPR
```

or is substantially similar to SEQ ID NO: 99, or is an active fragment of SEQ ID NO: 99. In some embodiments, the CAR comprises an amino acid sequence that is at least 90% identical to a sequence of SEQ ID NO: 99. In some embodiments, the CAR comprises an amino acid sequence that is at least 95% identical to a sequence of SEQ ID NO: 99. In some embodiments, the CAR comprises an amino acid sequence that is at least 98% identical to a sequence of SEQ ID NO: 99. In some embodiments, the CAR comprises an amino acid sequence of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR corresponds to amino acids 24-267 of SEQ ID NO: 99. In some embodiments, the CAR comprises an amino acid sequence that is at least 90% identical to a sequence of SEQ ID NO: 99, wherein the antigen binding domain of the CAR corresponds to amino acids 24-267 of SEQ ID NO: 99. In some embodiments, the CAR comprises an amino acid sequence that is at least 95% identical to a sequence of SEQ ID NO: 99, wherein the antigen binding domain of the CAR corresponds to amino acids 24-267 of SEQ ID NO: 99. In some embodiments, the CAR comprises an amino acid sequence that is at least 98% identical to a sequence of SEQ ID NO: 99, wherein the antigen binding domain of the CAR corresponds to amino acids 24-267 of SEQ ID NO: 99. In some embodiments, the CAR comprises an amino acid sequence of SEQ ID NO: 99, wherein the antigen binding domain of the CAR corresponds to amino acids 24-267 of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99. In some embodiments, the CAR comprises an amino acid sequence that is at least 90% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99. In some embodiments, the CAR comprises an amino acid sequence that is at least 95% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99. In some embodiments, the CAR comprises an amino acid sequence that is at least 98% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99. In some embodiments, the CAR comprises an amino acid sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR corresponds to amino acids 24-267 of SEQ ID NO: 99, a hinge domain of the CAR corresponds to amino acids 272-326 of SEQ ID NO: 99, a transmembrane domain of the CAR corresponds to amino acids 327-354 of SEQ ID NO: 99, a costimulatory domain of the CAR corresponds to amino acids 355-396 of SEQ ID NO: 99, and a signaling domain of the CAR corresponds to amino acids 397-508 of SEQ ID NO: 99. In some embodiments, the CAR comprises an amino acid sequence that is at least 90% identical to a sequence of SEQ ID NO: 99, wherein the antigen binding domain of the CAR corresponds to amino acids 24-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence that is at least 95% identical to a sequence of SEQ ID NO: 99, wherein the antigen binding domain of the CAR corresponds to amino acids 24-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence that is at least 98% identical to a sequence of SEQ ID NO: 99, wherein the antigen binding domain of the CAR corresponds to amino acids 24-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence of SEQ ID NO: 99, wherein the antigen binding domain of the CAR corresponds to amino acids 24-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99, a hinge domain of the CAR corresponds to amino acids 272-326 of SEQ ID NO: 99, a transmembrane domain of the CAR corresponds to amino acids 327-354 of SEQ ID NO: 99, a costimulatory domain of the CAR corresponds to amino acids 355-396 of SEQ ID NO: 99, and a signaling domain of the CAR corresponds to amino acids 397-508 of SEQ ID NO: 99. In some embodiments, the CAR comprises an amino acid sequence that is at least 90% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence that is at least 95% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence that is at least 98% identical to a sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99. In some embodiments, the CAR comprises an amino acid sequence of SEQ ID NO: 99, wherein the antigen binding domain of the CAR comprises a $V_H$ and a $V_L$, wherein the $V_H$ corresponds to amino acids 24-145 of SEQ ID NO: 99 and the $V_L$ corresponds to amino acids 161-267 of SEQ ID NO: 99, the hinge domain of the CAR corresponds to amino acids 272-326 of SEQ ID NO: 99, the transmembrane domain of the CAR corresponds to amino acids 327-354 of SEQ ID NO: 99, the costimulatory domain of the CAR corresponds to amino acids 355-396 of SEQ ID NO: 99, and the signaling domain of the CAR corresponds to amino acids 397-508 of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR comprises an amino acid sequence of SEQ ID NO: 92 and corresponds to amino acids 24-267 of SEQ ID NO: 99, a hinge domain of the CAR comprises an amino acid sequence of SEQ ID NO: 59 and corresponds to amino acids 272-326 of SEQ ID NO: 99, a transmembrane domain of the CAR comprises an amino acid sequence of SEQ ID NO: 61 and corresponds to amino acids 327-354 of SEQ ID NO: 99, a costimulatory domain of the CAR comprises an amino acid sequence of SEQ ID NO: 101 and corresponds to amino acids 355-396 of SEQ ID NO: 99, and a signaling domain of the CAR comprises an amino acid sequence of SEQ ID NO: 102 and corresponds to amino acids 397-508 of SEQ ID NO: 99.

(SEQ ID NO: 101)
KRGRKKLLYIFKQPFMRPVQTTQEEDGCSCRFPEEEEGGCEL (SEQ ID NO: 102)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

In some embodiments, the CAR comprises an amino acid sequence that is at least 90% identical to a sequence of SEQ ID NO: 99, wherein the antigen binding domain of the CAR comprises an amino acid sequence of SEQ ID NO: 92 and corresponds to amino acids 24-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence that is at least 95% identical to a sequence of SEQ ID NO: 99, wherein the antigen binding domain of the CAR comprises an amino acid sequence of SEQ ID NO: 92 and corresponds to amino acids 24-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence that is at least 98% identical to a sequence of SEQ ID NO: 99, wherein the antigen binding domain of the CAR comprises an amino acid sequence of SEQ ID NO: 92 and corresponds to amino acids 24-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence of SEQ ID NO: 99, wherein the antigen binding domain of the CAR comprises an amino acid sequence of SEQ ID NO: 92 and corresponds to amino acids 24-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99.

In some embodiments, the CAR comprises an amino acid sequence that is at least 85%, 86%, 87%, 88%, 89%, 90%, 91%, 92%, 93%, 94%, 95%, 96%, 97%, 98%, 99%, or 100% identical to a sequence of SEQ ID NO: 99, wherein the antigen binding domain of the CAR comprises a $V_H$ and a $V_L$, wherein the $V_H$ comprises an amino acid sequence of SEQ ID NO: 89 and corresponds to amino acids 24-145 of SEQ ID NO: 99 and the $V_L$ comprises an amino acid sequence of SEQ ID NO: 90 and corresponds to amino acids 161-267 of SEQ ID NO: 99, a hinge domain of the CAR comprises an amino acid sequence of SEQ ID NO: 59 and corresponds to amino acids 272-326 of SEQ ID NO: 99, a transmembrane domain of the CAR comprises an amino acid sequence of SEQ ID NO: 61 and corresponds to amino acids 327-354 of SEQ ID NO: 99, a costimulatory domain of the CAR comprises an amino acid sequence of SEQ ID NO: 101 and corresponds to amino acids 355-396 of SEQ ID NO: 99, and a signaling domain of the CAR comprises an amino acid sequence of SEQ ID NO: 102 and corresponds to amino acids 397-508 of SEQ ID NO: 99. In some embodiments, the CAR comprises an amino acid sequence that is at least 90% identical to a sequence of SEQ ID NO: 99, wherein the antigen binding domain of the CAR comprises a $V_H$ and a $V_L$, wherein the $V_H$ comprises an amino acid sequence of SEQ ID NO: 89 and corresponds to amino acids 24-145 of SEQ ID NO: 99 and the $V_L$ comprises an amino acid sequence of SEQ ID NO: 90 and corresponds to amino acids 161-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence that is at least 95% identical to a sequence of SEQ ID NO: 99, wherein the antigen binding domain of the CAR comprises a $V_H$ and a $V_L$, wherein the $V_H$ comprises an amino acid sequence of SEQ ID NO: 89 and corresponds to amino acids 24-145 of SEQ ID NO: 99 and the $V_L$ comprises an amino acid sequence of SEQ ID NO: 90 and corresponds to amino acids 161-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence that is at least 98% identical to a sequence of SEQ ID NO: 99, wherein the antigen binding domain of the CAR comprises a $V_H$ and a $V_L$, wherein the $V_H$ comprises an amino acid sequence of SEQ ID NO: 89 and corresponds to amino acids 24-145 of SEQ ID NO: 99 and the $V_L$ comprises an amino acid sequence of SEQ ID NO: 90 and corresponds to amino acids 161-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99. In some embodiments, the CAR comprises an amino acid sequence of SEQ ID NO: 99, wherein the antigen binding domain of the CAR comprises a $V_H$ and a $V_L$, wherein the $V_H$ comprises an amino acid sequence of SEQ ID NO: 89 and corresponds to amino acids 24-145 of SEQ ID NO: 99 and the $V_L$ comprises an amino acid sequence of SEQ ID NO: 90 and corresponds to amino acids 161-267 of SEQ ID NO: 99, the hinge domain of the CAR comprises an amino acid sequence of SEQ ID NO: 59 and corresponds to amino acids 272-326 of SEQ ID NO: 99, the transmembrane domain of the CAR comprises an amino acid sequence of SEQ ID NO: 61 and corresponds to amino acids 327-354 of SEQ ID NO: 99, the costimulatory domain of the CAR comprises an amino acid sequence of SEQ ID NO: 101 and corresponds to amino acids 355-396 of SEQ ID NO: 99, and the signaling domain of the CAR comprises an amino acid sequence of SEQ ID NO: 102 and corresponds to amino acids 397-508 of SEQ ID NO: 99.

In any of the preceding embodiments, the antigen binding domain of the CAR may be directly fused to the hinge domain of the CAR. In any of the preceding embodiments, the antigen binding domain of the CAR may be connected to the hinge domain of the CAR through a polypeptide linker, such as those provided for herein. In some embodiments, the polypeptide linker comprises an amino acid sequence of SGLD (SEQ ID NO: 100). In some embodiments, the polypeptide linker connects the C-terminus of the antigen binding domain to the N-terminus of the hinge region. In some embodiments, the antigen binding domain comprises a $V_H$ and a $V_L$ and the polypeptide linker connects the C-terminus of the $V_H$ to the N-terminus of the hinge region. In some embodiments, the antigen binding domain comprises a $V_H$ and a $V_L$ and the polypeptide linker connects the C-terminus of the $V_L$ to the N-terminus of the hinge region.

These are merely illustrative in nature and are not limiting to the present embodiments and any chimeric antigen receptor can be delivered in conjunction with the viral particles and vectors provided for herein. These are non-limiting examples of CARs and any CAR construct could be encoded for by the nucleic acid molecule.

In some embodiments, the pseudotyped viral particle further comprises a heterologous nucleic acid molecule encoding a cargo of interest. The nucleic acid molecule may be useful for modulating the expression of a target gene. In some embodiments, the cargo can be used to modulate the activity of a cell or express a protein that is trafficked to the surface of the target cell. Therefore, in some embodiments, the nucleic acid may comprise an siRNA or an shRNA. The nucleic acid may also encode for a cargo of interest. Therefore, in some embodiments, the cargo of interest may comprise a polypeptide or portion thereof, a protein or portion thereof, a chimeric antigen receptor or portion thereof, or a tumor antigen or a portion thereof. In some embodiments, the cargo of interest is an antibody that is produced by the virus, which can then be secreted by the cell that is infected with the virus. The term "protein" can refer to any polypeptide that carries a native function in a cellular environment. Therefore, in some embodiments, the protein encoded by the nucleic acid cargo of interest may comprise an enzyme, a nuclear receptor, a transporter, a ribosomal protein, a membrane bound protein, a cytoplasmic protein, a G-protein coupled receptor, a voltage gated ion channel, a secretory protein, a mitochondria protein, a cytokine, a chimeric antigen receptor, a tumor antigen, or a portion or chimeric species thereof.

Without being bound to any particular theory, the viral particle comprising a heterologous viral glycoprotein as provided for herein and comprising a targeting moiety as provided for herein can be used to express the heterologous molecule of interest in the target cell. Thus, for example, the CAR can be expressed in a T cell that is targeted by a viral particle pseudotyped with a VSV-G protein or a SVCV-G protein as provided for herein. Where the T cell is the intended target, the viral particle can comprise a targeting moiety that binds to a target on the surface of a T cell, such as, but not limited to CD2, CD3, CD4, CD5, CD7 or CD8. In some embodiments, the target is CD2. In some embodiments, the target is CD3. In some embodiments, the target is CD4. In some embodiments, the target is CD5. In some embodiments, the target is CD6. In some embodiments, the target is CD7. In some embodiments, the target is CD8. In some embodiments, the targeting moiety targeting CD7 is as provided for herein. In some embodiments, the targeting moiety targeting CD8 is as provided for herein.

In some embodiments, the pseudotyped viral particle is a recombinant lentivirus. In some embodiments, the recombinant pseudotyped viral particle is replication competent. In some embodiments, the recombinant pseudotyped viral particle is replication incompetent.

Exemplary Viral Particles Comprising a Targeting Moiety Comprising an Fc Domain

In some embodiments, a viral particle is provided, the viral particle comprising a heterologous viral glycoprotein and a targeting moiety comprising a polypeptide having a formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53; wherein the target binding domain comprises a sequence selected from SEQ ID NO: 38, SEQ ID NO: 39, SEQ ID NO: 50, or SEQ ID NO: 51; wherein the stalk portion $S_1$ comprises a variant Fc protein comprising a sequence that is a variant of SEQ ID NO: 26, SEQ ID NO: 27, or SEQ ID NO: 28; wherein the variant of SEQ ID NO: 26 comprises one or more mutations selected from the group consisting of L234A, L235A, N297A, P329G, I253A, H310A, and H435A; wherein the variant of SEQ ID NO: 27 comprises one or more mutations selected from the group consisting of N297A, P329G, 1253A, H310A, and H435A; wherein the variant of SEQ ID NO: 28 comprises one or more mutations selected from the group consisting of S228P, L235E, N297A, P329G, I253A, H310A, and H435A; and wherein the variant Fc protein further comprises a transmembrane domain comprising a sequence selected from SEQ ID NO: 61 or SEQ ID NO: 62. In some embodiments, the heterologous viral glycoprotein comprises a sequence of SEQ ID NO: 22. In some embodiments, the heterologous viral glycoprotein comprises a sequence of SEQ ID NO: 23. In some embodiments, the heterologous viral glycoprotein comprises a sequence of SEQ ID NO: 24. In some embodiments, the heterologous viral glycoprotein comprises a sequence of SEQ ID NO: 25. In some embodiments, the heterologous viral glycoprotein comprises a sequence of SEQ ID NO: 52. In some embodiments, the heterologous viral glycoprotein comprises a sequence of SEQ ID NO: 53. In some embodiments, the targeting moiety comprises an amino acid sequence of SEQ ID NO: 38. In some embodiments, the targeting moiety comprises an amino acid sequence of SEQ ID NO: 39. In some embodiments, the targeting moiety comprises an amino acid sequence of SEQ ID NO: 50. In some embodiments, the targeting moiety comprises an amino acid sequence of SEQ ID NO: 51. In some embodiments, the variant Fc protein is a variant of SEQ ID NO: 26 and comprises one or more mutations selected from the group consisting of L234A, L235A, N297A, P329G, I253A, H310A, and H435A. In some embodiments, the variant Fc protein is a variant of SEQ ID NO: 27 and comprises one or more mutations selected from the group consisting of N297A, P329G, I253A, H310A, and H435A. In some embodiments, the variant Fc protein is a variant of SEQ ID NO: 28 and comprises one or more mutations selected from the group consisting of S228P, L235E, N297A, P329G, I253A, H310A, and H435A. In some embodiments, the transmembrane domain has an amino acid sequence of SEQ ID NO: 61. In some embodiments, the transmembrane domain has an amino acid sequence of SEQ ID NO: 62. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, said particle comprising a heterologous viral glycoprotein and a targeting moiety comprising a polypeptide having a formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53; wherein the target binding domain comprises a sequence selected from SEQ ID NO: 38, SEQ ID NO: 39, SEQ ID NO: 50, or SEQ ID NO: 51; wherein the stalk portion $S_1$ comprises a formula of $L_1$-Fc-$L_2$-$X_1$; wherein $L_1$ is a linker comprising a sequence selected from SEQ ID NO: 54, SEQ ID NO: 55, SEQ ID NO: 56, SEQ ID NO: 57, SEQ ID NO: 58, SEQ ID NO: 73, SEQ ID NO: 74, SEQ ID NO: 75, or SEQ ID NO: 76, or is absent; Fc is a variant Fc protein comprising a sequence that is a variant of SEQ ID NO: 26, SEQ ID NO: 27, or SEQ ID NO: 28; wherein the variant of SEQ ID NO: 26 comprises one or more mutations selected from the group consisting of L234A, L235A, N297A, P329G, I253A, H310A, and H435A; wherein the variant of SEQ ID NO: 27 comprises one or more mutations selected from the group consisting of N297A, P329G, I253A, H310A, and H435A; wherein the variant of SEQ ID NO: 28 comprises one or more mutations selected from the group consisting of S228P, L235E, N297A, P329G, I253A, H310A, and H435A; $L_2$ is a linker comprising a sequence selected from SEQ ID NO: 54, SEQ ID NO: 55, SEQ ID NO: 56, SEQ ID NO: 57, SEQ ID NO: 58. SEQ ID NO: 73 SEQ ID NO: 74, SEQ ID NO: 75, or SEQ ID NO: 76, or is absent; and $X_1$ is a polypeptide comprising a transmembrane domain having a formula of ECD-$T_M$-ICD, wherein ECD is an extracellular domain having a sequence of SEQ ID NO: 59, SEQ ID NO: 60, or any fragment thereof, or is absent; $T_M$ is a transmembrane domain having a sequence of SEQ ID NO: 61 or SEQ ID NO: 62 or any fragment thereof, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64 or the ICD is absent. In some embodiments, the heterologous viral glycoprotein comprises a sequence of SEQ ID NO: 22. In some embodiments, the heterologous viral glycoprotein comprises a sequence of SEQ ID NO: 23. In some embodiments, the heterologous viral glycoprotein comprises a sequence of SEQ ID NO: 24. In some embodiments, the heterologous viral glycoprotein comprises a sequence of SEQ ID NO: 25. In some embodiments, the heterologous viral glycoprotein comprises a sequence of SEQ ID NO: 52. In some embodiments, the heterologous viral glycoprotein comprises a sequence of SEQ ID NO: 53. In some embodiments, T comprises an amino acid sequence of SEQ ID NO: 38. In some embodiments, T comprises an amino acid sequence of SEQ ID NO: 39. In some embodiments, T comprises an amino acid sequence of SEQ ID NO: 50. In some embodiments, T comprises an amino acid sequence of SEQ ID NO: 51. In some embodiments, $L_1$ is absent. In some embodiments, $L_1$ comprises an amino acid sequence of SEQ ID NO: 54. In some embodiments, $L_1$ comprises an amino acid sequence of SEQ ID NO: 55. In some embodiments, $L_1$ comprises an amino acid sequence of SEQ ID NO: 56. In some embodiments, $L_1$ comprises an amino acid sequence of SEQ ID NO: 57. In some embodiments, $L_1$ comprises an amino acid sequence of SEQ ID NO: 58. In some embodiments, $L_1$ comprises an amino acid sequence of SEQ ID NO: 73. In some embodiments, $L_1$ comprises an amino acid sequence of SEQ ID NO: 74. In some embodiments, $L_1$ comprises an amino acid sequence of SEQ ID NO: 75. In some embodiments, $L_1$ comprises an amino acid sequence of SEQ ID NO: 76. In some embodiments, the variant Fc protein is a variant of SEQ ID NO: 26 and comprises one or more mutations selected from the group consisting of L234A, L235A, N297A, P329G, I253A, H310A, and H435A. In some embodiments, the variant Fc protein is a variant of SEQ ID NO: 27 and comprises one or more mutations selected from the group consisting of N297A, P329G, 1253A, H310A, and H435A. In some embodiments, the variant Fc protein is a variant of SEQ ID NO: 28 and comprises one or more mutations selected from the group consisting of S228P, L235E, N297A, P329G, I253A, H310A, and H435A. In some embodiments, $L_2$ is absent. In some embodiments, $L_2$ comprises an amino acid sequence of SEQ ID NO: 54. In some embodiments, $L_2$ comprises an amino acid sequence of SEQ ID NO: 55. In some embodiments, $L_2$ comprises an amino acid sequence of SEQ ID NO: 56. In some embodiments, $L_2$ comprises an amino acid sequence of SEQ ID NO: 57. In some embodiments, $L_2$ comprises an amino acid sequence of SEQ ID NO:

58. In some embodiments, $L_2$ comprises an amino acid sequence of SEQ ID NO: 73. In some embodiments, $L_2$ comprises an amino acid sequence of SEQ ID NO: 74. In some embodiments, $L_2$ comprises an amino acid sequence of SEQ ID NO: 75. In some embodiments, $L_2$ comprises an amino acid sequence of SEQ ID NO: 76. In some embodiments, ECD is absent. In some embodiments, ECD comprises an amino acid sequence of SEQ ID NO: 59. In some embodiments, ECD comprises an amino acid sequence of SEQ ID NO: 60. In some embodiments, $T_M$ comprises an amino acid sequence of SEQ ID NO: 61. In some embodiments, $T_M$ comprises an amino acid sequence of SEQ ID NO: 62. In some embodiments, ICD is absent. In some embodiments, ICD is present and the env incorporation motif has an amino acid sequence of SEQ ID NO: 63. In some embodiments, ICD is present and the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, said particle comprising a heterologous viral glycoprotein and a targeting moiety comprising a polypeptide having a formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52, or SEQ ID NO: 53; wherein the target binding domain comprises a sequence selected from SEQ ID NO: 38, SEQ ID NO: 39, SEQ ID NO: 50, or SEQ ID NO: 51; wherein the stalk portion $S_1$ comprises a formula of $L_1$-Fc-$L_2$-$X_1$; wherein $L_1$ is a linker comprising a sequence of SEQ ID NO: 55 or is absent; Fc is a variant Fc protein comprising a sequence that is a variant of SEQ ID NO: 26, SEQ ID NO: 27, or SEQ ID NO: 28; wherein the variant of SEQ ID NO: 26 comprises one or more mutations selected from the group consisting of L234A, L235A, N297A, P329G, I253A, H310A, and H435A; wherein the variant of SEQ ID NO: 27 comprises one or more mutations selected from the group consisting of N297A, P329G, I253A, H310A, and H435A; wherein the variant of SEQ ID NO: 28 comprises one or more mutations selected from the group consisting of S228P, L235E, N297A, P329G, 1253A, H310A, and H435A; $L_2$ is a linker comprising a sequence of SEQ ID NO: 55 or is absent; and $X_1$ is a polypeptide comprising a transmembrane domain having a formula of ECD-$T_M$-ICD, wherein ECD is an extracellular domain having a sequence of SEQ ID NO: 60, or a fragment thereof, or is absent; $T_M$ is a transmembrane domain having a sequence of SEQ ID NO: 62 or a fragment thereof, and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64 or the ICD is absent. In some embodiments, the heterologous viral glycoprotein comprises a sequence of SEQ ID NO: 22. In some embodiments, the heterologous viral glycoprotein comprises a sequence of SEQ ID NO: 23. In some embodiments, the heterologous viral glycoprotein comprises a sequence of SEQ ID NO: 24. In some embodiments, the heterologous viral glycoprotein comprises a sequence of SEQ ID NO: 25. In some embodiments, the heterologous viral glycoprotein comprises a sequence of SEQ ID NO: 52. In some embodiments, the heterologous viral glycoprotein comprises a sequence of SEQ ID NO: 53. In some embodiments, T comprises an amino acid sequence of SEQ ID NO: 38. In some embodiments, T comprises an amino acid sequence of SEQ ID NO: 39. In some embodiments, T comprises an amino acid sequence of SEQ ID NO: 50. In some embodiments, T comprises an amino acid sequence of SEQ ID NO: 51. In some embodiments, $L_1$ is absent. In some embodiments, $L_1$ comprises an amino acid sequence of SEQ ID NO: 55. In some embodiments, the variant Fc protein is a variant of SEQ ID NO: 26 and comprises one or more mutations selected from the group consisting of L234A, L235A, N297A, P329G, I253A, H310A, and H435A. In some embodiments, the variant Fc protein is a variant of SEQ ID NO: 27 and comprises one or more mutations selected from the group consisting of N297A, P329G, I253A, H310A, and H435A. In some embodiments, the variant Fc protein is a variant of SEQ ID NO: 28 and comprises one or more mutations selected from the group consisting of S228P, L235E, N297A, P329G, I253A, H310A, and H435A. In some embodiments, $L_2$ is absent. In some embodiments, $L_2$ comprises an amino acid sequence of SEQ ID NO: 55. In some embodiments, ECD is absent. In some embodiments, ECD comprises an amino acid sequence of SEQ ID NO: 60. In some embodiments, $T_M$ comprises an amino acid sequence of SEQ ID NO: 62. In some embodiments, ICD is absent. In some embodiments, ICD is present and the env incorporation motif has an amino acid sequence of SEQ ID NO: 63. In some embodiments, ICD is present and the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, said particle comprising a heterologous viral glycoprotein and a targeting moiety comprising a polypeptide having a formula T-$S_1$, wherein T is a target binding domain and $S_1$ is a stalk portion, wherein the heterologous viral glycoprotein comprises a sequence of SEQ ID NO: 23 or SEQ ID NO: 25; wherein the target binding domain comprises a sequence of SEQ ID NO: 39; wherein the stalk portion $S_1$ comprises a formula of $L_1$-Fc-$L_2$-$X_1$; wherein $L_1$ is a linker comprising a sequence of SEQ ID NO: 55; Fc is a variant Fc protein comprising a sequence fo SEQ ID NO: 104; $L_2$ is a linker and is absent; and $X_1$ is a polypeptide comprising a transmembrane domain having a formula of ECD-$T_M$-ICD, wherein ECD is an extracellular domain having a sequence of SEQ ID NO: 60; $T_M$ is a transmembrane domain having a sequence of SEQ ID NO: 62, and ICD is an intracellular domain or protein that facilitates the incorporation of the targeting moiety into the envelope of the viral particle, wherein the ICD comprises an env incorporation motif comprising an amino acid sequence of SEQ ID NO: 63. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, said particle comprising a heterologous viral glycoprotein and a targeting moiety, wherein the heterologous viral glycoprotein comprises an amino acid sequence having at least 90% identity to SEQ ID NO: 23 or SEQ ID NO: 25, having at least 95% identity to SEQ ID NO: 23 or SEQ ID NO: 25, having at least 99% identity to SEQ ID NO: 23 or SEQ ID NO: 25, or having at least 100% identity to SEQ ID NO: 23 or SEQ ID NO: 25; and the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, said particle comprising a heterologous viral glycoprotein and a targeting moiety, wherein the heterologous viral glycoprotein comprises an amino acid sequence having at least 90% identity to SEQ ID NO: 52 or SEQ ID NO: 53, having at least 95% identity to SEQ ID NO: 52 or SEQ ID NO: 53, having at least 99% identity to SEQ ID NO: 52 or SEQ ID NO: 53, or having at least 100% identity to SEQ ID NO: 52 or SEQ ID NO: 53; and the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

Exemplary Viral Particles Comprising a Targeting Moiety Comprising a Flexible Polypeptide In some embodiments, a viral particle is provided, the viral particle comprising a heterologous viral structural protein and a targeting moiety, wherein the targeting moiety comprises a polypeptide having a formula of T-$S_1$, wherein T is a target binding domain and $S_1$ is a stalk portion; wherein the target binding domain comprises an amino acid sequence of SEQ ID NO: 38 or SEQ ID NO: 39; wherein the stalk portion $S_1$ comprises a formula of $L_3$-$X_1$; wherein $L_3$ is a flexible peptide linker having an amino acid sequence selected from SEQ ID NO: 54, SEQ ID NO: 55, SEQ ID NO: 56, SEQ ID NO: 57, or SEQ ID NO: 58; and $X_1$ is a polypeptide comprising a transmembrane domain having a formula ECD-$T_M$-ICD, wherein ECD is an extracellular domain having an amino acid sequence of SEQ ID NO: 59 or SEQ ID NO: 60, or is a fragment thereof, or is absent; $T_M$ is a transmembrane domain having an amino acid sequence of SEQ ID NO: 61 or SEQ ID NO: 62, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the target binding domain has an amino acid sequence of SEQ ID NO: 38. In some embodiments, the target binding domain has an amino acid sequence of SEQ ID NO: 39. In some embodiments, $L_3$ has an amino acid sequence of SEQ ID NO: 54. In some embodiments, $L_3$ has an amino acid sequence of SEQ ID NO: 55. In some embodiments, $L_3$ has an amino acid sequence of SEQ ID NO: 56. In some embodiments, $L_3$ has an amino acid sequence of SEQ ID NO: 57. In some embodiments, $L_3$ has an amino acid sequence of SEQ ID NO: 58. In some embodiments, the ECD has an amino acid sequence of SEQ ID NO: 59. In some embodiments, the ECD has an amino acid sequence of SEQ ID NO: 60. In some embodiments, the $T_M$ has an amino acid sequence of SEQ ID NO: 61. In some embodiments, the $T_M$ has an amino acid sequence of SEQ ID NO: 62. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, the viral particle comprising a heterologous viral structural protein and a targeting moiety, wherein the targeting moiety comprises a polypeptide having a formula of T-$S_1$, wherein T is a target binding domain and $S_1$ is a stalk portion; wherein the target binding domain comprises an amino acid sequence of SEQ ID NO: 50 or SEQ ID NO: 51; wherein the stalk portion $S_1$ comprises a formula of $L_3$-$X_1$; wherein $L_3$ is a flexible peptide linker having an amino acid sequence selected from SEQ ID NO: 54, SEQ ID NO: 55, SEQ ID NO: 56, SEQ ID NO: 57, or SEQ ID NO: 58; and $X_1$ is a polypeptide comprising a transmembrane domain having a formula ECD-$T_M$-ICD, wherein ECD is an extracellular domain having an amino acid sequence of SEQ ID NO: 59 or SEQ ID NO: 60, or is a fragment thereof, or is absent; $T_M$ is a transmembrane domain having an amino acid sequence of SEQ ID NO: 61 or SEQ ID NO: 62, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the target binding domain has an amino acid sequence of SEQ ID NO: 50. In some embodiments, the target binding domain has an amino acid sequence of SEQ ID NO: 51. In some embodiments, $L_3$ has an amino acid sequence of SEQ ID NO: 54. In some embodiments, $L_3$ has an amino acid sequence of SEQ ID NO: 55. In some embodiments, $L_3$ has an amino acid sequence of SEQ ID NO: 56. In some embodiments, $L_3$ has an amino acid sequence of SEQ ID NO: 57. In some embodiments, $L_3$ has an amino acid sequence of SEQ ID NO: 58. In some embodiments, the ECD has an amino acid sequence of SEQ ID NO: 59. In some embodiments, the ECD has an amino acid sequence of SEQ ID NO: 60. In some embodiments, the $T_M$ has an amino acid sequence of SEQ ID NO: 61. In some embodiments, the $T_M$ has an amino acid sequence of SEQ ID NO: 62. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, the viral particle comprising a heterologous viral structural protein and a targeting moiety, wherein the targeting moiety comprises a polypeptide having a formula of T-$S_1$, wherein the heterologous viral structural protein comprises a sequence of SEQ ID NO: 22, SEQ ID NO: 23, SEQ ID NO: 24, SEQ ID NO: 25, SEQ ID NO: 52, or SEQ ID NO: 53; wherein T is a target binding domain and $S_1$ is a stalk portion, wherein the target binding domain comprises an amino acid sequence of SEQ ID NO: 38, SEQ ID NO: 39, SEQ ID NO: 50, or SEQ ID NO: 51; wherein the stalk portion $S_1$ comprises a formula of $L_3$-$X_1$; wherein $L_3$ is a flexible peptide linker having an amino acid sequence selected from SEQ ID NO: 54, SEQ ID NO: 55, SEQ ID NO: 56, SEQ ID NO: 57, or SEQ ID NO: 58; and $X_1$ is a polypeptide comprising a transmembrane domain having a formula ECD-$T_M$-ICD, wherein ECD is an extracellular domain having an amino acid sequence of SEQ ID NO: 59 or SEQ ID NO: 60, or is a fragment thereof, or is absent; $T_M$ is a transmembrane domain having an amino acid sequence of SEQ ID NO: 61 or SEQ ID NO: 62, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the heterologous viral structural protein comprises a sequence of SEQ ID NO: 22. In some embodiments, the heterologous viral structural protein comprises a sequence of SEQ ID NO: 23. In some embodiments, the heterologous viral structural protein comprises a sequence of SEQ ID NO: 24. In some embodiments, the heterologous viral structural protein comprises a sequence of SEQ ID NO: 25. In some embodiments, the heterologous viral structural protein comprises a sequence of SEQ ID NO: 52. In some embodiments, the heterologous viral structural protein comprises a sequence of SEQ ID NO: 53. In some embodiments, the target binding domain has an amino acid sequence of SEQ ID NO: 38. In some embodiments, the target binding domain has an amino acid sequence of SEQ ID NO: 39. In some embodiments, the target binding domain has an amino acid sequence of SEQ ID NO: 50. In some embodiments, the target binding domain has an amino acid sequence of SEQ ID NO: 51. In some embodiments, $L_3$ has an amino acid sequence of SEQ ID NO: 54. In some embodiments, $L_3$ has an amino acid sequence of SEQ ID NO: 55. In some embodiments, $L_3$ has an amino acid sequence of SEQ ID NO: 56. In some embodiments, $L_3$ has an amino acid sequence of SEQ ID NO: 57. In some embodiments, $L_3$ has an amino acid sequence of SEQ ID NO: 58. In some embodiments, the ECD has an amino acid sequence of SEQ ID NO: 59. In some embodiments, the ECD has an amino acid sequence of SEQ ID NO: 60. In some embodiments, the $T_M$ has an amino acid sequence of SEQ ID NO: 61. In some embodiments, the $T_M$ has an amino acid sequence of SEQ ID NO: 62. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99. At least 99% identity to SEQ ID NO: 99, or at least 100% identity to SEQ ID NO: 99.

In some embodiments, a viral particle is provided, the viral particle comprising a heterologous viral structural protein and a targeting moiety, wherein the targeting moiety comprises a polypeptide having a formula of T-$S_1$, wherein the heterologous viral structural protein comprises a sequence of SEQ ID NO: 22, SEQ ID NO: 23, SEQ ID NO: 24, SEQ ID NO: 25, SEQ ID NO: 52, or SEQ ID NO: 53; wherein T is a target binding domain and $S_1$ is a stalk portion, wherein the target binding domain comprises an amino acid sequence of SEQ ID NO: 38, SEQ ID NO: 39, SEQ ID NO: 50, or SEQ ID NO: 51; wherein the stalk portion $S_1$ comprises a formula of $L_3$-$X_1$; wherein $L_3$ is a flexible peptide linker having an amino acid sequence of SEQ ID NO: 55; and $X_1$ is a polypeptide comprising a transmembrane domain having a formula ECD-$T_M$-ICD, wherein ECD is an extracellular domain having an amino acid sequence of SEQ ID NO: 59, or is a fragment thereof, or is absent; $T_M$ is a transmembrane domain having an amino acid sequence of SEQ ID NO: 61, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the heterologous viral structural protein comprises a sequence of SEQ ID NO: 22. In some embodiments, the heterologous viral structural protein comprises a sequence of SEQ ID NO: 23. In some embodiments, the heterologous viral structural protein comprises a sequence of SEQ ID NO: 24. In some embodiments, the heterologous viral structural protein comprises a sequence of SEQ ID NO: 25. In some embodiments, the heterologous viral structural protein comprises a sequence of SEQ ID NO: 52. In some embodiments, the heterologous viral structural protein comprises a sequence of SEQ ID NO: 53. In some embodiments, the target binding domain has an amino acid sequence of SEQ ID NO: 38. In some embodiments, the target binding domain has an amino acid sequence of SEQ ID NO: 39. In some embodiments, the target binding domain has an amino acid sequence of SEQ ID NO: 50. In some embodiments, the target binding domain has an amino acid sequence of SEQ ID NO: 51. In some embodiments, $L_3$ has an amino acid sequence of SEQ ID NO: 55. In some embodiments, the ECD has an amino acid sequence of SEQ ID NO: 59. In some embodiments, the $T_M$ has an amino acid sequence of SEQ ID NO: 61. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, the viral particle comprising a heterologous viral structural protein and a targeting moiety, wherein the targeting moiety comprises a polypeptide having a formula of T-$S_1$, wherein the heterologous viral structural protein comprises a sequence of SEQ ID NO: 23 or SEQ ID NO: 25; wherein T is a target binding domain and $S_1$ is a stalk portion, wherein the target binding domain comprises an amino acid sequence of SEQ ID NO: 39; wherein the stalk portion $S_1$ comprises a formula of $L_3$-$X_1$; wherein $L_3$ is a flexible peptide linker having an amino acid sequence of SEQ ID NO: 55; and $X_1$ is a polypeptide comprising a transmembrane domain having a formula ECD-$T_M$-ICD, wherein ECD is an extracellular domain having an amino acid sequence of SEQ ID NO: 59, or is a fragment thereof, or is absent; $T_M$ is a transmembrane domain having an amino acid sequence of SEQ ID NO: 61, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the heterologous viral structural protein comprises a sequence of SEQ ID NO: 23. In some embodiments, the heterologous viral structural protein comprises a sequence of SEQ ID NO: 25. In some embodiments, the target binding domain has an amino acid sequence of SEQ ID NO: 39. In some embodiments, $L_3$ has an amino acid sequence of SEQ ID NO: 55. In some embodiments, the ECD has an amino acid sequence of SEQ ID NO: 59. In some embodiments, the $T_M$ has an amino acid sequence of SEQ ID NO: 61. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a viral particle is provided, the viral particle comprising a heterologous viral structural protein and a targeting moiety, wherein the targeting moiety comprises a polypeptide having a formula of T-$S_1$, wherein the heterologous viral structural protein comprises a sequence of SEQ ID NO: 52 or SEQ ID NO: 53; wherein T is a target binding domain and $S_1$ is a stalk portion, wherein the target binding domain comprises an amino acid sequence of SEQ ID NO: 39; wherein the stalk portion $S_1$ comprises a formula of $L_3$-$X_1$; wherein $L_3$ is a flexible peptide linker having an amino acid sequence of SEQ ID NO: 55; and $X_1$ is a polypeptide comprising a transmembrane domain having a formula ECD-$T_M$-ICD, wherein ECD is an extracellular domain having an amino acid sequence of SEQ ID NO: 59, or is a fragment thereof, or is absent; $T_M$ is a transmembrane domain having an amino acid sequence of SEQ ID NO: 61, or a fragment thereof; and ICD is an intracellular domain or protein that facilitates the incorporation of the targeting moiety into the envelope of the viral particle or is absent, wherein the ICD comprises an env incorporation motif, said env incorporation motif having an amino acid sequence of SEQ ID NO: 63 or SEQ ID NO: 64. In some embodiments, the heterologous viral structural protein comprises a sequence of SEQ ID NO: 52. In some embodiments, the heterologous viral structural protein comprises a sequence of SEQ ID NO: 53. In some embodiments, the target binding domain has an amino acid sequence of SEQ ID NO: 39. In some embodiments, $L_3$ has an amino acid sequence of SEQ ID NO: 55. In some embodiments, the ECD has an amino acid sequence of SEQ ID NO: 59. In some embodiments, the $T_M$ has an amino acid sequence of SEQ ID NO: 61. In some embodiments, the env incorporation motif has an amino acid sequence of SEQ ID NO: 63. In some embodiments, the env incorporation motif has an amino acid sequence of SEQ ID NO: 64. In some embodiments, the viral particle further comprises a nucleic acid molecule encoding a heterologous molecule of interest. In some embodiments, the heterologous molecule of interest is as provided for herein. In some embodiments, the heterologous molecule of interest is a CAR as provided for herein. In some embodiments, the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

In some embodiments, a pharmaceutical composition is provided comprising the envelope pseudotyped viral particles or vectors as provided for herein, i.e. a particle that comprises a VSV-G mutant protein provided for herein.

In some embodiments, methods of delivering a cargo of interest to a cell are provided. In some embodiments, the methods comprise contacting the cell with the pseudotyped viral-like particles or viral vectors as provided for herein, or a pharmaceutical composition comprising the same.

In some embodiments, methods of delivering a cargo of interest to a cell in a subject are provided. In some embodiments, the methods comprise administering to the subject the pseudotyped viral-like particles or viral vectors as provided for herein, or a pharmaceutical composition comprising the same. In some embodiments, the cargo is a chimeric antigen receptor or as otherwise provided for herein.

In some embodiments, methods for of delivering a chimeric antigen receptor to a T-cell in a subject are provided. In some embodiments, the methods comprising administering to the subject the pseudotyped viral-like particles or viral vectors as provided for herein, or a pharmaceutical composition comprising the same, wherein the pseudotyped viral-like particle or viral vector comprises a heterologous nucleic acid molecule encoding the chimeric antigen receptor.

Also provided herein are nucleic acid molecules encoding a mutant VSV-G protein as provided for herein.

Methods of making the viral like particles or vectors comprising a mutant VSV-G protein are also provided. In some embodiments, the methods comprise transfecting or transducing a packaging cell line with the nucleic acid molecules encoding a mutant VSV-G protein as provided for herein under conditions sufficient to produce the pseudotyped viral-like particles or viral vectors. In some embodiments, the methods comprise transfecting or transducing a packaging cell line with the plurality of nucleic acid molecules provided for herein under conditions sufficient to produce the pseudotyped viral-like particles or viral vectors. In some embodiments, methods further comprise isolating the pseudotyped viral-like particle or viral vector. In some embodiments, the nucleic acid molecules also comprise a nucleic acid molecule encoding a targeting moiety and/or a cargo that is to be delivered by the viral vector that is produced.

Methods of Treating Cancer

Also provided for herein are methods of treating cancer in a subject. In some embodiments, the methods comprise administering to the subject the pseudotyped viral-like particles or viral vectors as provided for herein, or a pharmaceutical composition comprising the same, wherein the pseudotyped viral-like particle or viral vector comprises a heterologous nucleic acid molecule encoding the chimeric antigen receptor.

In some embodiments, the methods comprise administering to the subject immune cells that have been transduced by the pseudotyped viral-like particle or viral vectors as provided for herein. In some embodiments, the immune cells are first isolated from the subject prior to transduction by the pseudotyped viral-like particle or viral vectors as provided for herein.

Also provided herein are methods of treating a disease in a subject in need thereof.

In some embodiments, the methods provided include, but are not limited to, methods of treating a disease in a subject in need thereof, comprising administering to the subject the viral particle(s) provided herein to treat the disease.

In certain embodiments, the disease is a cancer. In addition, the compositions provided for herein can be used in methods for the treatment of any condition related to a cancer, such as a cell-mediated immune response against a tumor cell(s), where it is desirable to treat or alleviate the disease. The types of cancers to be treated include, but are not limited to, carcinoma, blastoma, sarcoma, certain leukemia or lymphoid malignancies, benign and malignant tumors, malignancies e.g., sarcomas, carcinomas, and melanomas. Other exemplary cancers include, but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a hematological tumor. In one embodiment, the cancer is a carcinoma. In one embodiment, the cancer is a sarcoma. In one embodiment, the cancer is a leukemia. In one embodiment the cancer is a solid tumor.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by the methods disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

In certain exemplary embodiments, the compositions provided herein can be used in methods to treat a myeloma, or a condition related to myeloma. Examples of myeloma or conditions related thereto include, without limitation, light chain myeloma, non-secretory myeloma, monoclonal gamopathy of undetermined significance (MGUS), plasmacytoma (e.g., solitary, multiple solitary, extramedullary plasmacytoma), amyloidosis, and multiple myeloma. In some embodiments, methods of treating multiple myeloma are provided. In some embodiments, the multiple myeloma is refractory myeloma. In some embodiments, the multiple myeloma is relapsed myeloma.

In certain exemplary embodiments, the in vivo modified immune cells produced using the compositions provided herein are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In some embodiments, the melanoma is cutaneous melanoma In some embodiments, the melanoma is refractory melanoma. In some embodiments, the melanoma is relapsed melanoma.

In some embodiments, the compositions provided herein are used to treat a sarcoma, or a condition related to sarcoma. Examples of sarcoma or conditions related thereto include, without limitation, angiosarcoma, chondrosarcoma, chordoma, endotheliosarcoma, Ewing's sarcoma, fibrosarcoma, gastrointestinal stromal tumor, leiomyosarcoma, liposarcoma, lymphangiosarcoma, lymphangioendotheliosarcoma, mesothelioma, malignant peripheral nerve sheath tumor, myxosarcoma, osteogenic sarcoma, osteosarcoma, pleomorphic sarcoma, rhabdomyosarcoma, synovioma, synovial sarcoma, and other soft tissue sarcomas. In some embodiments, the sarcoma is synovial sarcoma. In some embodiments, the sarcoma is liposarcoma such as myxoid/round cell liposarcoma, differentiated/dedifferentiated liposarcoma, or pleomorphic liposarcoma. In some embodiments, the sarcoma is myxoid/round cell liposarcoma. In some embodiments, the sarcoma is refractory sarcoma. In some embodiments, the sarcoma is relapsed sarcoma.

In some embodiments, the subject has been treated with a therapeutic agent targeting the disease or condition, e.g. the tumor, prior to administration of the composition. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the composition is administered prophylactically, e.g., to reduce the likelihood of or prevent relapse. In some aspects, the subject has not received prior treatment with another therapeutic agent.

The administration of the compositions may be carried out in any convenient manner known to those of skill in the art. For example, the compositions may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, intraperitoneally, intranasally, intracranially, or intraosseously. In other instances, the compositions is injected directly into a site of a local disease site in the subject, a lymph node, an organ, a tumor, and the like.

For the prevention or treatment of disease, the appropriate dosage may depend on the type of disease to be treated, the severity and course of the disease, whether the composition is administered for preventive or therapeutic purposes, previous therapy, the subject's clinical history and response to the treatment, and the discretion of the attending physician. The composition is, in some embodiments, suitably administered to the subject at one time or over a series of treatments.

In some embodiments, the composition is administered as part of a combination treatment, such as simultaneously with or sequentially with, in any order, another therapeutic intervention, such as an antibody or produced cell or receptor or agent, such as a cytotoxic or therapeutic agent. The composition(s), in some embodiments, is co-administered with one or more additional therapeutic agents or in connection with another therapeutic intervention, either simultaneously or sequentially in any order. In some contexts, the composition is co-administered with another therapy sufficiently close in time such that the composition enhances the effect of one or more additional therapeutic agents, or vice versa. In some embodiments, the composition is administered prior to the one or more additional therapeutic agents. In some embodiments, the composition is administered after the one or more additional therapeutic agents. In some embodiments, the one or more additional agents includes a cytokine, such as IL-2, for example, to enhance persistence. In some embodiments, the methods comprise administration of a chemotherapeutic agent. In some embodiments, the methods do not comprise the administration of a chemotherapeutic agent.

In certain embodiments, the compositions may be administered to a subject in combination with an immune checkpoint antibody (e.g., an anti-PD1, anti-CTLA-4, or anti-PDL1 antibody). For example, viral vectors may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVO®) or an antigen-binding fragment thereof. In certain embodiments, the compositions may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the composition may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the viral vector. In certain embodiments, combination treatment comprising an immune checkpoint modulator may increase the therapeutic efficacy of a therapy comprising a composition as provided herein. The other therapeutic can be administered simultaneously, before, or after the compositions provided herein are administered to the subject.

In certain embodiments, the subject is provided a secondary treatment. Secondary treatments include but are not limited to chemotherapy, radiation, surgery, and medications. In some embodiments, the subject is not provided a secondary treatment.

In some embodiments, the methods are performed without a lymphodepletion step, such as the administration of cyclophosphamide and/or fludarabine.

In some embodiments, the subject can be administered a conditioning therapy after the administration of the compositions to kill certain immune cells that are not transduced with the CAR encoded by the compositions. This can be done by including a selection marker that is encoded by the nucleic acid cargo of interest. In some embodiments, the conditioning therapy comprises administering an effective amount of cyclophosphamide to the subject. In some embodiments, the conditioning therapy comprises administering an effective amount of fludarabine to the subject. In some embodiments, the conditioning therapy comprises administering an effective amount of a combination of cyclophosphamide and fludarabine to the subject.

In some embodiments, a specific dosage regimen of the present disclosure includes a lymphodepletion step after the administration of the composition. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

It is known in the art that one of the adverse effects of the use of CAR T cells can be the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, in some embodiments, the methods comprise, following the diagnosis of CRS, appropriate CRS management strategies to mitigate the physiological symptoms of uncontrolled inflammation without dampening the antitumor efficacy of the in vivo generated cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) Biol Blood Marrow Transplant, doi.org/10.1016/j.bbmt.2018.12.758; Neelapu et al. (2018) Nat Rev Clin Oncology, 15:47; Teachey et al. (2016) Cancer Discov, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In some embodiments, methods of treating cancer in a subject in need thereof are provided, the methods comprising administering to the subject any of the compositions, such as the viral particle(s), provided herein.

The compositions disclosed herein can comprise a pharmaceutical composition, and for example include a pharmaceutically acceptable carrier, and/or a pharmaceutical formulation.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the composition, preferably those with activities complementary to the composition, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the composition in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the composition, by multiple bolus administrations of the composition, or by continuous infusion administration of the composition. In some embodiments, the pharmaceutical composition does not include a chemotherapeutic.

Formulations include those for oral, intravenous, intraperitoneal, subcutaneous, pulmonary, transdermal, intramuscular, intranasal, buccal, sublingual, or suppository administration. In some embodiments, the composition is administered parenterally. The term "parenteral," as used herein, includes intravenous, intramuscular, subcutaneous, rectal, vaginal, and intraperitoneal administration. In some embodiments, the composition is administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the composition in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The embodiments provided for herein can be used for many purposes, since the a pseudotyped virus capable of fusing with a target cell can be used to deliver a gene or other heterologous sequence of interest.

ENUMERATED EMBODIMENTS

In some embodiments, the following embodiments are provided:

1. A viral particle comprising a heterologous viral glycoprotein and a targeting moiety, wherein the targeting moiety comprises a polypeptide having the formula T-$S_1$, wherein T is a target binding domain and $S_1$ is a stalk portion.

2. The viral particle of embodiment 1, wherein the stalk portion $S_1$ comprises a variant Fc protein, wherein the variant Fc protein comprises a transmembrane domain, such as but not limited to a CD8 or CD28 transmembrane domain, and an effector mutation, wherein the effector mutation inhibits the interaction between the Fc protein and a Fc interacting protein, such as FcγR, C1q, FcRβ, or FcRn.

3. The viral particle of embodiment 2, wherein the $S_1$ stalk portion is attached to the surface of the viral particle through the transmembrane domain.

4. The viral particle of embodiments 2 or 3, wherein the Fc protein is a IgG1 Fc, IgG2 Fc or IgG4 Fc protein.

5. The viral particle of any one of embodiments 2-4, wherein the variant Fc protein comprises a variant of a sequence of SEQ ID NO: 26, SEQ ID NO: 27, or SEQ ID NO: 28.

6. The viral particle of any one of embodiments 2-5, wherein the variant Fc protein is a variant IgG1 Fc protein.

7. The viral particle of embodiment 6, wherein the variant IgG1 Fc protein comprises one or more of the mutations selected from the group consisting of: L234A, L235A, N297A, P329G, I253A, H310A, and H435A.

8. The viral particle of embodiments 6 or 7, wherein the variant IgG1 Fc protein comprises a mutation that corresponds to L234A and L235A of SEQ ID NO: 26.

9. The viral particle of any one of embodiments 6-8, wherein the variant IgG1 Fc protein comprises a mutation that corresponds to N297A of SEQ ID NO: 26.

10. The viral particle of any one of embodiments 6-9, wherein the variant IgG1 Fc protein comprises a mutation that corresponds to P329G of SEQ ID NO: 26.

11. The viral particle of any one of embodiments 6-10, wherein the variant IgG1 Fc protein comprises a mutation that corresponds to L234A, L235A, N297A, and P329G of SEQ ID NO: 26.

12. The viral particle of any one of embodiments 6-11, wherein the variant IgG1 Fc protein comprises a mutation that corresponds to I253A of SEQ ID NO: 26.

13. The viral particle of any one of embodiments 6-12, wherein the variant IgG1 Fc protein comprises a mutation that corresponds to H310A of SEQ ID NO: 26.

14. The viral particle of any one of embodiments 6-13, wherein the variant IgG1 Fc protein comprises a mutation that corresponds to H435A of SEQ ID NO: 26.

15. The viral particle of any one of embodiments 6-14, wherein the variant IgG1 Fc protein comprises a mutation that corresponds to I253A, H310A, and H435A of SEQ ID NO: 26.

16. The viral particle of any one of embodiments 6-15, wherein the variant IgG1 Fc protein comprises an amino acid sequence having at least 70% identity to SEQ ID NO: 103 and further comprises one or more mutations that correspond to L19A, L20A, N82A, P114G, I38A, H95A, and/or H220A of SEQ ID NO: 103.

17. The viral particle of any one of embodiments 6-16, wherein the variant IgG1 Fc protein comprises an amino acid sequence having at least 80% identity to SEQ ID NO: 104, at least 85% identity to SEQ ID NO: 104, at least 90% identity to SEQ ID NO: 104, at least 95% identity to SEQ ID NO: 104, at least 98% identity to SEQ ID NO: 104, or at least 100% identity to SEQ ID NO: 104.

18. The viral particle of any one of embodiments 2-5, wherein the variant Fc protein is a variant IgG2 Fc protein.

19. The viral particle of embodiment 18, wherein the variant IgG2 Fc protein comprises one or more mutations selected from the group consisting of: N297A, P329G, 1253A, H310A, and H435A.

20. The viral particle of embodiments 18 or 19, wherein the IgG2 Fc protein comprises a mutation that corresponds to N297A of SEQ ID NO: 27.

21. The viral particle of embodiments 18 or 19, wherein the IgG2 Fc protein comprises a mutation that corresponds to P329G of SEQ ID NO: 27.

22. The viral particle of any one of embodiments 18-21, wherein the IgG2 Fc protein comprises a mutation that corresponds to N297A and P329G of SEQ ID NO: 27.

23. The viral particle of any one of embodiments 18-22, wherein the variant IgG2 Fc protein comprises a mutation that corresponds to 1253A of SEQ ID NO: 27.

24. The viral particle of any one of embodiments 18-23, wherein the variant IgG2 Fc protein comprises a mutation that corresponds to H310A of SEQ ID NO: 27.

25. The viral particle of any one of embodiments 18-24, wherein the IgG2 Fc protein comprises a mutation that corresponds to H435A of SEQ ID NO: 27.

26. The viral particle of any one of embodiments 18-25, wherein the variant IgG2 Fc protein comprises a mutation that corresponds to I253A, H310A, and H435A of SEQ ID NO: 27.

27. The viral particle of any one of embodiments 2-5, wherein the variant Fc protein is a variant IgG4 Fc protein.

28. The viral particle of embodiment 27, wherein the variant IgG4 Fc protein comprises one or more mutations selected from the group consisting of: S228P, L235E, N297A, P329G, I253A, H310A, and H435A.

29. The viral particle of embodiments 27 or 28, wherein the IgG4 Fc protein comprises a mutation that corresponds to S228P of SEQ ID NO: 28.

30. The viral particle of any one of embodiments 27-29, wherein the IgG4 Fc protein comprises a mutation that corresponds to L235E of SEQ ID NO: 28.

31. The viral particle of any one of embodiments 27-30, wherein the IgG4 Fc protein comprises a mutation that corresponds to N297A of SEQ ID NO: 28.

32. The viral particle of any one of embodiments 27-31, wherein the IgG4 Fc protein comprises a mutation that corresponds to P329G of SEQ ID NO: 28.

33. The viral particle of any one of embodiments 27-32, wherein the IgG4 Fc protein comprises a mutation that corresponds to S228P, L235E, N297A, and P329G of SEQ ID NO: 28.

34. The viral particle of any one of embodiments 27-33, wherein the variant IgG4 Fc protein comprises a mutation that corresponds to I253A of SEQ ID NO: 28.

35. The viral particle of any one of embodiments 27-34, wherein the variant IgG4 Fc protein comprises a mutation that corresponds to H310A of SEQ ID NO: 28.

36. The viral particle of any one of embodiments 27-35, wherein the IgG4 Fc protein comprises a mutation that corresponds to H435A of SEQ ID NO: 28.

37. The viral particle of any one of embodiments 27-36, wherein the variant IgG4 Fc protein comprises a mutation that corresponds to I253A, H310A, and H435A of SEQ ID NO: 28.

38. The viral particle of any one of embodiments 2-37, wherein the targeting moiety having the formula T-$S_1$ comprises a stalk portion $S_1$ having a formula of $L_1$-Fc-$L_2$-$X_1$, wherein:

$L_1$ is a linker or absent;

Fc is a variant Fc protein;

$L_2$ is a linker or absent; and $X_1$ is a polypeptide comprising the transmembrane domain, wherein the targeting moiety having the formula T-$S_1$ has a formula of T-$L_1$-Fc-$L_2$-$X_1$.

39. The viral particle of embodiment 38, wherein $L_1$ and $L_2$ are each, independently, a polypeptide linker.

40. The viral particle of embodiment 39, wherein the polypeptide linker comprises $(GGGGA)_n$ (SEQ ID NO: 54), $(GGGGS)_n$ (SEQ ID NO: 55), $(EAAAK)_n$ (SEQ ID NO: 73), $A(EAAAK)_nA$ (SEQ ID NO: 74), $(XP)_n$ (SEQ ID NO: 75), wherein X is Ala, Lys, or Glu, GSAGSAAGSGEF (SEQ ID NO: 56), KESGSVSSEQLAQFRSLD (SEQ ID NO: 57), EGKSSGSGSESKST (SEQ ID NO: 58), AEAAAKEAAAKA (SEQ ID NO: 76), or a combination thereof, wherein each n is, independently, 1-5.

41. The viral particle of any one of embodiments 38-40, wherein $L_1$ is absent.

42. The viral particle of any one of embodiments 38-40, wherein $L_1$ is $(GGGGA)_n$ (SEQ ID NO: 54) or $(GGGGS)_n$ (SEQ ID NO: 55), and wherein each n is, independently, 1-5.

43. The viral particle of any one of embodiments 38-42, wherein $L_2$ is absent.

44. The viral particle of any one of embodiments 38-42, wherein $L_2$ is $(GGGGA)_n$ (SEQ ID NO: 54) or $(GGGGS)_n$ (SEQ ID NO: 55), and wherein each n is, independently, 1-5.

45. The viral particle of any one of embodiments 38-44, wherein $X_1$ comprises a polypeptide having a formula of ECD-$T_M$-ICD, wherein:

ECD is an extracellular domain, or a fragment thereof, of a cell surface protein, or absent;

$T_M$ is a transmembrane domain of a transmembrane protein; and

ICD is an intracellular domain or a protein that facilitates incorporation of the targeting moiety into the envelope of the viral particle, or absent, wherein the targeting moiety having the formula of T-$L_1$-Fc-$L_2$-$X_1$ has a formula of T-$L_1$-Fc-$L_2$-ECD-TM-ICD.

46. The viral particle of embodiment 45, wherein the ECD is absent.

47. The viral particle of embodiment 45, wherein the ECD is an extracellular domain, or fragment thereof, of CD8 or CD28.

48. The viral particle of embodiment 47, wherein the ECD comprises an amino acid sequence of SEQ ID NO: 59 or SEQ ID NO: 60.

49. The viral particle of embodiment 47, wherein the ECD comprises an amino acid sequence of SEQ ID NO: 60.

50. The viral particle of any one of embodiments 45-49, wherein $T_M$ is a transmembrane domain, or a fragment thereof, of CD8 or CD28.

51. The viral particle of embodiment 50, wherein the $T_M$ comprises an amino acid sequence of SEQ ID NO: 61 or SEQ ID NO: 62.

52. The viral particle of embodiment 50, wherein the $T_M$ comprises an amino acid sequence of SEQ ID NO: 62.

53. The viral particle of any one of embodiments 45-52, wherein the ICD is absent.

54. The viral particle of any one of embodiments 45-52, wherein the ICD comprises an Env incorporation motif.

55. The viral particle of embodiment 54, wherein the Env incorporation motif comprises an amino acid sequence of SEQ ID NO: 63 or SEQ ID NO: 64.

56. The viral particle of embodiment 1, wherein the stalk portion $S_1$ comprises a formula of $L_3$-$X_1$, wherein:

$L_3$ is a flexible peptide linker, and $X_1$ is a polypeptide comprising a transmembrane domain, wherein the targeting moiety having the formula T-$S_1$ has a formula of T-$L_3$-$X_1$.

57. The viral particle of embodiment 56, wherein $L_3$ comprises a polypeptide having a sequence of $(GGGGA)_n$ (SEQ ID NO: 54), $(GGGGS)_n$ (SEQ ID NO: 55), GSAGSAAGSGEF (SEQ ID NO: 56), KESGSVSSEQLAQFRSLD (SEQ ID NO: 57), EGKSSGSGSESKST (SEQ ID NO: 58), or any combination thereof, wherein each n is, independently, 1-4.

58. The viral particle of embodiment 57, wherein n is 1, 2, or 4.

59. The viral particle of any one of embodiments 56-58, wherein $X_1$ comprises a polypeptide having a formula of ECD-$T_M$-ICD, wherein:

ECD is an extracellular domain, or a fragment thereof, of a cell surface protein, or absent;

$T_M$ is a transmembrane domain of a transmembrane protein; and

ICD is an intracellular domain or a protein that facilitates the incorporation of the targeting moiety into the envelope of the viral particle, or absent, wherein the targeting moiety having the formula of T-$L_3$-$X_1$ has a formula of T-$L_3$-ECD-$T_M$-ICD.

60. The viral particle of embodiment 59, wherein the ECD is absent.

61. The viral particle of embodiment 59, wherein the ECD is an extracellular domain, or fragment thereof, or CD8 or CD28.

62. The viral particle of embodiment 61, wherein the ECD comprises an amino acid sequence of SEQ ID NO: 59 or SEQ ID NO: 60.

63. The viral particle of embodiment 61, wherein the ECD comprises an amino acid sequence of SEQ ID NO: 59.

64. The viral particle of any one of embodiments 59-63, wherein $T_M$ is a transmembrane domain, or a fragment thereof, of CD8 or CD28.

65. The viral particle of embodiment 64, wherein the $T_M$ comprises an amino acid sequence of SEQ ID NO: 61 or SEQ ID NO: 62.

66. The viral particle of embodiment 64, wherein the $T_M$ comprises an amino acid sequence of SEQ ID NO: 61.

67. The viral particle of any one of embodiments 59-66, wherein the ICD is absent.

68. The viral particle of any one of embodiments 59-66, wherein the ICD comprises an Env incorporation motif.

69. The viral particle of embodiment 68, wherein the Env incorporation motif comprises an amino acid sequence of SEQ ID NO: 63 or SEQ ID NO: 64.

70. The viral particle of any one of embodiments 1-69, wherein the target binding domain (T) binds to an immune cell, wherein the immune cell is any of a T cell, B cell; NK cell, dendritic cell, neutrophils, macrophages, a cancer cell; or, for example, CD3+ T cell; CD4+ T cell; CD7+ T cell, CD8+ T cell; CD19+B cell; CD19+ cancer cell; CD20+B cell; CD20+ cancer cell, CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

71. The viral particle of any one of embodiments 1-70, wherein the target binding domain (T) binds to CD7, CD8, cKit (CD117), CD4, CD3, CD5, CD6, CD2, TCR alpha, TCR beta, TCR gamma, TCR delta, CD10, CD34, CD110, CD33, CD14, CD68, CCR7, CD62L, CD25, CCR2, CCR3, CCR4, CCR5, CCR6, CCR7, or CXCR3, A glycosylated CD43 epitope expressed on acute leukemia or lymphoma but not on hematopoietic progenitors; A glycosylated CD43 epitope expressed on non-hematopoietic cancers; A kinase anchor protein 4 (AKAP-4); Adrenoceptor beta 3 (ADRB3); AFP; Anaplastic lymphoma kinase (ALK); Androgen receptor; Angiopoietin-binding cell surface receptor 2 (Tie 2); Auto antibody to desmoglein 1 (Dsg1); Auto antibody to desmoglein 3 (Dsg3); B7H3 (CD276); Biotin; Bone marrow stromal cell antigen 2 (BST2); BST1/CD157; Cancer/testis antigen 1 (NY-ESO-1); Cancer/testis antigen 2 (LAGE-la); Carbonic anhydrase IX (CA1X); Carcinoembryonic antigen (CEA); CCCTC-Binding Factor (Zinc Finger Protein)-Like (BORIS or Brother of the Regulator of lmprinted Sites); CCR4; CD5; CD19; CD20; CD22; CD24; CD30; CD32 (FCGR2A); CD33; CD34; CD38; CD44v6; CD72; CD79a; CD79b; CD97; CD99; CD123; CD171; CD179a; CD179b-IGL11; CD200R; CD276/B7H3; CD300 molecule-like family member f (CD300LF); CDH1-CD324; CDH6; CDH17; CDH19; Chromosome X open reading frame 61 (CXORF61); Claudin 6 (CLDN6); Claudin18.2 (CLD18A2 or CLDN18A.2); CMV pp65; C-MYC epitope Tag; Cripto; CS1 (also referred to as CD2 subset 1 or CRACC or SLAMF7 or CD319 or 19A24); CSF2RA (GM-CSFR-alpha); C-type lectin domain family 12 member A (CLEC12A); C-type lectin-like molecule-1 (CLL-1 or CLECL1); Cyclin B1; Cytochrome P450 IB 1 (CYP1B 1); DLL3; EBV-EBNA3c; EGF-bke module-containing mucin-like hormone receptor-like 2 (EMR2); Elongation factor 2 mutated (ELF2M); Ephrin B2; Ephrin type-A receptor 2 (EphA2); Epidermal growth factor receptor (EGFR); Epidermal growth factor receptor variant III (EGFRviii); Epithelial cell adhesion molecule (EPCAM); ERG; ETS translocation-variant gene 6 located on chromosome 12p (ETV6-AML); Fc fragment of IgA receptor (FCAR or CD89); Fc receptor-like 5 (FCRL5); Fibroblast activation protein alpha (FAP); FITC; Fms Like Tyrosine Kinase 3 (FLT3); Folate receptor alpha (Fra or FR1); Folate receptor beta (FRb); Follicle stimulating hormone receptor (FSHR); Fos-related antigen 1; Fucosyl-GM1; G protein coupled receptor class C group 5 member D (GPRC5D); G protein-coupled receptor 20 (GPR20); GAD; Ganglioside G2 (GD2); Ganglioside GD3 (aNeu5Ac(2-8)aNeu5Ac(2-3)bDGalp(1-4)bDGlcp(1-1)Cer); Ganglioside GM3 (aNeu5Ac(2-3)bDClalp(1-4) bDGlcp(1-1)Cer); GD3; GFRalpha4; Glycoprotein 100 (gplOO); Glypican-3 (GPC3); Gonadotropin Hormone receptor (CGHR or GR); GpA33; GpNMB; GPRC5D; Guanylyl cyclase C (GCC); Heat shock protein 70-2 mutated (mut hsp70-2); Hepatitis A virus cellular receptor 1 (HAVCR1); Hexasaccharide portion of globoH glycoceramide (GloboH); High molecular weight-melanoma associated antigen (HMWMAA); HIV1 envelope glycoprotein; HLA; HLA-DOA; HLA-A; HLA-A2; HLA-B; HLA-C; HLA-DM; HLA-DOB; HLA-DP; HLA-DQ; HLA-DR; HLA-G; HTLVI-Tax; Human papilloma virus E6 (HPV E6); Human papilloma virus E7 (HPV E7); Human Telomerase reverse transcriptase (hTERT); IgE; IL13Ra2; Ill 1Ra; Immunoglobulin lambda-like polypeptide 1 (IGLL1); Influenza A hemagglutinin (HA); Insulin-like growth factor 1 receptor (IGF-I receptor); Interleukin 11 receptor alpha (IL-11Ra); Interleukin-13 receptor subunit alpha-2 (IL-13Ra2 or CD213A2); Intestinal carboxyl esterase; KIT (CD117); KSHV K8.1; KSHV-gH; LAMP1; Legumain; Leukocyte immunoglobulin-like receptor subfamily A member 2 (LILRA2); Leukocyte-associated immunoglobulin-like receptor 1 (LAIR1); Leutenizing hormone receptor (LHR); Lewis(Y) antigen; Lews Ag; Livl; Locus K 9 (LY6K); Low conductance chloride channel; Lymphocyte antigen 6 complex; Lymphocyte antigen 75 (LY75); Lymphocyte-specific protein tyrosine kinase (LCK); Mammary gland differentiation antigen (NY-BR-1); Melanoma antigen recognized by T cells 1 (MelanA or MARTI); Melanoma-associated antigen 1 (MAGE-A1); Melanoma cancer testis antigen-1 (MAD-CT-1); Melanoma cancer testis antigen-2 (MAD-CT-2); Melanoma inhibitor of apoptosis (ML-IAP); Mesothelin; MPL; Mucin 1 cell surface associated (MUC1); N-Acetyl glucosaminyl-transferase V (NA17); Nectin-4; Neural cell adhesion molecule (NCAM); NKG2D; NYBR1; O-acetyl-GD2 ganglioside (OacGD2); Olfactory receptor 51E2 (OR51E2); Oncogene fusion protein consisting of breakpoint cluster region (BCR) and Abelson murine leukemia viral oncogene homolog 1 (Abl) (bcr-abl); P53 mutant; Paired box protein Pax-3 (PAX3); Paired box protein Pax-5 (PAX5); Pannexin 3 (PANX3); PDL1; P-glycoprotein; Placenta-specific 1 (PLAC1); Platelet-derived growth factor receptor beta (PDGFR-beta); Polysialic acid; Proacrosin binding protein sp32 (OY-TES1); Prostase; Prostate carcinoma tumor antigen-1 (PCT A-1 or Galectin 8); Prostate stem cell antigen (PSCA); Prostate-specific membrane antigen (PSMA); Prostatic acid phosphatase (PAP); Prostein; Protease Serine 21 (Testisin or PRSS21); Proteasome (Prosome Macropain) Subunit Beta Type 9 (LMP2); PTK7; Ras G12V; Ras Homolog Family Member C (RhoC); Rat sarcoma (Ras) mutant; Receptor for Advanced Gly cation Endproducts (RAGE-1); Receptor tyrosine kinase-like orphan receptor 1 (ROR1); Receptor tyrosine-protein kinase ERBB2 or Her-22/neu; Renal ubiquitous 1 (RU1); Renal ubiquitous 2 (RU2); Sarcoma translocation breakpoints; Serine 2 (TMPRSS2) ETS fusion gene; Sialyl Lewis adhesion molecule (sLe); SLAMF4; SLAMF6; Slea (CA19.9 or Sialyl Lewis Antigen); Sperm protein 17 (SPA17); Squamous Cell Carcinoma Antigen Recognized By T Cells 3 (SART3); Stage-specific embryonic antigen-4 (SSEA-4); STEAP1; Survivin; Synovial sarcoma X breakpoint 2 (SSX2); TCR Gamma Alternate Reading Frame Protein (TARP); TCR-beta1 chain; TCR-beta2 chain; TCR-delta chain; TCR-gamma chain; TCRgamma-delta; Telomerase; TGFbetaR2; The antigen recognized by TNT antibody; Thyroid stimulating hormone receptor (TSHR); Timl-/HVCR1; Tissue Factor 1 (TF1); Tn ag; Tn antigen ((Tn Ag) or (GalNAca-Ser/Thr)); TNF receptor family member B cell maturation (BCMA); Transglutaminase 5 (TGS5); Transmembrane protease; TROP2; Tumor endothelial marker 1 (TEM1/CD248); Tumor endothelial marker 7-related (TEM7R); Tumor protein p53 (p53); Tumor-associated glycoprotein 72 (TAG72); Tyrosinase; Tyrosinase-related protein 2 (TRP-2); Uroplakin 2 (UPK2); Vascular endothelial growth factor receptor 2 (VEGFR2); V-myc avian myelocytomatosis viral oncogene neuroblastoma derived homolog (MYCN); Wilms tumor protein (WT1); or X Antigen Family Member 1A (XAGE1).

72. The viral particle of embodiment 71, wherein the target binding domain (T) binds to CD7.

73. The viral particle of embodiment 72, wherein the target binding domain (T) comprises a polypeptide comprising: (i) a heavy chain comprising a heavy chain variable region comprising heavy chain CDR1, CDR2, and CDR3 sequences, wherein the heavy chain CDR1 sequence has the amino acid sequence of SEQ ID NO: 30; the heavy chain CDR2 has the amino acid sequence of SEQ ID NO: 31; and the heavy chain CDR3 sequence has the amino acid sequence of SEQ ID NO: 32, or variants of any of the foregoing; and (ii) a light chain comprising a light chain variable region comprising light chain CDR1, CDR2, and CDR3 sequences, wherein the light chain CDR1 sequence has the amino acid sequence of SEQ ID NO: 33; the light chain CDR2 sequence has the amino acid sequence of SEQ ID NO: 34; and the light chain CDR3 sequence has the amino acid sequence of SEQ ID NO: 35; or variants of any of the foregoing.

74. The viral particle of embodiment 73, wherein the heavy chain comprises a heavy chain variable region having at least 90% sequence identity to SEQ ID NO: 36, wherein the polypeptide comprises the sequences of HCDR1 as set forth in SEQ ID NO: 30; HCDR2 as set forth in SEQ ID NO: 31; and HCDR3 as set forth in SEQ ID NO: 32.

75. The viral particle of embodiments 73 or 74, wherein the light chain comprises: a light chain variable region having at least 90% sequence identity to SEQ ID NO: 37, wherein the polypeptide comprises the sequences of LCDR1 as set forth in SEQ ID NO: 33; LCDR2 as set forth in SEQ ID NO: 34; and LCDR3 as set forth in SEQ ID NO: 35.

76. The viral particle of any one of embodiments 73-75, wherein the polypeptide comprises a heavy chain and a light chain comprising: a heavy chain variable region of the heavy chain having at least 90% sequence identity to SEQ ID NO: 36, and a light chain variable region of the light chain having at least 90% sequence identity to SEQ ID NO: 37, wherein polypeptide comprises the sequences of HCDR1 as set forth in SEQ ID NO: 30; HCDR2 as set forth in SEQ ID NO: 31; HCDR3 as set forth in SEQ ID NO: 32; LCDR1 as set forth in SEQ ID NO: 33; LCD2 as set forth in SEQ ID NO: 34; and LCDR3 as set forth in SEQ ID NO: 35.

77. The viral particle of any one of embodiments 73-76, wherein the light chain and the heavy chain comprise: a heavy chain variable region of the heavy chain having at least 90% sequence identity to SEQ ID NO: 36; and a light chain variable region of the light chain having at least 90% sequence identity to SEQ ID NO: 37.

78. The viral particle of any one of embodiments 73-77, wherein the light chain and the heavy chain comprise: a heavy chain variable region of the heavy chain having at least 95% sequence identity to SEQ ID NO: 36; and a light chain variable region of the light chain having at least 95% sequence identity to SEQ ID NO: 37.

79. The viral particle of any one of embodiments 73-78, wherein the light chain and the heavy chain comprise: a heavy chain variable region of the heavy chain having at least 99% sequence identity to SEQ ID NO: 36; and a light chain variable region of the light chain having at least 99% sequence identity to SEQ ID NO: 37.

80. The viral particle of any one of embodiments 73-79, wherein the light chain and the heavy chain comprise: a heavy chain variable region comprising SEQ ID NO: 36, and a light chain variable region comprising SEQ ID NO: 37.

81. The viral particle of any one of embodiments 73-80, wherein the heavy chain variable region and the light chain variable region are linked by a linker, such as a peptide linker, which can be for example, a glycine/serine linker.

82. The viral particle of embodiment 81, wherein the peptide linker comprises a sequence of $(GGGGS)_n$, wherein n is independently 1-5.

83. The viral particle of any one of embodiments 73-80, wherein the heavy chain variable region and the light chain variable region are directly linked to one another and are not linked by a linker.

84. The viral particle of any one of embodiments 72-82, wherein the target binding domain (T) that binds to CD7 comprises a polypeptide comprising a sequence having at least 90% sequence identity to SEQ ID NO: 38, at least 95% sequence identity to SEQ ID NO: 38, at least 99% sequence identity to SEQ ID NO: 38, or a sequence as set forth in SEQ ID NO: 38.

85. The viral particle of any one of embodiments 72-82, wherein the target binding domain (T) that binds to CD7 comprises a polypeptide comprising a sequence having at least 90% sequence identity to SEQ ID NO: 39, having at least 95% sequence identity to SEQ ID NO: 39, having at least 99% sequence identity to SEQ ID NO: 39, or a sequence as set forth in SEQ ID NO: 39.

86. The viral particle of embodiment 71, wherein the target binding domain (T) binds to CD8.

87. The viral particle of embodiment 86, wherein the target binding domain (T) comprises a polypeptide that comprises: a heavy chain comprising a heavy chain variable region comprising heavy chain CDR1, CDR2, and CDR3 sequences, wherein the heavy chain CDR1 sequence has the amino acid sequence of SEQ ID NO: 42; the heavy chain CDR2 has the amino acid sequence of SEQ ID NO: 43; and the heavy chain CDR3 sequence has the amino acid sequence of SEQ ID NO: 44, or variants of any of the foregoing; and (ii) a light chain comprising a light chain variable region comprising light chain CDR1, CDR2, and CDR3 sequences, wherein the light chain CDR1 sequence has the amino acid sequence of SEQ ID NO: 45; the light chain CDR2 sequence has the amino acid sequence of SEQ ID NO: 46; and the light chain CDR3 sequence has the amino acid sequence of SEQ ID NO: 47; or variants of any of the foregoing.

88. The viral particle of embodiment 87, wherein the target binding domain (T) comprises a heavy chain comprising a heavy chain variable region having at least 90% sequence identity to SEQ ID NO: 48, wherein the polypeptide comprises the sequences of HCDR1 as set forth in SEQ ID NO: 42; HCDR2 as set forth in SEQ ID NO: 43; and HCDR3 as set forth in SEQ ID NO: 44.

89. The viral particle of embodiment 87 or 88, wherein the target binding domain (T) comprises a light chain comprising a light chain variable region having at least 90% sequence identity to SEQ ID NO: 49, wherein the polypeptide comprises the sequences of LCDR1 as set forth in SEQ ID NO: 45; LCDR2 as set forth in SEQ ID NO: 46; and LCDR3 as set forth in SEQ ID NO: 47.

90. The viral particle of any one of embodiments 87-89, wherein the target binding domain (T) comprises a polypeptide comprising a heavy chain and a light chain comprising: a heavy chain variable region of the heavy chain having at least 90% sequence identity to SEQ ID NO: 48, and a light chain variable region of the light chain having at least 90% sequence identity to SEQ ID NO: 49, wherein polypeptide comprises the sequences of HCDR1 as set forth in SEQ ID NO: 42; HCDR2 as set forth in SEQ ID NO: 43; HCDR3 as set forth in SEQ ID NO: 44; LCDR1 as set forth in SEQ ID NO: 45; LCD2 as set forth in SEQ ID NO: 46; and LCDR3 as set forth in SEQ ID NO: 47.

91. The viral particle of any one of embodiments 87-90, wherein the target binding domain (T) comprises a polypeptide comprising a light chain and a heavy chain comprising: a heavy chain variable region of the heavy chain having at least 90% sequence identity to SEQ ID NO: 48; and a light chain variable region of the light chain having at least 90% sequence identity to SEQ ID NO: 49.

92. The viral particle of any one of embodiments 87-90, wherein the target binding domain (T) comprises a polypeptide comprising a light chain and a heavy chain comprising: a heavy chain variable region of the heavy chain having at least 95% sequence identity to SEQ ID NO: 48; and a light chain variable region of the light chain having at least 95% sequence identity to SEQ ID NO: 49.

93. The viral particle of any one of embodiments 87-90, wherein the target binding domain (T) comprises a polypeptide comprising a light chain and a heavy chain comprising: a heavy chain variable region of the heavy chain having at least 99% sequence identity to SEQ ID NO: 48; and a light chain variable region of the light chain having at least 99% sequence identity to SEQ ID NO: 49.

94. The viral particle of embodiment 86, wherein the target binding domain (T) comprises a polypeptide comprising a light chain and a heavy chain comprising: wherein the heavy chain comprises a heavy chain variable region comprising SEQ ID NO: 48, and the light chain comprises a light chain variable region comprising SEQ ID NO: 49.

95. The viral particle of any one of embodiments 87-94, wherein the heavy chain variable region and the light chain variable region are linked by a linker, such as a peptide linker.

96. The viral particle of embodiment 95, wherein the peptide linker is a glycine/serine linker.

97. The viral particle of embodiments 95 or 96, wherein the peptide linker comprises a sequence of $(GGGGS)_n$ (SEQ ID NO: 55), wherein each n is independently 1-5.

98. The viral particle of any one of embodiments 87-94, wherein the heavy chain variable region and the light chain variable region are directly linked to one another and are not linked by a linker.

99. The viral particle of any one of embodiments 86-97, wherein the target binding domain (T) that binds to CD8 comprises a polypeptide comprising a sequence having at least 90% sequence identity to SEQ ID NO: 50, at least 95% sequence identity to SEQ ID NO: 50, at least 99% sequence identity to SEQ ID NO: 50, or a sequence as set forth in SEQ ID NO: 50.

100. The viral particle of any one of embodiments 86-97, wherein the target binding domain (T) that binds to CD8 comprises a polypeptide comprising a sequence having at least 90% sequence identity to SEQ ID NO: 51, having at least 95% sequence identity to SEQ ID NO: 51, having at least 99% sequence identity to SEQ ID NO: 51, or a sequence as set forth in SEQ ID NO: 51.

101. The viral particle of any one of embodiments 1-100, wherein the target binding domain (T) is an antibody, or an antigen-binding fragment thereof, such as scFv antibody.

102. The viral particle of any one of embodiments 1-101, wherein the heterologous viral glycoprotein is a SVCV-G polypeptide.

103. The viral particle of embodiment 102, wherein the SVCV-G polypeptide comprises a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 52 or SEQ ID NO: 53.

104. The viral particle of embodiment 102 or 103, wherein the SVCV-G polypeptide comprises a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 52.

105. The viral particle of embodiment 102 or 103, wherein the SVCV-G polypeptide comprises a polypeptide having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% identity to SEQ ID NO: 53.

106. The viral particle of embodiment 102 or 103, wherein the SVCV-G polypeptide comprises SEQ ID NO: 52 or SEQ ID NO: 53.

107. The viral particle of any one of embodiments 102, 103, or 106, wherein the SVCV-G polypeptide comprises SEQ ID NO: 52.

108. The viral particle of any one of embodiments 102, 103, or 106, wherein the SVCV-G polypeptide comprises SEQ ID NO: 53.

109. The viral particle of any one of embodiments 1-101, wherein the heterologous viral glycoprotein is a VSV-G polypeptide.

110. The viral particle 109, wherein the VSV-G polypeptide comprises a polypeptide of SEQ ID NO: 2 comprising a mutation that corresponds to a mutation at position 182 of SEQ ID NO: 2.

111. The viral particle 109, wherein the VSV-G polypeptide comprises an amino acid sequence having at least 70% identity to SEQ ID NO: 2 and comprising a mutation at position 182 as compared to SEQ ID NO: 2.

112. The viral particle of embodiment 110 or 111, wherein the VSV-G polypeptide comprises a I182E or I182D mutation as compared to SEQ ID NO: 2.

113. The viral particle of any one of embodiments 109-112, wherein the VSV-G polypeptide comprises the sequence having at least 70% identity to SEQ ID NO: 1 and comprising a mutation at position 198 as compared to SEQ ID NO: 1.

114. The viral particle of any one of embodiments 109-113, wherein the VSV-G polypeptide comprises a mutation that corresponds to I182D or I182E as compared to a sequence of SEQ ID NO: 2.

115. The viral particle of any one of embodiments 109-114, wherein the VSV-G polypeptide comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% to a sequence of SEQ ID NO: 4.

116. The viral particle of any one of embodiments 109-114, wherein the VSV-G polypeptide comprises a sequence of SEQ ID NO: 4.

117. The viral particle of any one of embodiments 109-114, wherein the VSV-G polypeptide comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% to a sequence of SEQ ID NO: 5.

118. The viral particle of any one of embodiments 109-114, wherein the VSV-G polypeptide comprises a sequence of SEQ ID NO: 5.

119. The viral particle of any one of embodiments 109-111 or 113, wherein the VSV-G polypeptide comprises a sequence at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% to a sequence of SEQ ID NO: 3.

120. The viral particle of any one of embodiments 109-111 or 113, wherein the VSV-G polypeptide comprises a sequence of SEQ ID NO: 53.

121. The viral particle of any one of embodiments 109-120, wherein the VSV-G polypeptide further comprises a mutation in the VSV-G protein that corresponds to a mutation as described in US 2020/0216502.

122. The viral particle of any one of embodiments 109-121, wherein the VSV-G polypeptide further comprises a mutation in the VSV-G protein that corresponds to a position of 8, 10, 47, 209 and/or 354 as compared to SEQ ID NO: 2.

123. The viral particle of any one of embodiments 109-122, wherein the VSV-G polypeptide further comprises a mutation that corresponds to a position 8 in SEQ ID NO: 2, wherein the mutation any amino acid different from the amino acid indicated at that position in the sequence SEQ ID NO: 2, except Y.

124. The viral particle of any one of embodiments 109-123, wherein the VSV-G polypeptide further comprises a mutation that corresponds to a position 209 in SEQ ID NO: 2, wherein the mutation any amino acid different from the amino acid indicated at that position in the sequence SEQ ID NO: 2, except H.

125. The viral particle of any one of embodiments 109-124, wherein the VSV-G polypeptide further comprises a mutation that corresponds to a position 47 in SEQ ID NO: 2, wherein the mutation any amino acid different from the amino acid indicated at that position in the sequence SEQ ID NO: 2, except K or R.

126. The viral particle of any one of embodiments 109-125, wherein the VSV-G polypeptide further comprises a mutation that corresponds to a position 354 in SEQ ID NO: 2, wherein the mutation any amino acid different from the amino acid indicated at that position in the sequence SEQ ID NO: 2, except K or R.

127. The viral particle of any one of embodiments 109-126, wherein the VSV-G polypeptide further comprises a mutation that corresponds to a position 10 in SEQ ID NO: 2, wherein the mutation any amino acid different from the amino acid indicated at that position in the sequence SEQ ID NO: 2, except Q or N.

128. The viral particle of any one of embodiments 109-127, wherein the VSV-G protein comprises a substitution at position 47 or at position 354, or at both positions 47 and 354, wherein each position is, independently, substituted by A, G, F, Q, or N.

129. The viral particle of any one of embodiments 109-128, wherein the VSV-G protein comprises a substitution at position 8, wherein the substitution is H8A, H8I, H8V, H8L, and the like.

130. The viral particle of any one of embodiments 109-129, wherein the VSV-G protein comprises a substitution at position 47, wherein the substitution is K47Q or K47N.

131. The viral particle of any one of embodiments 109-130, wherein the VSV-G protein comprises a substitution H8A and/or K47Q mutation.

132. The viral particle of any one of embodiments 109-131, wherein the VSV-G protein comprises a substitution at position 10, such as Q10A, Q10R, or Q10K substitution.

133. The viral particle of any one of embodiments 109-132, wherein the VSV-G protein further comprises a mutation that corresponds to a mutation at positions 214 and/or 352 of SEQ ID NO: 2.

134. The viral particle of embodiment 133, wherein the VSV-G polypeptide comprises a T214N and/or T352A mutation.

135. The viral particle of embodiment 109, wherein the VSV-G polypeptide comprises a substitution at positions I182 and at least one of T214, and T352 of SEQ ID NO: 2.

136. The viral particle of embodiment 135, wherein the VSV-G polypeptide comprises substitutions at positions I182, T214, and T352 of SEQ ID NO: 2.

137. The viral particle of embodiments 135 or 136, wherein the substitution at position 182 is I182D or I182E, the substitution at position 214 is T214N, and the substitution at position 352 is T352A.

138. The viral particle of any one of embodiments 135-137, wherein the VSV-G polypeptide comprises a sequence of SEQ ID NO: 22, SEQ ID NO: 23, SEQ ID NO: 24 or SEQ ID NO: 25.

139. The viral particle of any one of embodiments 135-137, wherein the VSV-G polypeptide comprises a sequence of SEQ ID NO: 22.

140. The viral particle of any one of embodiments 135-137, wherein the VSV-G polypeptide comprises a sequence of SEQ ID NO: 23.

141. The viral particle of any one of embodiments 135-137, wherein the VSV-G polypeptide comprises a sequence of SEQ ID NO: 24.

142. The viral particle of any one of embodiments 135-137, wherein the VSV-G polypeptide comprises a sequence of SEQ ID NO: 25.

143. The viral particle of any one of embodiments 1-142, wherein the viral particle further comprises a nucleic acid molecule encoding a heterologous molecule of interest.

144. The viral particle of embodiment 141, wherein the heterologous molecule of interest is an siRNA, an shRNA, a non-coding RNA (e.g. a guide RNA for a CRISPR system), a peptide, a polypeptide, a protein, a viral payload, a viral genome, or a combination thereof.

145. The viral particle of embodiments 143 or 144, wherein the heterologous molecule of interest is a chimeric antigen receptor ("CAR").

146. The viral particle of embodiment 145, wherein the CAR comprises an antigen binding domain comprising an antibody, or a fragment thereof.

147. The viral particle of embodiment 146, wherein the antibody, or fragment thereof is an antibody, a scFv antibody, an antigen binding domain, an ankyrin repeat, a VHH domain antibody, a nanobody, a single domain antibody, or an FN3 antibody.

148. The viral particle of embodiment 146 or 147, wherein the antigen binding domain of the CAR binds to CD20.

149. The viral particle of embodiment 148, wherein the antigen binding domain that binds to CD20 comprises a polypeptide comprising a light chain and a heavy chain comprising: a heavy chain variable region of the heavy chain having at least 90% identity to an amino acid sequence of SEQ ID NO: 89; and a light chain variable region of the light chain having at least 90% identity to an amino acid sequence of SEQ ID NO: 90.

150. The viral particle of embodiment 148, wherein the antigen binding domain that binds to CD20 comprises a polypeptide comprising a light chain and a heavy chain comprising: a heavy chain variable region of the heavy chain having at least 95% identity to an amino acid sequence of SEQ ID NO: 89; and a light chain variable region of the light chain having at least 95% identity to an amino acid sequence of SEQ ID NO: 90.

151. The viral particle of embodiment 148, wherein the antigen binding domain that binds to CD20 comprises a polypeptide comprising a light chain and a heavy chain comprising: a heavy chain variable region of the heavy chain having at least 99% identity to an amino acid sequence of SEQ ID NO: 89; and a light chain variable region of the light chain having at least 99% identity to an amino acid sequence of SEQ ID NO: 90.

152. The viral particle of embodiment 148, wherein the antigen binding domain that binds to CD20 comprises a polypeptide comprising a light chain and a heavy chain comprising: a heavy chain variable region of the heavy chain comprising an amino acid sequence of SEQ ID NO: 89; and a light chain variable region of the light chain comprising an amino acid sequence of SEQ ID NO: 90.

153. The viral particle of any one of embodiments 149-152, wherein the heavy chain variable region and the light chain variable region are directly linked to one another and are not linked by a linker.

154. The viral particle of any one of embodiments 149-152, wherein the antigen binding domain that binds to CD20 comprises a polypeptide comprising a sequence having at least 90% sequence identity to SEQ ID NO: 92, at least 95% sequence identity to SEQ ID NO: 92, at least 99% sequence identity to SEQ ID NO: 92, or a sequence as set forth in SEQ ID NO: 92.

155. The viral particle of any one of embodiments 149-152, wherein the antigen binding domain that binds to CD20 comprises a polypeptide comprising a sequence having at least 90% sequence identity to SEQ ID NO: 93, at least 95% sequence identity to SEQ ID NO: 93, at least 99% sequence identity to SEQ ID NO: 93, or a sequence as set forth in SEQ ID NO: 93.

156. The viral particle of embodiment 148, wherein the antigen binding domain that binds to CD20 comprises a polypeptide comprising a light chain and a heavy chain comprising: a heavy chain variable region of the heavy chain having at least 90% identity to an amino acid sequence of SEQ ID NO: 94; and a light chain variable region of the light chain having at least 90% identity to an amino acid sequence of SEQ ID NO: 95.

157. The viral particle of embodiment 148, wherein the antigen binding domain that binds to CD20 comprises a polypeptide comprising a light chain and a heavy chain comprising: a heavy chain variable region of the heavy chain having at least 95% identity to an amino acid sequence of SEQ ID NO: 94; and a light chain variable region of the light chain having at least 95% identity to an amino acid sequence of SEQ ID NO: 95.

158. The viral particle of embodiment 148, wherein the antigen binding domain that binds to CD20 comprises a polypeptide comprising a light chain and a heavy chain comprising: a heavy chain variable region of the heavy chain having at least 99% identity to an amino acid sequence of SEQ ID NO: 94; and a light chain variable region of the light chain having at least 99% identity to an amino acid sequence of SEQ ID NO: 95.

159. The viral particle of embodiment 148, wherein the antigen binding domain that binds to CD20 comprises a polypeptide comprising a light chain and a heavy chain comprising: a heavy chain variable region of the heavy chain comprising an amino acid sequence of SEQ ID NO: 94; and a light chain variable region of the light chain comprising an amino acid sequence of SEQ ID NO: 95.

160. The viral particle of any one of embodiments 156-159, wherein the heavy chain variable region and the light chain variable region are directly linked to one another and are not linked by a linker.

161. The viral particle of any one of embodiments 156-159, wherein the antigen binding domain that binds to CD20 comprises a polypeptide comprising a sequence having at least 90% sequence identity to SEQ ID NO: 96, at least 95% sequence identity to SEQ ID NO: 96, at least 99% sequence identity to SEQ ID NO: 96, or a sequence as set forth in SEQ ID NO: 96.

162. The viral particle of any one of embodiments 156-159, wherein the antigen binding domain that binds to CD20 comprises a polypeptide comprising a sequence having at least 90% sequence identity to SEQ ID NO: 97, at least 95% sequence identity to SEQ ID NO: 97, at least 99% sequence identity to SEQ ID NO: 97, or a sequence as set forth in SEQ ID NO: 97.

163. The viral particle of any one of embodiments 145-162, wherein the CAR further comprises a hinge domain, a transmembrane domain, a costimulatory domain, and a signaling domain.

164. The viral particle of embodiment 163, wherein the hinge domain comprises an amino acid sequence having at least 85%, 86%, 87%, 88%, 89%, 90%, 91%, 92%, 93%, 94%, 95%, 96%, 97%, 98%, 99%, or 100% identity to an amino acid sequence of SEQ ID NO: 59.

165. The viral particle of embodiment 163 or 164, wherein the transmembrane domain comprises an amino acid sequence having at least 85%, 86%, 87%, 88%, 89%, 90%, 91%, 92%, 93%, 94%, 95%, 96%, 97%, 98%, 99%, or 100% identity to an amino acid sequence of SEQ ID NO: 61.

166. The viral particle of any one of embodiments 163-165, wherein the costimulatory domain comprises an amino acid sequence having at least 85%, 86%, 87%, 88%, 89%, 90%, 91%, 92%, 93%, 94%, 95%, 96%, 97%, 98%, 99%, or 100% identity to an amino acid sequence of SEQ ID NO: 101.

167. The viral particle of any one of embodiments 163-166, wherein the signaling domain comprises an amino acid sequence having at least 85%, 86%, 87%, 88%, 89%, 90%, 91%, 92%, 93%, 94%, 95%, 96%, 97%, 98%, 99%, or 100% identity to an amino acid sequence of SEQ ID NO: 102.

168. The viral particle of embodiment 148, wherein the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

169. A method of infecting a cell, the method comprising contacting the cell with a viral particle of any one of embodiments 1-168.

170. A method of infecting a cell in a subject, the method comprising administering to the subject a pharmaceutical composition comprising a viral particle of any one of embodiments 1-168.

171. A method of delivering a heterologous molecule of interest to a cell, the method comprising contacting the cell with a viral particle of any one of embodiments 1-168, wherein the viral particle comprises a nucleic acid molecule encoding the heterologous molecule of interest.

172. A method of delivering a heterologous molecule of interest to a cell in a subject, the method comprising administering to the subject a viral particle of any one of embodiments 1-168, wherein the viral particle comprises a nucleic acid molecule encoding the heterologous molecule of interest.

173. The method of any one of embodiments 169-172, wherein the cell is an immune cell.

174. The method of any one of embodiments 169-173, wherein the cell is a T cell, B cell; NK cell, dendritic cell, neutrophils, macrophages, a cancer cell; or, for example, CD3+ T cell; CD4+ T cell; CD7+ T cell, CD8+ T cell; CD19+B cell; CD19+ cancer cell; CD20+B cell; CD20+ cancer cell, CD30+ lung epithelial cell; CD34+ haematopoietic stem cell; CD105+ endothelial cell; CD105+ haematopoietic stem cell; CD117+ haematopoietic stem cell; CD133+ cancer cell; EpCAM+ cancer cell; GluA2+ neuron; GluA4+ neuron; Haematopoietic stem cell; Hepatocyte; Her2/Neu+ cancer cell; NKG2D+ natural killer cell; SLC1A3+ astrocyte; SLC7A10+ adipocyte.

175. A method of treating a disease or disorder in a subject, the method comprising administering to the subject a viral particle of any one of embodiments 1-168, wherein the viral particle comprises a nucleic acid molecule encoding the heterologous molecule of interest to treat the disease or disorder.

176. The method of embodiment 175, wherein the disease or disorder is cancer (e.g. such as a T cell or B cell disorder or other type of cancer as described herein), an immune disorder, an auto-immune disorder, metabolic disorder, and the like.

177. A method of delivering a heterologous molecule to a target cell, the method comprising contacting the cell with a viral vector or particle of any one of embodiments 1-168, wherein the particle comprises a nucleic acid molecule encoding the heterologous molecule.

178. A viral particle comprising a heterologous viral glycoprotein and a targeting moiety comprising a polypeptide having the formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52 or SEQ ID NO: 53;

wherein the target binding domain comprises a sequence selected from SEQ ID NO: 38, SEQ ID NO: 39, SEQ ID NO: 50 or SEQ ID NO: 51;

wherein the stalk portion $S_1$ comprises a variant Fc protein comprising a sequence that is a variant of SEQ ID NO: 26, SEQ ID NO: 27, or SEQ ID NO: 28;

wherein the variant of SEQ ID NO: 26 comprises one or more mutations selected from the group consisting of L234A, L235A, N297A, P329G, 1253A, H310A, and H435A;

wherein the variant of SEQ ID NO: 27 comprises one or more mutations selected from the group consisting of N297A, P329G, I253A, H310A, and H435A;

wherein the variant of SEQ ID NO: 28 comprises one or more mutations selected from the group consisting of S228P, L235E, N297A, P329G, I253A, H310A, and H435A; and wherein the variant Fc protein further comprises a transmembrane domain comprising a sequence selected from SEQ ID NO: 61 or SEQ ID NO: 62.

179. A viral particle comprising a heterologous viral glycoprotein and a targeting moiety comprising a polypeptide having the formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52 or SEQ ID NO: 53;

wherein the target binding domain comprises a sequence selected from SEQ ID NO: 38, SEQ ID NO: 39, SEQ ID NO: 50 or SEQ ID NO: 51;

wherein the stalk portion $S_1$ comprises a formula of $L_1$-Fc-$L_2$-$X_1$, wherein:

$L_1$ is a linker comprising a sequence selected from SEQ ID NO: 54, SEQ ID NO: 55, SEQ ID NO: 56, SEQ ID NO: 57, SEQ ID NO: 58, SEQ ID NO: 73, SEQ ID NO: 74, SEQ ID NO: 75, or SEQ ID NO: 76 or is absent;

Fc is a variant Fc protein comprising a sequence that is a variant of SEQ ID NO: 26, SEQ ID NO: 27, or SEQ ID NO: 28;

wherein the variant of SEQ ID NO: 26 comprises one or more mutations selected from the group consisting of L234A, L235A, N297A, P329G, I253A, H310A, and H435A;

wherein the variant of SEQ ID NO: 27 comprises one or more mutations selected from the group consisting of N297A, P329G, 1253A, H310A, and H435A;

wherein the variant of SEQ ID NO: 28 comprises one or more mutations selected from the group consisting of S228P, L235E, N297A, P329G, I253A, H310A, and H435A;

$L_2$ is a linker comprising a sequence selected from SEQ ID NO: 54, SEQ ID NO: 55, SEQ ID NO: 56, SEQ ID NO: 57, SEQ ID NO: 58, SEQ ID NO: 73, SEQ ID NO: 74, SEQ ID NO: 75, or SEQ ID NO: 76 or is absent; and $X_1$ is a polypeptide comprising a transmembrane domain having a formula of ECD-$T_M$-ICD, wherein:

ECD is an extracellular domain having a sequence selected from SEQ ID NO: 59 or SEQ ID NO: 60 or a fragment thereof or is absent;

$T_M$ is a transmembrane domain having a sequence of SEQ ID NO: 61 or SEQ ID NO: 62, or a fragment thereof; and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64 or the ICD is absent.

180. A viral particle comprising a heterologous viral glycoprotein and a targeting moiety comprising a polypeptide having the formula T-$S_1$, wherein T is a target binding domain and $S_1$ is a stalk portion, wherein the heterologous viral glycoprotein comprises a sequence selected from SEQ ID NO: 22, SEQ ID NO: 23, SEQ ID NO: 24, SEQ ID NO: 25, SEQ ID NO: 52 or SEQ ID NO: 53;

wherein the target binding domain comprises a sequence selected from SEQ ID NO: 38, SEQ ID NO: 39, SEQ ID NO: 50 or SEQ ID NO: 51;

wherein the stalk portion $S_1$ comprises a formula of $L_1$-Fc-$L_2$-$X_1$, wherein:

$L_1$ is a linker comprising a sequence of SEQ ID NO: 55 or is absent;

Fc is a variant Fc protein comprising a sequence that is a variant of SEQ ID NO: 26, SEQ ID NO: 27, or SEQ ID NO: 28;

wherein the variant of SEQ ID NO: 26 comprises one or more mutations selected from the group consisting of L234A, L235A, N297A, P329G, I253A, H310A, and H435A;

wherein the variant of SEQ ID NO: 27 comprises one or more mutations selected from the group consisting of N297A, P329G, 1253A, H310A, and H435A;

wherein the variant of SEQ ID NO: 28 comprises one or more mutations selected from the group consisting of S228P, L235E, N297A, P329G, I253A, H310A, and H435A;

$L_2$ is a linker comprising a sequence of SEQ ID NO: 55 or is absent; and $X_1$ is a polypeptide comprising a transmembrane domain having a formula of ECD-$T_M$-ICD, wherein:

ECD is an extracellular domain having a sequence of SEQ ID NO: 60 or a fragment thereof or is absent;

$T_M$ is a transmembrane domain having a sequence of SEQ ID NO: 62, or a fragment thereof; and ICD is an intracellular domain or protein that facilitates the incorporation of the targeting moiety into the envelope of the viral particle, wherein the ICD comprises an env incorporation motif comprising an amino acid sequence of SEQ ID NO: 63 or SEQ ID NO: 64 or the ICD is absent.

181. The viral particle of any one of embodiments 178-180, wherein the variant Fc protein comprises an amino acid sequence having at least 85% identity to SEQ ID NO: 104, at least 90% identity to SEQ ID NO: 104, at least 95% identity to SEQ ID NO: 104, at least 98% identity to SEQ ID NO: 104, or comprises the amino acid sequence of SEQ ID NO: 104.

182. A viral particle comprising a heterologous viral glycoprotein and a targeting moiety comprising a polypeptide having the formula T-$S_1$, wherein T is a target binding domain and $S_1$ is a stalk portion, wherein the heterologous viral glycoprotein comprises a sequence of SEQ ID NO: 23 or SEQ ID NO: 25;

wherein the target binding domain comprises a sequence of SEQ ID NO: 39;

wherein the stalk portion $S_1$ comprises a formula of $L_1$-Fc-$L_2$-$X_1$, wherein:

$L_1$ is a linker comprising a sequence of SEQ ID NO: 55;

Fc is a variant Fc protein comprising a sequence of SEQ ID NO: 104;

$L_2$ is a linker and is absent;

$X_1$ is a polypeptide comprising a transmembrane domain having a formula of ECD-$T_M$-ICD, wherein:

ECD is an extracellular domain having a sequence of SEQ ID NO: 60;

$T_M$ is a transmembrane domain having a sequence of SEQ ID NO: 62; and

ICD is an intracellular domain or protein that facilitates the incorporation of the targeting moiety into the envelope of the viral particle, wherein the ICD comprises an env incorporation motif comprising an amino acid sequence of SEQ ID NO: 63.

183. A viral particle comprising a heterologous viral glycoprotein and a targeting moiety, wherein;

the heterologous viral glycoprotein comprises an amino acid sequence having at least 90% identity to SEQ ID NO: 23 or SEQ ID NO: 25, having at least 95% identity of SEQ ID NO: 23 or SEQ ID NO: 25, having at least 99% identity to SEQ ID NO: 23 or SEQ ID NO: 25, or having at least 100% identity to SEQ ID NO: 23 or SEQ ID NO: 25; and the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98.

184. A viral particle comprising a heterologous viral glycoprotein and a targeting moiety, wherein;

the heterologous viral glycoprotein comprises an amino acid sequence having at least 90% identity to of SEQ ID NO: 52 or SEQ ID NO: 53, having at least 95% identity to SEQ ID NO: 52 or SEQ ID NO: 53, having at least 99% identity to SEQ ID NO: 52 or SEQ ID NO: 53, or having at least 100% identity to SEQ ID NO: 52 or SEQ ID NO: 53; and the targeting moiety comprises an amino acid sequence having at least 90% identity to SEQ ID NO: 98, at least 95% identity to SEQ ID NO: 98, at least 99% identity to SEQ ID NO: 98, or at least 100% identity to SEQ ID NO: 98.

185. A viral particle comprising a heterologous viral structural protein and a targeting moiety comprising a polypeptide having the formula T-$S_1$, wherein T is a target binding domain and $S_1$ is a stalk portion;

wherein the target binding domain comprises an amino acid sequence of SEQ ID NO: 38 or SEQ ID NO: 39;

wherein the stalk portion $S_1$ comprises a formula of $L_3$-$X_1$; wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58; and $X_1$ is polypeptide comprising a transmembrane domain having a formula ECD-$T_M$-ICD, wherein:

ECD is an extracellular domain comprising an amino acid sequence of SEQ ID NO: 59 or SEQ ID NO: 60, or a fragment thereof, or is absent;

$T_M$ is a transmembrane domain comprising an amino acid sequence of SEQ ID NO: 61 or SEQ ID NO: 62, or a fragment thereof; and ICD is an intracellular domain or protein that facilitates the incorporation of the targeting moiety into the envelope of the viral particle or is absent, wherein the ICD comprises an env incorporation motif comprising an amino acid comprising a sequence of SEQ ID NO: 63 or SEQ ID NO: 64.

186. The viral particle of embodiment 185, wherein:

T comprises an amino acid sequence of SEQ ID NO: 38;

$L_3$ comprises an amino acid sequence of SEQ ID NO: 55;

ECD comprises an amino acid sequence of SEQ ID NO: 59;

$T_M$ comprises an amino acid sequence of SEQ ID NO: 61; and the ICD comprises an env incorporation motif comprising an amino acid sequence of SEQ ID NO: 63 or SEQ ID NO: 64.

187. The viral particle of embodiment 185, wherein:

T comprises an amino acid sequence of SEQ ID NO: 39;

$L_3$ comprises an amino acid sequence of SEQ ID NO: 55;

ECD comprises an amino acid sequence of SEQ ID NO: 59;

$T_M$ comprises an amino acid sequence of SEQ ID NO: 61; and the ICD comprises an env incorporation motif comprising an amino acid sequence of SEQ ID NO: 63 or SEQ ID NO: 64.

188. A viral particle comprising a heterologous viral structural protein and a targeting moiety comprising a polypeptide having the formula T-$S_1$, wherein T is a target binding domain and $S_1$ is a stalk portion;

wherein the target binding domain comprises an amino acid sequence of SEQ ID NO: 50 or SEQ ID NO: 51;

wherein the stalk portion $S_1$ comprises a formula of $L_3$-$X_1$; wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58; and $X_1$ is polypeptide comprising a transmembrane domain having a formula ECD-$T_M$-ICD, wherein:

ECD is an extracellular domain comprising an amino acid sequence of SEQ ID NO: 59 or SEQ ID NO: 60, or a fragment thereof, or is absent;

$T_M$ is a transmembrane domain comprising an amino acid sequence of SEQ ID NO: 61 or SEQ ID NO: 62, or a fragment thereof; and ICD is an intracellular domain or protein that facilitates the incorporation of the targeting moiety into the envelope of the viral particle or is absent, wherein the ICD comprises an env incorporation motif comprising an amino acid comprising a sequence of SEQ ID NO: 63 or SEQ ID NO: 64.

189. The viral particle of embodiment 188, wherein:

T comprises an amino acid sequence of SEQ ID NO: 50;

$L_3$ comprises an amino acid sequence of SEQ ID NO: 55;

ECD comprises an amino acid sequence of SEQ ID NO: 59;

$T_M$ comprises an amino acid sequence of SEQ ID NO: 61; and the ICD comprises an env incorporation motif comprising an amino acid sequence of SEQ ID NO: 63 or SEQ ID NO: 64.

190. The viral particle of embodiment 188, wherein:

T comprises an amino acid sequence of SEQ ID NO: 51;

$L_3$ comprises an amino acid sequence of SEQ ID NO: 55;

ECD comprises an amino acid sequence of SEQ ID NO: 59;

$T_M$ comprises an amino acid sequence of SEQ ID NO: 61; and the ICD comprises an env incorporation motif comprising an amino acid sequence of SEQ ID NO: 63 or SEQ ID NO: 64.

191. A viral particle comprising a heterologous viral structural protein and a targeting moiety comprising a polypeptide having the formula T-$S_1$;

wherein the heterologous viral structural protein comprises a sequence of SEQ ID NO: 22, SEQ ID NO: 23, SEQ ID NO: 24, SEQ ID NO: 25, SEQ ID NO: 52 or SEQ ID NO: 53;

wherein T is a target binding domain and $S_1$ is a stalk portion;

wherein the target binding domain comprises an amino acid sequence of SEQ ID NO: 38, SEQ ID NO: 39, SEQ ID NO: 50 or SEQ ID NO: 51;

wherein the stalk portion $S_1$ comprises a formula of $L_3$-$X_1$; wherein $L_3$ is a flexible peptide linker comprising an amino acid sequence of SEQ ID NO: 54, SEQ ID NO: 55, SEQ ID NO: 56, SEQ ID NO: 57, or SEQ ID NO: 58; and $X_1$ is polypeptide comprising a transmembrane domain having a formula ECD-$T_M$-ICD, wherein:

ECD is an extracellular domain comprising an amino acid sequence of SEQ ID NO: 59 or SEQ ID NO: 60, or a fragment thereof, or is absent;

$T_M$ is a transmembrane domain comprising an amino acid sequence of SEQ ID NO: 61 or SEQ ID NO: 62, or a fragment thereof; and ICD is an intracellular domain or protein that facilitates the incorporation of the targeting moiety into the envelope of the viral particle, wherein the ICD comprises an env incorporation motif comprising an amino acid comprising a sequence of SEQ ID NO: 63 or SEQ ID NO: 64.

192. A viral particle comprising a heterologous viral structural protein and a targeting moiety comprising a polypeptide having the formula T-$S_1$;

wherein the heterologous viral structural protein comprises a sequence of SEQ ID NO: 22, SEQ ID NO: 23, SEQ ID NO: 24, SEQ ID NO: 25, SEQ ID NO: 52 or SEQ ID NO: 53;

wherein T is a target binding domain and $S_1$ is a stalk portion;

wherein the target binding domain comprises an amino acid sequence of SEQ ID NO: 38, SEQ ID NO: 39, SEQ ID NO: 50 or SEQ ID NO: 51;

wherein the stalk portion $S_1$ comprises a formula of $L_3$-$X_1$; wherein $L_3$ is a flexible peptide linker comprising an amino acid sequence of SEQ ID NO: 55; and $X_1$ is polypeptide comprising a transmembrane domain having a formula ECD-$T_M$-ICD, wherein:

ECD is an extracellular domain comprising an amino acid sequence of SEQ ID NO: 59 or a fragment thereof, or is absent;

$T_M$ is a transmembrane domain comprising an amino acid sequence of SEQ ID NO: 61 or a fragment thereof; and ICD is an intracellular domain or protein that facilitates the incorporation of the targeting moiety into the envelope of the viral particle or is absent, wherein the ICD comprises an env incorporation motif comprising an amino acid comprising a sequence of SEQ ID NO: 63 or SEQ ID NO: 64.

193. A viral particle comprising a heterologous viral structural protein and a targeting moiety comprising a polypeptide having the formula T-$S_1$;

wherein the heterologous viral structural protein comprises a sequence of SEQ ID NO: 23 or SEQ ID NO: 25;

wherein T is a target binding domain and $S_1$ is a stalk portion;

wherein the target binding domain comprises an amino acid sequence of SEQ ID NO: 39;

wherein the stalk portion $S_1$ comprises a formula of $L_3$-$X_1$; wherein $L_3$ is a flexible peptide linker comprising an amino acid sequence of SEQ ID NO: 55; and $X_1$ is polypeptide comprising a transmembrane domain having a formula ECD-$T_M$-ICD, wherein:

ECD is an extracellular domain comprising an amino acid sequence of SEQ ID NO: 59;

$T_M$ is a transmembrane domain comprising an amino acid sequence of SEQ ID NO: 61; and ICD is an intracellular domain or protein that facilitates the incorporation of the targeting moiety into the envelope of the viral particle, wherein the ICD comprises an env incorporation motif comprising an amino acid comprising a sequence of SEQ ID NO: 63 or SEQ ID NO: 64.

194. A viral particle comprising a heterologous viral structural protein and a targeting moiety comprising a polypeptide having the formula T-$S_1$;

wherein the heterologous viral structural protein comprises a sequence of SEQ ID NO: 52 or SEQ ID NO: 53;

wherein T is a target binding domain and $S_1$ is a stalk portion;

wherein the target binding domain comprises an amino acid sequence of SEQ ID NO: 39;

wherein the stalk portion $S_1$ comprises a formula of $L_3$-$X_1$; wherein $L_3$ is a flexible peptide linker comprising an amino acid sequence of SEQ ID NO: 55; and $X_1$ is polypeptide comprising a transmembrane domain having a formula ECD-$T_M$-ICD, wherein:

ECD is an extracellular domain comprising an amino acid sequence of SEQ ID NO: 59;

$T_M$ is a transmembrane domain comprising an amino acid sequence of SEQ ID NO: 61; and ICD is an intracellular domain or protein that facilitates the incorporation of the targeting moiety into the envelope of the viral particle, wherein the ICD comprises an env incorporation motif comprising an amino acid comprising a sequence of SEQ ID NO: 63 or SEQ ID NO: 64.

195. The viral particle of any one of embodiments 178-194, wherein the viral particle further comprises a nucleic acid molecule encoding a heterologous molecule of interest.

196. The viral particle of embodiment 195, wherein the heterologous molecule of interest is a CAR.

197. The viral particle of embodiment 195, wherein the CAR comprises an amino acid sequence having at least 85% identity to SEQ ID NO: 99, at least 90% identity to SEQ ID NO: 99, at least 95% identity to SEQ ID NO: 99, at least 99% identity to SEQ ID NO: 99, or at least 100% identity to SEQ ID NO: 99.

198. A polypeptide comprising a variant Fc polypeptide.

199. The polypeptide of embodiment 198, wherein the variant Fc is a variant of an IgG1 Fe, an IgG2 Fc, or an IgG4 Fc.

200. The polypeptide of embodiment 198 or embodiment 199, wherein the variant Fc is a variant of a Fc polypeptide comprising the amino acid sequence of SEQ ID NO: 26, SEQ ID NO: 27, or SEQ ID NO: 28.

201. The polypeptide of any one of embodiments 198-200, wherein the variant comprises an N-terminal deletion.

202. The polypeptide of embodiment 201, wherein the N-terminal deletion does not comprise up to 100 amino acid residues from the N-terminus of SEQ ID NO: 26, SEQ ID NO: 27, or SEQ ID NO: 28.

203. The polypeptide of embodiment 201, wherein the N-terminal deletion does not comprise up to 98 amino acid residues from the N-terminus of SEQ ID NO: 26, SEQ ID NO: 27, or SEQ ID NO: 28.

204. The polypeptide of embodiment 201, wherein the N-terminal deletion does not comprise up to 1-98 amino acid residues from the N-terminus of SEQ ID NO: 26, SEQ ID NO: 27, or SEQ ID NO: 28.

205. The polypeptide of any one of embodiments 198-204, wherein the variant Fe does not comprise the amino acid sequence of SEQ ID NO: 105.

206. The polypeptide of any one of embodiments 198-205, wherein the variant Fc comprises the amino acid sequence of SEQ ID NO: 103.

207. The polypeptide of any one of embodiments 198-206, wherein the variant Fc polypeptide comprises one or more mutations at a position that corresponds to L234, L235, M297, P329, 1253, H310, or H435.

208. The polypeptide of embodiments 207, wherein the variant Fc polypeptide does not comprise an N-terminal deletion.

209. The polypeptide of embodiments 207, wherein the variant Fc polypeptide comprises an N-terminal deletion.

210. A polypeptide comprising a variant Fc polypeptide, wherein the variant Fc polypeptide comprises an amino acid sequence that is at least 85%, 90%, 91%, 92%, 93%, 94%, 95%, 96%, 97%, 98%, or 99% identical to the amino acid sequence of SEQ ID NO: 103, wherein the variant Fc polypeptide does not comprise the amino acid sequence of SEQ ID NO: 105, and wherein the variant Fc polypeptide comprises one or more mutations that correspond to L234A, L235A, M297A, P329G, 1253A, H310A, or H435A.

211. A polypeptide comprising a variant Fc polypeptide, wherein the variant Fc polypeptide comprises an amino acid sequence that is at least 85%, 90%, 91%, 92%, 93%, 94%, 95%, 96%, 97%, 98%, or 99% identical to the amino acid sequence of SEQ ID NO: 103, wherein the variant Fc polypeptide does not comprise the amino acid sequence of SEQ ID NO: 105, and wherein the variant Fc polypeptide comprises mutations that correspond to L234A, L235A, M297A, P329G, I253A, H310A, or H435A.

212. A polypeptide comprising a variant Fc polypeptide, wherein the variant Fc polypeptide comprises an amino acid sequence that is at least 85%, 90%, 91%, 92%, 93%, 94%, 95%, 96%, 97%, 98%, or 99% identical to the amino acid sequence of SEQ ID NO: 104 and does not comprise the amino acid sequence of SEQ ID NO: 105.

213. A polypeptide comprising a variant Fc polypeptide, wherein the variant Fc polypeptide comprises an amino acid sequence of SEQ ID NO: 104 and does not comprise the amino acid sequence of SEQ ID NO: 105.

214. A viral particle comprising the polypeptide of any one of embodiments 198-213.

The following examples are illustrative, but not limiting, of the compounds, compositions and methods described herein. Other suitable modifications and adaptations known to those skilled in the art are within the scope of the following embodiments.

EXAMPLES

Example 1: Mutation at Position 182 of VSV-G Abrogates LDL-R Interaction, but Retains Fusing Properties Plasmids/Sequences. All VSV-G plasmids were derived from pCMV-VSV-G Envelope Vector (Cell Bio Labs, catalog RV-110). Point mutations and combinations thereof were introduced using site directed mutagenesis (New England Biolabs). Individual mutations H8A and K47Q were previously shown to partially "blind" VSV-G, reducing its binding to LDL-R, the native cellular receptor for VSV (PMID: 29531262, DOI: 10.1038/s41467-018-03432-4). In this experiment, a single binder molecule consisting of a CD7-targeting scFv (clone MT701) fused to an IgG "stalk" bearing a CD28 transmembrane domain was used.

Cells. HEK293T cells were grown in DMEM with 10% FBS. SupT1 cells were maintained in RPMI media with 10% FBS. Human PBMCs were purchased from AllCells and cultured in X-Vivo 10 (Lonza) supplemented with 20 ng/mL IL-2 (Peprotech). PBMCs were activated 48 hours prior to transduction using anti-CD3/CD28 Dynabeads (Cell Therapy Systems).

Generation of lentiviral particles. The recombinant lentiviral particles co-expressing VSV-G glycoprotein and binder molecules were generated by plasmid transection into HEK293T cells using Lipofectamine 3000 (ThermoFisher Scientific). A total of 5 plasmids were transfected: (1) plasmid expressing the VSV-G glycoprotein, (2) plasmid expressing the binder protein (3) plasmid expressing the lentiviral transfer genome encoding for eGFP, (4) plasmid expressing gag-pol, and (5) plasmid expressing rev. Transfected cell supernatant was harvested 48 hours later. Virus in the cell supernatant was concentrated by centrifugation through a sucrose cushion and resuspended in PBS. Lentiviral particle titer was determined using the Lenti-X p24 Rapid Titer Kit (Takara Bio, San Jose, CA).

Lentivirus transduction assay. A series of 10-fold dilutions (in cell culture media) of the concentrated lentivirus was performed and used to infect SupT1 and activated human PBMCs. Media was replaced 6 hours later, and the transduced cells were analyzed by flow cytometry on days 4 and 7 after transduction. Cells were stained with a viability stain and an anti-CD7 antibody to detect CD7 positive cells (PeCy7 mouse-anti-human CD7, clone CD7-6B7, BD Biosciences). Expression of eGFP was measured to calculate transduction efficiency.

Structure-guided design of novel blinding mutations. Using a published crystal structures of VSV-G bound to CR2 and CR3 of the LDL-R (pdb 50YL and 50Y9, respectively), two putative positions in VSV-G with side chains oriented toward the binding interface on LDL-R were identified (FIG. 1). Residue Q10 (SEQ ID NO: 2) appeared to form several interactions with residues in both CR2 and CR3. In CR3, this included interactions with a positively charged arginine residue. Thus, three substitutions were tested: Q10A to reduce side-chain interactions that potentially stabilize LDL-R binding and Q10R and Q10K to create electrostatic repulsion.

Residue I182 (SEQ ID NO: 2) appeared to contact several residues in both CR2 and CR3 as well. Three substitutions were tested: I182A to reduce side-chain interactions that potentially stabilize LDL-R binding and I182D and I182E to create electrostatic repulsion against the primary binding interfaces on LDL-R.

Addition of negative charges in the binding interface ablate native tropism without altering fusogenicity. Titration of viral supernatants on the CD7+ T cell line SupT1 validated the structural predictions for residue I182. In the absence of any compensatory binder molecule, WT VSV-G reached titers of 3.0e8 while both I182D and I182E were ~3 orders of magnitude lower (FIG. 2). Substitutions at residue I182 preserved fusogenicity, as titers were restored to 1e8 in the presence of a binder redirecting the virions to CD7.

Figure 2A:
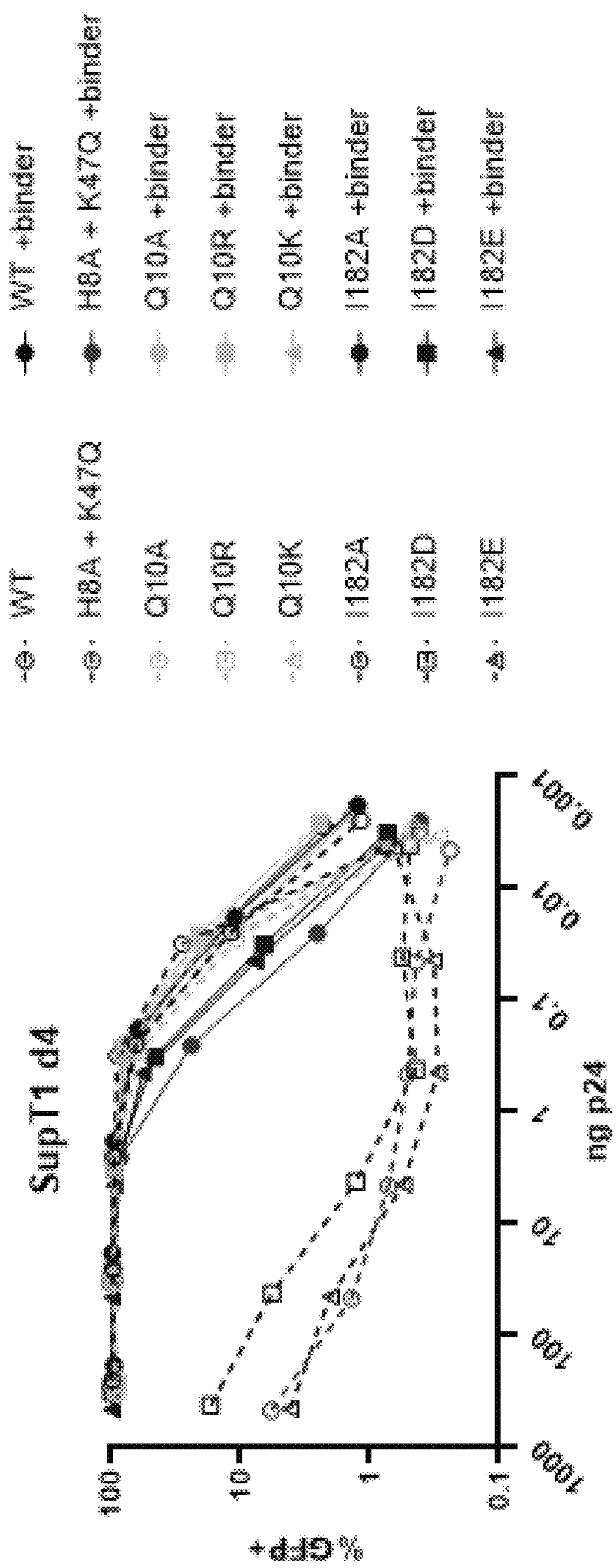
FIG. 2A and FIG. 2B illustrate the effect of adding negatively charged amino acids to the VSV-G:LDL-R binding interface on native tropism and fusogenicity.
Figure 2B:
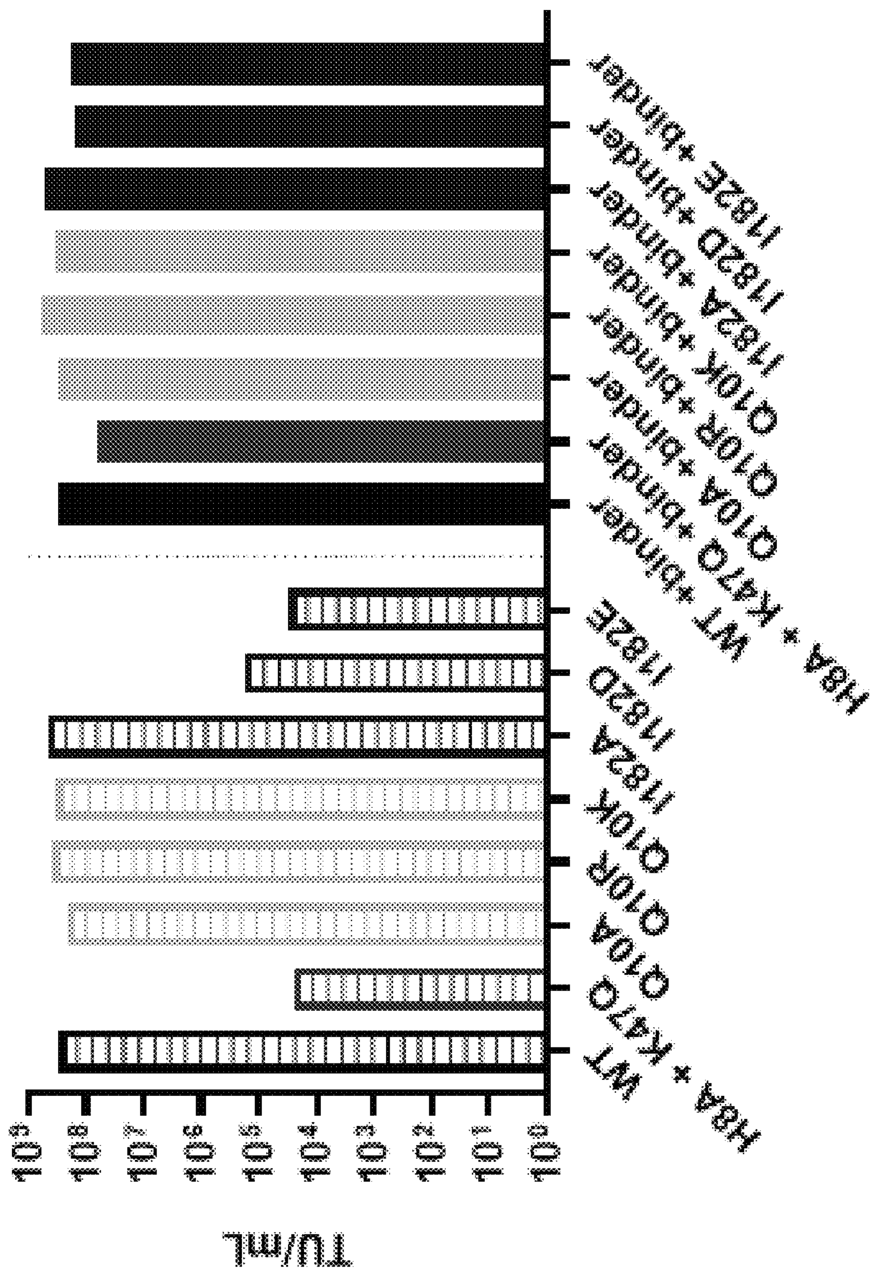

The data is illustrated in FIG. 2, which shows that the addition of negative charges in the binding interface ablate native tropism without altering fusogenicity. FIG. 2A shows the titration of VSV-G constructs on SupT1 cells. Plotted is the percentage of SupT1 cells expressing GFP at each amount of viral input in terms of p24 antigen. Dashed lines/open circles indicate VSV-G constructs alone, solid lines/filled circles indicate the same construct with a CD7 targeting molecule expressed in trans. FIG. 2B illustrates Functional titer of each construct calculated from the titration in A, expressed as transducing units per mL of concentrated virus supernatant (TU/mL).

Thus these examples demonstrate that a mutation position 182 is sufficient to abrogate the LDL-R interaction, but retain fusogenic properties when combining with a targeting moiety that binds to a target on the target cell.

Example 2: Serum Stable VSV-G Protein

WT VSV-G is reported to be sensitive to inactivation by naïve human serum, with inactivation ranging from minimal change to about 100-fold decrease depending on study parameters. Accordingly, it was assessed i) whether substitution at position I182 produced a variant VSV-G with similar sensitivity to serum and ii) whether incorporation of known serum stabilizing VSV-G mutations into the I182 substituted constructs had an effect on the serum stability of the constructs.

Figure 4:
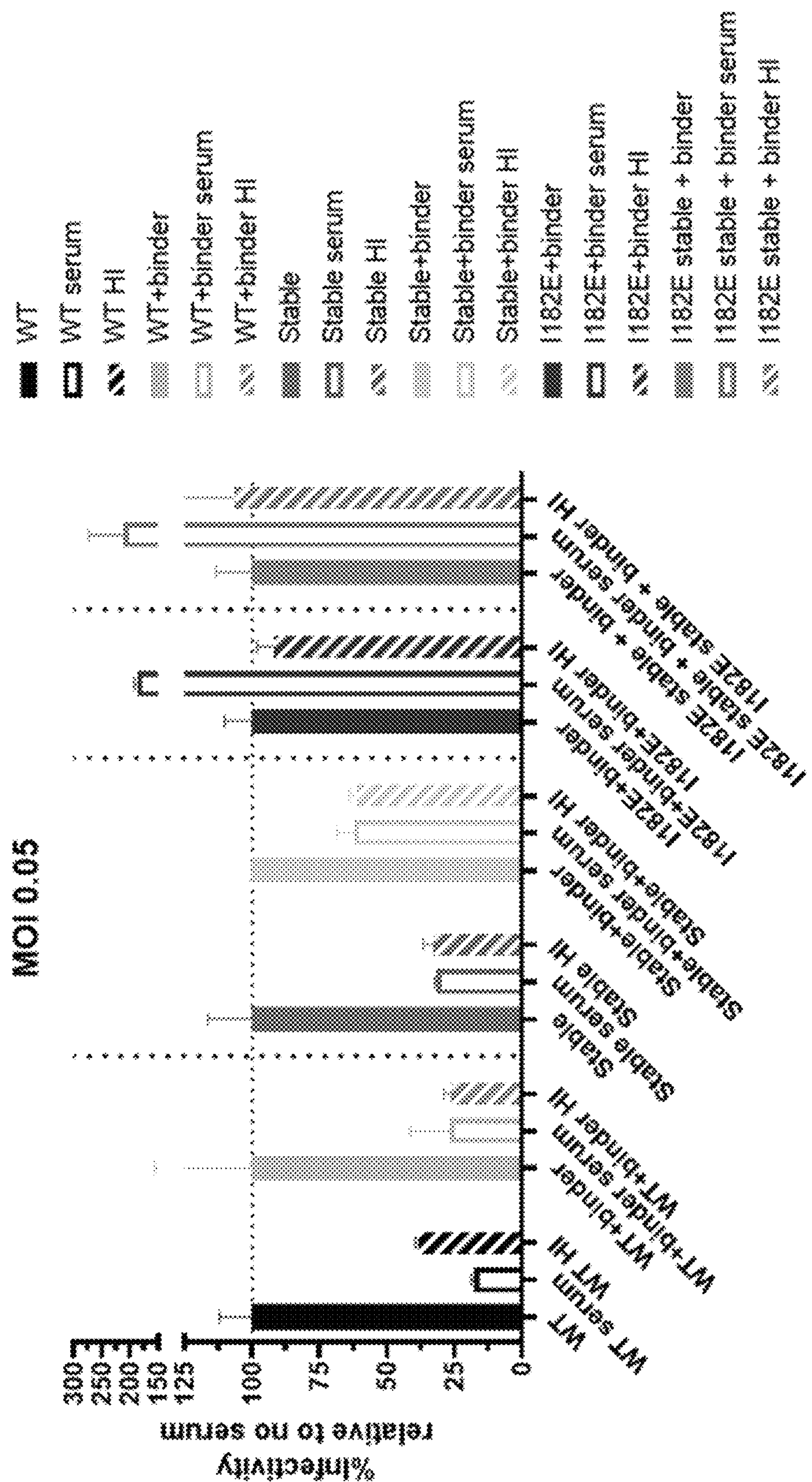
FIG. 4 illustrates the effect of various VSV-G mutations on the serum stability of viral constructs in combination with a CD7 binder.

WT VSV-G, Serum Stable VSV-G (T214N, T352A), LDL-R de-targeted VSV-G (I182E), and LDL-R de-targeted serum stable VSV-G (I182E, T214N, T352A) were tested for their ability to infect SupT1 cells in the presence or absence of naïve serum or heat inactivated serum (HI) (FIG. 4). As expected WT VSV-G had a dramatic decrease in percent infectivity when administered in the presence of serum with a mild rescue of infectivity if serum was heat inactivated (FIG. 4, columns 1-3). The inclusion of the CD7 targeting moiety on an IgG1 Fc stalk (WT) did not rescue the serum inactivation (FIG. 4, columns 4-6). The VSV-G constructs harboring the T214N and T352A mutations showed a similar reduction in infectivity in the presence of serum with no distinction between naïve or HI serum (FIG. 4, columns 7-9). However, the inclusion of the targeting moiety was able to partially rescue the inactivation in either serum condition (FIG. 4, columns 10-12). Surprisingly, the LDL-R de-targeted VSV-G (I182E) showed no reduction in infectivity percentage in the presence of either serum condition (FIG. 4, columns 13-15), but rather showed increased infectivity in the presence of naïve serum as compared to serum free or HI serum conditions. Further inclusion of the known serum stable mutations into VSV-G (I182E, T214N, T352A) also demonstrated increased infectivity in the presence of serum as compared to serum free conditions (FIG. 4, columns 16-18). Further, the I182E, T214N, T352A construct also demonstrates increased infectivity in the presence of HI serum (FIG. 4, column 18), which indicates that the triple mutant construct has a higher degree of serum stability than the other constructs examined.

Figure 5:
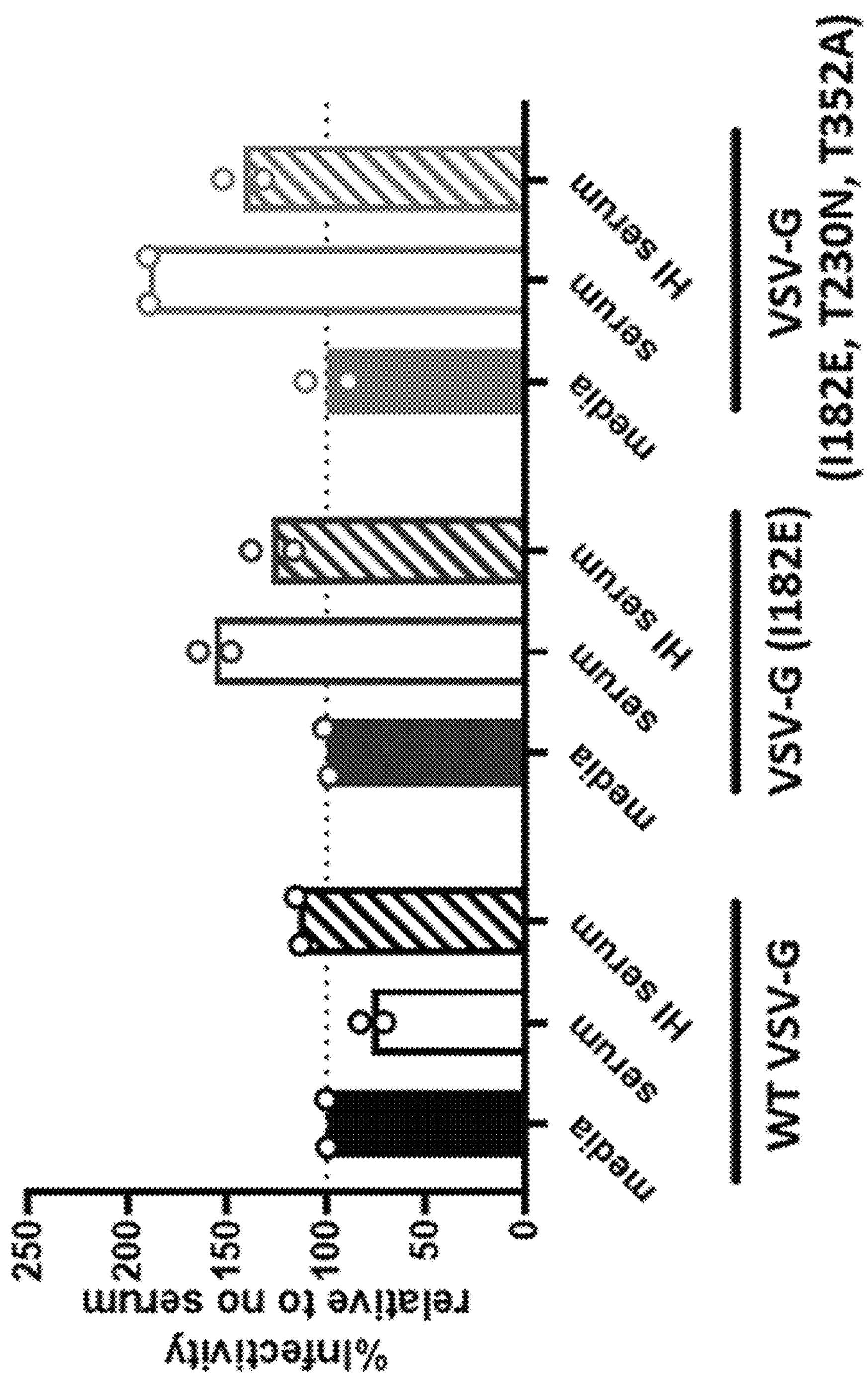
FIG. 5 illustrates the effect of various VSV-G mutations on the serum stability of viral constructs in combination with a CD7 binder.

To further characterize the effect of including serum stabilizing mutations in the viral constructs of the present application, WT VSV-G, VSV-G (I182E), and VSV-G (I182E, T230N, T352A) were assessed at a lower dose of vector (FIG. 5). In agreement with the previous assessment, WT VSV-G showed decreased infectivity in serum as compared to no-serum conditions (FIG. 5, columns 1 and 2). However, heat inactivation (HI) of serum did appear to have a rescuing effect on WT VSV-G infectivity (FIG. 5, column 3). In further agreement with the previous assessment, VSV-G (I182E) demonstrated enhanced infectivity in the presence of serum as compared to no serum conditions (FIG. 5, columns 4 and 5). The presence of HI serum also resulted in an increased infectivity compared to no serum, with a smaller effect than naïve serum (FIG. 5, column 6). VSV-G (I182E, T214N, T352A) also demonstrated increased infectivity in serum and HI serum conditions as compared to no serum conditions (FIG. 5, columns 7-9), in agreement with the previous assessment. Further, when compared to the respective no serum condition, VSV-G (I182E, T230N, T352A) results in a greater percent increased infectivity compared to VSV-G (I182E), suggesting that inclusion of all three mutations results in greater serum stability than just I182E alone.

Thus, these examples demonstrate that i) the LDL-R detargeting mutation I182E affords an unexpected level of protection against the serum inactivation observed for WT VSV-G, ii) the LDL-R detargeting mutation I182E does not abrogate the serum stabilizing effect of the T230N+T352A mutations, and iii) the combined mutation construct VSV-G (I182E, T230N, T352A) appears to have a greater serum stabilizing effect than either I182E alone or T230N+T352A alone. Thus, VSV-G (I182E, T230N, T352A) is able to ablate native tropoism without alternating fusogenicity and additionally demonstrates a more stable profile and is not neutralized in serum.

Example 3: Spring Viremia of Carp Virus G Protein can Facilitate Cell Specific Fusion Methods Plasmids/Sequences. All rhabdovirus GP sequences were codon optimized and synthesized by Genscript. Sequences are shown below, with accession numbers found in the following table, which are hereby incorporated by reference in its entirety, Table 1:

TABLE 1

Rhadovirus glycoprotein sequences used.

| Rhabdovirus | Genbank Accession |
|---|---|
| Spodoptera frugiperda rhabdovirus isolate Sf - G | KF947078.1 |
| Drosophila obscura sigma virus 10A - G | GQ410979.1 |
| Wuhan insect virus 7 - G | YP_009301742.1 |
| Perch rhabdovirus - G | YP_007641366.1 |
| Spring viremia of carp virus - G | CAA85735.1 |

The targeting moiety comprises an anti-CD7 antibody (clone MT701, in single chain format) anchored to the membrane via an IgG based Fc stalk, which comprises a CD28 transmembrane domain.

Cells. HEK293T cells were grown in DMEM with 10% FBS. SupT1 cells were maintained in RPMI media with 10% FBS. Human PBMCs were purchased from AllCells and cultured in X-Vivo 10 (Lonza) supplemented with 20 ng/mL IL-2 (Peprotech). PBMCs were activated 48 hours prior to transduction using anti-CD3/CD28 Dynabeads (Cell Therapy Systems).

Generation of lentiviral particles. The recombinant lentiviral particles co-expressing rhabdovirus-G glycoproteins and binder molecules were generated by plasmid transection into HEK293T cells using Lipofectamine 3000 (ThermoFisher Scientific). A total 5 plasmids were transfected: (1) plasmid expressing the rhabdovirus G glycoprotein, (2) plasmid expressing the binder protein (where indicated), (3) plasmid expressing the lentiviral transfer genome encoding for CAR20, (4) plasmid expressing gag-pol, and (5) plasmid expressing rev. Transfected cell supernatant was harvested 48 hours later. Virus in the cell supernatant was concentrated by centrifugation through a sucrose cushion and resuspended in x-vivo medium. Lentiviral particle titer was determined using the Lenti-X p24 Rapid Titer Kit (Takara Bio, San Jose, CA).

Lentivirus transduction assay. A series of 5-fold dilutions (in cell culture media) of the concentrated lentivirus was performed and used to infect SupT1 and activated human PBMCs. Media was replaced 6 hours later, and the transduced cells were analyzed by flow cytometry on days 4 and 7 after transduction. Cells were stained with a viability stain, an anti-CD7 antibody to detect CD7 positive cells, and an anti-CAR antibody to detect CAR20 expression as a measure of transduction efficiency.

Results:

SVCV-G mediates fusion into human cells. Most non-mammalian rhabdovirus G proteins failed to mediate transduction in human cells, with the exception of Spring viremia of carp virus G (SVCV-G). This glycoprotein did not target SupT1 or human PBMC cells on its own as transduction was very inefficient (~1 log lower than blinded VSV-G I182E) in the absence of the CD7 binder. Targeted transduction mediated by the CD7 binder reached comparable titers to retargeted VSV-G I182E.

Figure 6:
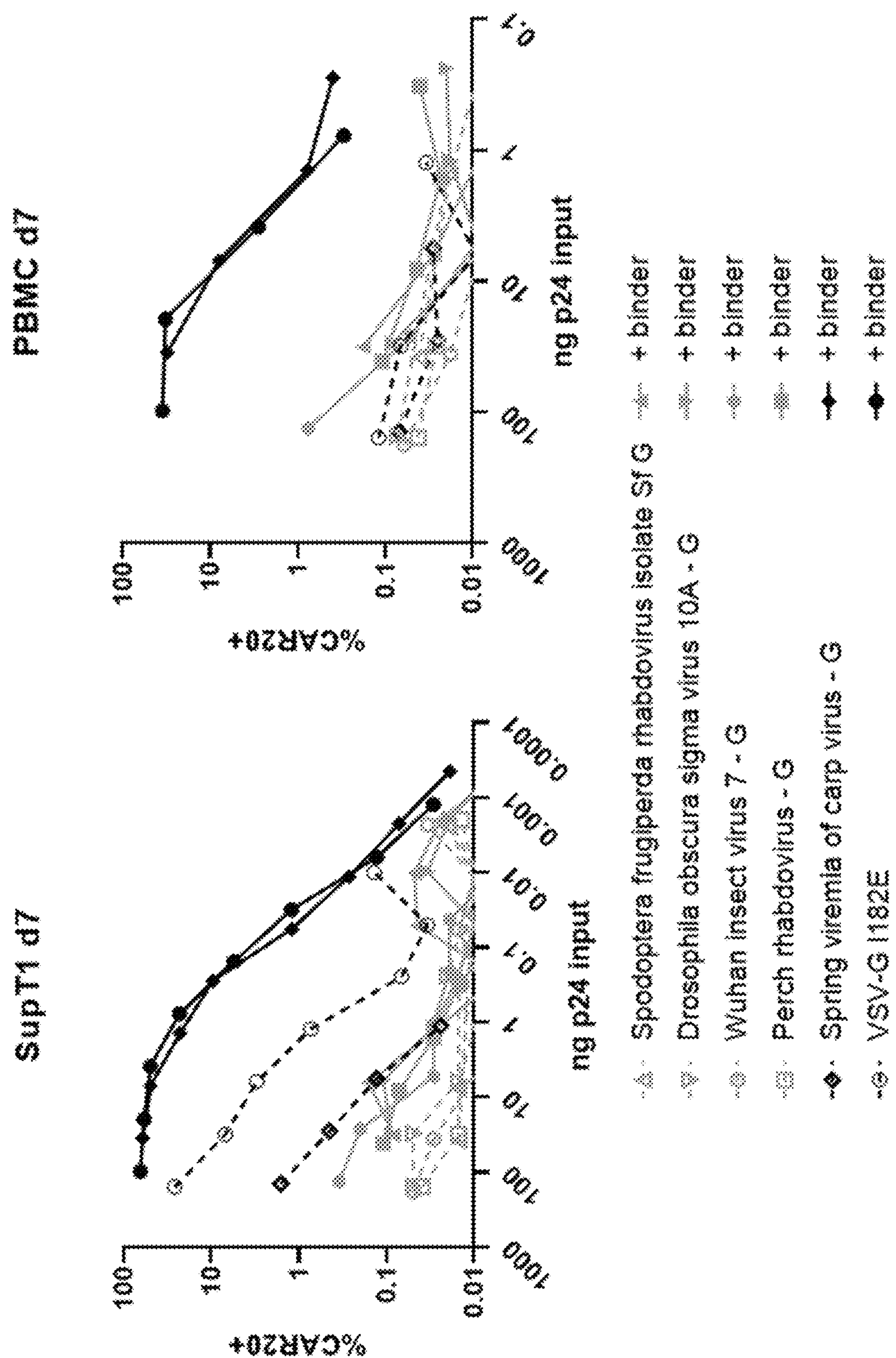
FIG. 6 illustrates the ability of various rhabdovirus G proteins to transduce SupT1 and PBMC cells alone or in combination with a CD7 binder.

This surprising and unexpected result demonstrates that a viral structural protein that cannot infect an immune cell on its own can be used to infect a cell when the virus also expresses a targeting moiety, such as one that comprises an anti-CD7 scFv. This result could not have been predicted and is shown not to be an effect of the anti-CD7 scFv on its own as the presence of the anti-CD7 scFv targeting moiety was not sufficient to induce infections utilizing other non-human rhabdovirus GP proteins. The data is illustrated in FIG. 6.

Example 4: CD7 Targeting Moiety can be Linked to a Fc Stalk to Transduce PBMCs

Generation of Plasmids and Sequences.

The amino acid sequence including CDRs of the CD7 binder was determined via mass spectrometry (Rapid Novor). CD7 binder sequences were synthesized by IDT or GenScript (Piscataway, NJ) using codon optimization for human expression and inserted onto viral glycoprotein or IgG-based stalks and flanked by a G4S linker. An example viral glycoprotein is a Nipah-G protein with the CD7 binder attached to the extracellular region. An example IgG-based stalk was a human IgG1 Fc dimer with a CD8 or CD28 transmembrane region and an envelope incorporating motif with the CD7 binder attached to the extracellular region. The resulting binders were expressed under the direction of a CMV promoter.

Generation of Engineered Lentiviral Particles.

The recombinant lentiviral particles expressing the CD7 binder incorporated on the surface were generated by plasmid transection into HEK293T cells using Lipofectamine 3000 (ThermoFisher Scientific). In some embodiments, a total of 5 plasmids were transfected: (1) plasmid expressing the CD7 binder with the IgG stalk or a plasmid expressing the CD7 binder on a Nipah-G protein, (2) plasmid expressing a detargeted-VSV-G protein, (3) lentiviral genome expressing eGFP, (4) plasmid expressing gag-pol, (5) plasmid expressing rev.In some embodiments, a total of 5 plasmids were transfected: (1) plasmid expressing the CD7 binder with the Nipah-G protein, (2) plasmid expressing Nipah-F protein, (3) lentiviral genome expressing eGFP, (4) plasmid expressing gag-pol, (5) plasmid expressing rev. Media was changed 6 hours after transfection and cells were harvested 48 hours later. Virus in the media was concentrated by centrifugation through a sucrose cushion and resuspended in media. Lentiviral particle titer was determined using the Lenti-X p24 Rapid Titer Kit (Takara Bio, San Jose, CA)

CD7 binders attach to both human and non-human primate PBMCs, leading to CD7+ cell transduction.

Figures 7A, 7B, 7C, 7D:
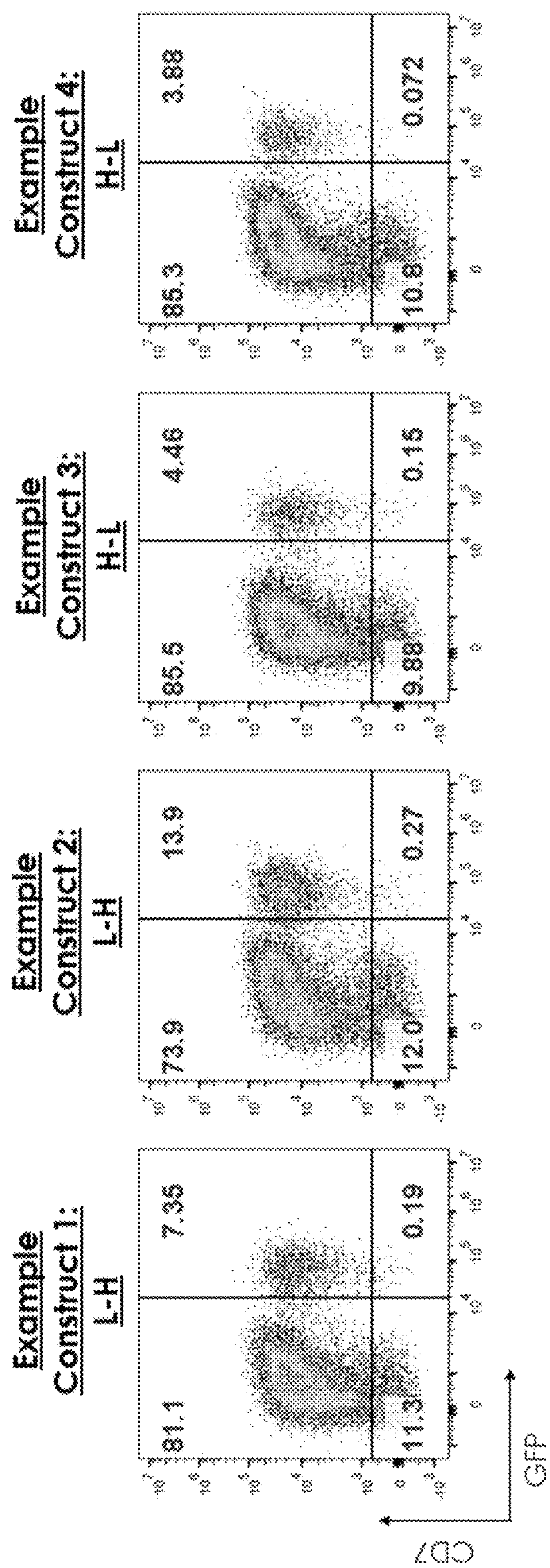
FIG. 7A-L show flow cytometry data of human PBMCs transduced with exemplary vectors comprising CD7 binders as disclosed herein.
Figures 7E, 7F, 7G, 7H:
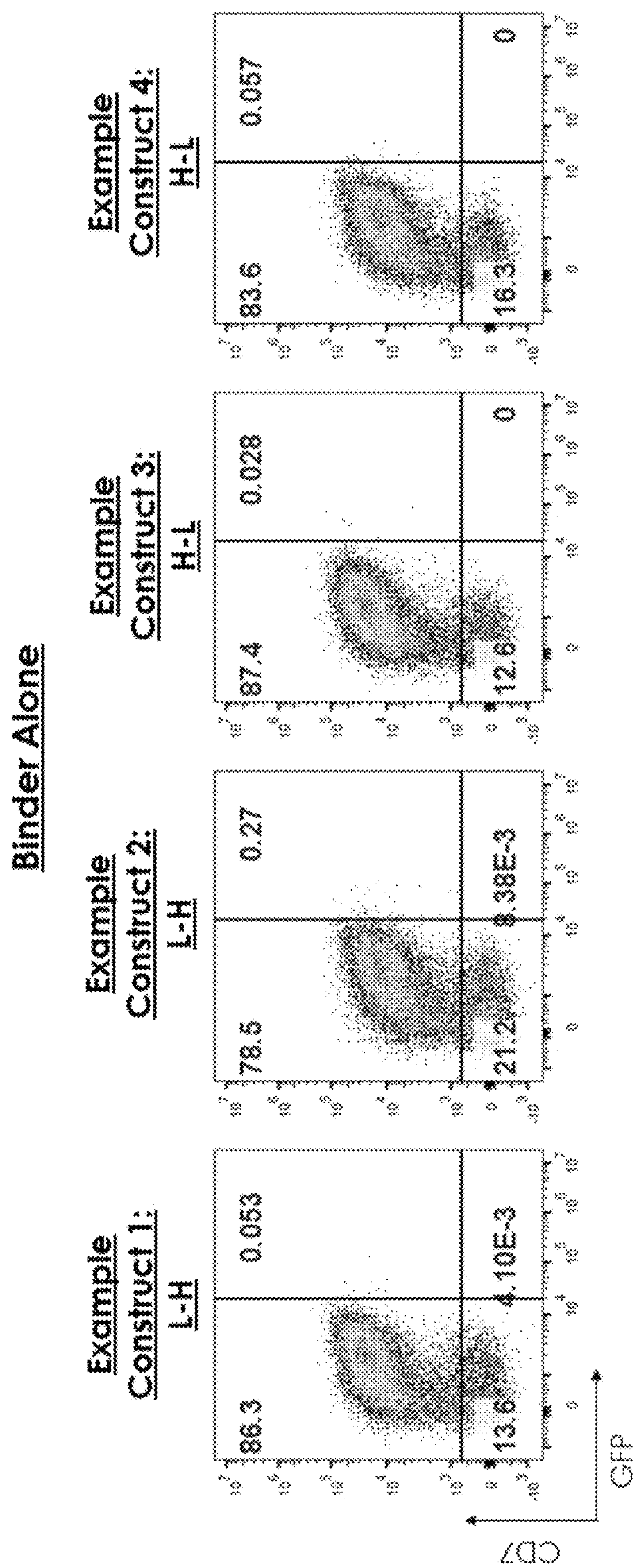
Figures 7I, 7J, 7K, 7L:
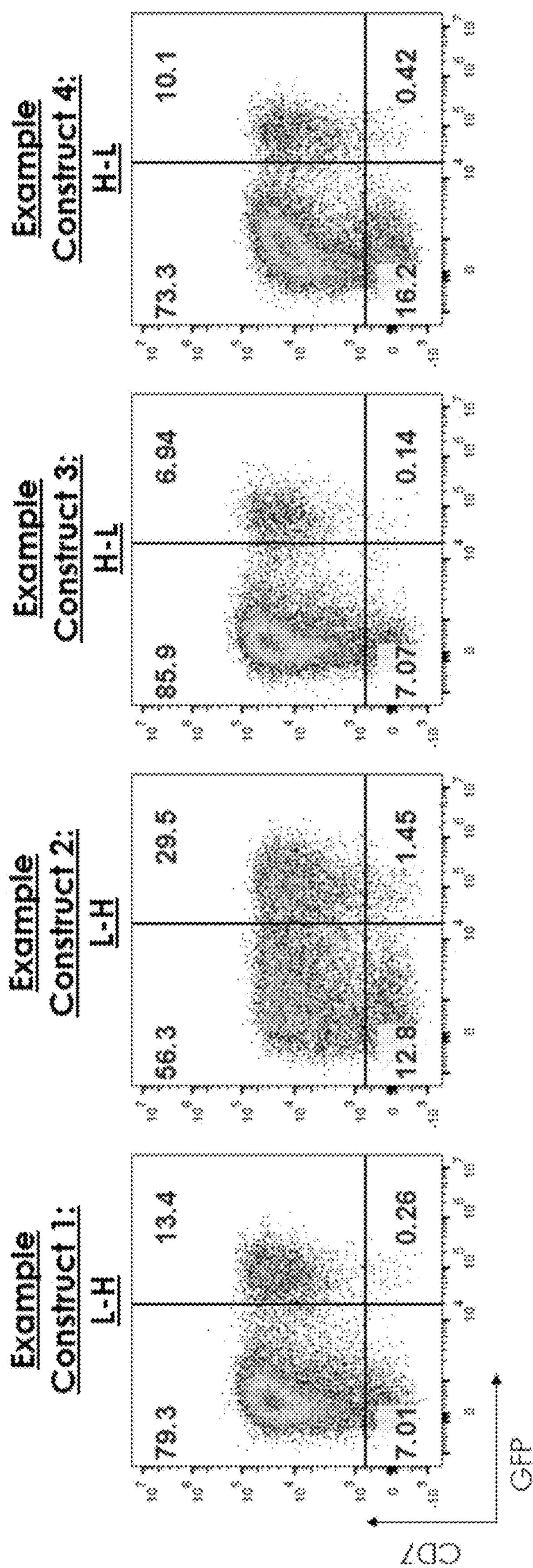
Figure 7M:
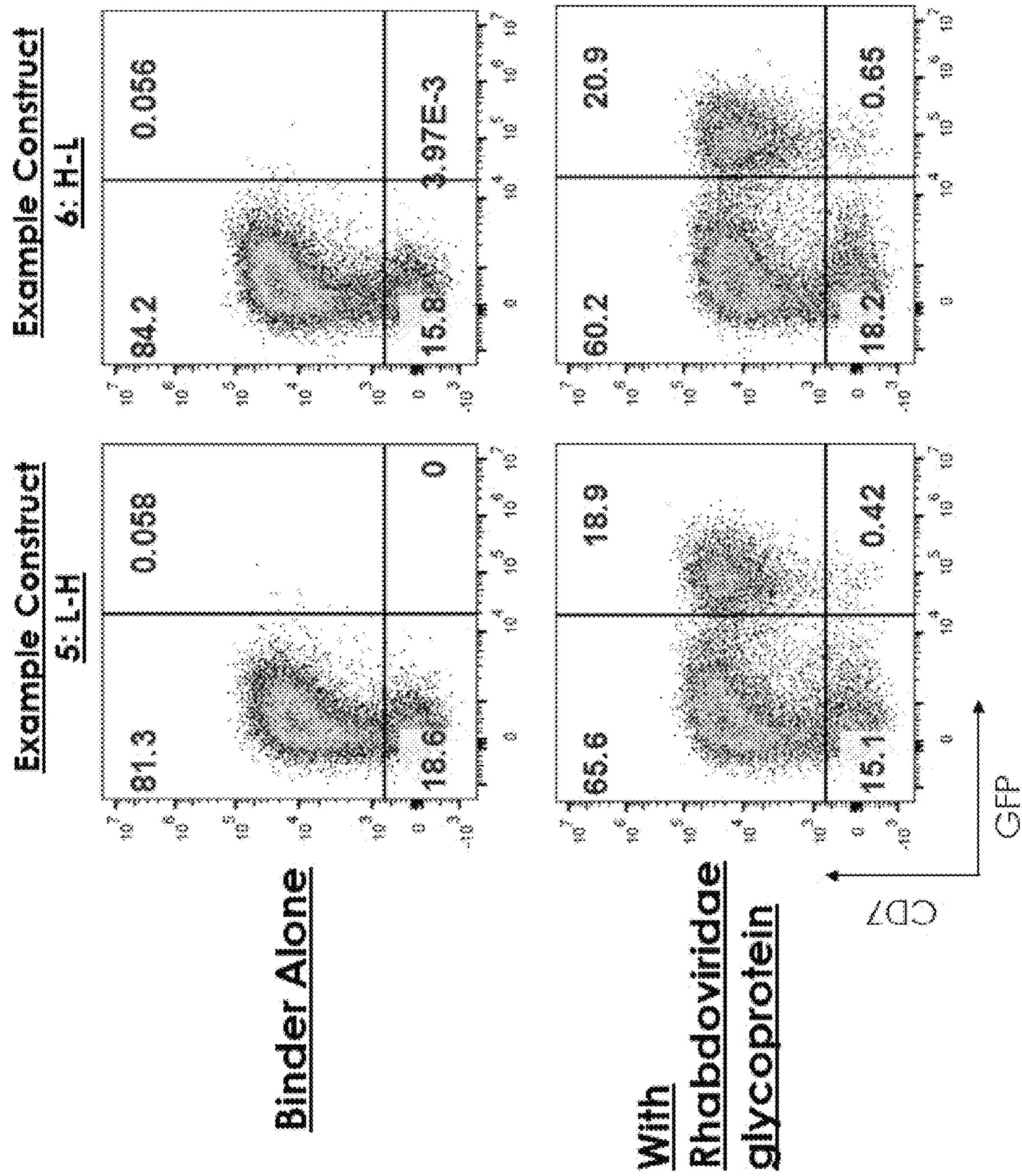
FIG. 7M shows flow cytometry data of human PBMCs transduced with exemplary vectors comprising CD7 binders as disclosed herein.
Figures 8A, 8B, 8C, 8D:
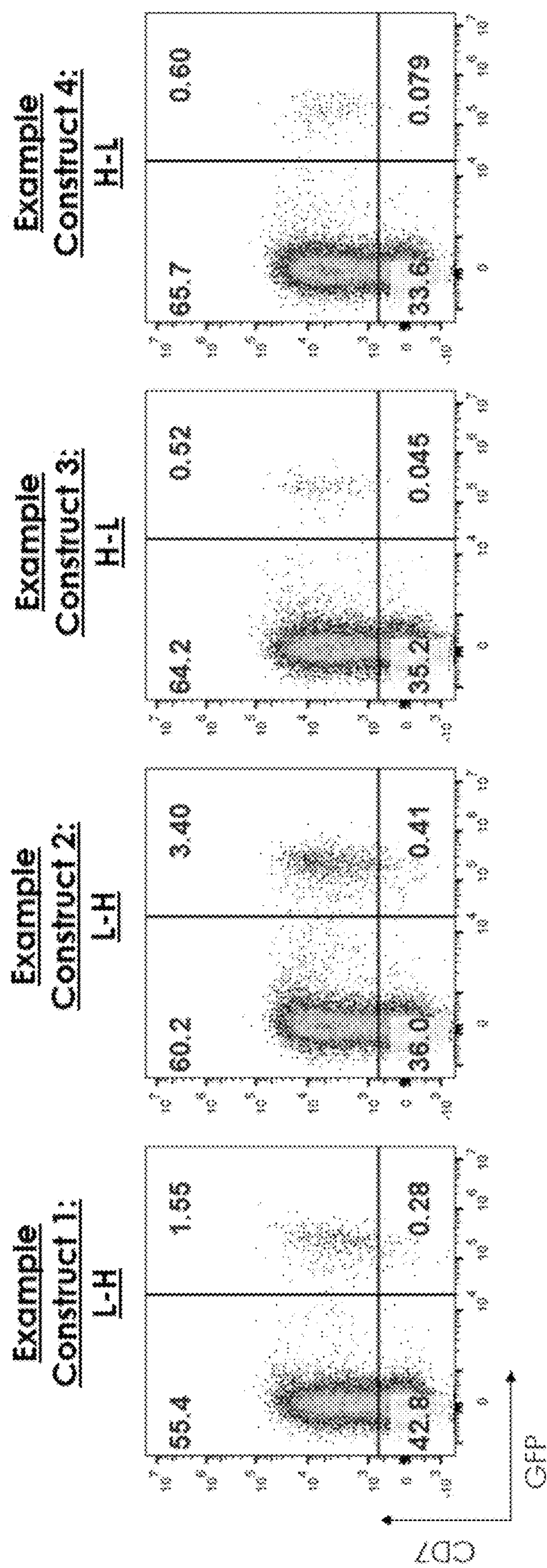
FIG. 8A-L shows flow cytometry data of non-human primate PBMCs transduced with exemplary vectors comprising CD7 binders as disclosed herein.
Figures 8E, 8F, 8G, 8H:
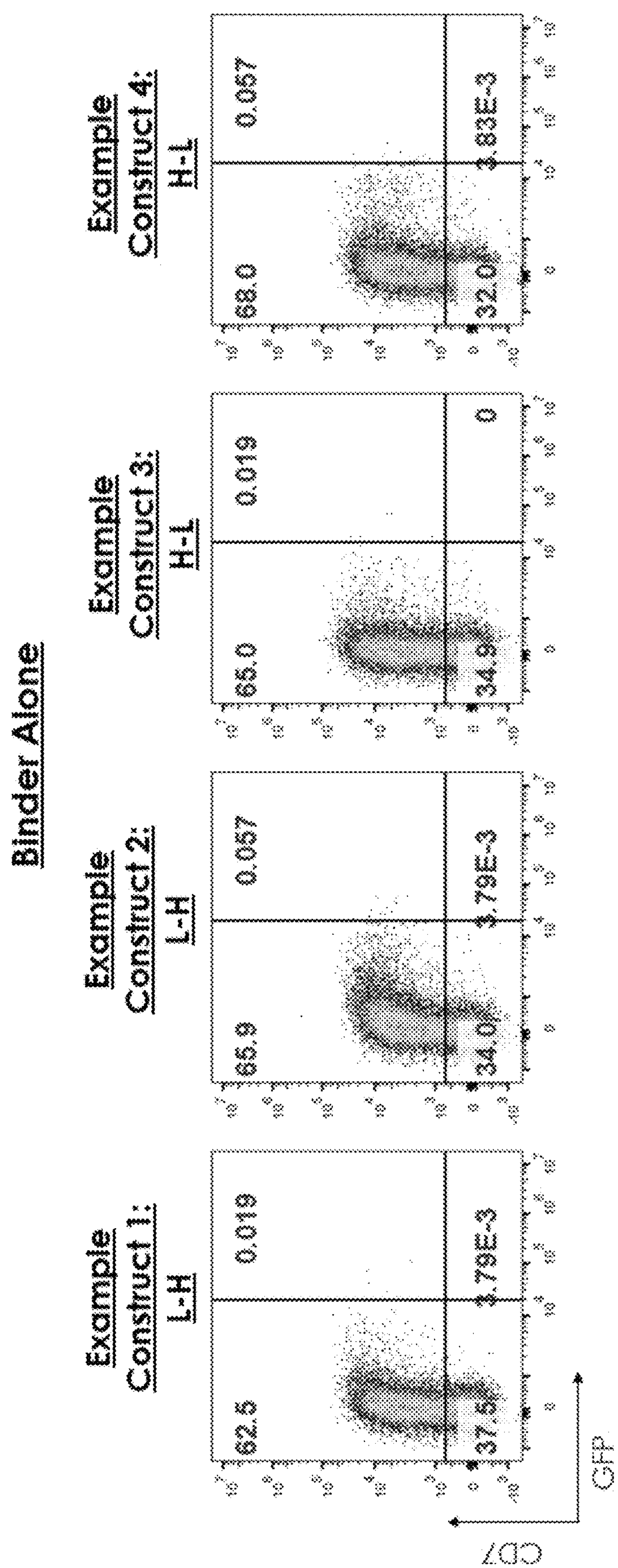
Figures 8I, 8J, 8K, 8L:
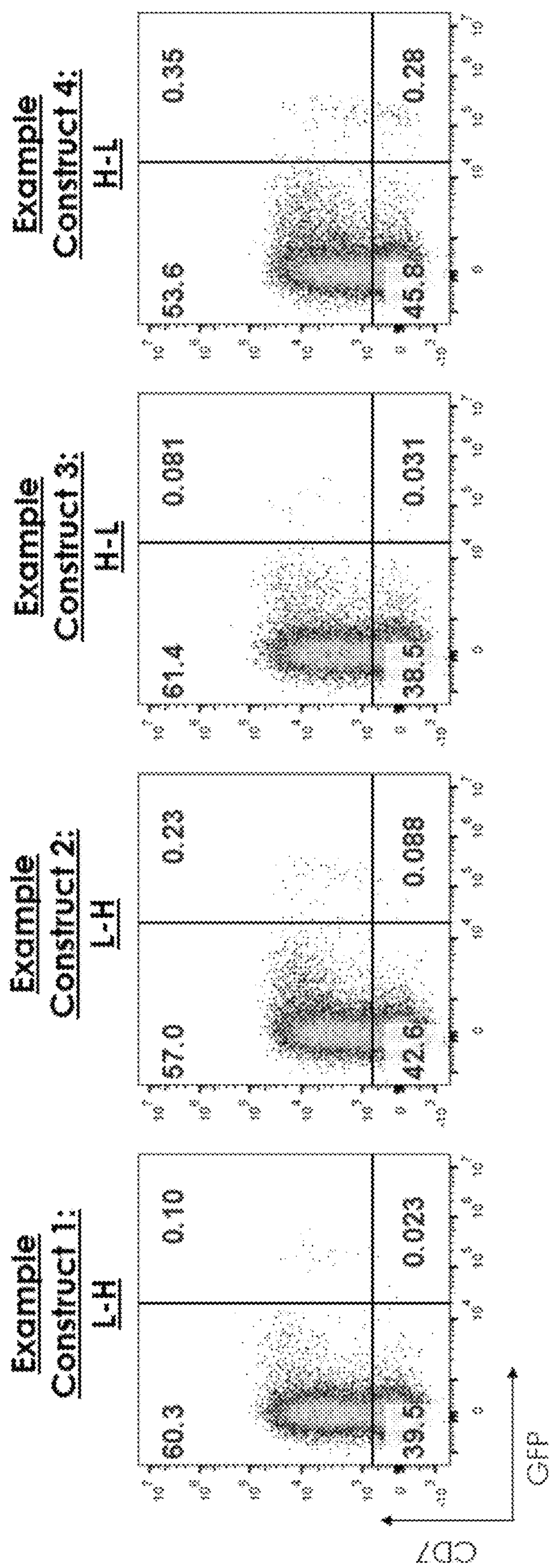
Figure 8M:
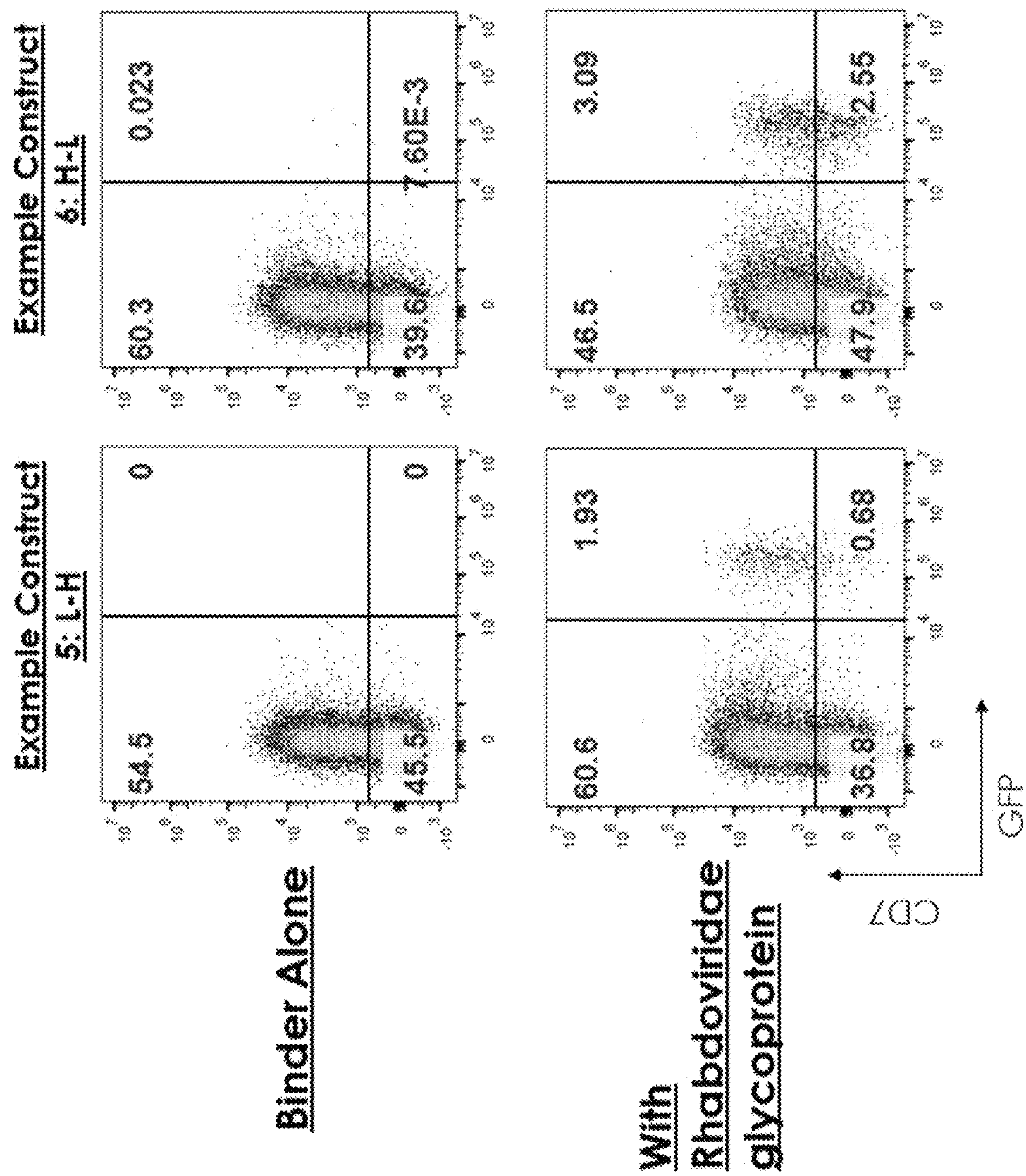
FIG. 8M shows flow cytometry data of non-human primate PBMCs transduced with exemplary vectors comprising CD7 binders as disclosed herein.

Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on days 4 and 7 after transduction. Cells were stained with an anti-CD7 antibody to detect CD7 positive cells (PE-Cy7 mouse-anti-human CD7, clone MT-701, Biolegend) as well as GFP expression. Cell viability was also determined. CD7 binders adhered to Paramyxoviridae glycoproteins, such as Nipah-G with Nipah-(FIGS. 7A-D and FIGS. 8A-D) or with Rhabdoviridae glycoproteins, such as VSV-G (FIGS. 7I-L and FIGS. 8I-L) successfully transduced human PBMCs (FIGS. 7A-L) or NHP PBMCs (FIGS. 8A-L) compared to the binder alone (FIGS. 7E-H and FIGS. 8E-H) which shows no transduction. When CD7 with an IgG stalk was tested, the binder alone (top row) again did not transduce human (FIG. 7M) or NHP PBMCs (FIG. 8M) but when administered with blinded VSV-G, transduction was seen in both human (FIG. 7M, bottom panel) and NHP PBMCs (FIG. 8M, bottom panel).

These examples and embodiments demonstrate that the polypeptides can be used to bind to CD7 and target viral particles to cells expressing CD7 to transduce the cells expressing CD7.

Example 5: CD8 Targeting Moiety can be Linked to a Fc Stalk to Transduce PBMCs

Generation of Plasmids and Sequences.

The amino acid sequence including CDRs of the CD8 binder was determined via mass spectrometry (Rapid Novor). CD8 binder sequences were synthesized by IDT or GenScript (Piscataway, NJ) using codon optimization for human expression and inserted onto viral glycoprotein or IgG-based stalks and flanked by a G4S linker. An example viral glycoprotein is a Nipah-G protein with the CD8 binder attached to the extracellular region. An example IgG-based stalk was a human IgG1 Fc dimer with a CD8 or CD28 transmembrane region and an envelope incorporating motif with the CD8 binder attached to the extracellular region. The resulting binders were expressed under the direction of a CMV promoter.

Generation of Engineered Lentiviral Particles.

The recombinant lentiviral particles expressing the CD8 binder incorporated on the surface were generated by plasmid transection into HEK293T cells using Lipofectamine 3000 (ThermoFisher Scientific). In some embodiments, a total of 5 plasmids were transfected: (1) plasmid expressing the CD8 binder with the IgG stalk, (2) plasmid expressing a detargeted-VSV-G protein, (3) lentiviral genome expressing eGFP, (4) plasmid expressing gag-pol, (5) plasmid expressing rev. In some embodiments, the lentiviral genome expressing eGFP was replaced with a CAR molecule. Media was changed 6 hours after transfection and cells were harvested 48 hours later. Virus in the media was concentrated by centrifugation through a sucrose cushion and resuspended in media. Lentiviral particle titer was determined using the Lenti-X p24 Rapid Titer Kit (Takara Bio, San Jose, CA).

CD8 binders attach to both human and non-human primate PBMCs, leading to CD8+ cell transduction.

Figure 9B:
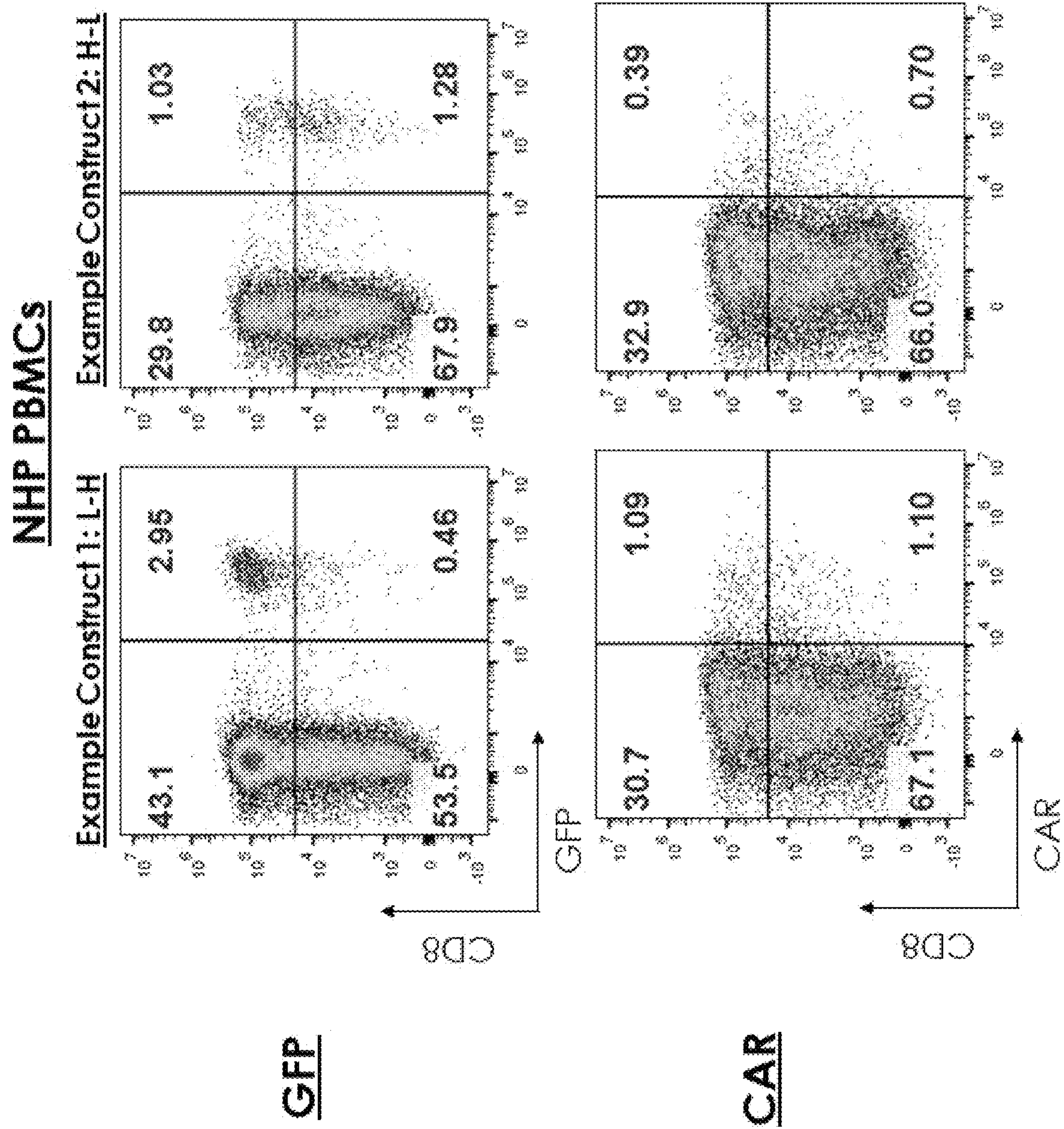
FIG. 9B shows flow cytometry data of non-human primate PBMCs transduced with exemplary vectors comprising CD8 binders as disclosed herein.

Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on day 6 after transduction. Cells were stained with an anti-CD8 antibody to detect CD8 positive cells (BV421 mouse-anti-human CD8, clone RPA-T8, Biolegend) as well as GFP or CAR20 expression. Cell viability was also determined. CD8 binders with detargeted VSV-G successfully transduced human PBMCs (FIG. 9A) or NHP PBMCs (FIG. 9B) with GFP (FIG. 9A-9B, top row) and CAR20 (FIGS. 9A-9B, bottom row).

These examples and embodiments demonstrate that the polypeptides can be used to bind to CD8 and target viral particles to cells expressing CD8 to transduce the cells expressing CD8.

Figure 10A:
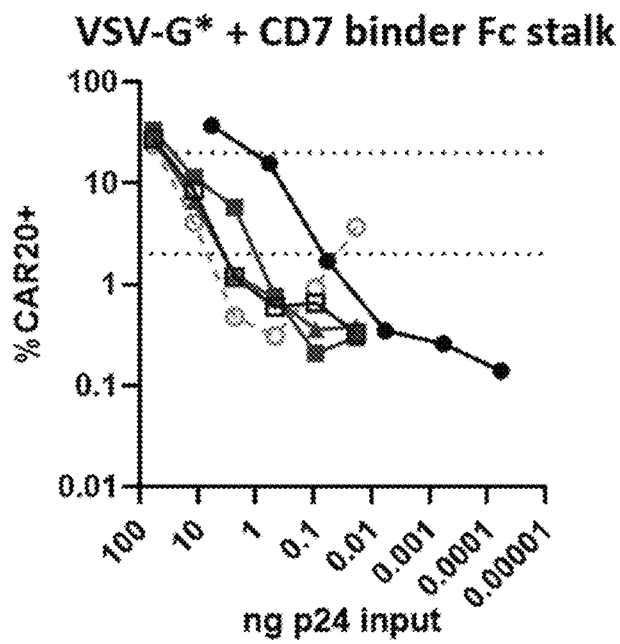
FIG. 10A illustrates the ability of VSV-G* pseudotyped lentiviral particles harboring a CD7 binder with a variant Fc stalk to transduce SupT1 cells as well as human and non-human primate PBMCs.
Figure 10B:
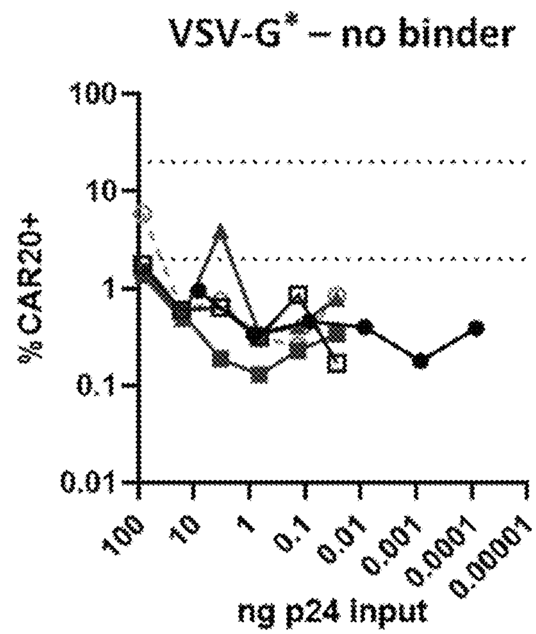
FIG. 10B illustrates the transduction of cells in the absence of the CD7 binder.
Figure 10C:
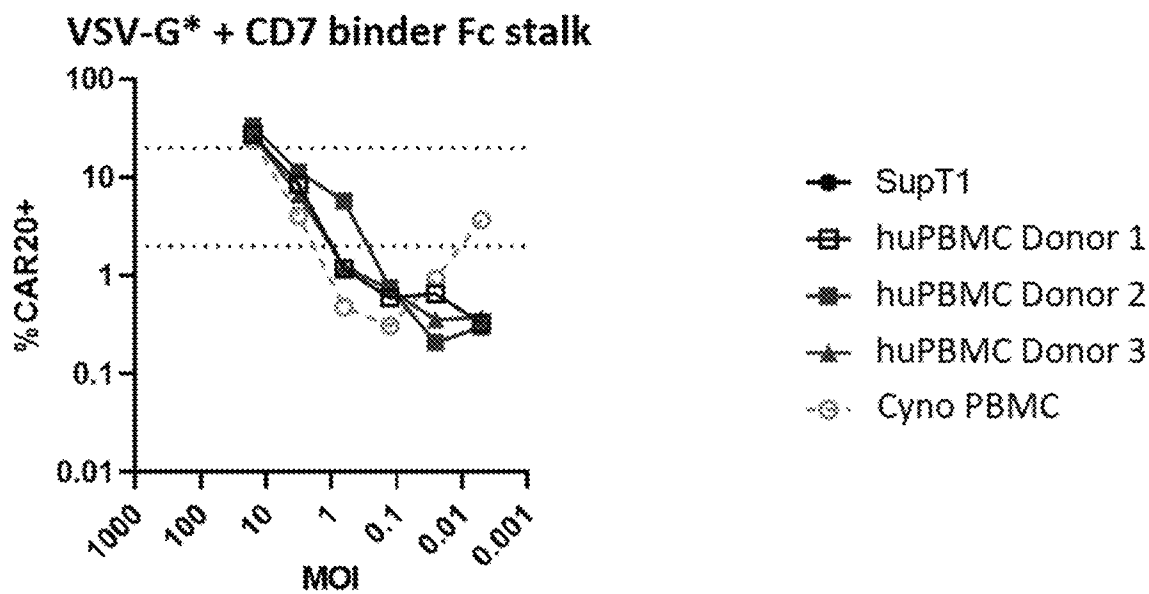
FIG. 10C illustrates the transduction of human and non-human primate PBMCs in terms of MOI calculated from SupT1 titration. VSV-G* denotes VSV-G (I182E, T214N, T352A).

Example 6: VSV-G* Pseudotyped Lentiviruses Harboring Fc Stalk Binder Transduce PBMCs Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. The binder constructs utilized for VSV-G* pseudotyped lentiviruses in the present example are the same as the CD7 binder constructs utilized in previous examples. Media was replaced 24 hours later, and the transduced cells were analyzed by flow cytometry on day 7 after transduction to determine CAR transduction. CAR expression was observed in all human and non-human primate PBMCs assessed (FIG. 10A) compared to the binder alone (FIG. 10B) which shows no transduction. Data are also presented as percent CAR expression vs multiplicity of infection (FIG. 10C).

These examples and embodiments demonstrate that the VSV-G* pseudotyped lentiviruses are able to successfully transduce a variety of human and non-human primate PMBCs.

Figure 11A:
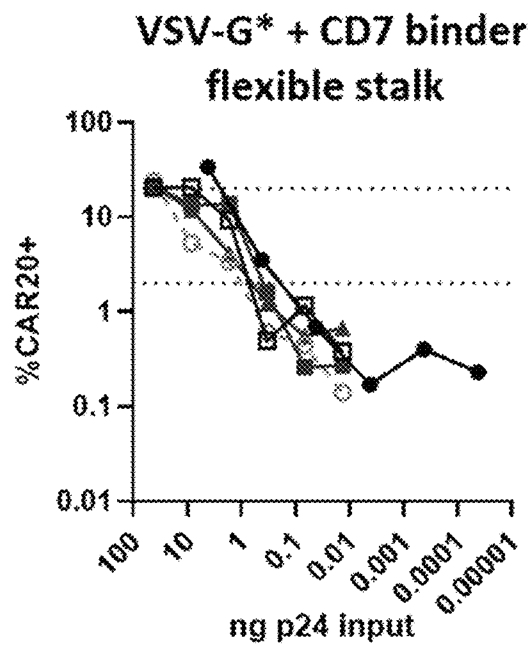
FIG. 11A illustrates the ability of VSV-G* pseudotyped lentiviral particles harboring a CD7 binder with a flexible stalk to transduce SupT1 cells as well as human and non-human primate PBMCs.
Figure 11B:
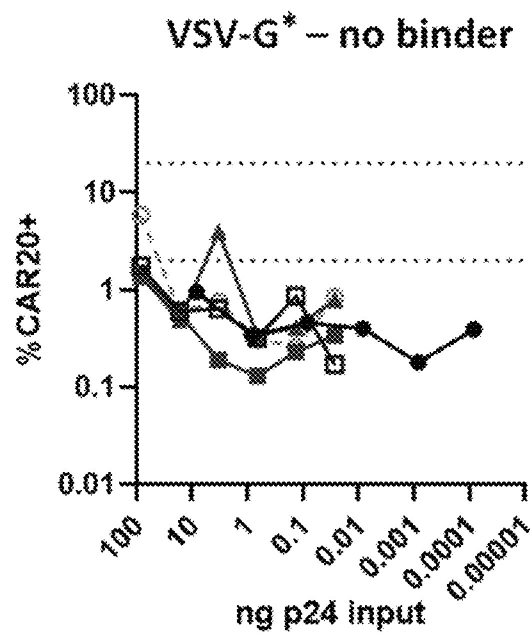
FIG. 11B illustrates the transduction of cells in the absence of the CD7 binder.
Figure 11C:
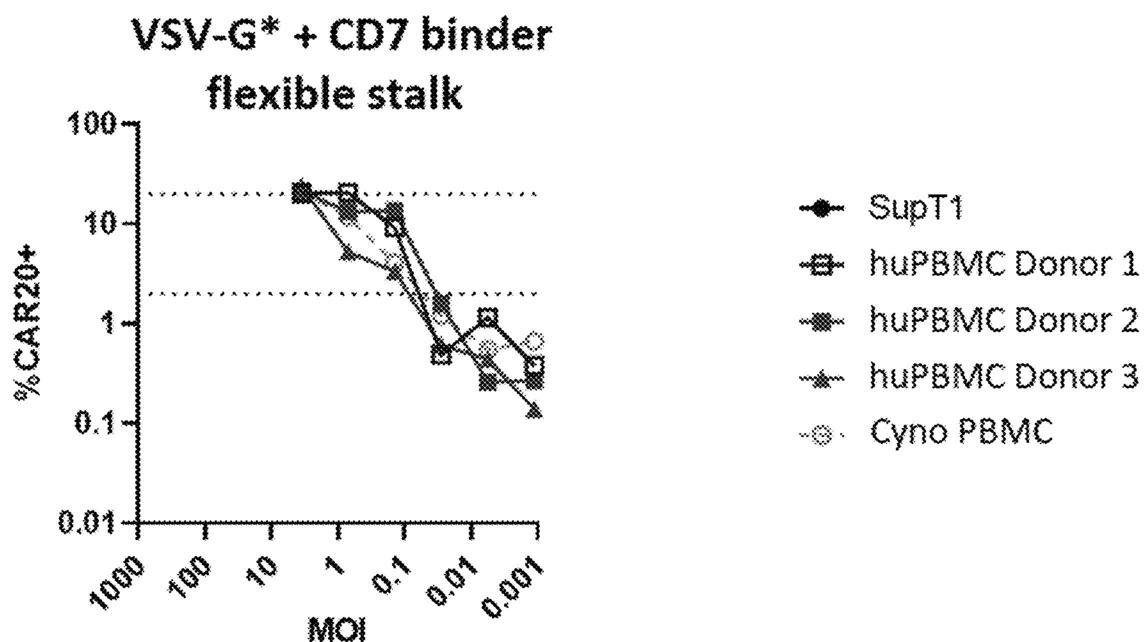
FIG. 11C illustrates the transduction of human and non-human primate PBMCs in terms of MOI calculated from SupT1 titration. VSV-G* denotes VSV-G (I182E, T214N, T352A).

Example 7: CD7 Targeting Moiety can be Linked to a Flexible Stalk to Transduce PBMCs Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Media was replaced 24 hours later, and the transduced cells were analyzed by flow cytometry on day 7 after transduction to determine CAR transduction. CAR expression was observed in all human and non-human primate PBMCs assessed (FIG. 11A) compared to no binder (FIG. 11B) which shows no transduction. Data are also presented as percent CAR expression vs multiplicity of infection (FIG. 11C).

Figure 12A:
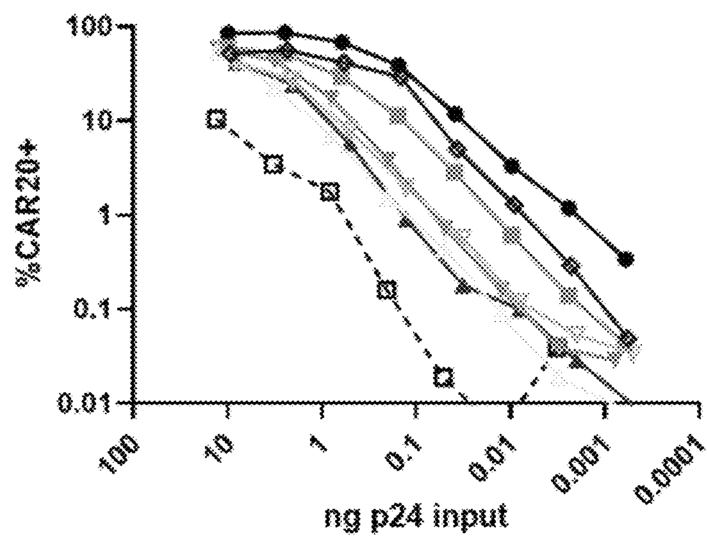
FIG. 12A illustrates the ability of viral particles harboring a CD7 binder with flexible stalks of varying length to transduce SupT1 cells in comparison to other IgG based binders.
Figure 12B:
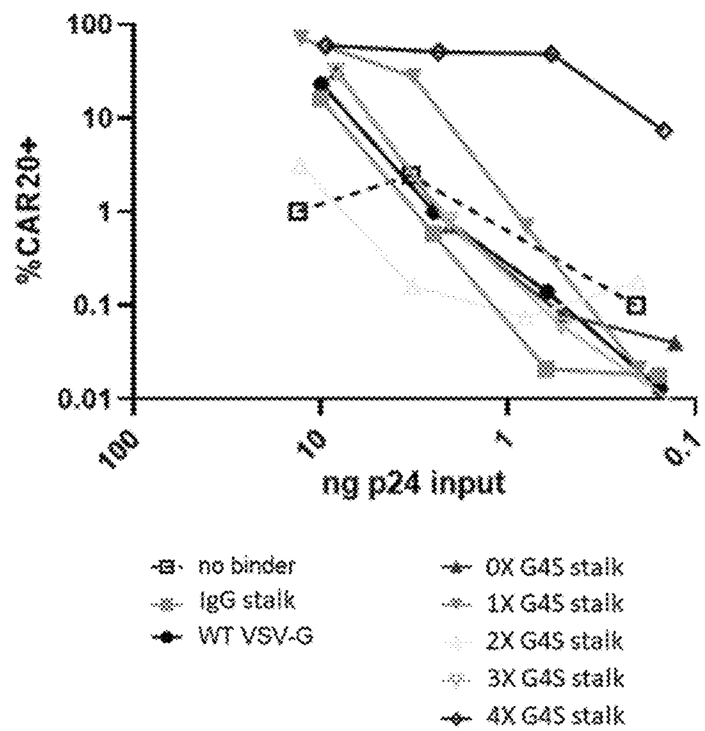
FIG. 12B illustrates the ability of viral particles harboring a CD7 binder with flexible stalks of varying length to transduce activated PBMC cells in comparison to other IgG based binders.

These examples and embodiments demonstrate that a CD7 binder with a flexible stalk is able to successfully transduce human and non-human primate PBMCs. This represents a surprising and unexpected result in light of a recent report by Dobson and colleagues (Dobson C S, Reich A N, Gaglione S, Smith B E, Kim E J, Dong J, Ronsard L, Okonkwo V, Ling wood D, Dougan M, Dougan S K, Birnbaum M E. Antigen identification and high-throughput interaction mapping by reprogramming viral entry. Nat Methods. 2022 April; 19(4):449-460. doi: 10.1038/41592-022-01436-z. Epub 2022 Apr. 8. PMID: 35396484: PMCID: PMC9012700) which showed that a VSVG (K47Q, R354A)

psuedotyped virus utilizing IL-13 as a target binding domain was unable to transduce IL-13Rα1-expressing cells when utilizing a flexible $(G_4S)_3$ surface architecture. To determine whether the number of $G_4S$ repeats is an essential variable for transduction, various constructs were utilized harboring between 0 and 4 $G_4S$ repeats (FIG. 12). Viruses comprising the various $G_4S$ stalks each with an anti-CD7 binding domain were transfected along with a packaging plasmid set consisting of VSV-G*, xHIV packaging, rev, and a SIN lentivector genome encoding an anti-CD20 CAR (CAR20) in HEK293T cells. Control samples were either the packaging set alone without a binder, the packaging set with an IgG Fc stalk with an anti-CD7 binding domain, or the packaging set without a binder substituting VSV-G* with VSV-G wild-type. Viral supernatant was purified by centrifugation over a 20% sucrose cushion and resuspended in X-Vivo media. Resuspended virus was analyzed by a p24 assay to determine viral protein content in solution. 10-fold dilutions by p24 mass of virus were administered to SupT1 and human PBMCs as indicated. Flow cytometry was utilized to assess the fraction of cells with CAR20 protein on the surface at seven days after transduction. In SupT1 cells (FIG. 12A), $(G_4S)_1$ resulted in greater CAR expression than $(G_4S)_2$ or $(G_4S)_3$ constructs. Surprisingly, constructs harboring a $(G_4S)_4$ flexible stalk did not follow the trend established for $(G_4S)_{1-3}$ and instead the $(G_4S)_4$ flexible stalk constructs resulted in greater CAR expression than any of the other $(G_4S)_n$ constructs tested. A similar result was found in human PBMCs (FIG. 12B).

Figure 13A:
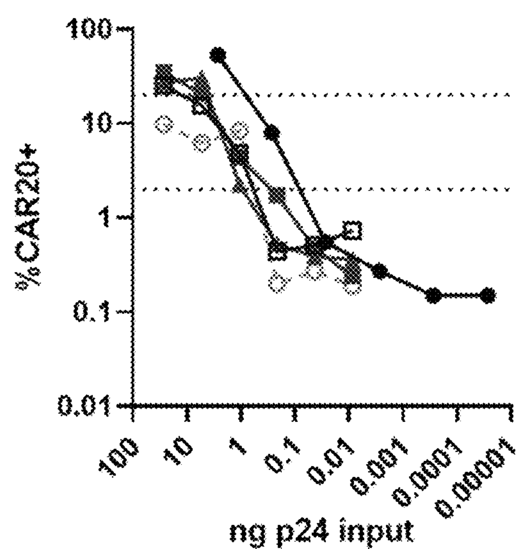
FIG. 13A illustrates the ability of SVCV-G pseudotyped lentiviral particles harboring a CD7 binder with a variant Fc stalk to transduce SupT1 cells as well as human and non-human primate PBMCs.
Figure 13B:
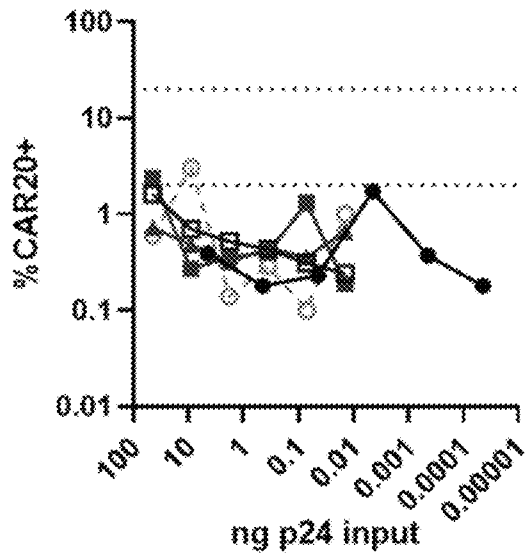
FIG. 13B illustrates the transduction of cells in the absence of the CD7 binder.
Figure 13C:
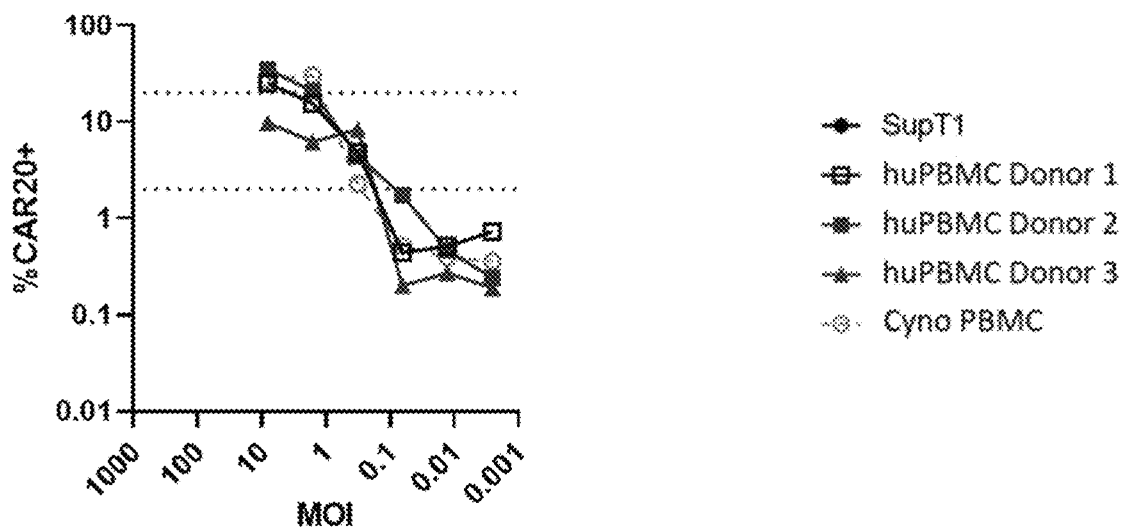
FIG. 13C illustrates the transduction of human and non-human primate PBMCs in terms of MOI calculated from SupT1 titration.
Figure 15A:
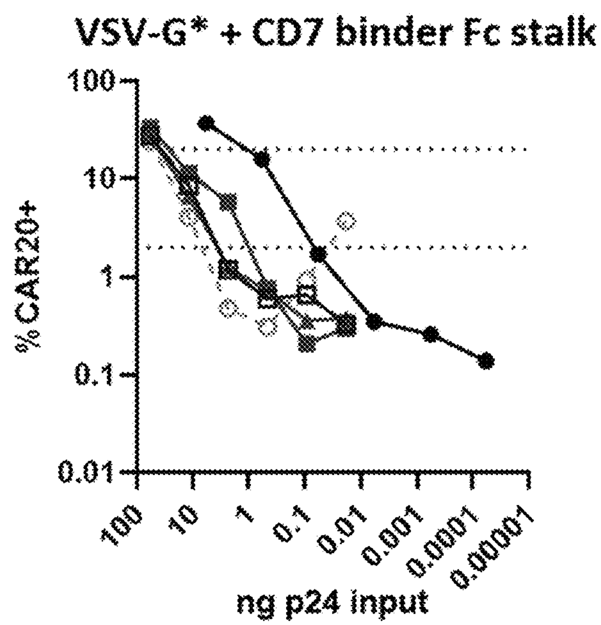
FIG. 15A-D is a comparison of the ability of VSV-G* pseudotyped lentiviral particles (panels A and B) and SVCV-G pseudotyped lentiviral particles (panels C and D) to transduce SupT1 cells as well as human and non-human primate PBMCs. VSV-G* denotes VSV-G (I182E, T214N, T352A).
Figure 15B:
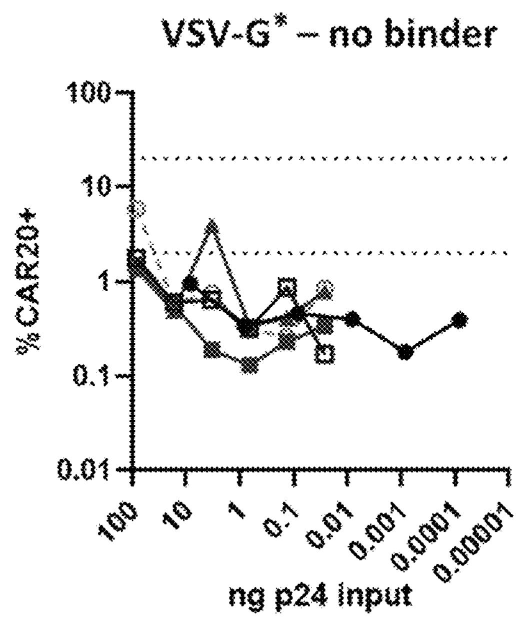
Figure 15C:
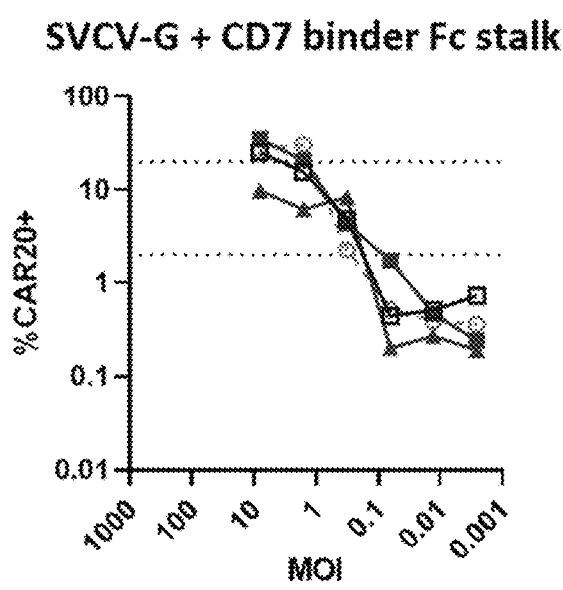
Figure 15D:
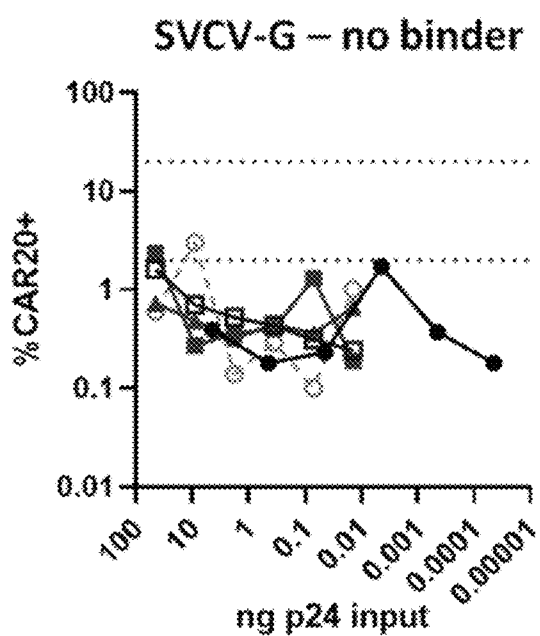
Figure 16A:
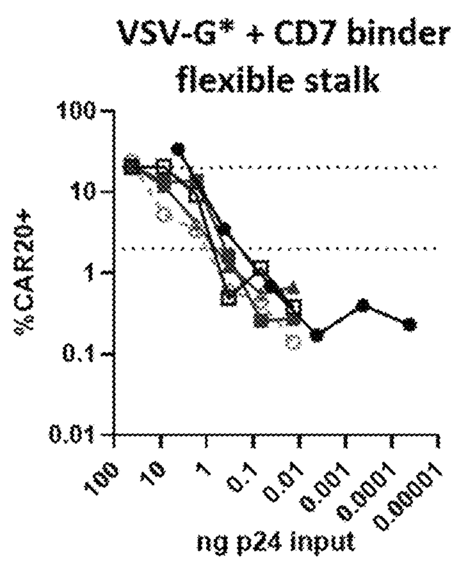
FIG. 16A-D is a comparison of the ability of VSV-G* pseudotyped lentiviral particles (panels A and B) and SVCV-G pseudotyped lentiviral particles (panels C and D) to transduce SupT1 cells as well as human and non-human primate PBMCs. VSV-G* denotes VSV-G (I182E, T214N, T352A).
Figure 16B:
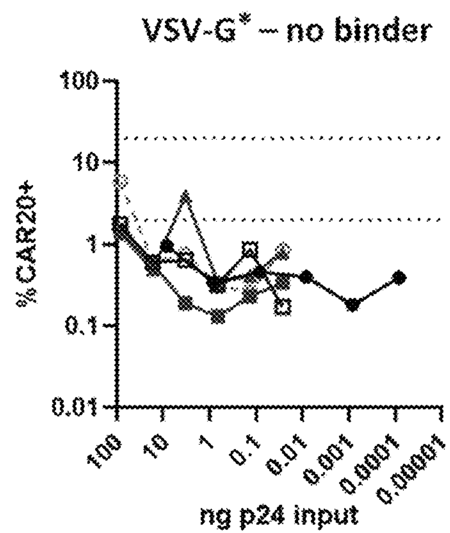
Figure 16C:
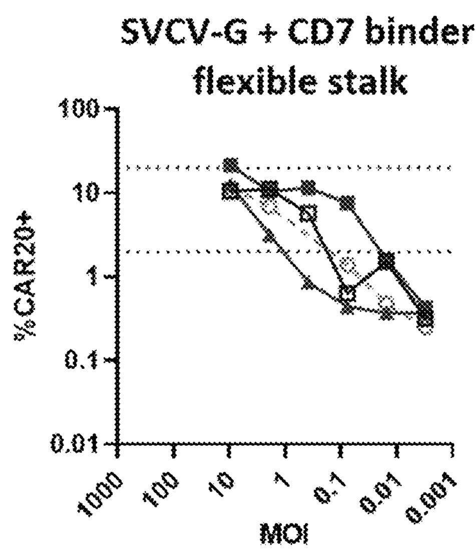
Figure 16D:
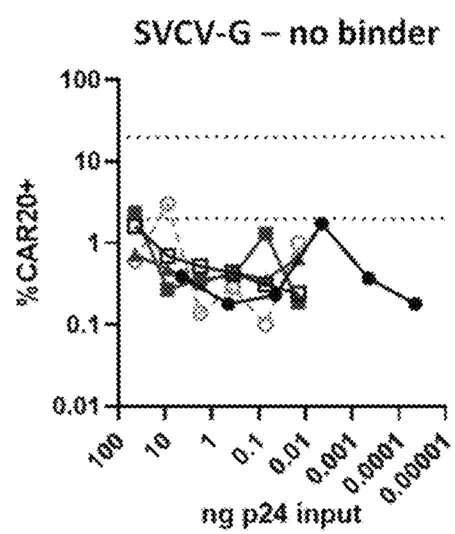

Example 8: SVCV-G Pseudotyped Lentiviruses Harboring Fc Stalk Binder Transduce PBMCs Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. The CD7 binder constructs utilized for SVCV-G pseudotyped lentiviruses of the present example are the same as those utilized in previous examples. Media was replaced 24 hours later, and the transduced cells were analyzed by flow cytometry on day 7 after transduction to determine CAR transduction. CAR expression was observed in all human and non-human primate PBMCs assessed (FIG. 13A) compared to no binder (FIG. 13B) which shows no transduction. Data are also presented as percent CAR expression vs multiplicity of infection (FIG. 13C).

These examples and embodiments demonstrate that the i) SVCV-G pseudotyped lentiviruses are able to successfully transduce PMBCs and ii) the variant Fc stalks of the present disclosure are not limited to just VSV-G pseudotyped embodiments.

Example 9: SVCV-G Pseudotyped Lentiviruses Harboring a CD7/Flexible Stalk Binder Transduce PBMCs Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. The binder constructs utilized for SVCV-G pseudotyped lentiviruses are the same as those utilized in previous example 4. Media was replaced 24 hours later, and the transduced cells were analyzed by flow cytometry on day 7 after transduction to determine CAR transduction. CAR expression was observed in all human and non-human primate PBMCs assessed (FIG. 14A) compared to no binder (FIG. 14B) which shows no transduction. Data are also presented as percent CAR expression vs multiplicity of infection (FIG. 14C).

These examples and embodiments demonstrate that the i) SVCV-G pseudotyped lentiviruses are able to successfully transduce PMBCs and ii) the flexible stalk constructs are not limited to just VSV-G pseudotyped embodiments.

Example 10: SVCV-G Pseudotyped Lentiviruses are Comparable to VSV-G* Pseudotyped Lentiviruses The transduction efficiency of SVCV-G and VSV-G* pseudotyped lentiviruses harboring a CD7 binder with a Fc stalk were compared. Lentivirus generation and cell transduction assays were performed as in the previous examples. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on day 7 after transduction to determine CAR transduction. CAR expression was comparable between VSV-G* and SVCV-G pseudotyped constructs across in SupT1 cells as well as several human PBMC lines and non-human primate PBMC lines (FIG. 15).

The transduction efficiency of SVCV-G and VSV-G* pseudotyped lentiviruses harboring a CD7 binder with a flexible stalk were also compared. Lentivirus generation and cell transduction assays were performed as in the previous examples. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Human PBMC cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect human and non-human primate cells. Media was replaced 24 hours later, and the transduced cells were analyzed by flow cytometry on day 7 after transduction to determine CAR transduction. CAR expression was comparable between VSV-G* and SVCV-G pseudotyped constructs across in SupT1 cells as well as several human PBMC lines and non-human primate PBMC lines (FIG. 16).

These examples and embodiments demonstrate that both VSV-G* and SVCV-G pseudotyped viral particles are able to transduce SupT1 and PBMC cells with similar potency when using a CD7 binder with either the variant Fc stalks of the present disclosure or the flexible peptide stalks of the present disclosure, suggesting that both VSV-G* and SVCV-G constructs may be useful in transducing a wide array of cell types.

Example 11: PBMC Transduction Profile of PBMCs Transduced with VSV-G* Pseudotyped Lentiviruses Harboring Fc Stalk Binder To verify that the intended cell targets were being transduced, primary human PBMCs were transduced with VSV-G* pseudotyped lentiviruses harboring a CD7 binder having the sequence of SEQ ID NO: 98 and were subsequently assessed for transgene (GFP) expression. Human PBMC cells were maintained in X-Vivo10 media with 5% human serum and 20 ng/mL of human IL-2. Concentrated lentivirus was used to infect the PBMCs. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Media was replaced 24 hours later, and the transduced cells were analyzed by flow cytometry.

Figure 17A:
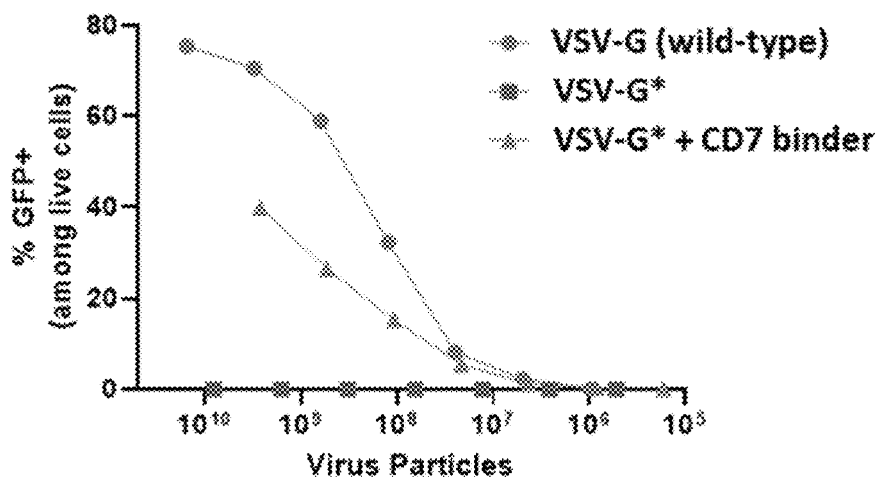
FIG. 17A illustrates the ability of VSV-G* pseudotyped lentiviral particles to ablate GFP transduction driven by WT-VSV-G in activated PBMCs, and that the inclusion of a CD7 binder restores GFP transduction.
Figure 17B:
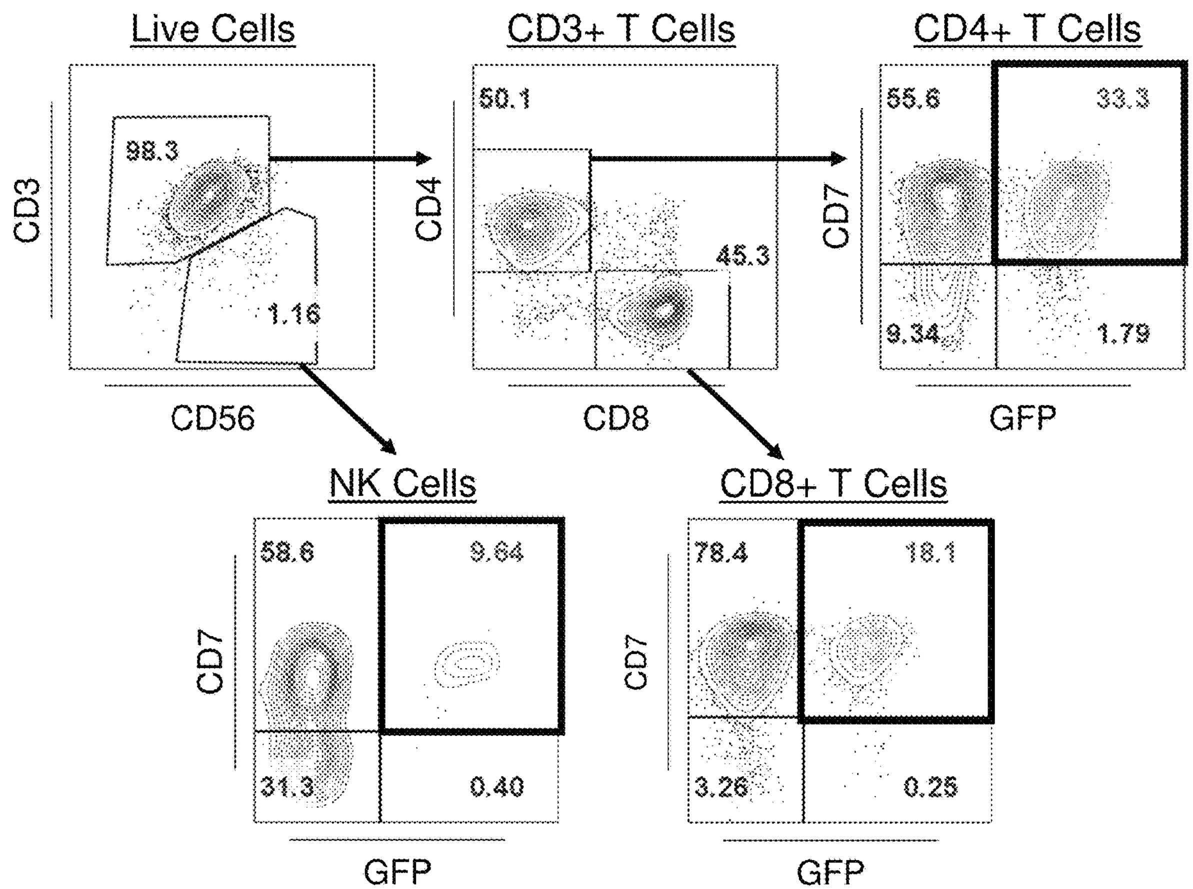
FIG. 17B illustrates the specific cell populations transduced by the VSV-G*, CD-7 binder pseudotyped lentiviral particles.

As shown in FIG. 17A, viral particles comprising wild-type VSV-G demonstrated a robust transgene expression, which was eliminated by use of the VSV-G* glycoprotein. Inclusion of the CD7 binder rescued GFP transgene expression. This data again illustrates that the VSV-G* glycoprotein is able to ablate the promiscuous reactivity of the WT-VSV-G glycoprotein, and that inclusion of a directed binder will result in targeted transgene expression. The GFP positive PBMCs were further assessed by cell type. As shown in FIG. 17B, the VSV-G* pseudotyped lentiviruses harboring a CD7 binder having the sequence of SEQ ID NO: 98 successfully transduced CD4+ T cells, CD8+ T cells, and NK Cells, as evidenced by the population of GFP positive, cell marker positive cells for each of these cell types. This data demonstrates the ability of the viral particles provided for herein to successfully transduce the intended CD7 positive cell targets in PBMCs.

Figures 18A, 18B:
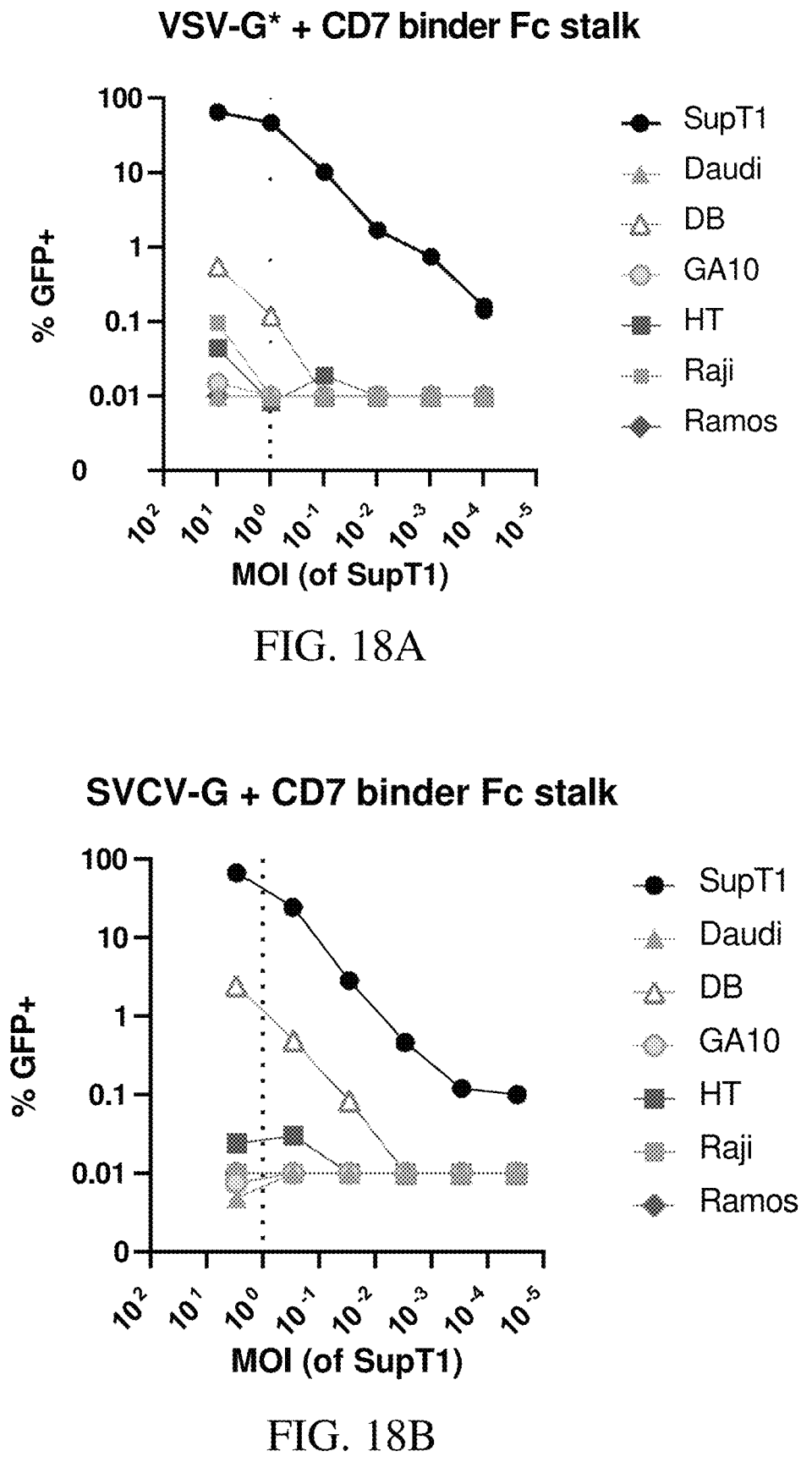

Example 12: VSV-G* and SVCV-G Pseudotyped Lentiviruses Harboring a CD7/Fc Stalk Binder Exhibit Minimal Off Target Transduction The off target transduction of B-cells via VSV-G* and SVCV-G pseudotyped lentiviral constructs utilizing Fc binder stalks was assessed in several B-cell populations. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. B-cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect the various B-cell populations. The CD7 binder constructs utilized for the VSV-G* and SVCV-G pseudotyped lentiviruses are the same as those utilized in previous examples. Media was replaced 24 hours later, and the transduced cells were analyzed by flow cytometry on day 5 after transduction to determine GFP transduction. As a control, SupT1 cells were also infected with the same lentiviral constructs. None of the B-cell populations assessed demonstrated any significant level of GFP expression (FIG. 18). The percent of GFP positive cells only exceeded 1% in line DB when utilizing the SVCV-G pseudotyped construct at the highest concentration of lentivirus utilized.

Figures 19A, 19B:
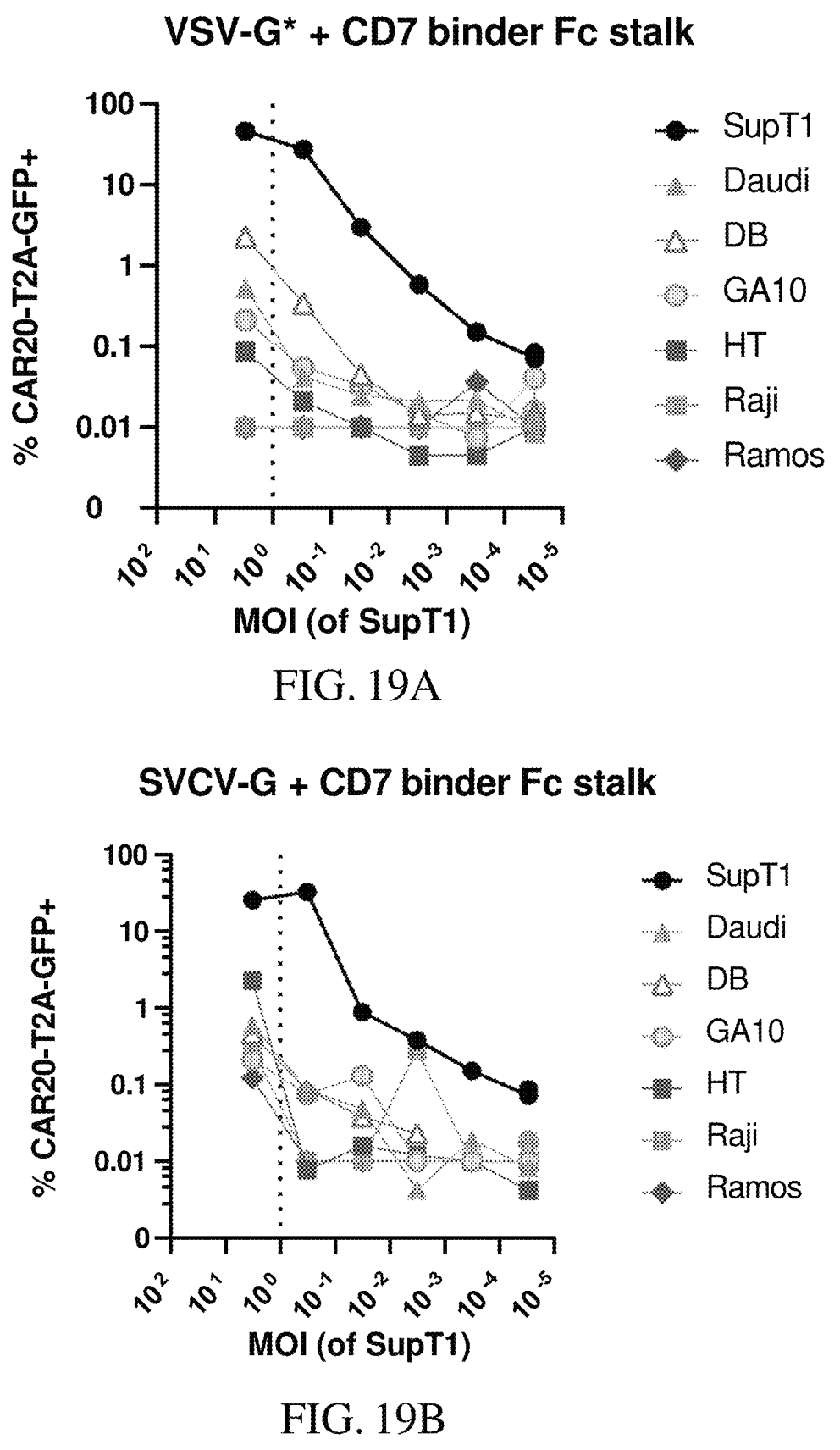

Lentiviral constructs delivering a CAR20-T2A-GFP transgene were also assessed in a similar manner (FIG. 19). VSV-G* pseudotyped lentiviruses utilizing the Fc binder stalk still exhibited minimal off target transduction of B-cells in all cell populations tested (FIG. 19). The percent of CAR-T2A-GFP positive cells only exceeded 1% in line DB at the highest lentiviral concentrations utilized. SVCV-G pseudotyped lentiviruses utilizing the Fc stalk also exhibited minimal off target transduction of B-cells in five of the six cell populations assessed (FIG. 19A). The percent of CAR-T2A-GFP positive cells only exceeded 1% in line HT at the highest concentration of lentivirus utilized.

Figure 20A:
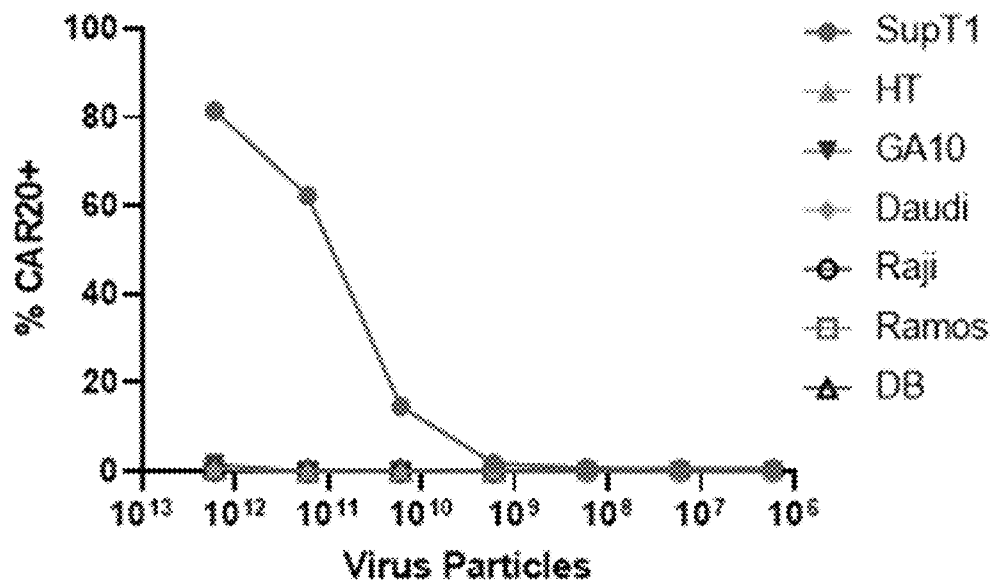
FIG. 20A and FIG. 20B illustrate the assessment of off target transduction by VSV-G* pseudotyped lentiviral particles harboring a CD7 binder with a variant Fc stalk.
Figure 20B:
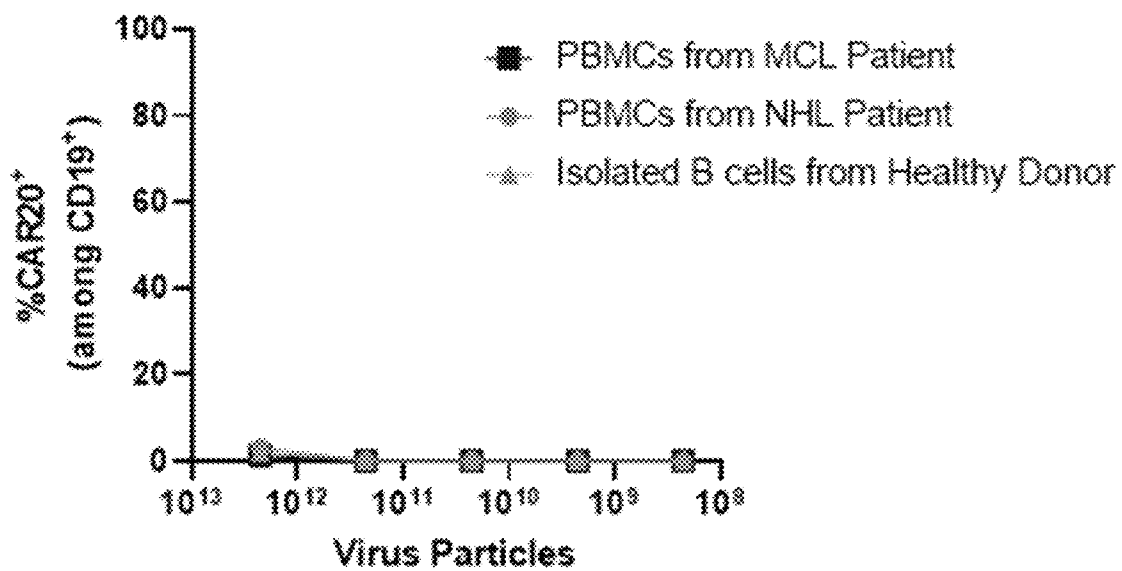

The off target experiments were repeated utilizing a VSV-G* pseudotyped lentiviruses harboring a CD7 binder having the sequence of SEQ ID NO: 98 (FIG. 20A). As with previous experiments, the VSV-G* pseudotyped lentiviruses did not exhibit appreciable transduction of the CD20 CAR in the B-cell tumor lines. As a further control, the VSV-G* pseudotyped lentiviruses harboring a CD7 binder having the sequence of SEQ ID NO: 98 were also tested for their ability to inappropriately transduce B cells from patients with B-cell malignancies (FIG. 20B). PBMCs were isolated from the patients and a healthy donor and were transduced with the viral construct. B cells were then isolated by flow selecting for CD19 positive B cells, and the amount of CAR20 positive B cells was assessed. As shown in FIG. 20B, the viral constructs did not inappropriately transduce CD19 positive B cells from either the healthy control or those with B-cell malignancies.

These examples and embodiments demonstrate that the i) VSV-G* and SVCV-G pseudotyped lentiviruses utilizing the Fc stalks of the present disclosure have low off target transduction of B-cells, ii) delivery of a CAR20 transgene instead of a GFP transgene does not significantly increase off target transduction in B-cells, iii) the CD7 binder of SEQ ID NO: 98 did not result in significant off target transduction of B-cells, and iv) the viral constructs provided for herein did not inappropriately transduce primary B-cells from patients with B-cell malignancies.

Figures 21A, 21B:
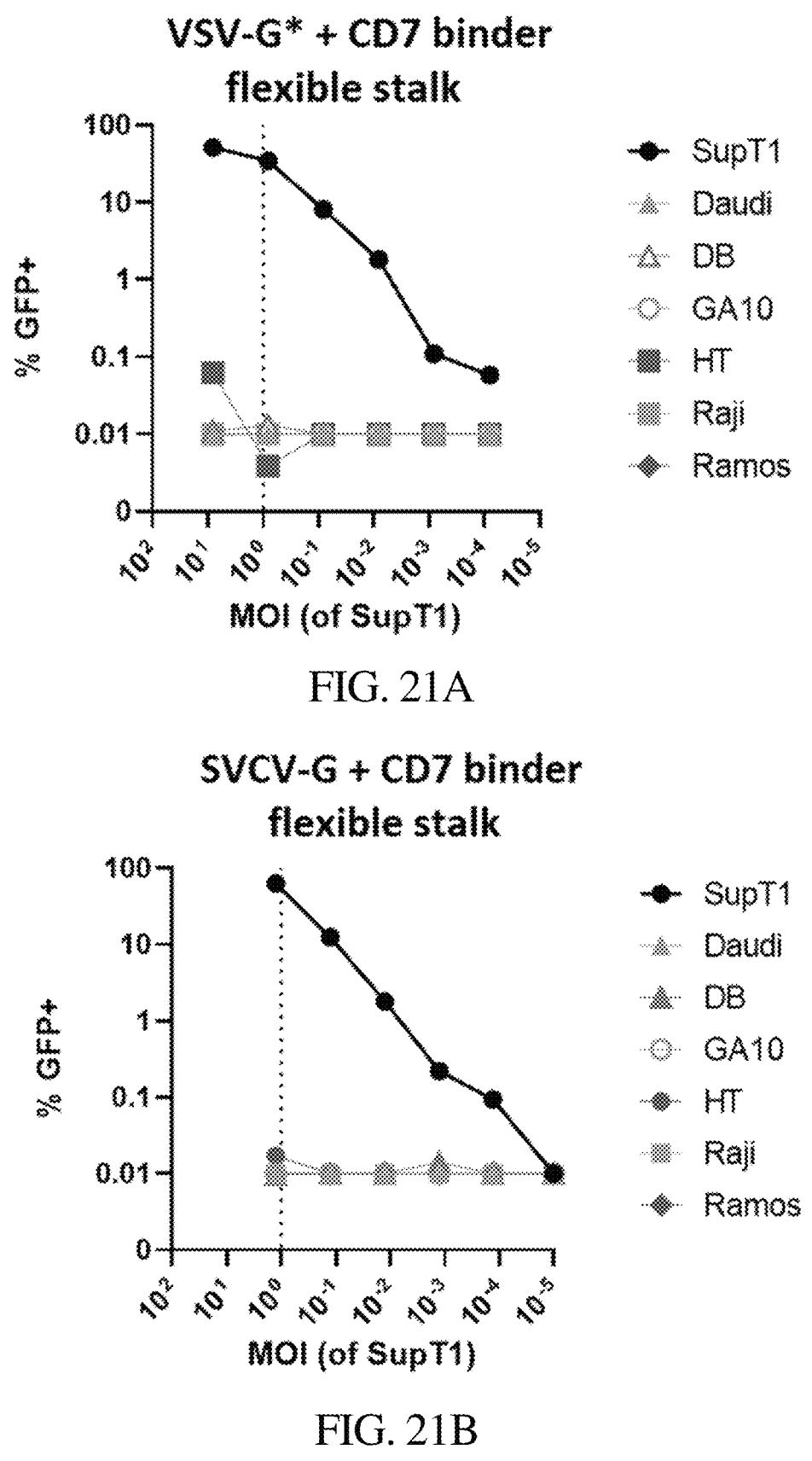

Example 13: VSV-G* and SVCV-G Pseudotyped Lentiviruses Harboring a CD7/Flexible Stalk Binder Exhibit Minimal Off Target Transduction The off target transduction of B-cells via VSV-G* and SVCV-G pseudotyped lentiviral constructs utilizing flexible binder stalks was assessed in several B-cell populations. The utilized VSV-G protein was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. B-cells were maintained in X-Vivo10 media with 5% human serum and 20 ng/mL of human IL-2. Non-human primate cells were maintained in RPMI media with 10% FBS, 1% Pen/Strep with 1 mM Sodium Pyruvate and 100 units/mL hIL-2. Concentrated lentivirus was used to infect the various B-cell populations. The binder constructs utilized for the VSV-G* and SVCV-G pseudotyped lentiviruses are the same as those utilized in previous Examples 4 and 6. Media was replaced 24 hours later, and the transduced cells were analyzed by flow cytometry on day 5 after transduction to determine GFP transduction. As a control, SupT1 cells were also infected with the same lentiviral constructs. None of the B-cell populations assessed demonstrated any significant level of GFP expression (FIG. 21).

Figure 22A:
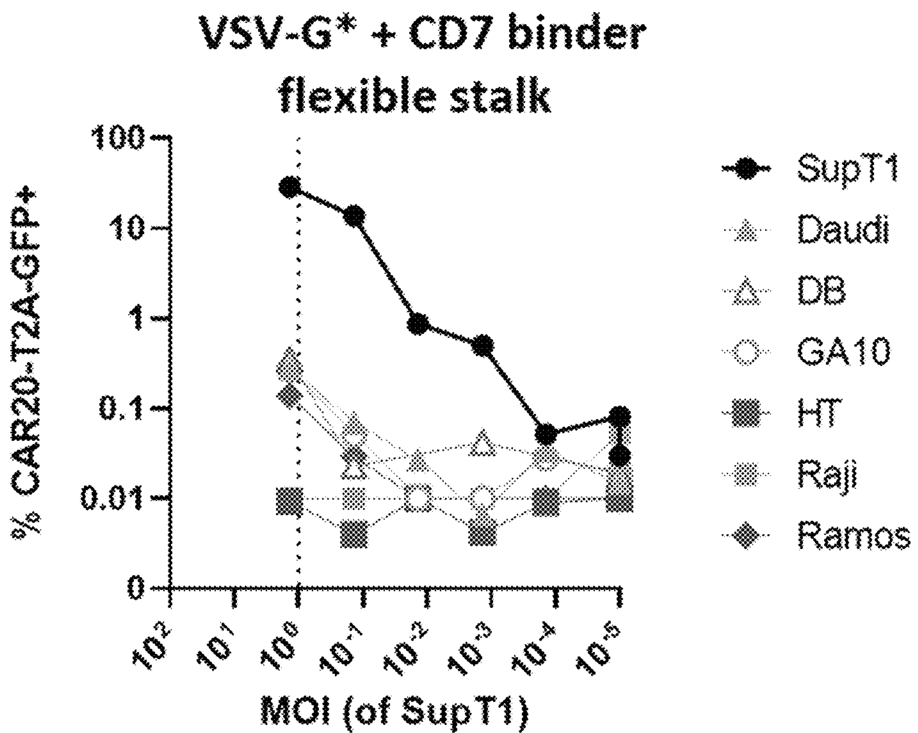
FIG. 22A and FIG. 22B is a comparison of the off target transduction of a CAR20-T2A-GFP construct in a panel of B-cell cell lines as compared to control SupT1.
Figure 22B:
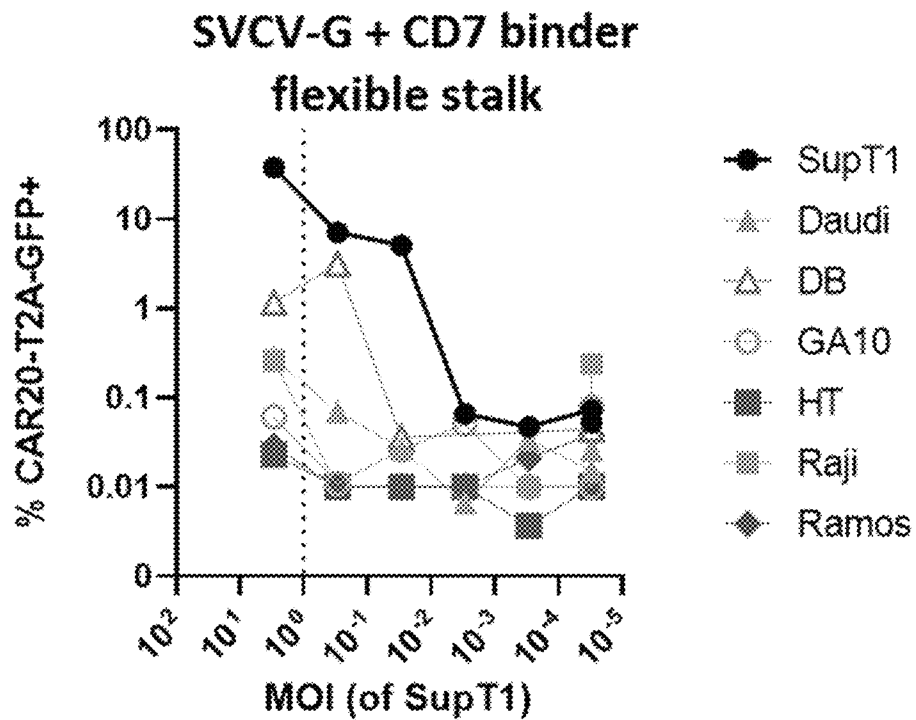

Lentiviral constructs delivering a CAR20-T2A-GFP transgene were also assessed in a similar manner (FIG. 20). VSV-G* pseudotyped lentiviruses utilizing the flexible binder stalk still exhibited minimal off target transduction of B-cells in all cell populations tested (FIG. 22). The percent of CAR-T2A-GFP positive cells did not exceed 1% in any of the B-cell cell populations at any of the lentiviral concentrations utilized. SVCV-G pseudotyped lentiviruses utilizing the flexible binder stalk also exhibited minimal off target transduction of B-cells in five of the six cell populations assessed (FIG. 22A). The percent of CAR-T2A-GFP positive cells did not exceed 1% in the Daudi, GA10, HT, Raji, or Ramos cell lines at any of the lentiviral concentrations utilized. The B-cell cell line DB did rise above 1% positive at two of the higher lentiviral concentrations utilized, but still remained less than the control SupT1 cell line.

These examples and embodiments demonstrate that the i) VSV-G* and SVCV-G pseudotyped lentiviruses utilizing a flexible binder stalk have low off target transduction of B-cells and ii) delivery of a CAR20 transgene instead of a GFP transgene does not significantly increase off target transduction in B-cells.

Example 14: VSV-G* Pseudotyped Lentiviruses with CD20-CAR Transgene Payload Kills CD20 Positive Lymphoma Cells In Vitro The ability of VSV-G* pseudotyped lentiviral constructs with a CD20-CAR transgene to kill CD20 positive lymphoma cells in vitro was assessed. The VSV-G* pseudotyped lentiviral constructs utilized a CD7 binder having the sequence of SEQ ID NO: 98. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. Human PBMCs were transduced with a lentiviral construct carrying a CD20-CAR (CAR20) transgene. The CAR20 transgene comprised the sequence of SEQ ID NO: 99.

Figure 23A:
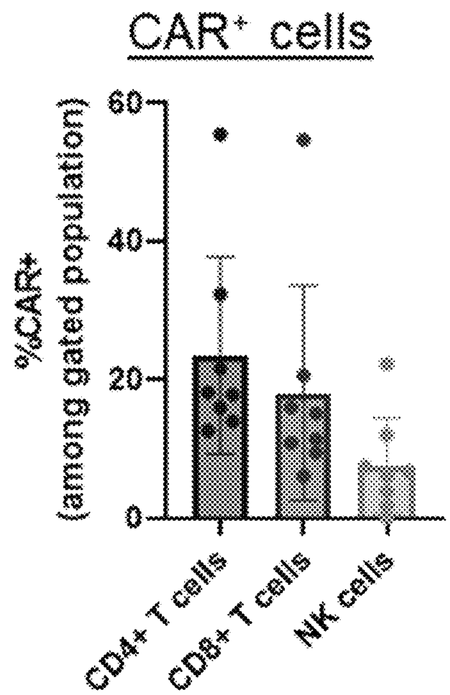
FIG. 23A-C illustrate the ability of PBMCs transduced with CD20 CAR constructs as provided herein to kill lymphoma cell lines.
Figure 23B:
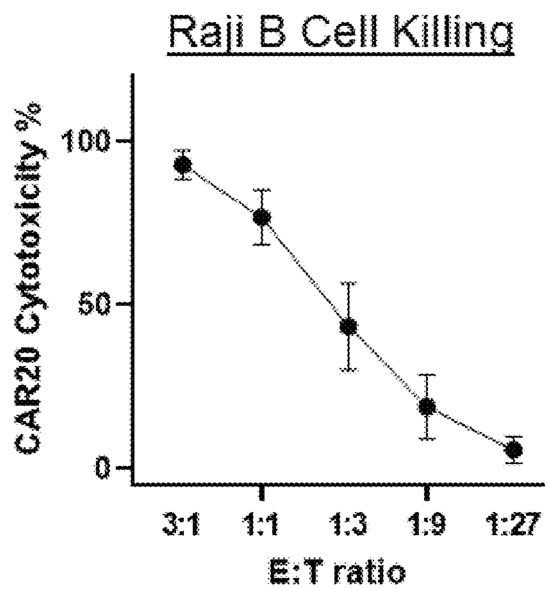
Figure 23C:
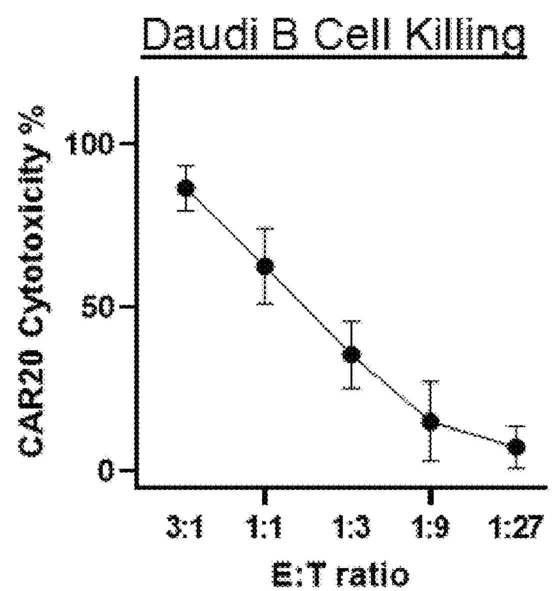

The CAR20 positive cells were first assessed to identify the population of cells transduced by the lentiviral construct. In agreement with previous examples, the CAR20 positive cells were identified as being CD4+ T cells, CD8+ T cells, and KN cells. CD20 positive lymphoma cells were then added to the CAR20 cells at a given effector to target ratio (E:T). The CAR20 positive PBMCs produced a dose dependent killing of both CD20 positive lymphoma cells assessed (FIGS. 23B and 23C)

These examples and embodiments demonstrate that the VSV-G* pseudotyped lentiviruses utilizing the CD7 binder having a sequence of SEQ ID NO: 98 delivering a CAR transgene of SEQ ID NO: 99 not only transduce the appropriate target cells, but also produce PBMCs expressing the CAR construct and capable of a robust and dose dependent killing of CD20 positive lymphoma cells in vitro.

Figure 24A:
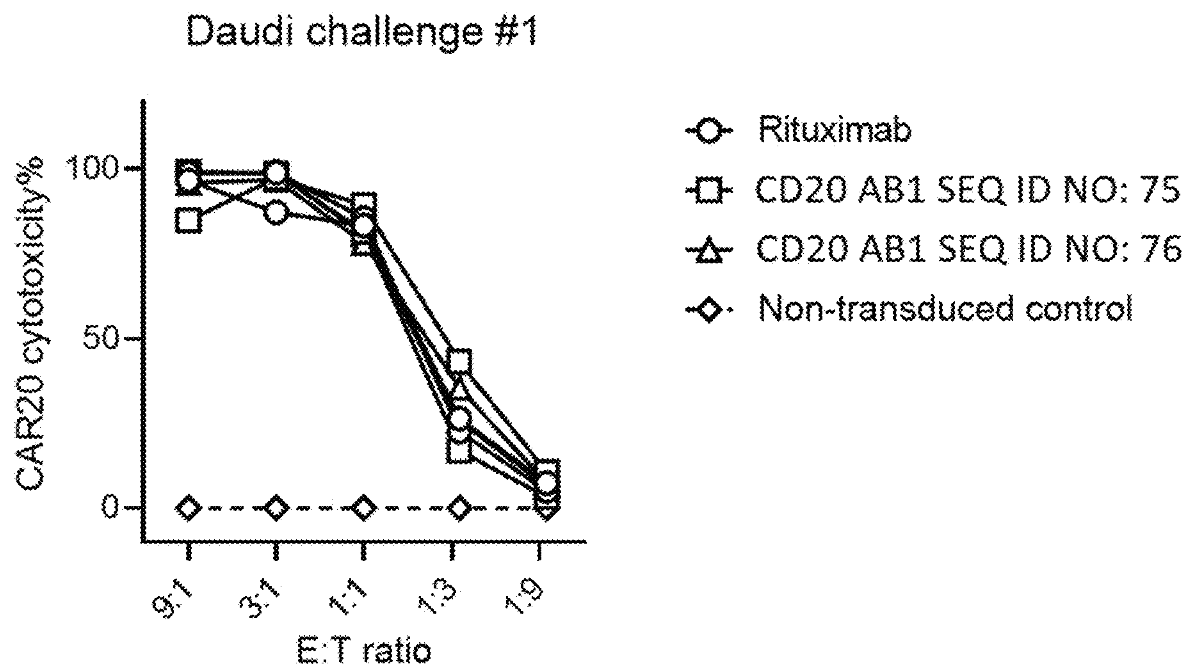
FIGS. 24A and 24B illustrate the ability of VSV-G* pseudotyped lentiviral particles utilizing CD7 binders and a CD20-CAR transgene as provided for herein to kill Daudi lymphoma cells (FIG. 24A) or Raji lymphoma cells (FIG. 24B). CAR20 constructs utilized antigen binding domains comprising rituximab, or CD20AB1 SEQ ID NOs 92 or 93 as provided for herein.
Figure 24B:
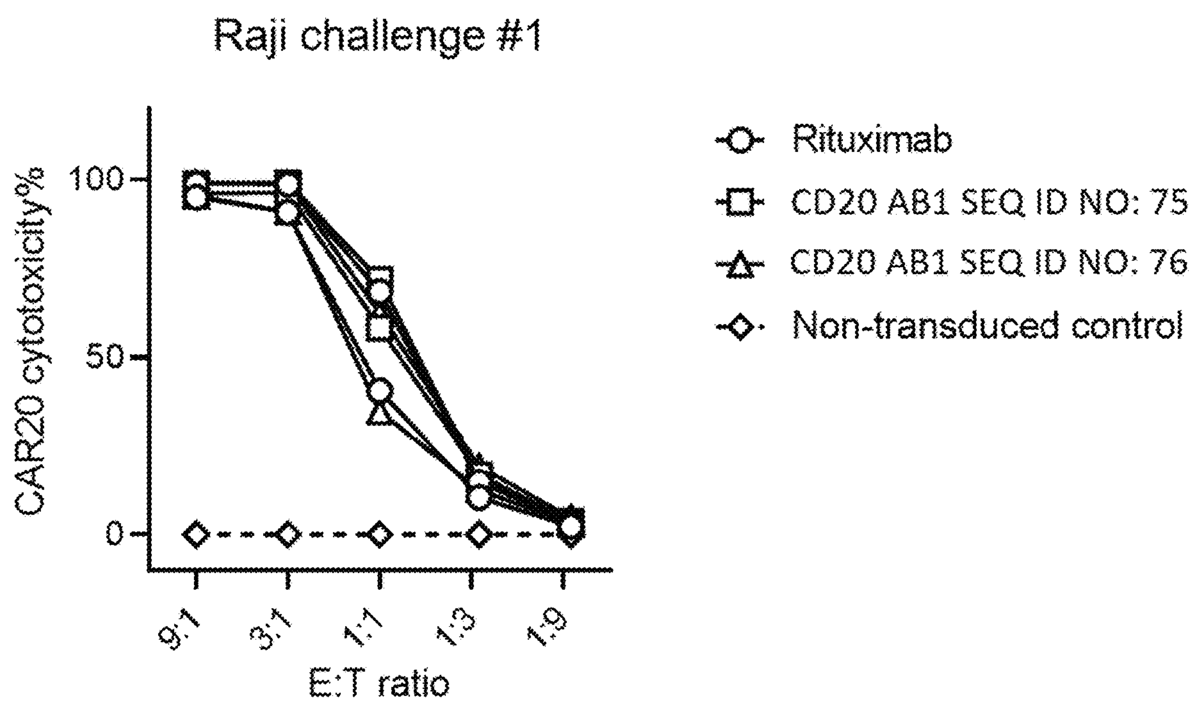

Example 15: VSV-G* Pseudotyped Lentiviruses with CD20-CAR Transgene Payload Kills CD20 Positive Lymphoma Cells In Vitro The ability of VSV-G* pseudotyped lentiviral constructs with a CD20-CAR transgene to kill CD20 positive lymphoma cells in vitro was assessed. The VSV-G* pseudotyped lentiviral constructs utilized CD7 binders as provided for herein. The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein. Human PBMCs were transduced with a lentiviral construct carrying a CD20-CAR (CAR20) transgene. The CAR20 transgenes comprised antigen binding domains of SEQ ID NO: 92 or SEQ ID NO: 93. CD20 positive lymphoma cells were then added to the CAR20 cells at a given effector to target ratio (E:T). The CAR20 positive PBMCs produced a dose dependent killing of CD20 positive lymphoma cells (FIG. 24)

These examples and embodiments demonstrate that the VSV-G* pseudotyped lentiviruses utilizing the CD7 binders of the present disclosure not only transduce the appropriate target cells as demonstrated by the previous examples, but also produce robust and dose dependent killing of CD20 positive lymphoma cells in vivo.

Figure 25A:
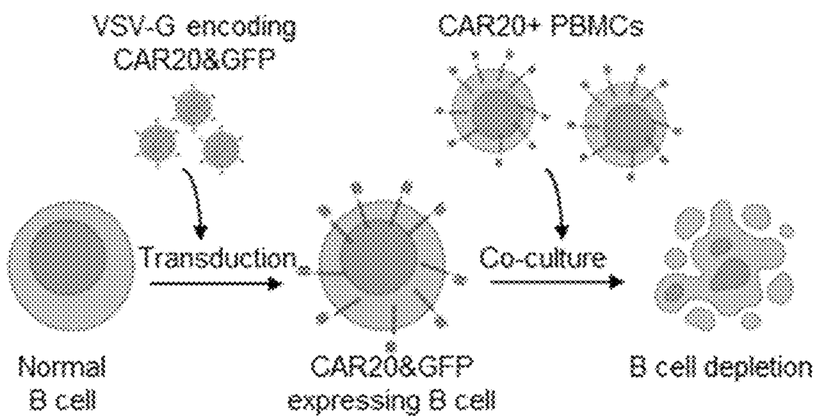
FIG. 25A-C illustrate the results of an experiment to assess risk of generating CAR-resistant B cell tumors.

Example 16: Assessment of Potential for Generation of CAR Resistant B-Cell Tumors An experiment was performed to assess the risk of unintended B cell transduction resulting in CAR-resistant B cell tumors. The experimental process is outlined in FIG. 25A. As shown, normal B cells were first transduced with viral constructs as provided for herein to generate B cells harboring a GFP transgene or a CAR20 transgene and a GFP transgene. The generated B cells were then exposed to CAR20 positive PBMCs at a given effector to target ratio (E:T). The possibility of enriching for transgene positive B cells was also assessed. CAR20 positive PBMCs were generated as described in previous examples with a VSV-G* pseudotyped lentiviral constructs utilizing a CD7 binder having the sequence of SEQ ID NO: 98 and delivering a CAR transgene having the sequence of SEQ ID NO: 99. The results are illustrated in FIGS. 25B and 25C.

Figure 25B:
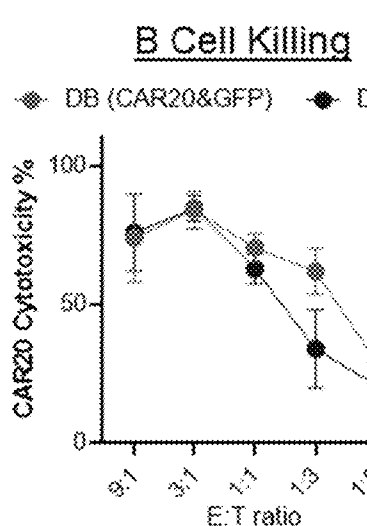
Figure 25C:
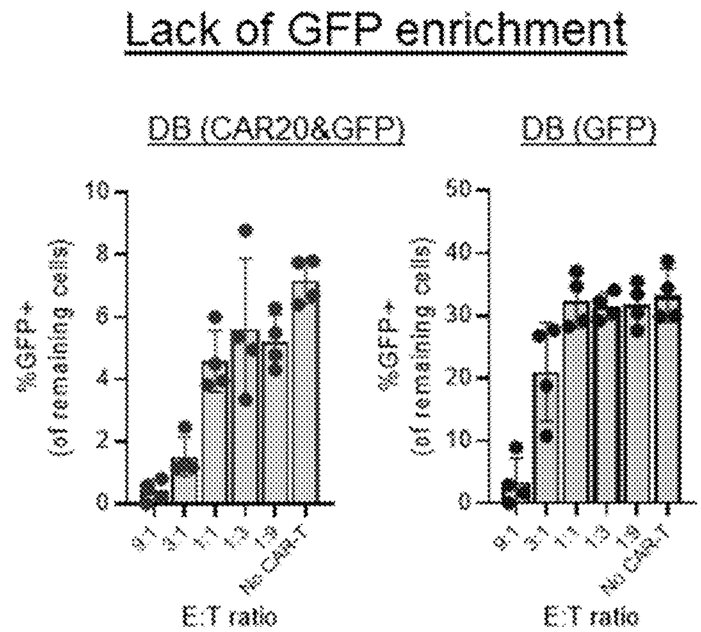

As shown in FIG. 25B, CAR20 positive PBMCs were still able to kill CAR20 positive B cells at a similar potency to the killing of GFP only positive B cells. As shown in FIG. 25C, the CAR20 positive B cells were not selectively spared from CAR20 positive PBMCs, as demonstrated by the lack of enrichment for GFP in the CAR20 positive GFP positive condition.

The data of the present example further highlight the favorable risk profile of the viral particles provided for herein. As demonstrated in previous examples, the viral particles provided for herein have minimal off target transduction of B-cells. The data of the present example demonstrate that even if B-cells were unintentionally transduced, this transduction does not confer resistance to the B-cells, which are still susceptible to the CAR20 positive PBMCs.

Example 17: VSV-G* Pseudotyped Lentiviruses Deplete B-Cells in Mice

Figure 26A:
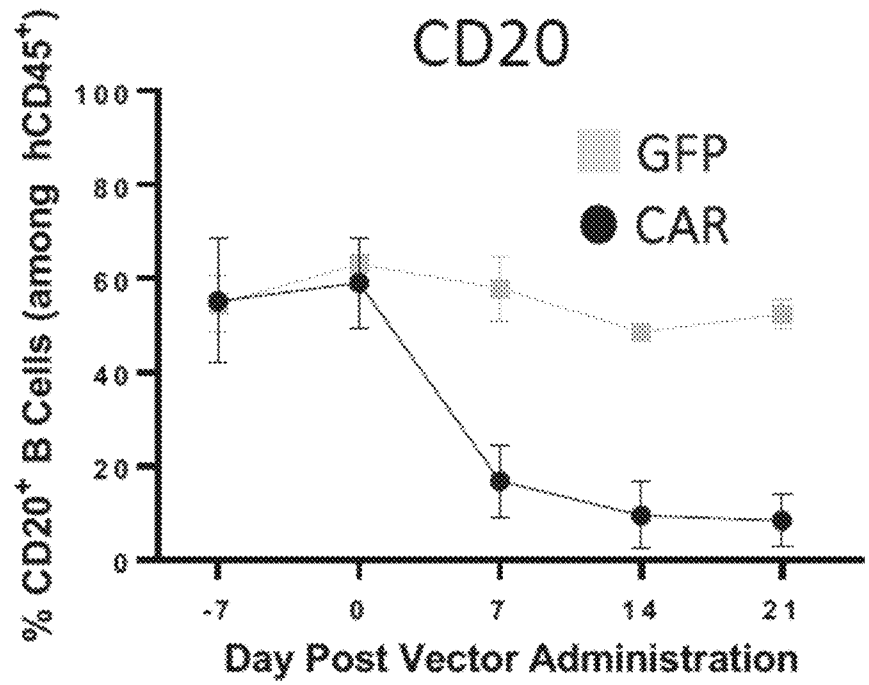
FIGS. 26A and 26B illustrate the ability of VSV-G* pseudotyped lentiviral particles utilizing CD7 binders and a CD20-CAR transgene as provided for herein to deplete B-cells in vivo in huCD34 NSG mice. B-cells were detected via assessment for CD20 (FIG. 26A) or CD19 (FIG. 26B).
Figure 26B:
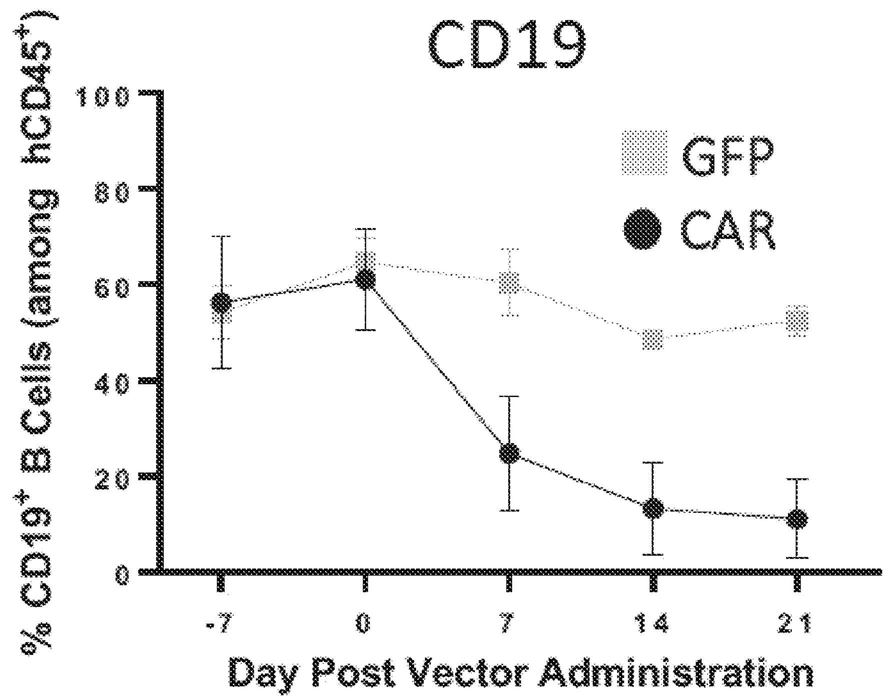

The ability of VSV-G* pseudotyped lentiviral constructs to deplete B-cell populations in vivo was assessed. The VSV-G* pseudotyped lentiviral constructs utilized CD7 binders as provided for herein (i.e., SEQ ID NO: 98). The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23, SEQ ID NO: 25), as provided for herein. Mice were injected with lentiviral particles expressing a GFP transgene, or a CD20-CAR transgene (SEQ ID NO: 99). The mice utilized were huCD34 NSG mice which have circulating human T and B cells. Mice receiving lentiviral constructs expressing GFP saw no loss of CD20 (FIG. 26A) or CD19 (FIG. 26B) B cells. Mice receiving the CD20-CAR transgene saw a dramatic and sustained loss of B cells over three weeks as exhibited by a dramatic loss of both CD20 positive B cells (FIG. 26A) and CD19 positive B cells (FIG. 26B).

Figure 27A:
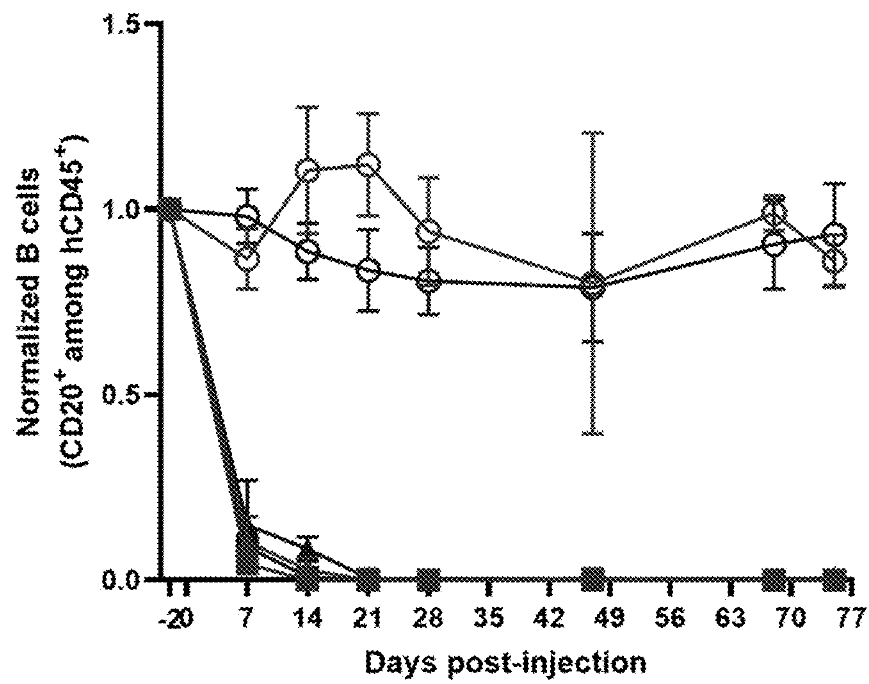
FIGS. 27A and 27B illustrates the ability of VSV-G* pseudotyped lentiviral particles utilizing CD7 binders and a CD20-CAR transgene as provided for herein to deplete B-cells in vivo in huCD34 NSG mice.
Figure 27B:
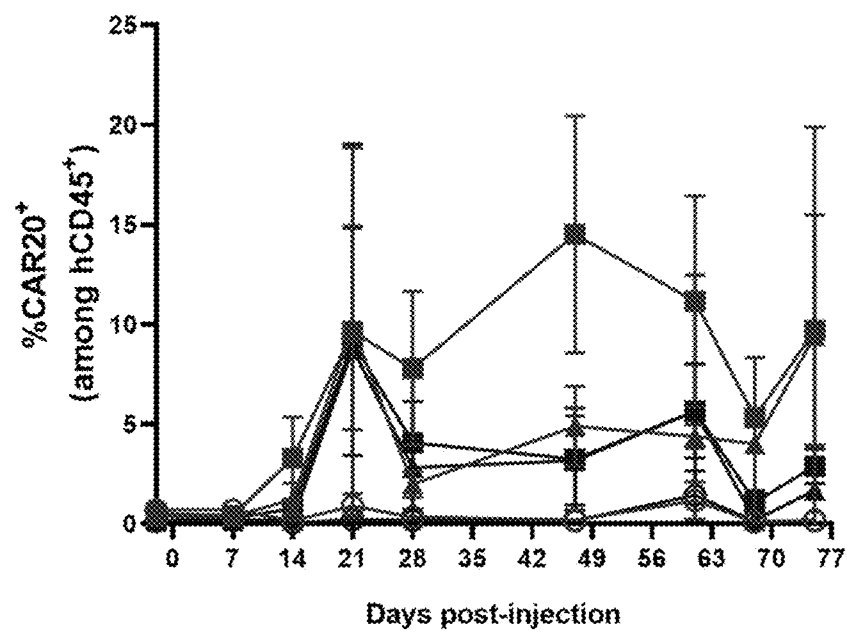

The B cell depletion assessment described above was repeated utilizing multiple viral doses (FIG. 27). Further, the huCD34 NSG mice utilized in the follow up experiment were generated from two separate human donors, thereby allowing for the assessment of donor variability. As shown in FIG. 27A, all viral doses tested for both donor sets resulted in dramatic and sustained loss of B cells over the timeline of the experiment. The mice were also periodically assessed for the presence of CAR20 positive cells in the blood, which would indicate the stable generation of CAR20+ PBMCs in vivo. As shown in FIG. 27B, the mice of the present example had detectable CAR20+ cells in the blood starting around 14 days post injection which was sustained for the duration of the study.

The data of the present example demonstrate the ability of the viral particles provided for herein to generate CAR20+ cells in vivo, resulting in in vivo depletion of B cells. Further, the detection of sustained CAR20+ cells in the blood indicate that in the absence of an immune response against the CAR molecule, the CAR20+ cells generated by the viral particles are maintained and active.

Figure 28A:
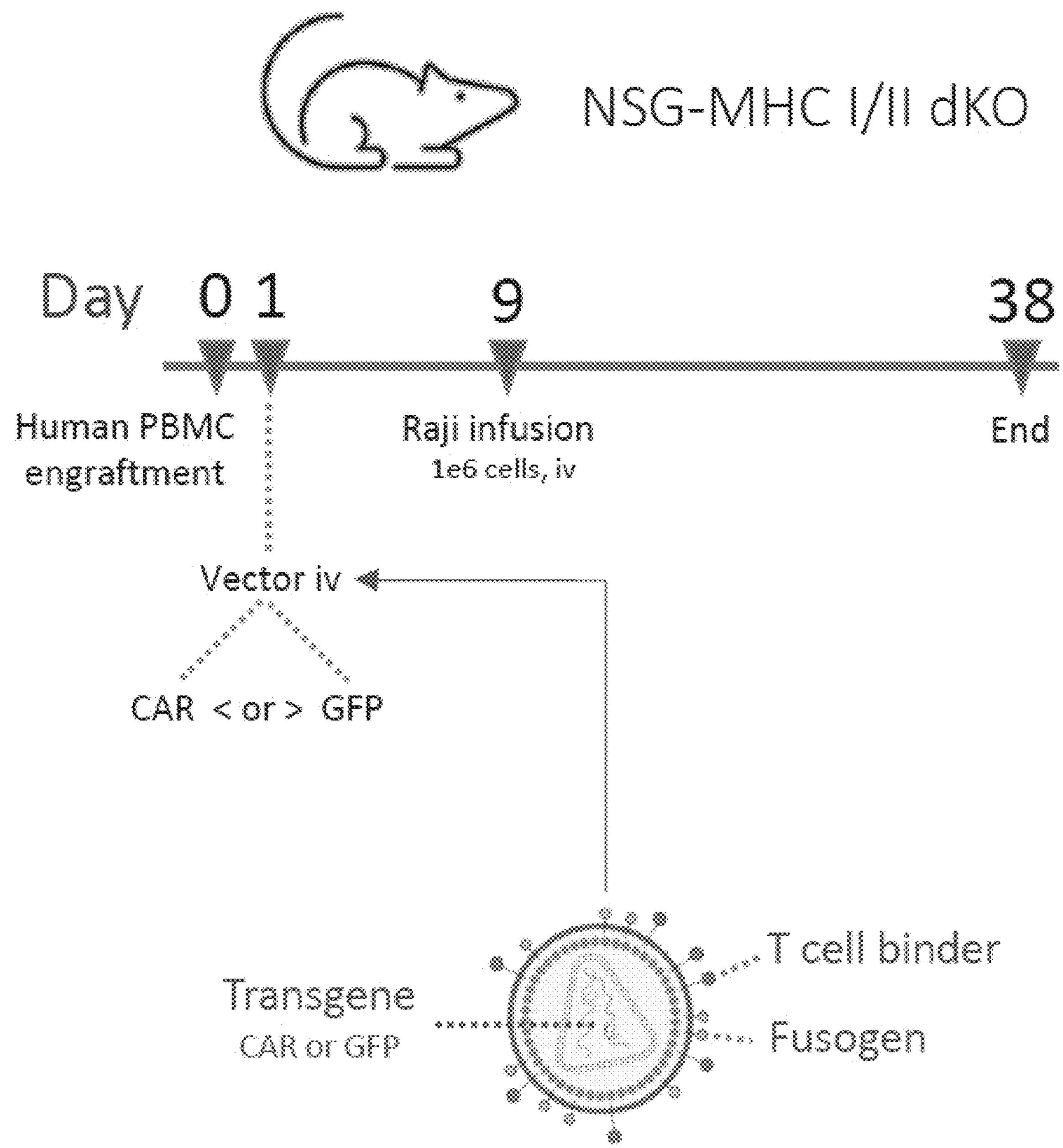
FIGS. 28A and 28B illustrate the ability of VSV-G* pseudotyped lentiviral particles utilizing CD7 binders and a CD20-CAR transgene as provided for herein to prevent tumor formation in vivo.
Figure 28B:
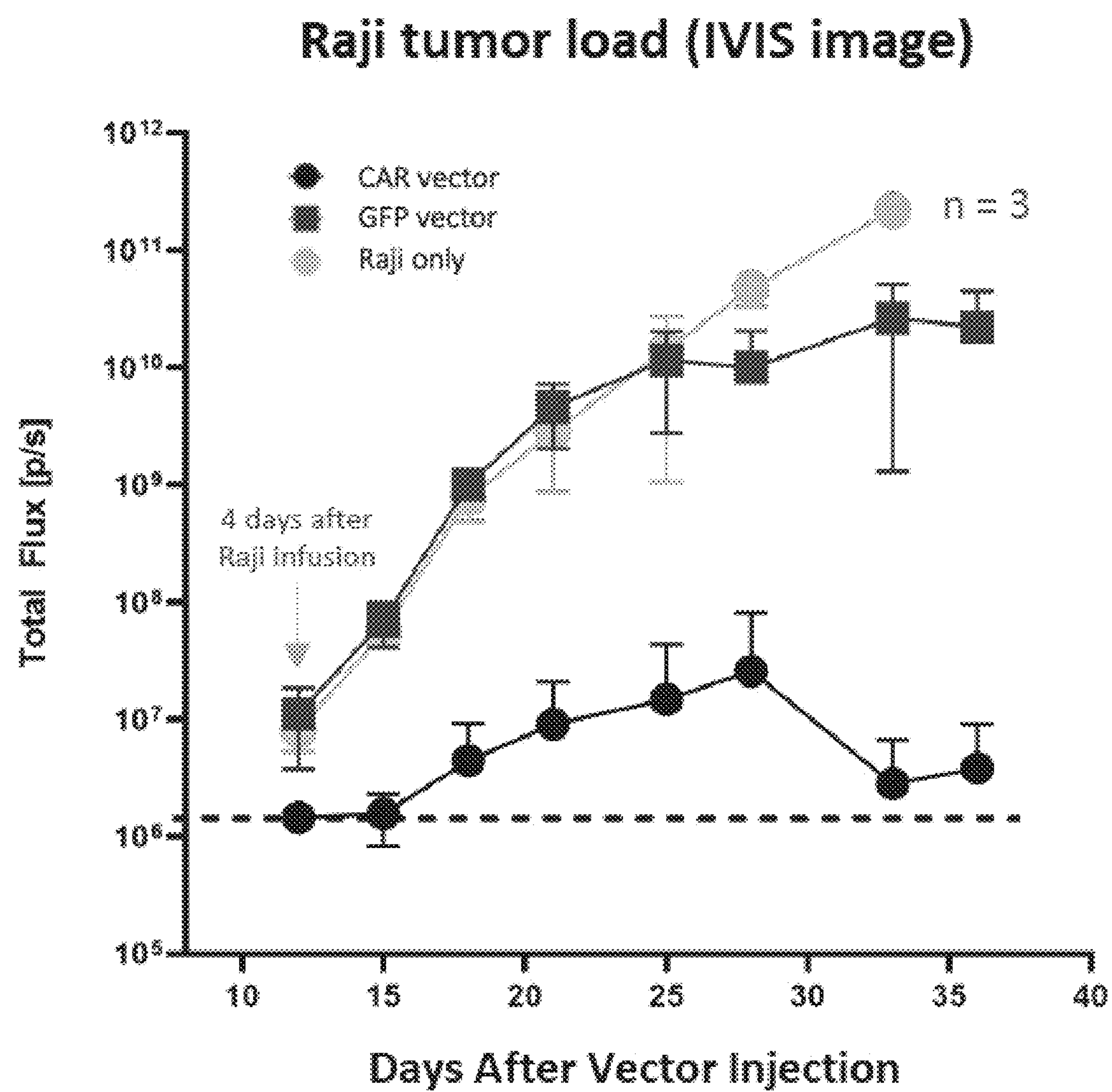

Example 18: VSV-G* Pseudotyped Lentiviruses Eliminate Established Tumors in Mice To further characterize the in vivo efficacy of the viral particles, the ability of VSV-G* pseudotyped lentiviral constructs to prevent tumor formation was assessed. Mice were injected with viral particles expressing a GFP transgene or a CD20-CAR transgene (i.e. SEQ ID NO: 99) on protocol Day 1. On Day 9, mice were infused with Raji tumor cells and tumor progression was monitored. The experimental protocol is illustrated in FIG. 28A. Mice receiving no treatment or lentiviral constructs expressing GFP demonstrated progressive tumor development and spread as determined by IVIS imaging. In contrast, mice receiving lentiviral constructs expressing the CD20-CAR transgene demonstrated no tumor development after Raji cell infusion (FIG. 28B).

Figure 29A:
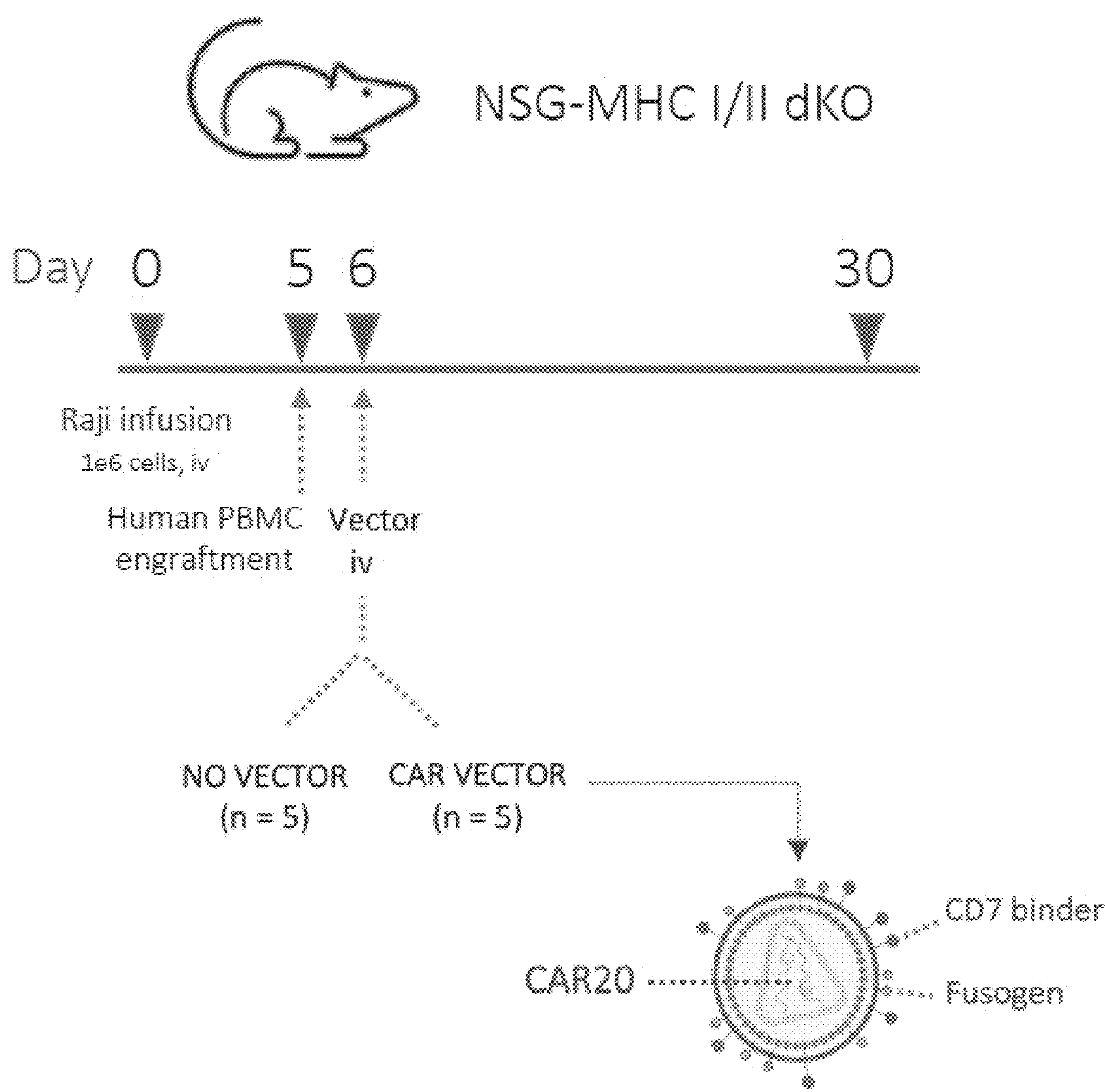
FIG. 29A-D illustrate the ability of VSV-G* pseudotyped lentiviral particles utilizing CD7 binders and a CD20-CAR transgene as provided for herein to eliminate established Raji tumors in vivo.
Figure 29B:
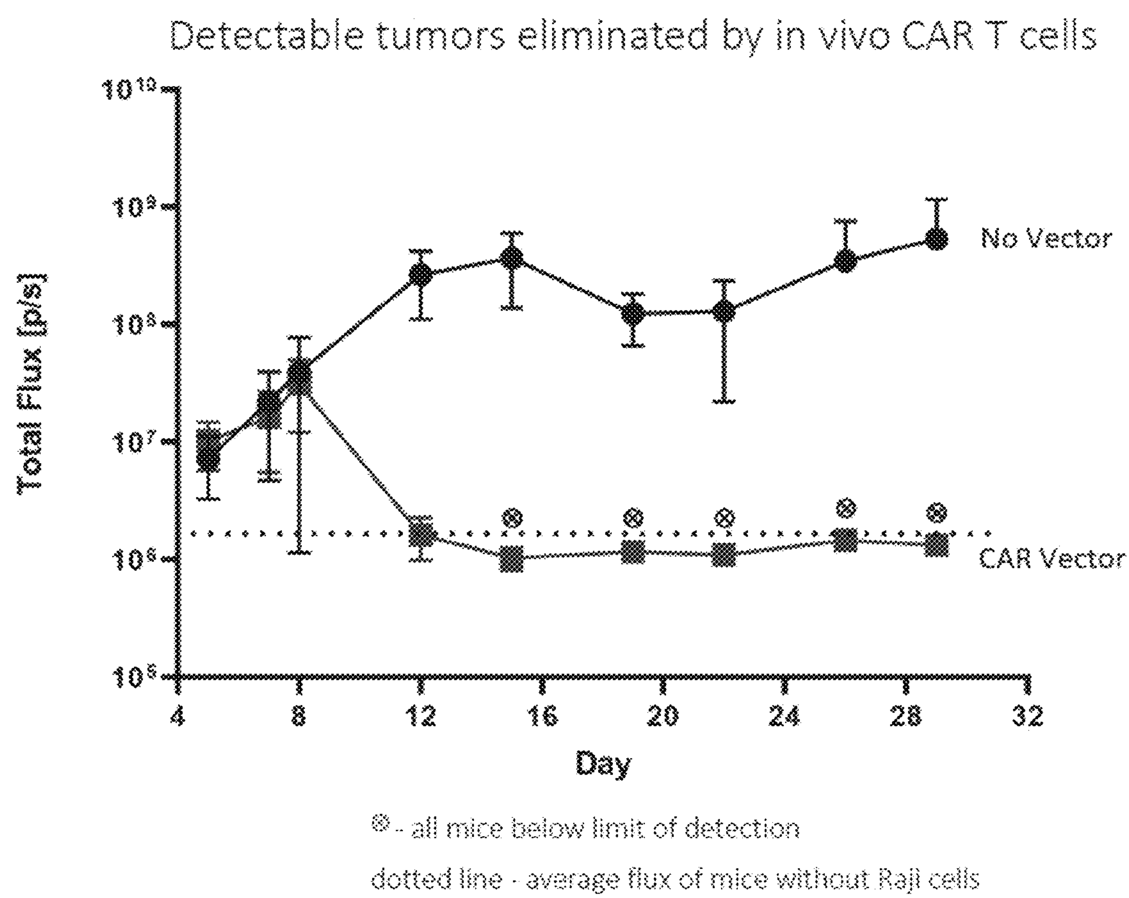

The ability of the viral particles to affect established tumors in vivo was also assessed. Mice were infused with Raji tumor cells on protocol Day 0. Mice were humanized via human PBMC engraftment on protocol Day 5, and mice were either not injected with viral particles (control) or injected with viral particles expressing a CD20-CAR transgene on protocol Day 6. Tumor progression was monitored through protocol Day 30. The experimental protocol is illustrated in FIG. 29A. Control and virus treated mice demonstrated comparable tumor load on Day 5 (prior to virus administration), Day 7, and Day 8 as determined by IVIS imaging, indicating that Raji tumors were established in both groups. At Day 12, control mice continued to exhibit increased tumor load, whereas virus treated mice exhibited a dramatic decrease in tumor load. The decreased tumor load was sustained throughout the duration of the experiment (FIG. 29B).

Figure 29C:
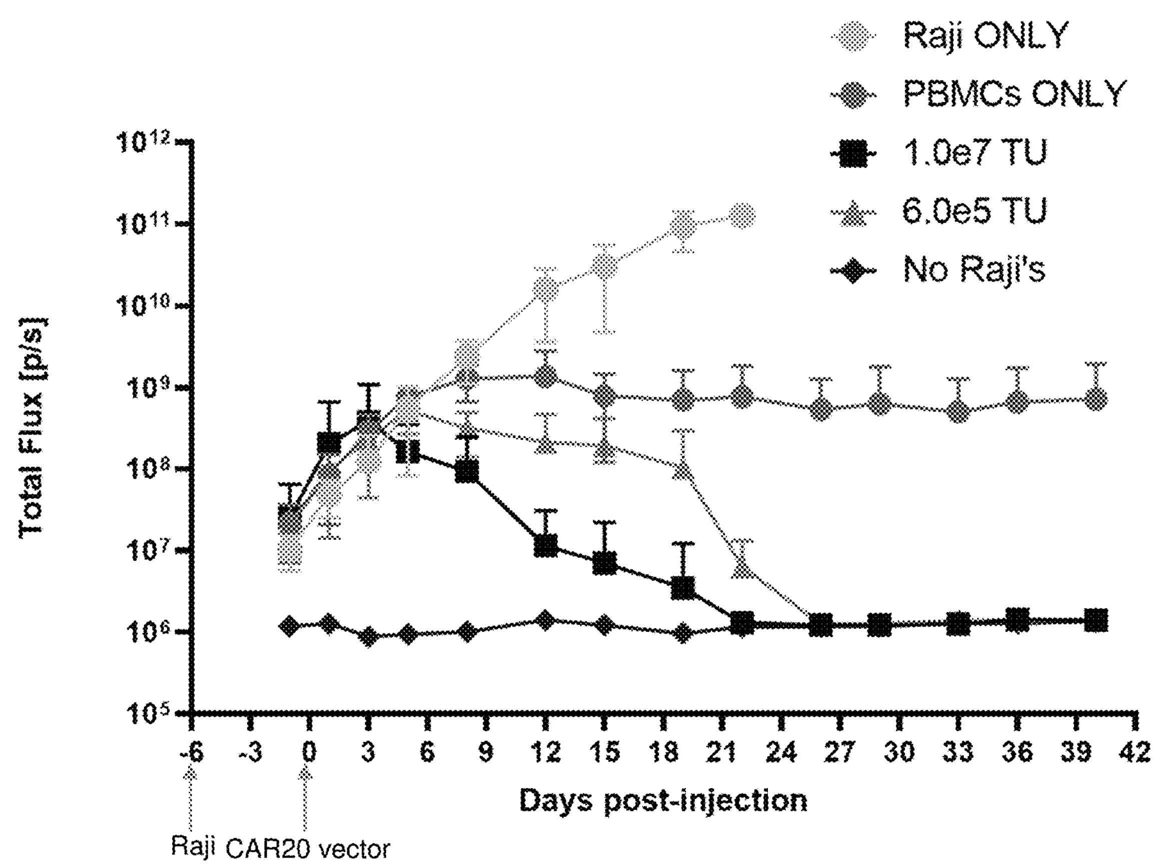
Figure 29D:
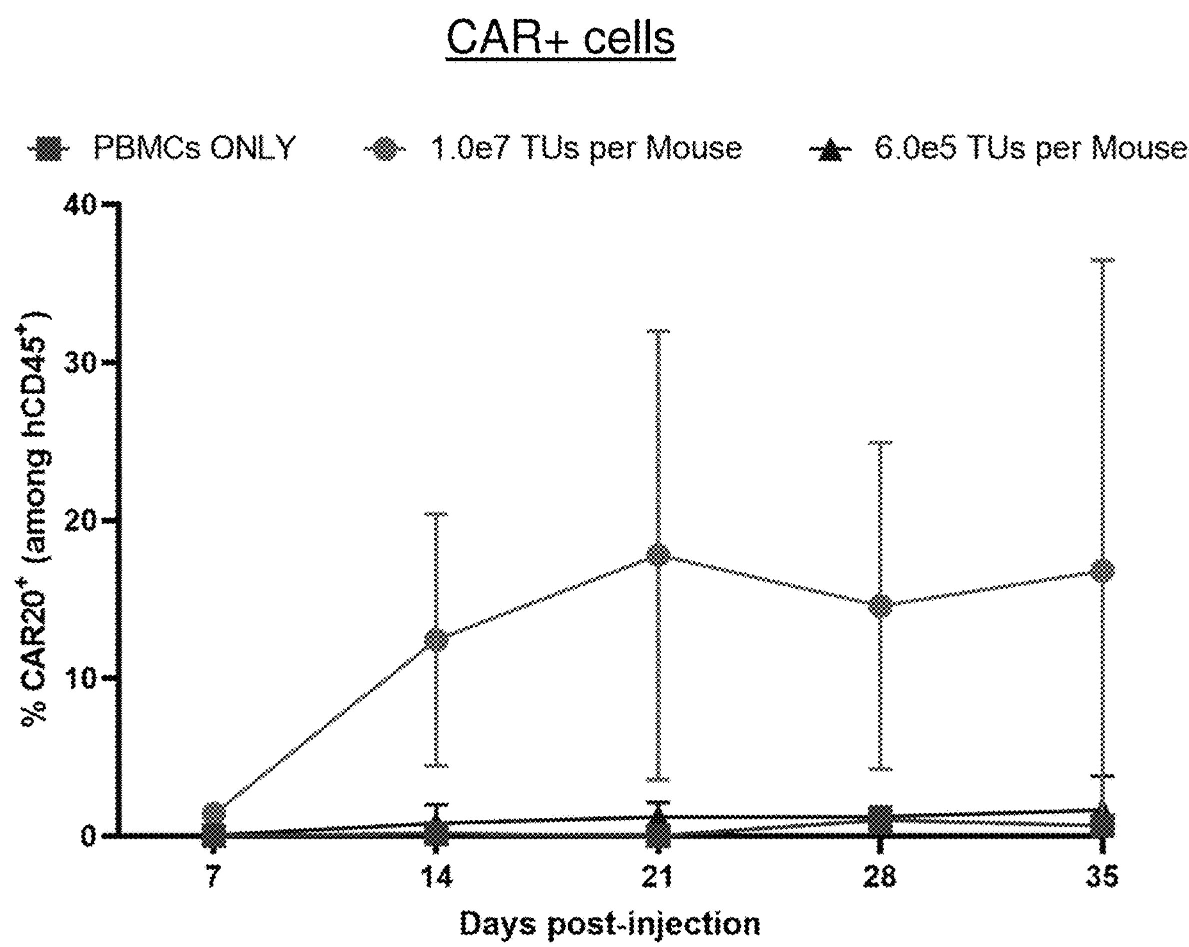
Figure 30A:
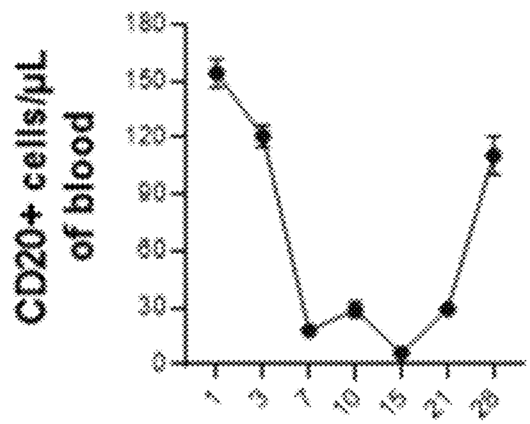
FIG. 30A-F illustrates the ability of VSV-G* pseudotyped lentiviral particles utilizing CD7 binders and a CD20-CAR transgene as provided for herein to deplete B-cells in vivo in NHPs.
Figure 30B:
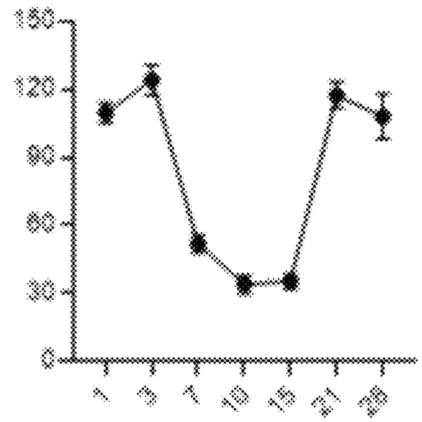
Figure 30C:
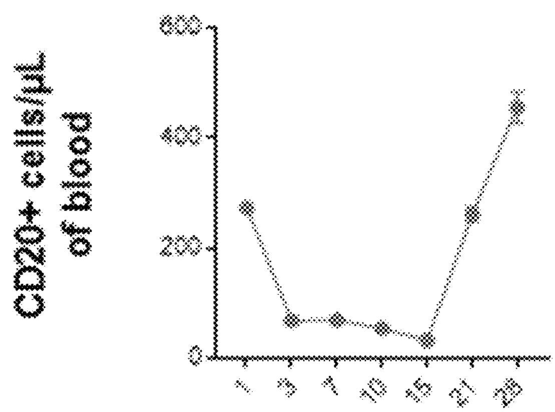
Figure 30D:
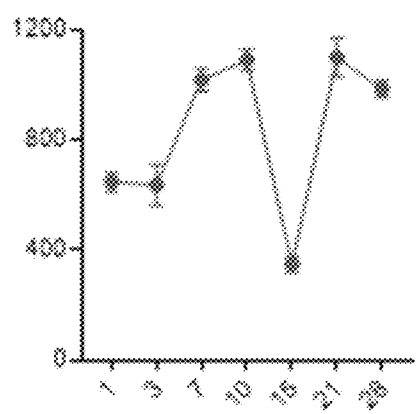
Figure 30E:
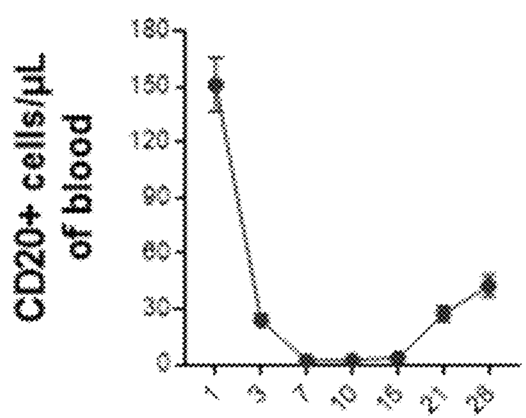
Figure 30F:
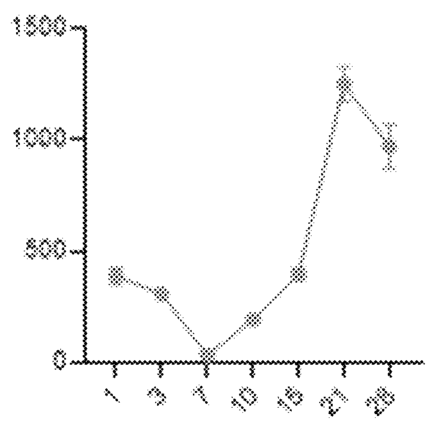

The same experimental setup as depicted in FIG. 29A was repeated with varying viral doses. As shown in FIG. 29C, both doses of virus utilized result in depletion of the established Raji tumors. Additionally, the mice were also assessed for the presence of CAR20+ cells in the blood throughout the duration of the study. As shown in FIG. 29D, at the highest dose of virus utilized CAR20+ cells were detected in the blood of the mice.

These examples and embodiments demonstrate that the VSV-G* pseudotyped lentiviral constructs of the present disclosure are able to properly target B-cells in vivo, prevent tumor formation in vivo, eliminate established tumors in vivo, and generate sustained and detectable CAR20+ cells in vivo.

Example 19: VSV-G* Pseudotyped Lentiviruses Deplete B-Cells in Non-Human Primates The ability of VSV-G* pseudotyped lentiviral constructs to deplete B-cell populations in vivo was also assessed in non-human primates (Macaques). The VSV-G* pseudotyped lentiviral constructs utilized CD7 binders as provided for herein (i.e. SEQ ID NO: 98). The VSV-G protein utilized was a variant VSV-G protein harboring a mutation to prevent binding of VSV-G to the LDL-R. The variant VSV-G is denoted VSV-G* and corresponds to VSV-G (I182E, T214N, T352A) (e.g. SEQ ID NO: 23), as provided for herein.

Figure 31:
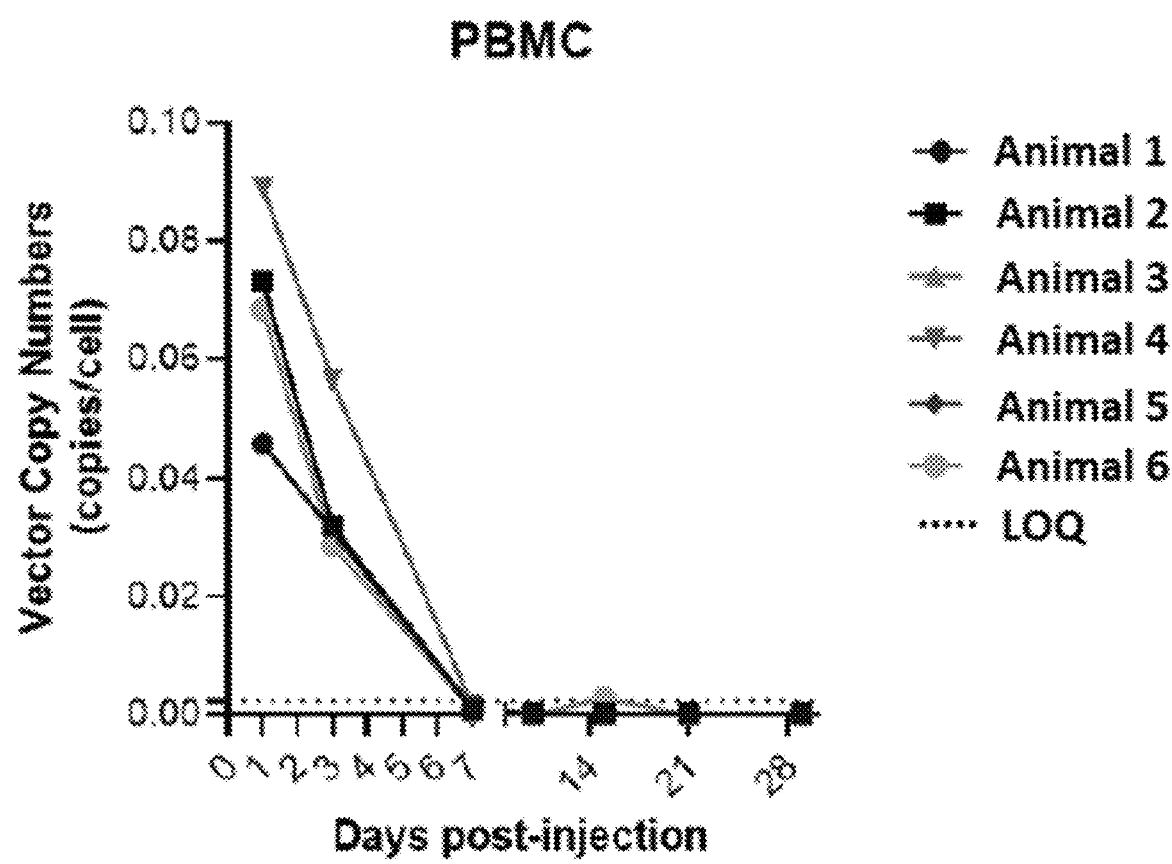
FIG. 31 illustrates the detection of provirus DNA in the PBMCs of NHPs. The animals of FIG. 31 correspond to the same animals as FIG. 30A-F.
Figure 32A:
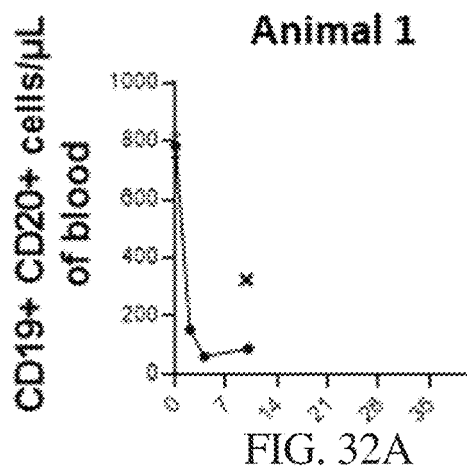
FIG. 32A-F illustrates the ability of VSV-G* pseudotyped lentiviral particles utilizing CD7 binders and a CD20-CAR transgene as provided for herein to deplete B-cells in vivo in NHPs.
Figure 32B:
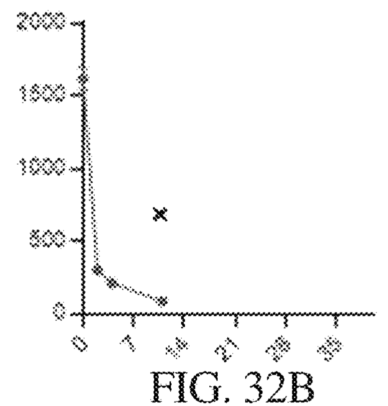
Figure 32C:
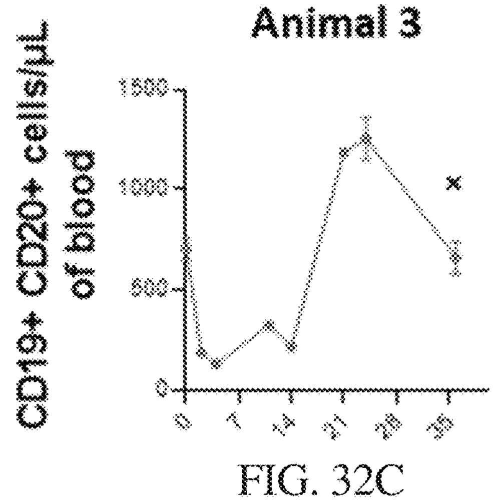
Figure 32D:
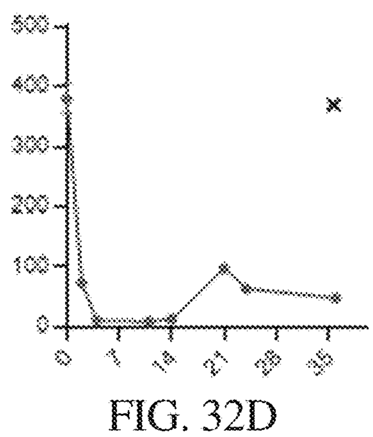
Figure 32E:
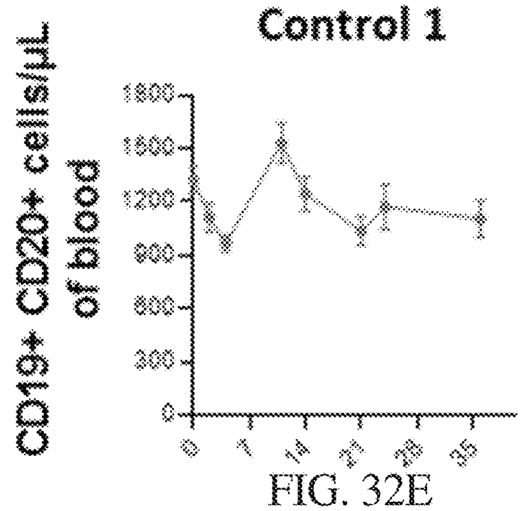
Figure 32F:
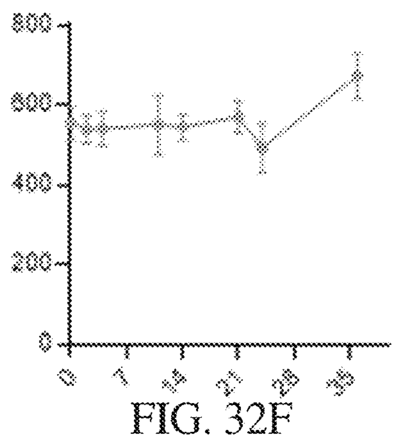

In a first cohort, six male macaques were injected with lentiviral particles on protocol Day 0 and their CD20+ cells were monitored. The CD20 CAR construct utilized for this experiment had an antigen binding domain corresponding to SEQ ID NO: 96. Injection of the lentiviral particles results in B-cell depletion in all 6 macaques tested (FIG. 30A-F). PBMCs were isolated at various time points and evidence of successful viral transduction was assessed. CAR20 positive cells were not directly detected, however transduced cells were detected using a multiplex droplet digital PCR assay specific for the provirus DNA and the albumin gene (FIG. 31). These results indicate that the lentiviral particle delivering the CD20 CAR were able to successfully transduce CD7 positive cells in vivo and the resulting CAR20 positive CD7 positive cells were able to deplete B-cells in non-human primates (NHP). As expected, immune responses (mediated by T and B cells) to non-macaque sequences in the CAR are associated with eventual B cell rebound in most NHPs. The rebound in B cell counts coincided with increased frequency in B cells expressing proliferation marker Ki67+, suggesting that the increase in B cells in circulation was due to B cell replenishment by progenitor cells (data not shown). Despite evidence of an immune response, no indications of toxicity or other safety concerns were observed in any of the NHPs receiving the lentivirus. No NHPs showed clinical signs of CRS such as high fever, behavioral changes, signs of organ dysfunction, other clinical observations or neurotoxicity.

Figure 33:
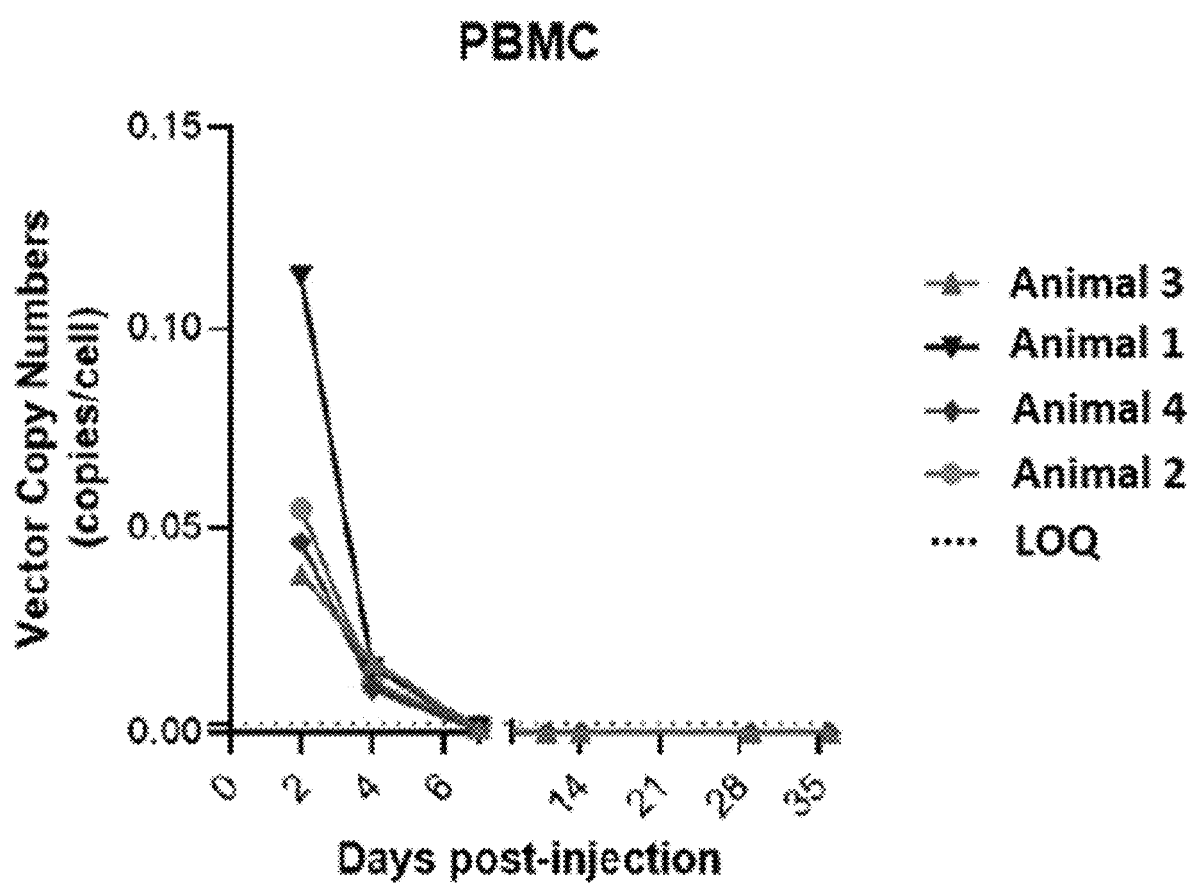
FIG. 33 illustrates the detection of provirus DNA in the PBMCs of NHPs. The animals of FIG. 33 correspond to the same animals as FIG. 32A-D.
Figure 34A:
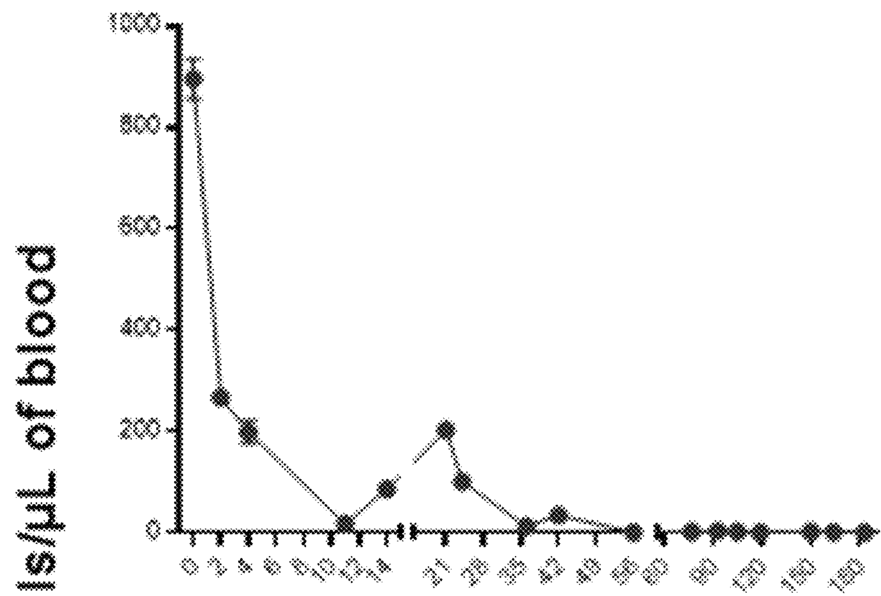
FIG. 34A-H illustrates the ability of VSV-G* pseudotyped lentiviral particles utilizing CD7 binders and a CD20-CAR transgene as provided for herein to deplete B-cells in vivo in NHPs.
Figure 34B:
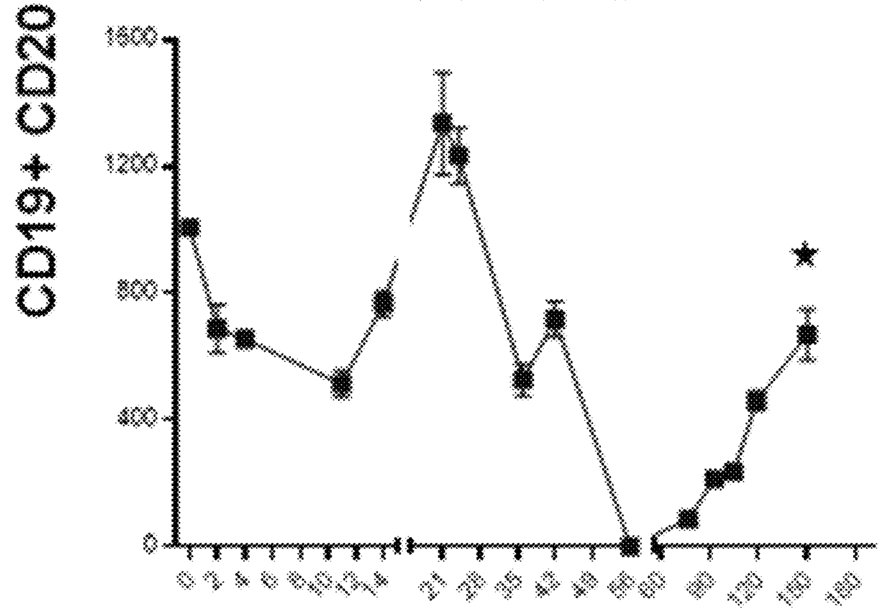
Figure 34C:
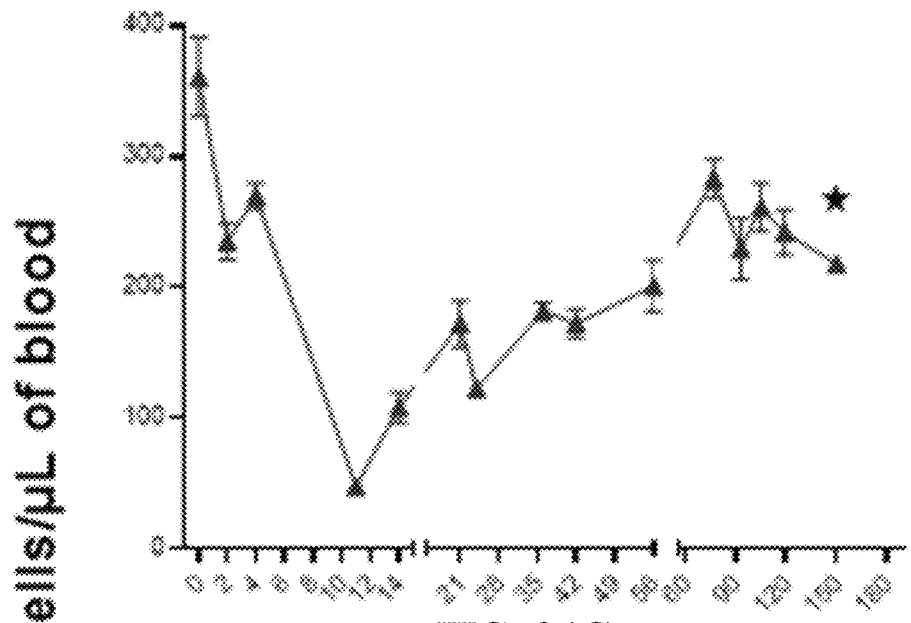
Figure 34D:
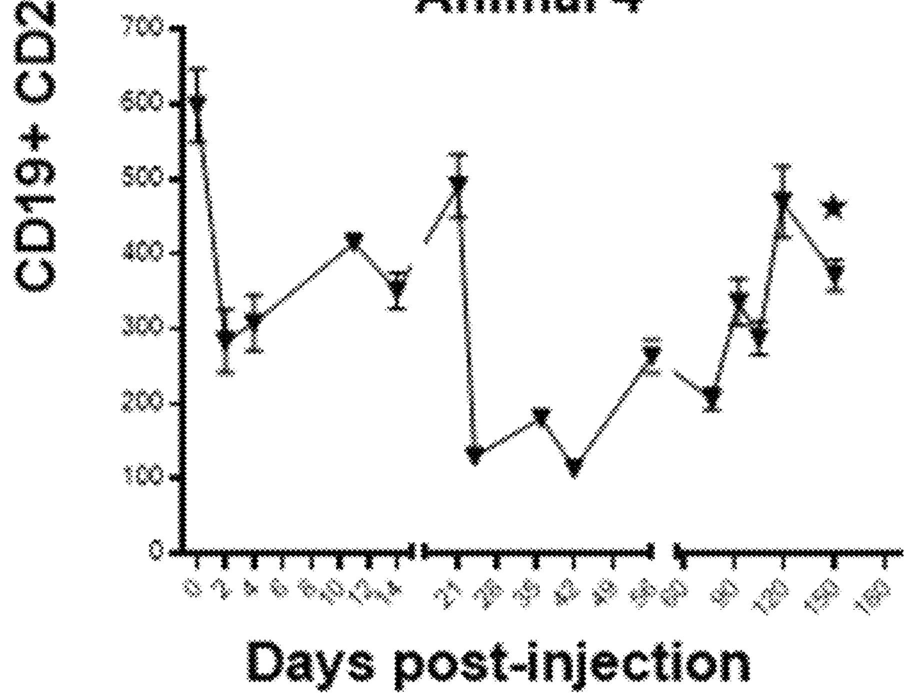
Figure 34E:
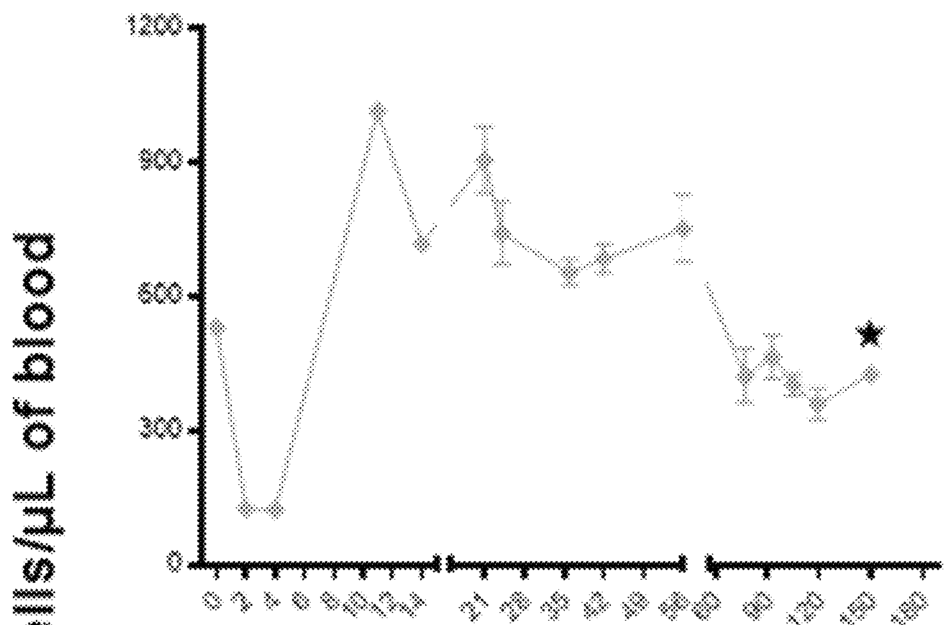
Figure 34F:
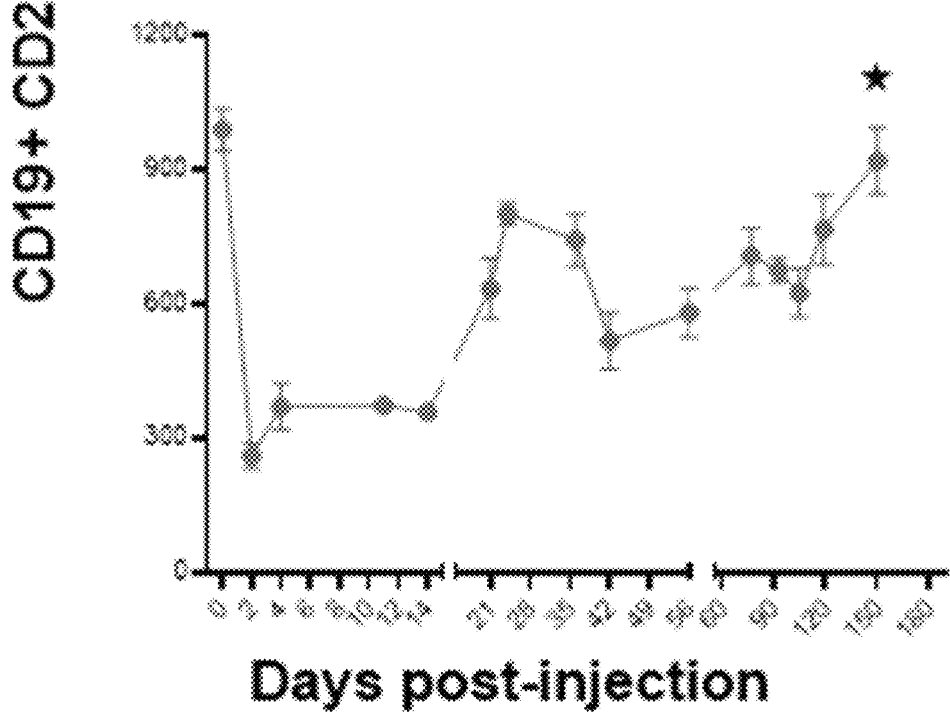
Figure 34G:
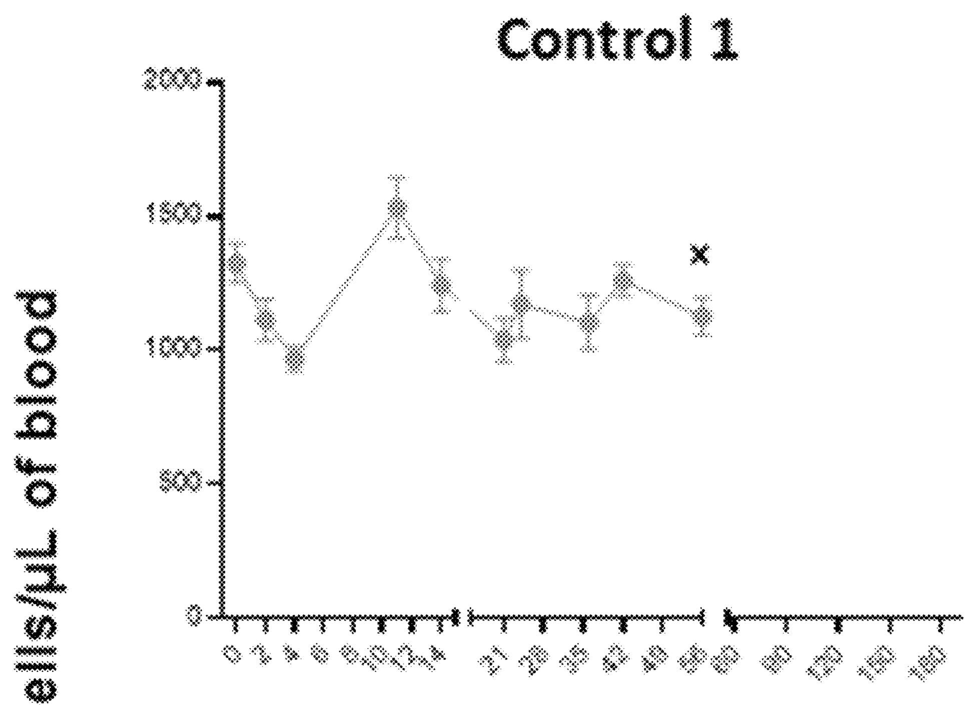
Figure 34H:
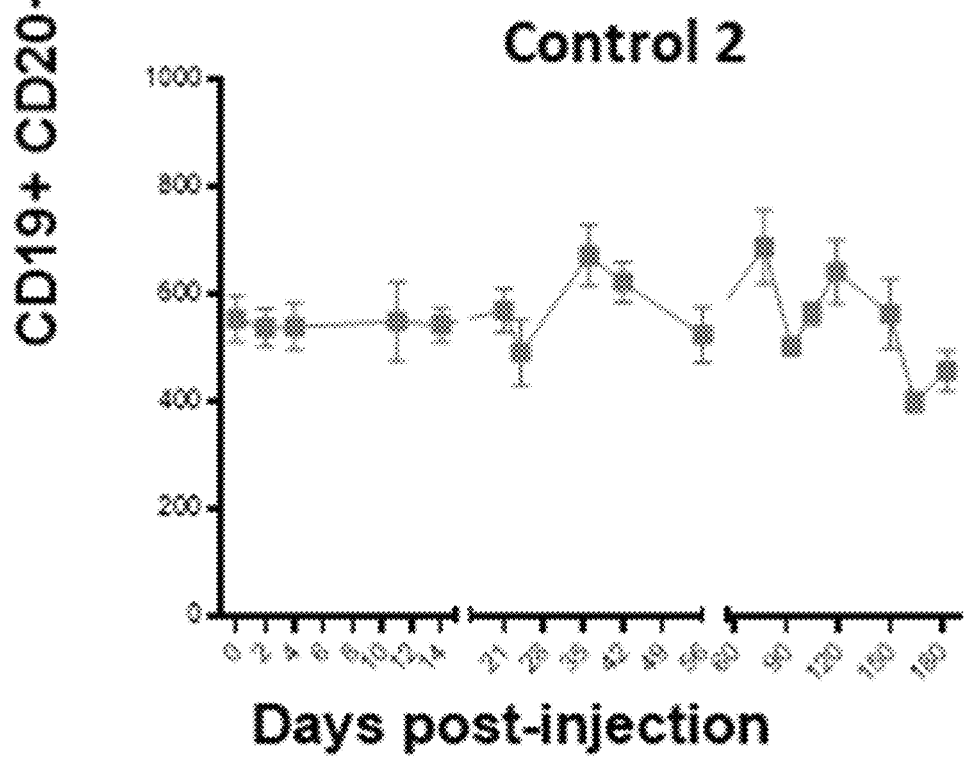

The results of the first cohort of macaques was confirmed in a second cohort (FIG. 32A-F). In the second cohort, four male macaques were injected with the same lentivirus construct as the first cohort on protocol day 0 and their CD20+ cells were monitored. Two control macaques received buffer only. Two lentiviral treated animals were necropsied on protocol days 10/11 to provide data on biodistribution. The remaining two lentiviral treated animals were necropsied on days 36/37. Consistent with the results of the first cohort, all four NHPs receiving lentiviral vector exhibited a depletion of B-cells, where the two animals receiving buffer injections exhibited no such depletion. As with the first cohort, provirus DNA was detected in isolated PBMCs of lentiviral vector treated animals (FIG. 33), demonstrating that injection of lentiviral particles was successfully resulting in in vivo transduction of the target cells.

Figure 35:
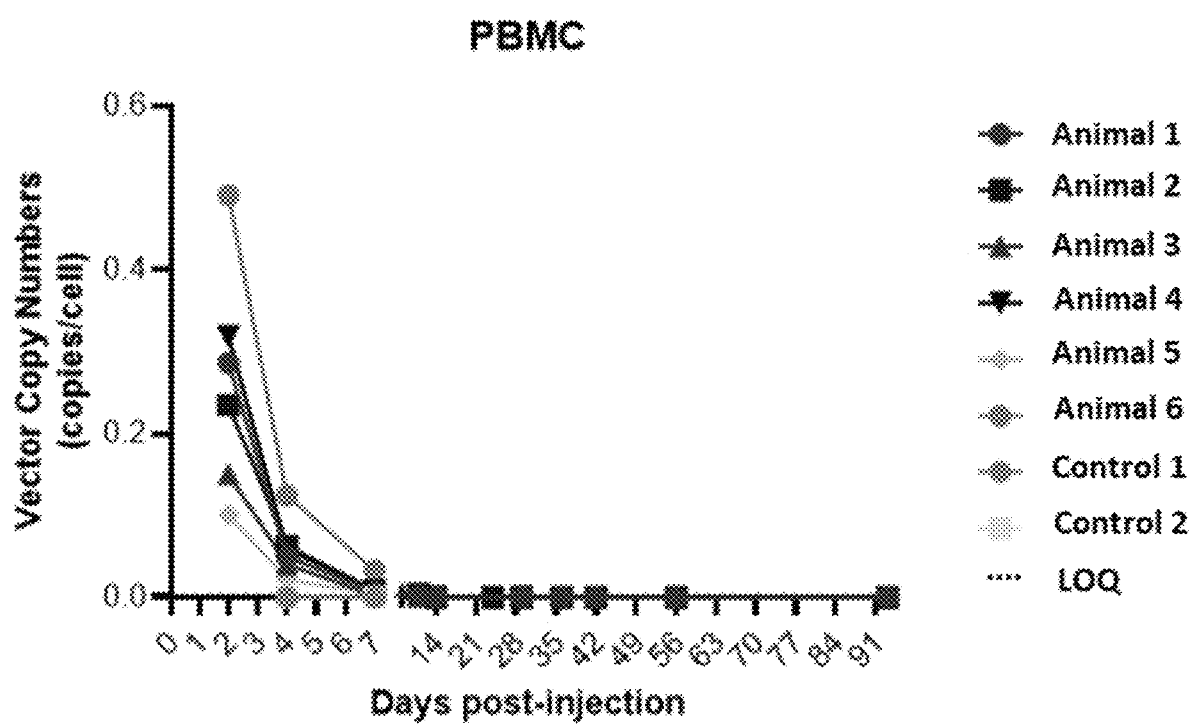
FIG. 35 illustrates the detection of provirus DNA in the PBMCs of NHPs. The animals of FIG. 35 correspond to the same animals as FIG. 34A-H.
Figures 36A, 36B:
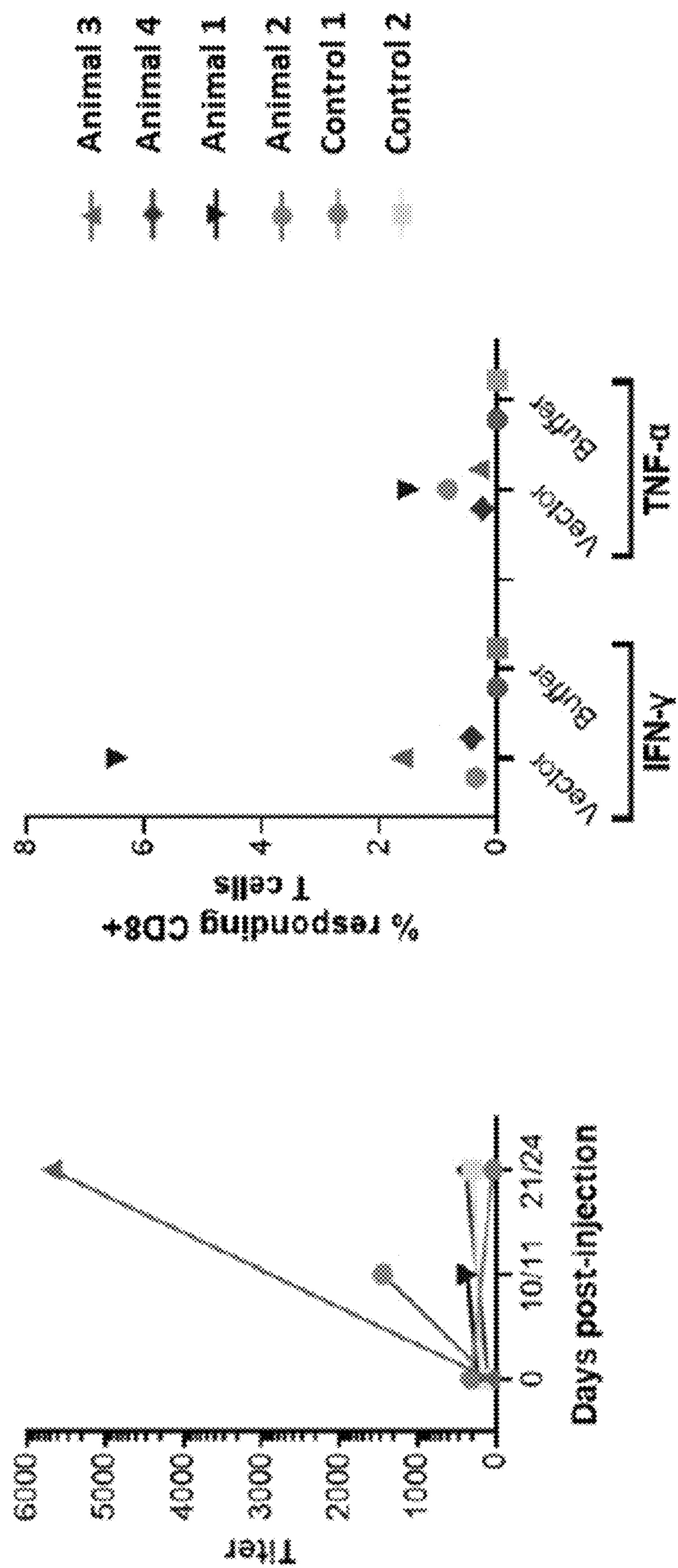
FIG. 36A-D illustrates the assessment of a CD20 CAR specific immune response across different cohorts of NHP receiving different CD20 CAR transgenes.
Figures 36C, 36D:
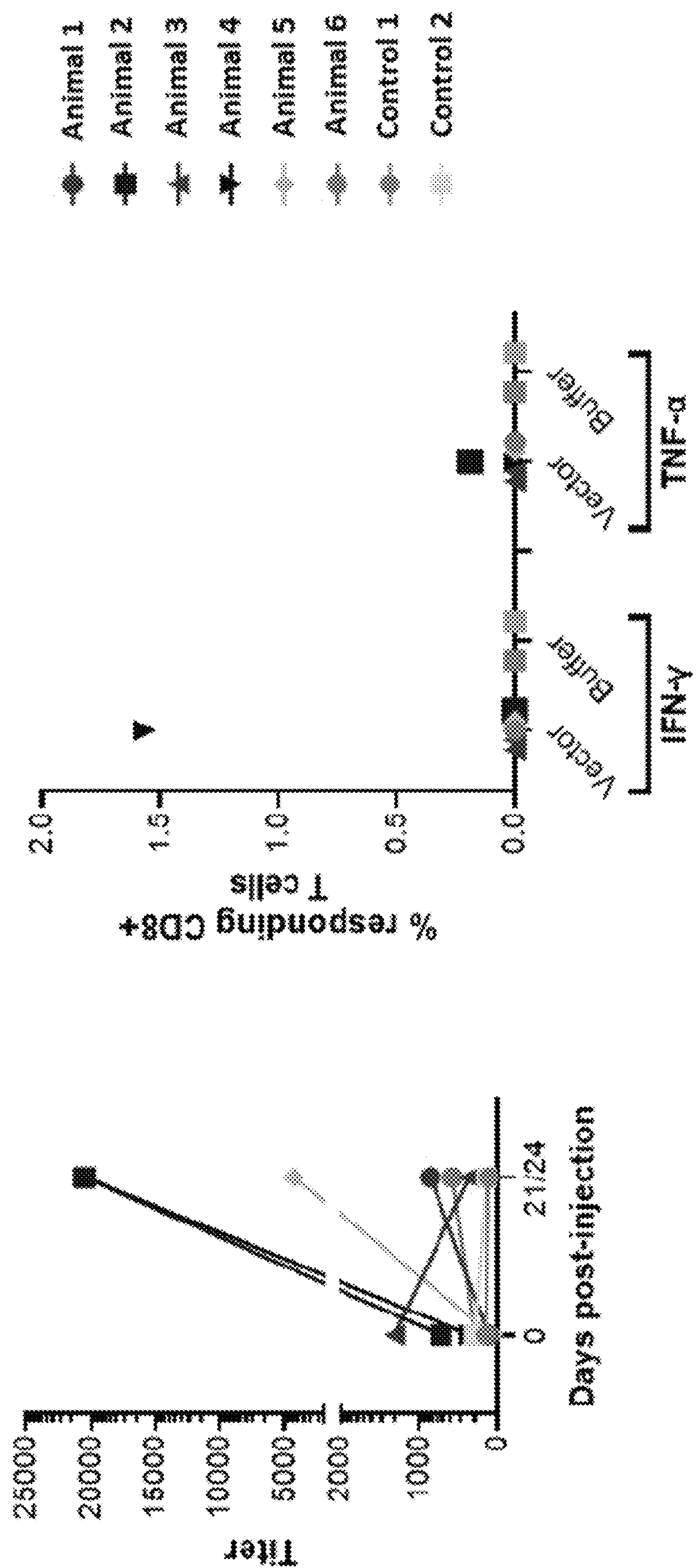

To address the immune response to the CAR sequence, a second CD20 CAR construct was examined in a third cohort of animals. The CD20 CAR construct utilized for the third cohort had an antigen binding domain corresponding to SEQ ID NO: 92, and expression of the CAR was under control of a T-cell specific promoter. In the third cohort, six male macaques were injected with lentiviral particles and two male macaques were injected with buffer only on protocol Day 0 and their CD20+ cells were monitored (FIG. 34A-H). All six NHPs receiving lentiviral vector exhibited a depletion of B-cells, where the two animals receiving buffer injections exhibited no such depletion. As with previous cohorts, provirus DNA was detected in isolated PBMCs of lentiviral vector treated animals (FIG. 35). To test if the second CD20 CAR construct had a reduced immune response, animals from cohort two and cohort three were assessed for the presence of anti-CD20 CAR antibodies in plasma as well as for signs of CAR specific T cell response (FIG. 36A-D; FIGS. 36A and B are data from cohort 2, FIGS. 36C and D are data from cohort 3). As shown in FIG. 36A and FIG. 36C, both CD20 CAR constructs result in the generation of anti-CD20 antibodies in the plasma. All four animals in cohort 2 exhibited elevated INFγ and TNF-α over buffer treated animals, indicative of a CAR specific T cell response (FIG. 36B). However, the cohort three animals exhibited a blunted CAR specific T cell response, as only Animal 4 had elevated INF-γ over control and only Animal 2 had elevated TNF-α (FIG. 36D). These results indicate that CD20 CAR constructs having an antigen binding domain of SEQ ID NO: 96 or SEQ ID NO: 92 are both able to deplete B-cells in vivo in NHPs, and that the CD20 CAR having the antigen binding domain of SEQ ID NO: 92 may be less immunogenic in NHPs than the CD20 CAR having the antigen binding domain of SEQ ID NO: 96.

Figure 37:
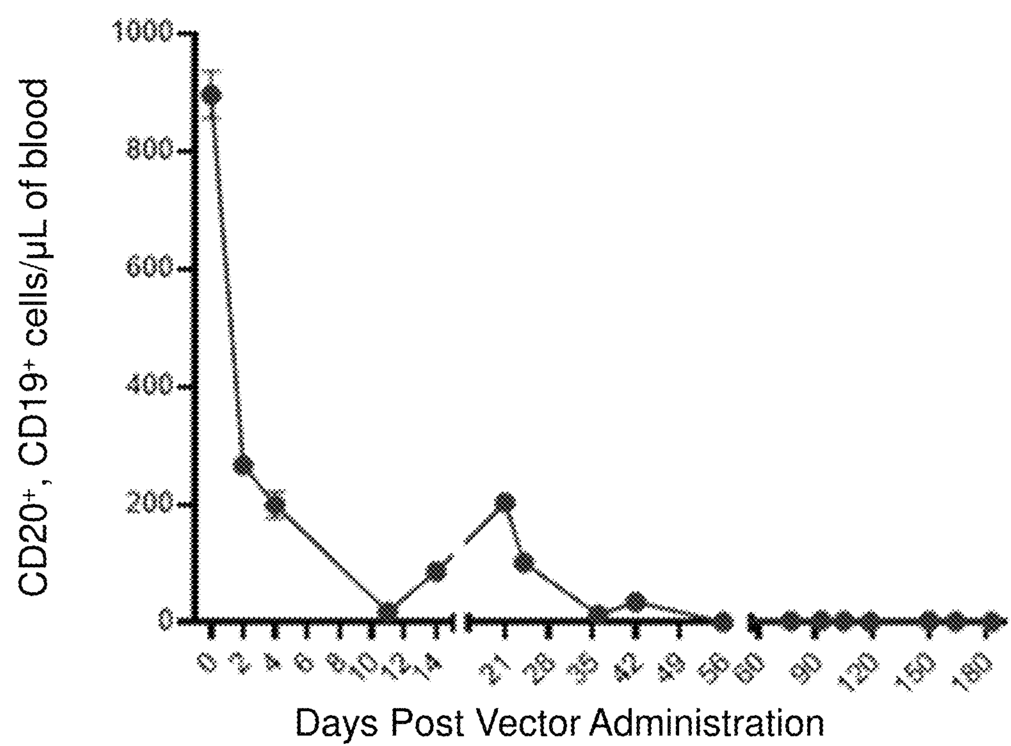
FIG. 37 illustrates the results of a B cell depletion study in cynomolgus macaques. Data are from three animals that did not generate an immune response to the humanized CAR transgene, indicating that in the absence of an immune response the VSV-G* pseudotyped lentiviral particles utilizing CD7 binders and a CD20-CAR transgene as provided for herein can stimulate sustained depletion of B-cells.
Figures 38A, 38B:
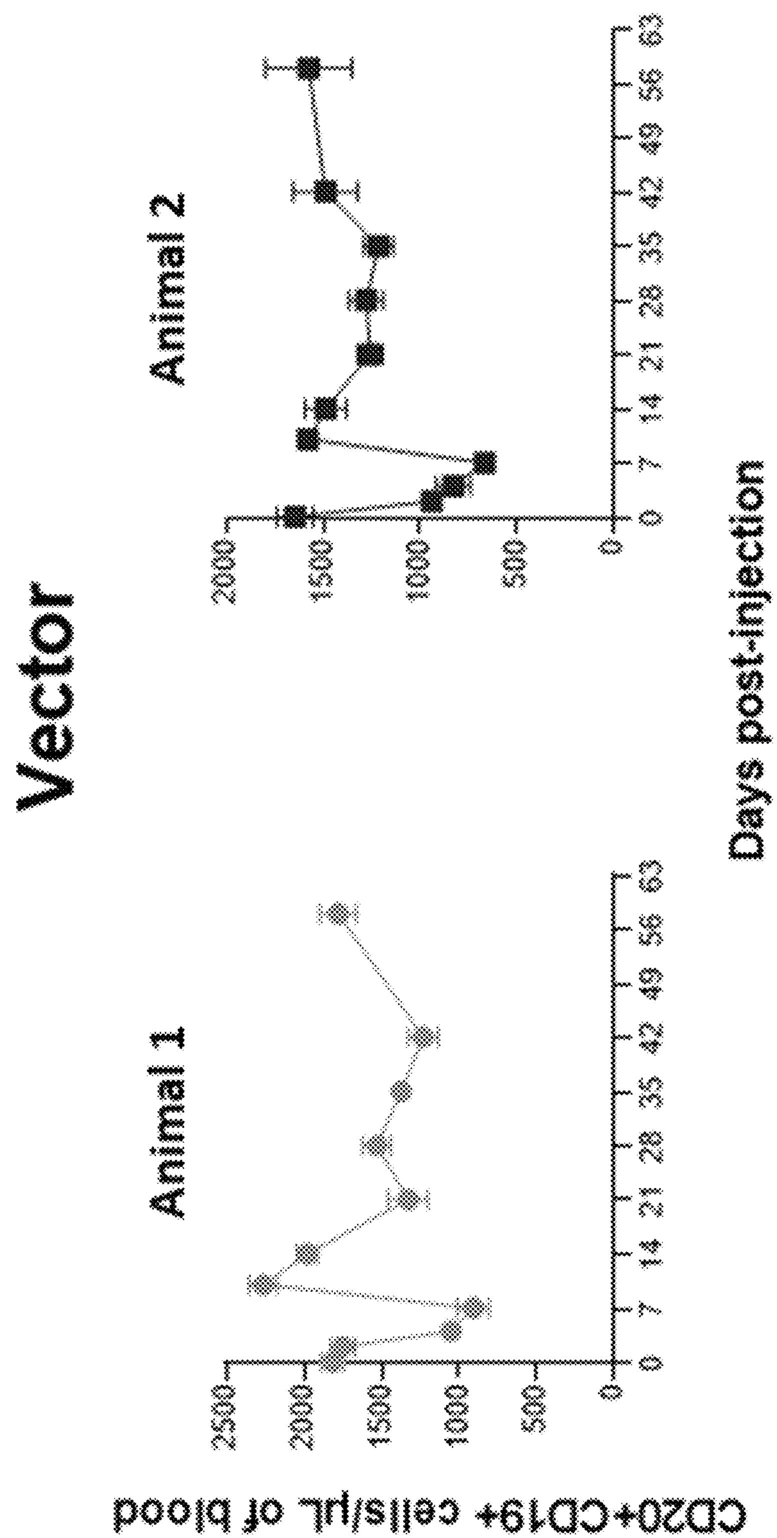
FIG. 38A-D illustrates the ability of VSV-G* pseudotyped lentiviral particles utilizing CD7 binders and a CD20-CAR transgene as provided for herein to deplete B-cells in vivo in NHPs.
Figures 38C, 38D:
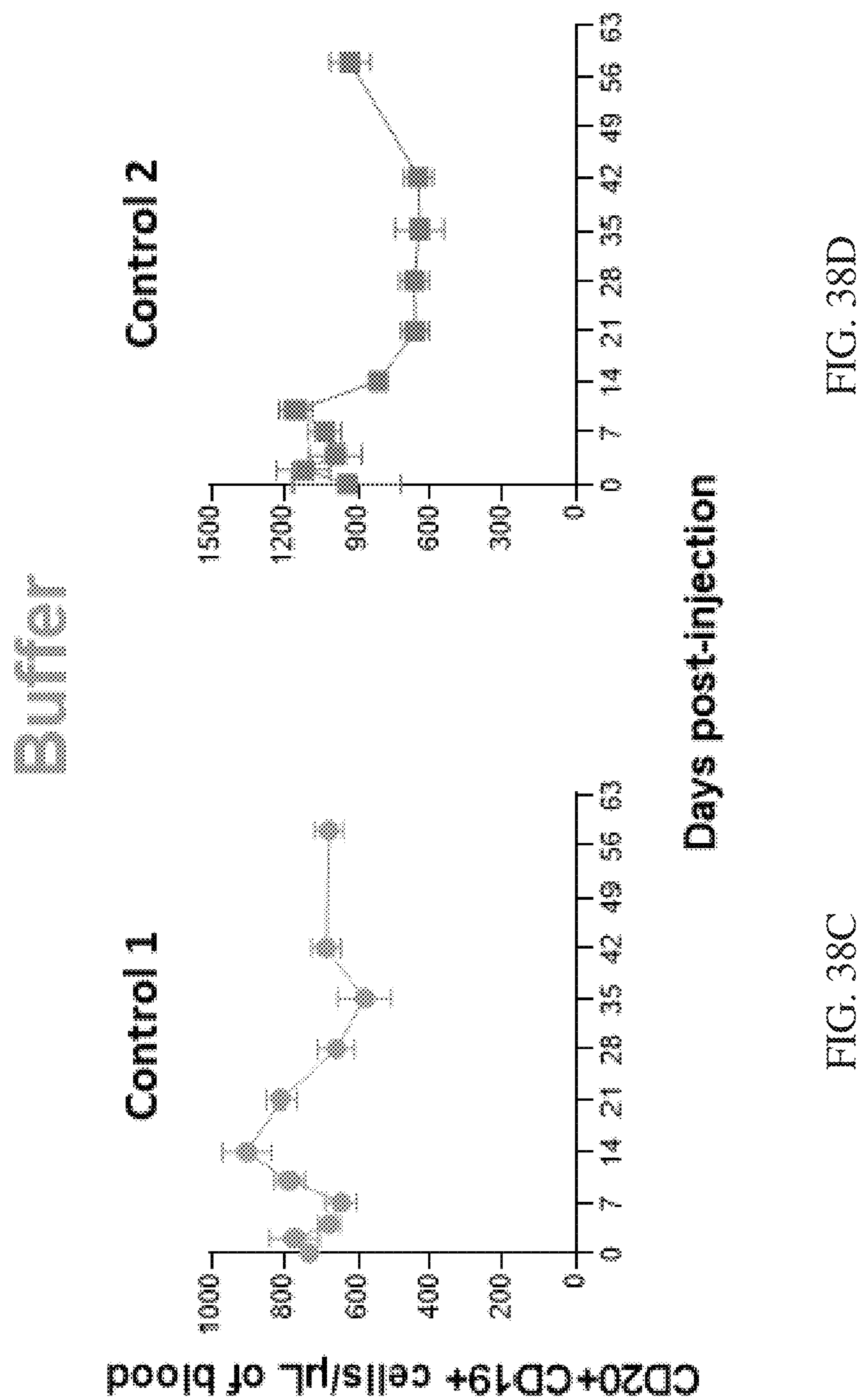

Interestingly, three animals from cohort three did not exhibit an immune response against the CAR20 sequences utilized. These were Animal 1, Animal 3, and Animal 6. These animals exhibited minimal detection of anti-CD20 CAR antibodies in the plasma and no detection of IFN-γ or TNF-α (FIG. 36C and FIG. 36D). Closer examination of the number of CD20 positive cells for these animals reveled that Animals 1, 3, and 6 exhibited a more sustained B cell depletion profile over the duration of the study (FIG. 34A-H). The CD20 cell count plot for Animal 1 is shown again in FIG. 37. As shown, Animal 1 exhibited an initial B cell depletion in the weeks following vector administration, and has exhibited a sustained depletion of B cells throughout the duration of the study. These data shows that in the absence of an immune response against the CAR construct, the vector particles provided for herein are able to generate a sustained reduction in B cells in NHPs.

Figure 39:
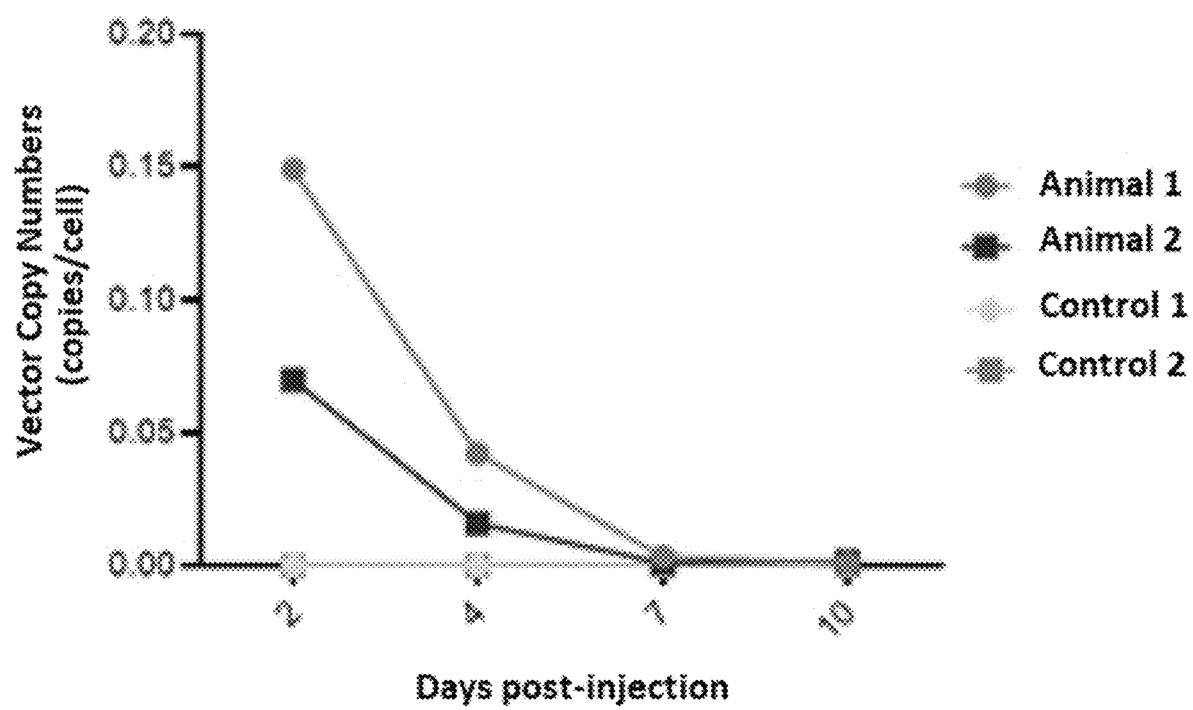
FIG. 39 illustrates the detection of provirus DNA in the PBMCs of NHPs. The animals of FIG. 39 correspond to the same animals as FIG. 38A-D.

A fourth cohort of animals was tested in a similar manner as above. The CD20 CAR construct utilized for the fourth cohort had an antigen binding domain corresponding to SEQ ID NO: 92, and expression of the CAR was under control of a EF1-α promoter. In the fourth cohort, two male macaques were injected with lentiviral particles and two male macaques were injected with buffer only on protocol Day 0 and their CD20+ cells were monitored (FIG. 38A-D). As with prior cohorts, the lentiviral vector treated animals exhibited a transient depletion of B-cells that was not observed in the control animals. As with previous cohorts, provirus DNA was detected in isolated PBMCs of lentiviral vector treated animals (FIG. 39). These data demonstrate that injection of lentiviral particles successfully results in in vivo transduction of the target cells and subsequent depletion of B-cells. Taken together, these data demonstrate that the viral particles of the present application are able to successfully target the desired target cells in vivo, successfully transduce the target cells in vivo with the CD20 CAR molecules of the present application, and that the in vivo generated target cells comprising the CD20 CAR molecules of the present application are able to successfully target and deplete B-cells as intended.

This specification contains numerous citations to patents, patent applications, and publications. Each is hereby incorporated by reference for all purposes.

The specification also makes reference to various sequences, such as those provided herein and below.

VSV-G Indiana Full length WT:

(SEQ ID NO: 1)

MKCLLYLAFLFIGVNCKFTIVFPHNQKGNWKNVPSNYHYCPSSSDLNWHNDLIGTALQVKMPKSHKAIQADGWMCHA

SKWVTTCDFRWYGPKYITHSIRSFTPSVEQCKESIEQTKQGTWLNPGFPPQSCGYATVIDAEAVIVQVTPHHVLVDE

YTGEWVDSQFINGKCSNYICPTVHNSTTWHSDYKVKGLCDSNLISMDITFFSEDGELSSLGKEGTGERSNYFAYETG

GKACKMQYCKHWGVRLPSGVWFEMADKDLFAAARFPECPEGSSISAPSQTSVDVSLIQDVERILDYSLCQETWSKIR

AGLPISPVDLSYLAPKNPGTGPAFTIINGTLKYFETRYIRVDIAAPILSRMVGMISGTTTERELWDDWAPYEDVEIG

PNGVLRTSSGYKFPLYMIGHGMLDSDLHLSSKAQVFEHPHIQDAASQLPDDESLFFGDTGLSKNPIELVEGWFSSWK

SSIASFFFIIGLIIGLFLVLRVGIHLCIKLKHTKKRQIYTDIEMNRLGK

VSV-G Indiana Ectodomain WT:

(SEQ ID NO: 2)

KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGITTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

-continued

VSV-G Indiana ectodomain I182A:

(SEQ ID NO: 3)

KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLASMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain I182D:

(SEQ ID NO: 4)

KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLQSMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

VSV-G Indiana ectodomain I182E:

(SEQ ID NO: 5)

KFTIVFPHNQKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLESMDITFFSEDGELSSLGKEGTGERSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWESSWKSSIASFFFIIGLIIGL

FLVLRVGIHLCIKLKHTKKRQIYTDIEMNRLGK

VSV-G Indiana ectodomain H8A + K47Q:

(SEQ ID NO: 6)

KFTIVFPANQKGNWKNVPSNYHYCPSSSDLNWHNDLIGTALQVKMP@SHKAIQADGWMCHASKWVTTCDFRWYGPKY

ITHSIRSFTPSVEQCKESIEQTKQGTWLNPGFPPQSCGYATVTDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWESSWKSSIASFFFIIGLIIGL

FLVLRVGIHLCIKLKHTKKRQIYTDIEMNRLGK

VSV-G Indiana ectodomain Q10A:

(SEQ ID NO: 7)

KFTIVFPHNAKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWFSSWKSSIASFFFIIGLIIGL

FLVLRVGIHLCIKLKHTKKRQIYTDIEMNRLGK

-continued

VSV-G Indiana ectodomain Q10R:

(SEQ ID NO: 8)

KFTIVFPHNRKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWESSWKSSIASFFFIIGLIIGL

FLVLRVGIHLCIKLKHTKKRQIYTDIEMNRLGK

VSV-G Indiana ectodomain Q10K:

(SEQ ID NO: 9)

KFTIVFPHNXKGNWKNVPSNYHYCPSSSDLNWHNDLIGTALQVKMPKSHKAIQADGWMCHASKWVTTCDFRWYGPKY

ITHSIRSFTPSVEQCKESIEQTKQGTWLNPGFPPQSCGYATVIDAEAVIVQVTPHHVLVDEYTGEWVDSQFINGKCS

NYICPTVHNSTTWHSDYKVKGLCDSNLISMDITFFSEDGELSSLGKEGTGFRSNYFAYETGGKACKMQYCKHWGVRL

PSGVWFEMADKDLFAAARFPECPEGSSISAPSQTSVDVSLIQDVERILDYSLCQETWSKIRAGLPISPVDLSYLAPK

NPGTGPAFTIINGTLKYFETRYIRVDIAAPILSRMVGMISGTTTERELWDDWAPYEDVEIGPNGVLRTSSGYKFPLY

MIGHGMLDSDLHLSSKAQVFEHPHIQDAASQLPDDESLFFGDTGLSKNPIELVEGWESSWKSSIASFFFIIGLIIGL

FLVLRVGIHLCIKLKHTKKRQIYTDIEMNRLGK

VSV-G New Jersey Full length WT:

(SEQ ID NO: 10)

MLSYLIFALVVSPILGKIEIVFPQHTTGDWKRVPHEYNYCPTSADKNSHGTQTGIPVELTMPKGLTTHQVDGEMCHS

ALWMTTCDFRWYGPKYITHSIHNEEPTDYQCLEAIKAYKDGVSFNPGFPPQSCGYGTVTDAEAHIVTVTPHSVKVDE

YTGEWIDPHFIGGRCKGQICETVHNSTKWFTSSDGESVCSQLFTLVGGTFFSDSEEITSMGLPETGIRSNYFPYVST

EGICKMPFCRKPGYKLKNDLWFQITDPDLDKTVRDLPHIKDCDLSSSIVTPGEHATDISLISDVERILDYALCQNTW

SKIEAGEPITPVDLSYLGPKNPGAGPVFTIINGSLHYFMSKYLRVELESPVIPRMEGKVAGTRIVRQLWDQWFPFGE

VEIGPNGVLKTKQGYKFPLHIIGTGEVDNDIKMERIVKHWEHPHIEAAQTFLKKDDTEEVLYYGDTGVSKNPVELVE

GWFSGWRSSIMGVLAVIIGFVILIFLIRLIGVLSSLFRQKRRPIYKSDVEMAHFR

VSV-G New Jersey ectodomain WT:

(SEQ ID NO: 11)

KIEIVFPQHTTGDWKRVPHEYNYCPTSADKNSHGTQTGIPVELTMPKGLTTHQVDGFMCHSALWMTTCDERWYGPKY

ITHSIHNEEPTDYQCLEAIKAYKDGVSFNPGFPPQSCGYGTVTDAEAHIVTVTPHSVKVDEYTGEWIDPHFIGGRCK

GQICETVHNSTKWFTSSDGESVCSQLFTLVGGTFFSDSEEITSMGLPETGIRSNYFPYVSTEGICKMPFCRKPGYKL

KNDLWFQITDPDLDKTVRDLPHIKDCDLSSSIVTPGEHATDISLISDVERILDYALCQNTWSKIEAGEPITPVDLSY

LGPKNPGAGPVFTIINGSLHYFMSKYLRVELESPVIPRMEGKVAGTRIVRQLWDQWFPFGEVEIGPNGVLKTKQGYK

FPLHIIGTGEVDNDIKMERIVKHWEHPHIEAAQTFLKKDDTEEVLYYGDTGVSKNPVELVEGWFSGWRSSIMGVLAV

IIGFVILIFLIRLIGVLSSLFRQKRRPIYKSDVEMAHFR

VSV-G Marraba Full length WT:

(SEQ ID NO: 12)

MLRLFLFCFLALGAHSKFTIVFPHHQKGNWKNVPSTYHYCPSSSDQNWHNDLTGVSLHVKIPKSHKAIQADGWMCHA

AKWVTTCDFRWYGPKYITHSIHSMSPTLEQCKTSIEQTKQGVWINPGFPPQSCGYATVIDAEVVVVQATPHHVLVDE

YTGEWIDSQLVGGKCSKEVCQTVHNSTVWHADYKITGLCESNLASVDITFFSEDGQKTSLGKPNTGFRSNHFAYESG

EKACRMQYCTQWGIRLPSGVWFELVDKDLFQAAKLPECPRGSSISAPSQTSVDVSLIQDVERILDYSLCQETWSKIR

AKLPVSPVDLSYLAPKNPGSGPAFTIINGTLKYFETRYIRVDISNPIIPHMVGTMSGITTERELWNDWYPYEDVEIG

PNGVLKTPTGFKFPLYMIGHGMLDSDLHKSSQAQVFEHPHAKDAASQLPDDETLFFGDTGLSKNPVELVEGWFSSWK

STLASFFLIIGLGVALIFIIRIIVAIRYKYKGRKTQKIYNDVEMSRLGNK

-continued

VSV-G Marraba ectodomain WT:

(SEQ ID NO: 13)

KFTIVFPHHQKGNWKNVPSTYHYCPSSSDQNWHNDLTGVSLHVKIPKSHKAIQADGWMCHAAKWVTTCDFRWYGPKY
ITHSIHSMSPTLEQCKTSIEQTKQGVWINPGFPPQSCGYATVIDAEVVVVQATPHHVLVDEYTGEWIDSQLVGGKCS
KEVCQTVHNSTVWHADYKITGLCESNLASVDITFFSEDGQKTSLGKPNTGERSNHFAYESGEKACRMQYCTQWGIRL
PSGVWFELVDKDLFQAAKLPECPRGSSISAPSQTSVDVSLIQDVERILDYSLCQETWSKIRAKLPVSPVDLSYLAPK
NPGSGPAFTIINGTLKYFETRYIRVDISNPIIPHMVGTMSGTTTERELWNDWYPYEDVEIGPNGVLKTPTGFKFPLY
MIGHGMLDSDLHKSSQAQVFEHPHAKDAASQLPDDETLFFGDTGLSKNPVELVEGWFSSWKSTLASFFLIIGLGVAL
IFIIRIIVAIRYKYKGRKTQKIYNDVEMSRLGNK

VSV-G Carajas Full length WT:

(SEQ ID NO: 14)

MKMKMVIAGLILCIGILPAIGKITISFPQSLKGDWRPVPKGYNYCPTSADKNLHGDLIDIGLRLRAPKSFKGISADG
WMCHAARWITTCDFRWYGPKYITHSIHSFRPSNDQCKEAIRLINEGNWINPGFPPQSCGYASVTDSESVVVTVTKHQ
VLVDEYSGSWIDSQFPGGSCTSPICDTVHNSTLWHADHTLDSICDQEFVAMDAVLFTESGKFEEFGKPNSGIRSNYF
PYESLKDVCQMDFCKRKGFKLPSGVWFEIEDAEKSHKAQVELKIKRCPHGAVISAPNQNAADINLIMDVERILDYSL
CQATWSKIQNKEALTPIDISYLGPKNPGPGPAFTIINGTLHYENTRYIRVDIAGPVTKEITGFVSGTSTSRVLWDQW
FPYGENSIGPNGLLKTASGYKYPLFMVGTGVLDADIHKLGEATVIEHPHAKEAQKVVDDSEVIFFGDTGVSKNPVEV
VEGWFSGWRSSLMSIFGIILLIVCLVLIVRILIALKYCCVRHKKRTIYKEDLEMGRIPRRA

VSV-G Carajas ectodomain WT:

(SEQ ID NO: 15)

KITISFPQSLKGDWRPVPKGYNYCPTSADKNLHGDLIDIGLRLRAPKSFKGISADGWMCHAARWITTCDFRWYGPKY
ITHSIHSFRPSNDQCKEAIRLINEGNWINPGFPPQSCGYASVTDSESVVVTVTKHQVLVDEYSGSWIDSQFPGGSCT
SPICDTVHNSTLWHADHTLDSICDQEFVAMDAVLFTESGKFEEFGKPNSGIRSNYFPYESLKDVCQMDFCKRKGEKL
PSGVWFEIEDAEKSHKAQVELKIKRCPHGAVISAPNQNAADINLIMDVERILDYSLCQATWSKIQNKEALTPIDISY
LGPKNPGPGPAFTIINGTLHYENTRYIRVDIAGPVTKEITGFVSGTSTSRVLWDQWFPYGENSIGPNGLLKTASGYK
YPLFMVGTGVLDADIHKLGEATVIEHPHAKEAQKVVDDSEVIFFGDTGVSKNPVEVVEGWFSGWRSSLMSIFGIILL
IVCLVLIVRILIALKYCCVRHKKRTIYKEDLEMGRIPRRA

VSV-G Alagoa Full length WT:

(SEQ ID NO: 16)

MTPAFILCMLLAGSSWAKFTIVFPQSQKGDWKDVPPNYRYCPSSADQNWHGDLLGVNIRAKMPKVHKAIKADGWMCH
AAKWVTTCDYRWYGPQYITHSIHSFIPTKAQCEESIKQTKEGVWINPGFPPKNCGYASVSDAESIIVQATAHSVMID
EYSGDWLDSQFPTGRCTGSTCETIHNSTLWYADYQVTGLCDSALVSTEVTFYSEDGLMTSIGRQNTGYRSNYFPYEK
GAAACRMKYCTHEGIRLPSGVWFEMVDKELLESVQMPECPAGLTISAPTQTSVDVSLILDVERMLDYSLCQETWSKV
HSGLPISPVDLGYIAPKNPGAGPAFTIVNGTLKYFDTRYLRIDIEGPVLKKMTGKVSGTPTKRELWTEWFPYDDVEI
GPNGVLKTPEGYKFPLYMIGHGLLDSDLQKTSQAEVFHHPQIAEAVQKLPDDETLFFGDTGISKNPVEVIEGWFSNW
RSSVMAIVFAILLLVITVLMVRLCVAFRHFCCQKRHKIYNDLEMNQLRR

VSV-G Alagoa ectodomain WT:

(SEQ ID NO: 17)

KFTIVFPQSQKGDWKDVPPNYRYCPSSADQNWHGDLLGVNIRAKMPKVHKAIKADGWMCHAAKWVTTCDYRWYGPQY
ITHSIHSFIPTKAQCEESIKQTKEGVWINPGFPPKNCGYASVSDAESIIVQATAHSVMIDEYSGDWLDSQFPTGRCT
GSTCETIHNSTLWYADYQVTGLCDSALVSTEVTFYSEDGLMTSIGRQNTGYRSNYFPYEKGAAACRMKYCTHEGIRL
PSGVWFEMVDKELLESVQMPECPAGLTISAPTQTSVDVSLILDVERMLDYSLCQETWSKVHSGLPISPVDLGYIAPK
NPGAGPAFTIVNGTLKYFDTRYLRIDIEGPVLKKMTGKVSGTPTKRELWTEWFPYDDVEIGPNGVLKTPEGYKFPLY
MIGHGLLDSDLQKTSQAEVFHHPQIAEAVQKLPDDETLFFGDTGISKNPVEVIEGWFSNWRSSVMAIVFAILLLVIT
VLMVRLCVAFRHFCCQKRHKIYNDLEMNQLRR

-continued

VSV-G Cocal Full length WT:

(SEQ ID NO: 18)

MNFLLLTFIVLPLCSHAKFSIVFPQSQKGNWKNVPSSYHYCPSSSDQNWHNDLLGITMKVKMPKTHKAIQADGWMCH

AAKWITTCDFRWYGPKYITHSIHSIQPTSEQCKESIKQTKQGTWMSPGFPPQNCGYATVTDSVAVVVQATPHHVLVD

EYTGEWIDSQFPNGKCETEECETVHNSTVWYSDYKVTGLCDATLVDTEITFFSEDGKKESIGKPNTGYRSNYFAYEK

GDKVCKMNYCKHAGVRLPSGVWFEFVDQDVYAAAKLPECPVGATISAPTQTSVDVSLILDVERILDYSLCQETWSKI

RSKQPVSPVDLSYLAPKNPGTGPAFTIINGTLKYFETRYIRIDIDNPIISKMVGKISGSQTERELWTEWFPYEGVEI

GPNGILKTPTGYKFPLFMIGHGMLDSDLHKTSQAEVFEHPHLAEAPKQLPEEETLFFGDTGISKNPVELIEGWFSSW

KSTVVTFFFAIGVFILLYVVARIVIAVRYRYQGSNNKRIYNDIEMSRFRK

VSV-G Cocal ectodomain WT:

(SEQ ID NO: 19)

KFSIVFPQSQKGNWKNVPSSYHYCPSSSDQNWHNDLLGITMKVKMPKTHKAIQADGWMCHAAKWITTCDFRWYGPKY

ITHSIHSIQPTSEQCKESIKQTKQGTWMSPGFPPQNCGYATVTDSVAVVVQATPHHVLVDEYTGEWIDSQFPNGKCE

TEECETVHNSTVWYSDYKVTGLCDATLVDTEITFFSEDGKKESIGKPNTGYRSNYFAYEKGDKVCKMNYCKHAGVRL

PSGVWFEFVDQDVYAAAKLPECPVGATISAPTQTSVDVSLILDVERILDYSLCQETWSKIRSKQPVSPVDLSYLAPK

NPGTGPAFTIINGTLKYFETRYIRIDIDNPIISKMVGKISGSQTERELWTEWFPYEGVEIGPNGILKTPTGYKFPLF

MIGHGMLDSDLHKTSQAEVFEHPHLAEAPKQLPEEETLFFGDTGISKNPVELIEGWFSSWKSTVVTFFFAIGVFILL

YVVARIVIAVRYRYQGSNNKRIYNDIEMSRFRK

VSV-G Morreton Full length WT:

(SEQ ID NO: 20)

MLVLYLLLSLLALGAQCKFTIVFPHNQKGNWKNVPANYQYCPSSSDLNWHNGLIGTSLQVKMPKSHKAIQADGWMCH

AAKWVTTCDFRWYGPKYVTHSIKSMIPTVDQCKESIAQTKQGTWLNPGFPPQSCGYASVTDAEAVIVKATPHQVLVD

EYTGEWVDSQFPTGKCNKDICPTVHNSTTWHSDYKVTGLCDANLISMDITFFSEDGKLTSLGKEGTGFRSNYFAYEN

GDKACRMQYCKHWGVRLPSGVWFEMADKDIYNDAKFPDCPEGSSIAAPSQTSVDVSLIQDVERILDYSLCQETWSKI

RAHLPISPVDLSYLSPKNPGTGPAFTIINGTLKYFETRYIRVDIAGPIIPQMRGVISGTTTERELWTDWYPYEDVEI

GPNGVLKTATGYKFPLYMIGHGMLDSDLHISSKAQVFEHPHIQDAASQLPDDETLEFGDTGLSKNPIELVEGWFSGW

KSTIASFFFIIGLVIGLYLVLRIGIALCIKCRVQEKRPKIYTDVEMNRLDR

VSV-G Morreton ectodomain WT:

(SEQ ID NO: 21)

KFTIVFPHNQKGNWKNVPANYQYCPSSSDLNWHNGLIGTSLQVKMPKSHKAIQADGWMCHAAKWVTTCDFRWYGPKY

VTHSIKSMIPTVDQCKESIAQTKQGTWLNPGFPPQSCGYASVTDAEAVIVKATPHQVLVDEYTGEWVDSQFPTGKCN

KDICPTVHNSTTWHSDYKVTGLCDANLISMDITFFSEDGKLTSLGKEGTGFRSNYFAYENGDKACRMQYCKHWGVRL

PSGVWFEMADKDIYNDAKFPDCPEGSSIAAPSQTSVDVSLIQDVERILDYSLCQETWSKIRAHLPISPVDLSYLSPK

NPGTGPAFTIINGTLKYFETRYIRVDIAGPIIPQMRGVISGTTTERELWTDWYPYEDVEIGPNGVLKTATGYKFPLY

MIGHGMLDSDLHISSKAQVFEHPHIQDAASQLPDDETLFFGDTGLSKNPIELVEGWFSGWKSTIASFFFIIGLVIGL

YLVLRIGIALCIKCRVQEKRPKIYTDVEMNRLDR

Fc IgG1 (Accession No. P01857)

(SEQ ID NO: 26)

ASTKGPSVFPLAPSSKSTSGGTAALGCLVKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVLDSDGSFFLYSKLTVDKSRWQQGNVFSC

SVMHEALHNHYTQKSLSLSPGK

Fc IgG2 (Accession No. AAN76043)

(SEQ ID NO: 27)

STKGPSVFPLAPCSRSTSESTAALGCLVKDYFPEPVTVSWNSGALTSGVHTFPAVLQSSGLYSLSSVVTVPSSSLGT

QTYTCNVDHKPSNTKVDKTVERKCCVECPPCPAPPVAGPSVFLFPPKPKDTLMISRTPEVTCVVVDVSHEDPEVQFN

-continued

WYVDGVEVHNAKTKPREEQFNSTFRVVSVLTVVHQDWLNGKEYKCKVSNKGLPAPIEKTISKTKGQPREPQVYTLPP

SREEMTKNQVSLTCLVKGFYPSDIAVEWESNGQPENNYKTTPPMLDSDGSFFLYSKLTVDKSRWQQGNVFSCSVMHE

ALHNHYTQKSLSLSPGK

Fc IgG4 (Accession No. AAB59394)

(SEQ ID NO: 28)

STKGPSVFPLAPCSRSTSESTAALGCLVKDYFPEPVTVSWNSGALTSGVHTFPAVLQSSGLYSLSSVVTVPSSSLGT

KTYTCNVDHKPSNTKVDKRVESKYGPPCPSCPAPEFLGGPSVFLFPPKPKDTLMISRTPEVTCVVVDVSQEDPEVQF

NWYVDGVEVHNAKTKPREEQFNSTYRVVSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDGSFFLYSRLTVDKSRWQEGNVFSCSVMH

EALHNHYTQKSLSLSLGK

What is claimed:

1. A viral particle comprising a heterologous viral glycoprotein and a targeting moiety, wherein the targeting moiety comprises a polypeptide having the formula T-$S_1$, wherein T is a target binding domain and Sis a stalk portion, wherein the heterologous viral glycoprotein is a VSV-G polypeptide comprising an amino acid sequence having at least 95% identity to SEQ ID NO: 2;

wherein the target binding domain (T) comprises a scFv antibody that binds to CD7, wherein the scFv comprises a heavy chain variable region and a light chain variable region, wherein the heavy chain variable region comprises a heavy chain complementarity determining region 1 (HCDR1) comprising the amino acid sequence of SEQ ID NO: 30, a HCDR2 comprising the amino acid sequence of SEQ ID NO: 31, and a HCDR3 comprising the amino acid sequence of SEQ ID NO: 32; and wherein the light chain variable region comprises a light chain complementarity determining region 1 (LCDR1) comprising the amino acid sequence of SEQ ID NO: 33, a LCDR2 comprising the amino acid sequence of SEQ ID NO: 34, and a LCDR3 comprising the amino acid sequence of SEQ ID NO: 35; and wherein the stalk portion $S_1$ comprises a Fc protein comprising an amino acid sequence having at least 95% identity to the amino acid sequence of SEQ ID NO: 103, and wherein the S1 stalk portion is attached to the surface of the viral particle through a transmembrane domain.

2. The viral particle of claim 1, wherein the heavy chain variable region comprises an amino acid sequence having at least 95% identity to the amino acid sequence of SEQ ID NO: 36; and the light chain variable region comprises an amino acid sequence having at least 95% identity to the amino acid sequence of SEQ ID NO: 37.

3. The viral particle of claim 1, wherein the scFv comprises an amino acid sequence having at least 95% sequence identity to the amino acid sequence of SEQ ID NO: 38.

4. The viral particle 1, wherein the VSV-G polypeptide comprises a mutation at position 182 as compared to SEQ ID NO: 2.

5. The viral particle 1, wherein the VSV-G polypeptide comprises a I182E or I182D mutation as compared to SEQ ID NO: 2.

6. The viral particle of claim 4, wherein the VSV-G polypeptide further comprises a mutation at position 214 and/or position 352 of SEQ ID NO: 2.

7. The viral particle of claim 6, wherein the mutation at position 182 is I182D or I182E, the mutation at position 214 is T214N, and the mutation at position 352 is T352A.

8. A method of infecting a cell, the method comprising contacting the cell with the viral particle of claim 1.

9. The viral particle of claim 1, wherein the heavy chain variable region comprises an amino acid sequence having at least 98% identity to the amino acid sequence of SEQ ID NO: 36; and the light chain variable region comprises an amino acid sequence having at least 98% identity to the amino acid sequence of SEQ ID NO: 37.

10. The viral particle of claim 1, wherein the heavy chain variable region comprises the amino acid sequence of SEQ ID NO: 36; and the light chain variable region comprises the amino acid sequence of SEQ ID NO: 37.

11. The viral particle of claim 1, wherein the scFv comprises an amino acid sequence having at least 98% sequence identity to the amino acid sequence of SEQ ID NO: 38.

12. The viral particle of claim 1, wherein the scFv comprises the amino acid sequence of SEQ ID NO: 38.

13. The viral particle of claim 1, wherein the VSV-G polypeptide comprises the amino acid sequence of SEQ ID NO: 23.

14. The viral particle of claim 1, wherein the Fc protein comprises one or more mutations that correspond to L19A, L20A, N82A, P114G, 138A, H95A, or H220A of SEQ ID NO: 103.

15. The viral particle of claim 1, wherein:

the VSV-G polypeptide comprises an amino acid sequence that is at least 95% identical to SEQ ID NO: 2 and an I182E or an I182D mutation as compared to SEQ ID NO: 2;

the target binding domain (T) comprises an scFv comprising an amino acid sequence that is at least 95% identical to SEQ ID NO: 38, wherein the scFv comprises a HCDR1 comprising the amino acid sequence of SEQ ID NO: 30; a HCDR2 comprising the amino acid sequence of SEQ ID NO: 31; a HCDR3 comprising the amino acid sequence of SEQ ID NO: 32; a LCDR1 comprising the amino acid sequence of SEQ ID NO: 33; a LCDR2 comprising the amino acid sequence of SEQ ID NO: 34; and a LCDR3 comprising the amino acid sequence of SEQ ID NO: 35; and wherein the Fc protein comprises an amino acid sequence having at least 95% identity to the amino acid sequence of SEQ ID NO: 104, provided that the Fc protein comprises the mutations of L19A, L20A, N82A, P114G, I38A, H95A, and H220A.

16. The viral particle of claim 1, wherein:

the VSV-G polypeptide comprises an amino acid sequence that is at least 98% identical to SEQ ID NO: 2 and an I182E or an I182D mutation as compared to SEQ ID NO: 2;

the target binding domain (T) comprises an scFv comprising an amino acid sequence that is at least 98% identical to SEQ ID NO: 38, wherein the scFv comprises a HCDR1 comprising the amino acid sequence of SEQ ID NO: 30; a HCDR2 comprising the amino acid sequence of SEQ ID NO: 31; a HCDR3 comprising the amino acid sequence of SEQ ID NO: 32; a LCDR1 comprising the amino acid sequence of SEQ ID NO: 33; a LCDR2 comprising the amino acid sequence of SEQ ID NO: 34; and a LCDR3 comprising the amino acid sequence of SEQ ID NO: 35; and wherein the Fc protein comprises an amino acid sequence having at least 98% identity to the amino acid sequence of SEQ ID NO: 104, provided that the Fc protein comprises the mutations of L19A, L20A, N82A, P114G, I38A, H95A, and H220A.

17. The viral particle of claim 1, wherein:

the VSV-G polypeptide comprises an amino acid sequence that is at least 98% identical to SEQ ID NO: 2 and an I182E mutation as compared to SEQ ID NO: 2;

the target binding domain (T) comprises an scFv comprising an amino acid sequence that is at least 98% identical to SEQ ID NO: 38, wherein the scFv comprises a HCDR1 comprising the amino acid sequence of SEQ ID NO: 30; a HCDR2 comprising the amino acid sequence of SEQ ID NO: 31; a HCDR3 comprising the amino acid sequence of SEQ ID NO: 32; a LCDR1 comprising the amino acid sequence of SEQ ID NO: 33; a LCDR2 comprising the amino acid sequence of SEQ ID NO: 34; and a LCDR3 comprising the amino acid sequence of SEQ ID NO: 35; and wherein the Fc protein comprises an amino acid sequence having at least 98% identity to the amino acid sequence of SEQ ID NO: 104, provided that the Fc protein comprises the mutations of L19A, L20A, N82A, P114G, I38A, H95A, and H220A.

18. The viral particle of claim 1, wherein:

the VSV-G polypeptide comprises an amino acid sequence that is at least 95% identical to SEQ ID NO: 2 and an I182E or an I182D mutation as compared to SEQ ID NO: 2; and the targeting moiety comprises an amino acid sequence having at least 95% identity to SEQ ID NO: 98.

19. The viral particle of claim 1, wherein:

the VSV-G polypeptide comprises an amino acid sequence that is at least 98% identical to SEQ ID NO: 2 and an I182E or an I182D mutation as compared to SEQ ID NO: 2; and the targeting moiety comprises an amino acid sequence having at least 98% identity to SEQ ID NO: 98.

20. The viral particle of claim 1, wherein:

the VSV-G polypeptide comprises an amino acid sequence that is at least 98% identical to SEQ ID NO: 2 and an I182E mutation as compared to SEQ ID NO: 2; and the targeting moiety comprises an amino acid sequence having at least 98% identity to SEQ ID NO: 98.

21. The viral particle of claim 1, wherein the viral particle further comprises a nucleic acid molecule encoding a CAR.

22. The viral particle of claim 21, wherein the CAR comprises an antigen binding domain that binds to CD20.

23. The viral particle of claim 22, wherein the antigen binding domain that binds to CD20 comprises a polypeptide comprising a light chain and a heavy chain comprising: a heavy chain variable region of the heavy chain having at least 95% identity to an amino acid sequence of SEQ ID NO: 89; and a light chain variable region of the light chain having at least 95% identity to an amino acid sequence of SEQ ID NO: 90.

24. The viral particle of claim 22, wherein the CAR comprises an amino acid sequence having at least 95% identity to an amino acid sequence of SEQ ID NO: 99.

25. The viral particle of claim 22, wherein the CAR comprises an amino acid sequence having at least 98% identity to an amino acid sequence of SEQ ID NO: 99.

26. The viral particle of claim 22, wherein the CAR comprises the amino acid sequence of SEQ ID NO: 99.

27. The viral particle of claim 1, wherein:

the VSV-G polypeptide comprises the amino acid sequence of SEQ ID NO: 23; and the targeting moiety comprises the amino acid sequence of SEQ ID NO: 98.

28. The viral particle of claim 27, wherein the viral particle further comprises a nucleic acid molecule encoding a CAR.

29. The viral particle of claim 28, wherein the CAR comprises an antigen binding domain that binds to CD20.

30. The viral particle of claim 29, wherein the antigen binding domain that binds to CD20 comprises a polypeptide comprising a light chain and a heavy chain comprising: a heavy chain variable region of the heavy chain having at least 95% identity to an amino acid sequence of SEQ ID NO: 89; and a light chain variable region of the light chain having at least 95% identity to an amino acid sequence of SEQ ID NO: 90.

31. The viral particle of claim 29, wherein the CAR comprises an amino acid sequence having at least 95% identity to an amino acid sequence of SEQ ID NO: 99.

32. The viral particle of claim 29, wherein the CAR comprises an amino acid sequence having at least 98% identity to an amino acid sequence of SEQ ID NO: 99.

33. The viral particle of claim 29, wherein the CAR comprises the amino acid sequence of SEQ ID NO: 99.

* * * * *

UNITED STATES PATENT AND TRADEMARK OFFICE
CERTIFICATE OF CORRECTION

PATENT NO. : 12,252,512 B2
APPLICATION NO. : 18/358358
DATED : March 18, 2025
INVENTOR(S) : Bruce C. Schnepp and Philip R. Johnson Page 1 of 1

It is certified that error appears in the above-identified patent and that said Letters Patent is hereby corrected as shown below:

In the Claims

In Claim 1, Column 219, Line 15, replace:
"Sis"
With:
--$S_1$ is--

In Claim 1, Column 219, Line 38, replace:
"S1"
With:
--$S_1$--

Signed and Sealed this
Twenty-ninth Day of April, 2025

Coke Morgan Stewart
*Acting Director of the United States Patent and Trademark Office*